United States Patent
Sällberg et al.

(10) Patent No.: US 7,566,812 B2
(45) Date of Patent: Jul. 28, 2009

(54) TRANSGENIC MOUSE MODELS OF HEPATITIS C VIRUS (HCV) AND IDENTIFICATION OF HCV THERAPEUTICS

(75) Inventors: Matti Sällberg, Stockholm (SE); Lars Frelin, Tumba (SE)

(73) Assignee: Tripep AB, Huddinge (SE)

( * ) Notice: Subject to any disclaimer, the term of this patent is extended or adjusted under 35 U.S.C. 154(b) by 0 days.

(21) Appl. No.: 11/660,878

(22) PCT Filed: Aug. 26, 2005

(86) PCT No.: PCT/IB2005/003736

§ 371 (c)(1), (2), (4) Date: May 6, 2008

(87) PCT Pub. No.: WO2006/021896

PCT Pub. Date: Mar. 2, 2006

(65) Prior Publication Data

US 2008/0295185 A1    Nov. 27, 2008

Related U.S. Application Data

(60) Provisional application No. 60/649,975, filed on Feb. 4, 2005, provisional application No. 60/605,030, filed on Aug. 27, 2004.

(51) Int. Cl.
*A01K 67/027* (2006.01)
*A01K 67/033* (2006.01)
*A01K 67/00* (2006.01)

(52) U.S. Cl. .............................. 800/18; 800/8
(58) Field of Classification Search .............. 800/18, 800/8

See application file for complete search history.

(56) References Cited

FOREIGN PATENT DOCUMENTS

WO    WO 99/61039    * 12/1999

* cited by examiner

*Primary Examiner*—Michael C. Wilson
(74) *Attorney, Agent, or Firm*—Knobbe Martens Olson & Bear LLP

(57) ABSTRACT

Disclosed herein is the discovery of novel NS3/4A compositions with enhanced expression abilities. Embodiments of the invention include codon optimized NS3/4A compositions and compositions with the Semliki forest virus replicon. Additional embodiments include transgenic organisms containing these NS3/4A compositions, methods or using these transgenic mice to screen and refine drugs, and the drugs refined by these methods. Additional embodiments include protease activity dependent molecules that can indicate the presence or absence of a protease inhibitor.

13 Claims, 30 Drawing Sheets

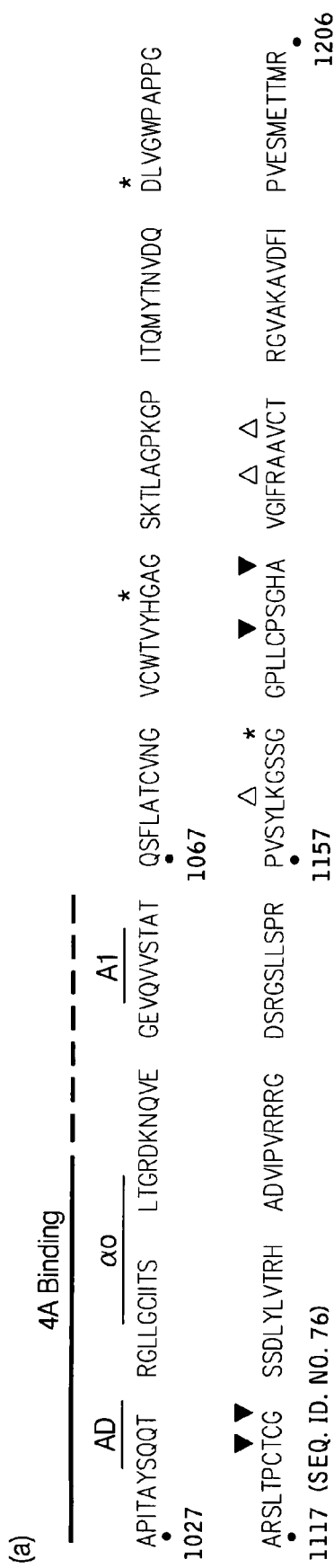
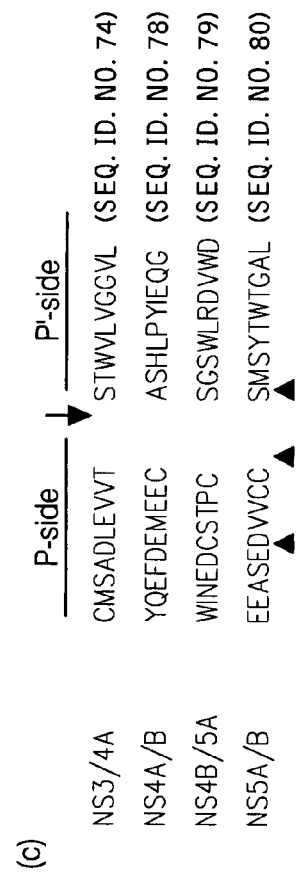
FIG. 13A
FIG. 13B

Wild type HBeAg

P25 pre core protein ->
    Secretory HBeAg ->
        Particulate HBcAg ->

HBe   MQLFHLCLIISCSCPTVQAS-KLCLGWLWG-MDIDPYKEF..   SEQ ID NO: 45
Signal seq Secretory seq HBeAg with an artificially introduced NS3/4A proteolytic site at HBcAg position 3
(cleavage will destroy secretion of HBeAg)

HBcAg 1-149->

HBeM1 MQLFHLCLIISCSCPTVQAS-KLCLGWLWG-MDI-LEVVT-STWVL-DPYKEF.. SEQ ID NO: 46
Signal seq Secretory seq * * P1 P1'
NS3/4A site

FIG. 14D

FIG. 18E  LPS activated nuclear extracts
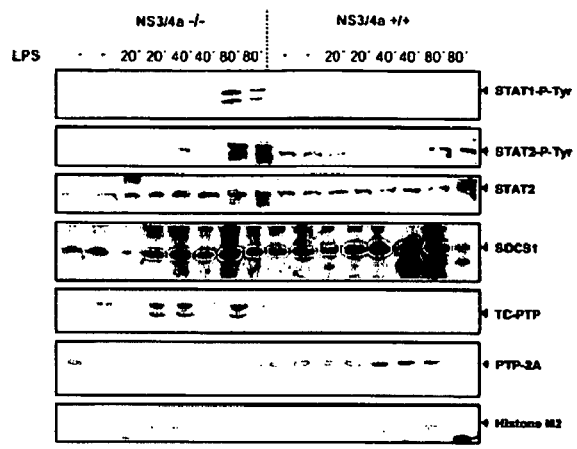
FIG. 18F  αIFN activated nuclear extracts
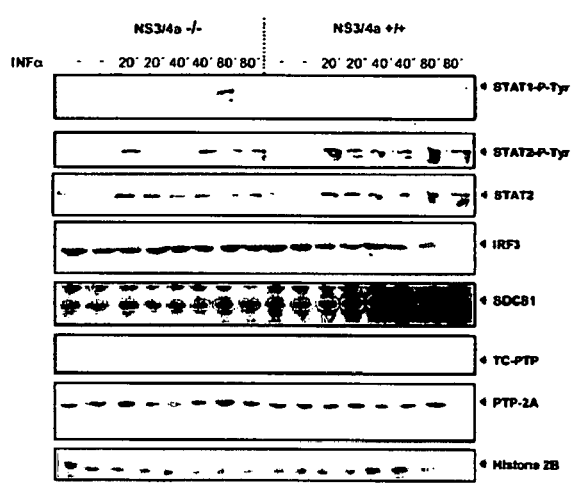
FIG. 18G  γIFN activated nuclear extracts
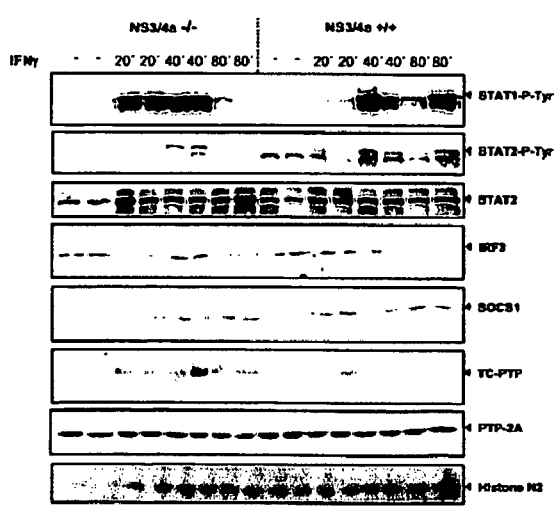

TRANSGENIC MOUSE MODELS OF HEPATITIS C VIRUS (HCV) AND IDENTIFICATION OF HCV THERAPEUTICS

CROSS REFERENCE TO RELATED APPLICATION

This application claims the benefit and priority to and is a U.S. National Phase of PCT International Application Number PCT/IB2005/003736, filed on Aug. 26, 2005, designating the United States of America, which claims priority under 35 U.S.C. § 119 to U.S. Provisional Patent Application No. 60/649,975 filed on Feb. 4, 2005 and U.S. Provisional Patent Application No. 60/605,030 filed on Aug. 27, 2004. The disclosures of the above- described applications are hereby incorporated by reference in their entirety.

FIELD OF THE INVENTION

Aspects of the invention concern the use of genes encoding the hepatitis C virus (HCV) nonstructural proteins (NS3/4A) to create transgenic mice, which can be used to identify compounds that inhibit HCV infection. Embodiments include the exogenous nucleic acids used to create NS3/4A-containing transgenic mice, the exogenous peptides encoded by said nucleic acids, genetically modified mice containing said compositions, and methods of using said genetically modified mice to identify compositions that treat or prevent HCV infection. Preferred embodiments include pharmaceuticals and dietary supplements comprising an inhibitor of a kinase (e.g., a p38 Map kinase), which can be provided to subjects infected with HCV or subjects at risk of becoming infected with HCV.

BACKGROUND OF THE INVENTION

The HCV genome is approximately 9.4 kb in length, and encodes at least ten polypeptides. (Kato, *Microb. Comp. Genomics*, 5:129-151 (2000)). The genomic RNA is translated into one single polyprotein that is subsequently cleaved by viral and cellular proteases to yield the functional polypeptides. (Id.) The polyprotein is cleaved to three structural proteins (core protein, E1 and E2), to p7 of unknown function, and to six non-structural (NS) proteins (NS2, NS3, NS4A/B, NS5A/B). (Id.) NS3 encodes a serine protease that is responsible for some of the proteolytic events required for virus maturation (Kwong et al., *Antiviral Res.*, 41:67-84 (1999)) and NS4A acts as a co-factor for the NS3 protease. (Id.) NS3 further displays NTPase activity, and possesses RNA helicase activity in vitro. (Kwong et al., *Curr. Top. Microbiol. Immunol.*, 242:171-96 (2000)).

HCV infection typically progresses from an acute to a chronic phase. (*Virology*, Fields ed., third edition, Lippencott-Raven publishers, pp. 1041-47 (1996)). Acute infection is characterized by high viral replication and high viral load in liver tissue and peripheral blood. (Id. at 1041-42.) The acute infection is cleared by the patient's immune defense system in roughly 20-40% of the infected individuals; in the other 60-80% the virus establishes a chronic, persistent infection. (Lawrence, *Adv. Intern. Med.*, 45:65-105 (2000)). During the chronic phase replication takes place in the liver and the virus is readily detected in peripheral blood. (*Virology*, supra, pp. 1042).

The infected host mounts both a humoral and a cellular immune response against the HCV virus but in most cases the response fails to prevent establishment of the chronic disease. Following the acute phase, the infected patient produces antiviral antibodies including neutralizing antibodies to the envelope proteins E1 and E2. (Id. at 1045). This antibody response is sustained during chronic infection. (Id.) In chronically infected patients, the liver is also infiltrated by both CD8+ and CD4+ lymphocytes. (Id. at 1044-45). Additionally, infected patients produce interferons as an early response to the viral infection. (Id. at 1045). It is likely that the vigor of the initial immune response against the infection determines whether the virus will be cleared or whether the infection will progress to a chronic phase. (Pape et al., *J. Viral. Hepat.*, 6 Supp. 1:36-40 (1999)).

Although a humoral and cellular immune response targeted against the NS3 protein appears to be important in patients who clear an acute HCV infection (see Diepolder H M et al., *Lancet*, 346(8981):1006-7 (1995) and Missale G., et al., *J Clin Invest*, 98(3):706-14 (1996)), the HCV proteins that are responsible for inducing an HCV phenotype is largely unknown.

The need for compositions that treat or prevent HCV infection is manifest. This goal is complicated by the fact that the creation of an animal model for HCV infection has proven difficult. So far, human, chimpanzees, and tree shrews are the primary animals that are susceptible for infection with human HCV (Xie et al. Virology 244:513-20 (1998)). HCV has been reported to infect primary cultures of human hepatocytes; however, the cells do not support the production of progeny virons (Fournier et al. *J Gen Virol* 79 (Pt 10):2367-74 (1998)). Current animal models either do not exhibit the normal course of infection or require the use of previously infected human liver cells, or both. (See, e.g., WO 99/16307; Galun et al. J. Infect. Dis. 172:25-30 (1995); Bronowicki et al. Hepatology 28:211-8 (1998); and Lerta et al. Hepatology 28 (4Pt2):498A (1998). Two exceptions to this are that Chimpanzees and uPA-Scid mice repopulated with human liver can both be infected in vivo (Mercer et al., Hepatitis C virus replication in mice with chimeric human livers. *Nat. Med.*, 7(8):927-33 (2001)).

One recent attempt to overcome these obstacles was described in U.S. Pat. No. 6,509,514, issued Jan. 21, 2003 to Kneteman et al., herein expressly incorporated by reference in its entirety; however, the production of Kneteman's modified mouse required engrafting human hepatocytes into a mouse liver, a time consuming and laborious process. Another drawback of this approach is that the mice were found to be immunocompromised.

Another attempt to overcome these obstacles was described in U.S. Pat. No. 6,201,166, issued Mar. 13, 2001 to Kohara et al. (involving the use of a Cre-loxP switch system to attempt to drive expression of particular HCV proteins), herein expressly incorporated by reference in its entirety. Kohara et al., however, only expressed certain types of HCV proteins (CN2, N24 or CR) and the approach required activation of the Cre-loxP system in order to induce HCV protein expression. There remains a need for more transgenic models of HCV infection and compositions that treat or prevent HCV infection.

SUMMARY OF THE INVENTION

It was discovered that exogenous nucleic acid constructs comprising hepatitis C virus (HCV) nonstructural protein 3 (NS3) and nonstructural protein 4A (NS4A) can be introduced into mice, thereby creating HCV NS3/4A transgenic mice, which express appreciable amounts of NS3 and/or NS4A proteins in the livers of said genetically modified mice (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 micrograms NS3 and/or NS4A protein per gram of liver tissue). HCV NS3/4A transgenic mice created, as described herein, have a reduced sensitivity or an increased resistance to TNF-alpha, as compared to wild-type mice of the same variety that have not been genetically modified to contain NS3/4A. That is, some of the genetically modified mice, created as described herein, survive contact with an amount of TNF-alpha that is lethal to wild-type mice of the same variety. Some of the genetically modified mice created as described herein also revert to a TNF-alpha sensitive phenotype when said mice are contacted with a p38 MAP kinase inhibitor, such as SB203580 or SB202190. That is, some of the genetically modified mice created as described herein, which have a reduced sensitivity or increased resistance to TNF-alpha, can be induced to become as sensitive to TNF-alpha as a wild-type mouse of the same variety by contacting the genetically modified mouse with an inhibitor of p38 MAP kinase.

Genetically modified mice that express NS3/4A are used as models for HCV infection and provide an in vivo system for the analysis and testing of compounds that inhibit HCV replication and/or HCV infection. Optionally, signal molecules and secretory signals can be included on said nucleic acid constructs used to create said genetically modified mice so as to facilitate the analysis and testing of said compounds for anti-HCV activity. By some approaches, the genetically modified mice, created as described herein, are contacted with a compound and an indicator of HCV infection, such as expression of NS3, NS3 protease activity, or TNF-alpha sensitivity is analyzed. Compounds that inhibit HCV replication (e.g., inhibitors of NS3 expression or protease activity or compounds that restore TNF-alpha sensitivity) are identified using the methods described herein and said identified compounds (e.g., p38 MAP kinase inhibitors such as, SB203580 or SB202190) can be incorporated into pharmaceuticals and/or dietary supplements, which can be provided to HCV infected individuals or individuals at risk of becoming infected with HCV. That is, aspects of the invention described herein concern the use of p38 MAP kinase inhibitors such as, SB203580 or SB202190, to prepare a medicament for the treatment and/or prevention of HCV infection and methods of using said medicaments in HCV treatment or prophylactic methods.

Accordingly, some embodiments relate to a transgenic non-human mammal (e.g., a rodent such as, a mouse) containing an exogenous DNA sequence stably integrated in its genome, wherein said exogenous DNA sequence comprises a mouse major urinary promoter (MUP) operably linked to an HCV NS3 gene. The genetically modified non-human mammal can comprise an allele comprising an HCV NS3 gene and an HCV NS4A gene. The non-human mammal preferably expresses HCV NS3 and/or NS4A proteins in the liver. In some embodiments, the NS3 gene and the NS4A genes are codon optimized. In some embodiments, the only hepatitis C virus genes in the allele consist of a NS3/4A gene. The NS3 and NS4A genes that are inserted into mice can be codon optimized for mice or humans. Codon-optimized sequences can be generated by software, for example, DNABUILDER.

It was also discovered that various NS3/4A cleavage site nucleic acid and amino acid constructs can be created so as to create secretion dependent indicators of NS3 protease activity. These indicators (PADSI, for Protease Activity Dependent Secreted Indicators) can be used to monitor the activity of a NS3 protease in vivo by looking for the presence or absence of detectable markers (indicators) in various localities in an organism.

In some embodiments, a method of identifying a compound that inhibits hepatitis C virus replication is provided. By some approaches, a genetically modified mouse created as described above, is contacted with a test compound, and a marker for the inhibition of HCV replication (e.g., protease activity or TNF-alpha sensitivity) is analyzed. In some embodiments, the marker for the inhibition of HCV is identified by analyzing a liver cell or liver tissue of the mouse contacted with the test compound and analyzing a liver cell or liver tissue of a second mouse, which was not contacted with the test compound.

In some aspects, a method of making a genetically modified non-human mammal, such as a mouse is provided. The method comprises providing a NS3/4A gene targeting construct, introducing the NS3/4A gene and a selectable marker sequence into a non-human mammal embryonic stem cell, introducing the non-human mammal embryonic stem cell into a non-human mammal embryo, transplanting the embryo into a pseudopregnant non-human mammal, allowing the embryo to develop to term, and identifying a genetically modified non-human mammal whose genome comprises the NS3/4A gene in an allele.

In some embodiments, the NS3 protein that is expressed in said transgenic mice is detectable via a western blot. In some embodiments, the NS3 protein that is expressed in said transgenic mice is restricted to expression in the cytoplasm of hepatocytes. In some embodiments, the genetically modified mouse has a liver with a significantly increased weight relative to a mouse without NS3 protein expression. In some embodiments, the genetically modified mouse has a lower number of nuclei per unit area in its liver tissue relative to a mouse without NS3 protein being expressed in the mouse.

In some embodiments, the genetically modified mouse, created as described herein, comprises an altered intrahepatic distribution of immune cells. In some embodiments, the genetically modified mouse has a reduced number of intrahepatic inflammatory foci than a mouse that does not comprise an NS3 and/or NS4A gene (e.g., a wild-type mouse). In some embodiments, the frequency of such foci occurring in the genetically modified mouse is reduced as compared to that of a non-transgenic mouse that does not contain the NS3 and/or NS4A genes. In some embodiments the frequency is reduced at least two fold or at least four fold. In some embodiments, the genetically modified mouse has a reduced number of intra-hepatic inflammatory foci, as compared to a non-transgenic mouse that does not comprise a an NS3 and/or NS4A gene. In some embodiments, the liver in the genetically modified mouse has a NS3/4A protein distribution and tissue localization consistent with HCV infection (e.g., protein expression in the liver).

In some aspects, the liver in the mouse having an allele with an NS3 and NS4A gene has an altered hepatic distribution of immune cells. In some embodiments, NS3 and/or NS4A protein expression is restricted to hepatocytes. In some embodiments, NS3 and/or NS4A protein expression in said genetically modified mice is in the hepatic venules and portal tracts. In some embodiments, the amount of NS3 protein that is expressed in said genetically modified mice is an amount that is sufficient for detection by immuno histochemistry (e.g., expression in at least 1% of the hepatocytes of the mouse). That is, in some embodiments, the genetically modified mice, created as described herein, comprise an amount of hepatocytes that express NS3 and/or NS4A, which is at least, more than, or equal to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 31%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) of the total number of hepatocytes of the mouse.

In some aspects, a genetically modified mouse with a persistent expression of NS3 and/or NS4A proteins is provided. In some embodiments, the only HCV proteins produced by the mouse are NS3 and/or NS4A proteins. In some embodiments, the amount of persistent NS3 protein produced is detectable and limited to liver cells. In some embodiments, the term "persistent" means an expression of NS3 and/or NS4A that lasts for more than 1 week, 2 weeks, 3 weeks, 1 month, two months, three months, four months, five months, six months, seven months, eight months, nine months ten months, eleven months, one year, 13 months, fourteen months, fifteen months, sixteen months, seventeen months, or eighteen months.

In some embodiments, a composition for analyzing compounds for their ability to inhibit the activity of a protease is provided. The composition comprises a NS3 gene, a gene encoding a detectable marker attached to the NS3 gene, a NS3/4A cleavage site, and a secretory gene encoding a secretory protein signal. Cleavage of the NS3/4A cleavage site results in a change in localization of the detectable marker.

In some aspects, a nucleic acid encoding a PADSI protein is provided. The PADSI nucleic acid comprises a nucleic acid section encoding a NS3 protein, a nucleic acid section encoding a cleavage site protein, a nucleic acid section encoding a secretory protein signal, and a nucleic acid section encoding a detectable marker. The nucleic acid sections are associated together so that their translation results in a single contiguous protein and cleavage of the cleavage site results in a change in localization of the detectable maker.

In some embodiments, a PADSI protein that comprises a NS3 protein segment, a cleavage site segment, a secretory protein signal segment, and a detectable marker segment is provided. The segments are associated in one contiguous piece and cleavage of the cleavage site results in a change in localization of the detectable maker. In some embodiments of the preceding aspects, the cleavage of the protein cleavage site results in the separation of the secretory protein signal and the detectable marker from the NS3 protein segment. In some embodiments of the preceding aspects, the cleavage of the cleavage site results in an increase in a presence of the detectable marker in a venous blood of an organism. In some embodiments of the preceding aspects, the NS3 protein is not autocatalytic for the cleavage of the cleavage site.

In some aspects, a nucleic acid encoding a PADSI protein is provided. It comprises a nucleic acid section encoding a cleavage site, a nucleic acid section encoding a secretory protein signal, and a nucleic acid section encoding a detectable marker. The cleavage site section, detectable marker, and secretory protein signal are associated together so that their translation results in a single contiguous protein. Cleavage of the cleavage site results in a change in localization of the detectable maker. In some embodiments, the compositions above further comprise a nucleic acid section encoding a NS3 protein.

In some aspects, a PADSI protein that comprises a cleavage site segment, a secretory protein signal segment, and a detectable marker segment is provided. The cleavage site segment and the secretory protein signal segment are associated in one contiguous piece, and cleavage of the cleavage site results in a change in localization of the detectable marker. In some embodiments, the protein further comprises a NS3 protein segment. In some embodiments of the previous aspects, the cleavage site is positioned between the secretory protein signal and the detectable marker.

In some embodiments, the constructs described above are incorporated into a transgenic organism (e.g., a mouse). Accordingly, cleavage at the protease cleavage site results in two separate protein segments such that one segment comprises the secretory protein signal and the other section comprises the detectable marker. In some embodiments of the previous aspects, the cleavage of the cleavage site segment results in the retention of the marker protein in a cell in which the PADSI is located. In some embodiments, the detectable marker is selected from the group consisting of: beta galactosidase, lac Z, Green Fluorescent Protein, and Luciferase. In some embodiments, the secretory signal is from an IG kappa sequence. In some embodiments, the cleavage site is selected from the group consisting of NS4A/4B, NS4B/5A, NS5A/5B, NS2/3, and NS3/4. In some embodiments, the change in localization is between the cells in which the uncleaved PADSI protein is located and the venous blood.

In some embodiments, a system for determining a NS3 protease inhibitor is provided. The system comprises a PADSI nucleic acid. The PADSI nucleic acid comprises a nucleic acid encoding a secretory section connected to a nucleic acid encoding a cleavage site, which is connected to a nucleic acid encoding a detectable marker and a transgenic organism. The transgenic organism produces NS3. In some embodiments, the transgenic organism further comprises the NS4A gene. In some embodiments, the PADSI nucleic acid is capable of being administered to the transgenic organism via a virus.

In some aspects, a system for determining a NS3 protease inhibitor is provided. The system comprises a PADSI protein that comprises a secretory protein signal connected to a NS3/4A cleavage site which in turn is connected to a detectable marker and a transgenic organism containing NS3/4A. The transgenic organism produces the NS3 protease. In some embodiments, the PADSI protein is administered to the transgenic organism in a viral vector and the transgenic organism is a transgenic mouse.

In some aspects, a system for determining a NS3 protease inhibitor is provided. The system comprises a PADSI nucleic acid. The PADSI nucleic acid comprises a nucleic acid encoding a NS3 protein connected to a nucleic acid encoding a NS3/4A cleavage site that in turn is connected to a nucleic acid encoding a detectable marker and a nucleic acid encoding a secretory protein signal.

The PADSI nucleic acid is expressed in an organism that is transgenic for the PADSI nucleic acid. In some aspects, a system for determining a NS3 protease inhibitor is provided. The system comprises a PADSI protein. The PADSI protein comprises a NS3 protein connected to a NS3/4A cleavage site that in turn is connected to a detectable marker and a secretory protein signal. The PADSI protein is in an organism that is transgenic for the PADSI nucleic acid. In some embodiments of the previous aspects, the detectable marker is detectable in venous blood. In some embodiments, the detectable marker is detectable via fluorescence. In some embodiments of the previous aspects, the detectable marker is luciferase.

In some aspects, a method of identifying a protease inhibitor is provided. The method comprises determining an initial level of detectable marker in the venous blood of one of the genetically modified mice described herein, contacting a candidate protease inhibitor to the mouse, determining the level of detectable marker in the venous blood of the mouse. A change in the level of detectable marker indicates the presence of a protease inhibitor. In some embodiments, the PADSI protein comprises a NS3 protein connected to a NS3/4A cleavage site. The NS3/4A cleavage site is connected to a secretory signal, the secretory signal is, in turn, connected to a detectable marker. A decrease in the amount of detectable marker in the venous blood of the organism indicates the presence of a protease inhibitor. In some embodiments, the PADSI protein comprises a secretory signal connected to a NS3 cleavage site that in turn is connected to a marker protein. The transgenic mouse is a NS3/4A-containing transgenic mouse. Cleavage of the NS3 cleavage site results in the marker protein remaining in a cell and, thus, an increase in the detectable marker in the venous blood indicates the presence of a protease inhibitor. In some of these embodiments the detection of the detectable marker is accomplished fluorescently. In some of these embodiments, the detection of the detectable marker is accomplished on the outside of the transgenic mouse's body. In some embodiments, a protease inhibitor detected by any of the above methods is formulated into a pharmaceutical or dietary supplement.

In some aspects, a genetically modified mouse that comprises a NS3 gene and a NS4A gene displays an increased resistance to an adverse effect of an application of TNF-alpha to the genetically modified mouse compared to a standard resistance of a wild-type mouse to the application of TNF-alpha. In some embodiments, the adverse effect is death of the mouse. In some embodiments, the adverse effect is death of a plurality of cells (e.g., death of liver cells). In some contexts, the term "TNF-alpha sensitivity" refers amount of cell death (e.g., liver cell death) in an animal after contact with TNF-alpha. In some contexts, the term "TNF-alpha sensitivity" refers to death of the animal. Accordingly, in some embodiments, the genetically modified mice created as described herein have a reduced TNF-alpha sensitivity as compared to a wild-type mouse of the same variety, which can be that the genetically modified mouse comprising NS3/4A exhibits less cell death (e.g., liver cell death) than a wild-type mouse of the same variety or that the NS3/4A-containing transgenic mouse survives contact with an amount of TNF-alpha that is lethal to a wild-type mouse of the same variety.

In some aspects, a method for screening for an inhibitor of suppressor of cytokine signaling-1 (SOCS1) inhibitor is provided. The method comprises providing a candidate SOCS1 inhibitor to a transgenic mouse, created as described herein, providing a lethal amount of TNF-alpha to the transgenic mouse, determining the impact of TNF-alpha on said transgenic mouse, comparing the impact of TNF-alpha administration on said transgenic mouse with the impact of TNF-alpha administration on a control mouse (e.g., a wild-type mouse of the same variety), and selecting an inhibitor of SOCS1 based on the observation that the impact of TNF-alpha on the transgenic mouse in the presence of the candidate inhibitor is approximately the same as the impact of TNF-alpha on the control mouse. In some embodiments, the impact of TNF-alpha is ascertained by analyzing the amount of cell death in the mouse, which can include an analysis of the liver cells or livers of the mice, such as, a measurement of liver cell death. In some embodiments, the amount of cell death is measured by determining survival of the mouse after contact with TNF-alpha.

In some embodiments, a method of identifying a p38 MAP kinase inhibitor is provided. The method comprises providing a candidate p38 inhibitor to a transgenic mouse created as described herein, providing an amount of TNF-alpha to said transgenic mouse, determining a first amount of cell death resulting from the contact of TNF-alpha to the transgenic mouse, comparing the first amount of cell death with a standard amount of cell death due to the contact of the amount of TNF-alpha to a control mouse (e.g., a wild-type mouse of the same variety), and selecting an inhibitor of p38 based on the fact that the first amount of cell death and the standard amount of cell death are about the same.

In some embodiments, a method for preventing, treating, or ameliorating an HCV related symptom in a patient is provided. The method comprises identifying a subject having an HCV related symptom and providing said identified subject a compound identified in by the methods described herein. In some embodiments, the compound is a p38 inhibitor. In some embodiments, the HCV treatment is a SOCS1 inhibitor. In some embodiments, the p38 inhibitor functions by preventing the phosphorylation of p38 kinase. In some embodiments, the p38 inhibitor is selected from the group consisting of SB 203580, SB 202190, KN62, U0126, PD 98059, Wortmannin, rapamycin, Ro 31-8220, Bis-1, Go 6976, UCN01, Indirubin-3'-monoxime, kenpaullone, alsterpaullone, PP1, PP2, SU 6656, SP 600125, ML-9, PD 169316, p38 MAP Kinase inhibitor, SB202190 hydrochloride, SB 203580 hydrochloride, SB 203580 Iodo, SC68376, SKF-86002, ZM 3363772, Anti-p38/HOG-1 antibody, and anti-p38 MAP Kinase antibody. In some embodiments, the p38 inhibitor is SB203580. In some embodiments, the p38 inhibitor is SB202190. In some embodiments, the HCV treatment is selected from the group that consists of: a SOCS1 inhibitor, an IFR3 enhancer, type-I IFN, typeI/II hepatic DC, STAT1 activator, STAT2 activator, siRNA to SOCS1, siRNA to p38, siRNA to PP2A, a blocking antibody to SOCS1, a blocking antibody to p38, a blocking antibody to PP2A, an activating antibody to IFR3, an activating antibody to STAT1, an activating antibody to STAT2, and a PP2A inhibitor. In some embodiments, the compound is an inhibitor of PP2A and it lowers the activity of PP2A in a NS3/4A transgenic mouse to a level similar to that of an activity of PP2A in a wild type mouse. In some embodiments, the compound is an inhibitor of SOCS1 and it lowers the activity of SOSC1 in a NS3/4A transgenic mouse to a level similar to that of an activity of SOCS1 in a wild type mouse. In some embodiments, the compound is an enhancer of the IFR3 activity and it increases the activity of IFR3 in a NS3/4A transgenic mouse to a level similar to that of an activity of IFR3 in a wild type mouse. In some embodiments, the enhancer of IFR3 activity functions by phosphorylating IFR3.

In some embodiments, a dietary supplement comprising one or more of the aforementioned compounds is provided to a subject (e.g., an individual identified as having HCV) for the purpose of improving the general health or welfare of said subject, improving the immune system function or function of the liver. Accordingly, some embodiments include methods of improving the general health or welfare of a subject, methods of improving the function of the immune system, or methods of improving the function of the liver by providing a subject in need (e.g., a subject infected with HCV) with a dietary supplement comprising any one or more of the compounds described above, or Kunitz trypsin inhibitor (KTI) and a Bowman-Birk trypsin inhibitor (BBI), soy bean extract, grape seed extract, quercitin, flavinoids, carotenoids, *brassica* extract, phytoestrogens, or troglitazone. Some of these methods also include the step of identifying an HCV infected subject. Thus, use of one of the aforementioned compounds, preferably, Kunitz trypsin inhibitor (KTI) and a Bowman-Birk trypsin inhibitor (BBI), soy bean extract, grape seed extract, quercitin, flavinoids, carotenoids, *brassica* extract, phytoestrogens, or troglitazone, for the preparation of a dietary supplement for the improvement of the general health or welfare of a subject (e.g., an HCV infected subject), the improvement of the immune system of a subject (e.g., an HCV infected subject), or the improvement of the function of the liver of a subject (e.g., an HCV infected subject) are embodiments. Further, the use of any one or more of the aforementioned compositions for the preparation of a medicament for the treatment or prevention or HCV infection is contemplated. That is, aspects of the invention also include methods of treating or preventing HCV infection comprising identifying a subject in need of a compound that inhibits proliferation or replication of HCV, and providing said subject a Kunitz trypsin inhibitor (KTI) and a Bowman-Birk trypsin inhibitor (BBI), soy bean extract, grape seed extract, quercitin, flavinoids, carotenoids, *brassica* extract, phytoestrogens, or troglitazone.

Particularly preferred embodiments include a genetically modified mouse comprising a reduced sensitivity to TNF-alpha, as compared to a wild-type mouse of the same variety and an exogenous nucleic acid construct that comprises a promoter operably linked to a gene encoding a hepatitis C virus (HCV) nonstructural protein 3 (NS3). The genetically modified mouse can further comprise a gene encoding a HCV nonstructural protein 4A (NS4A). In some embodiments, the genetically modified mice described above have the proviso that said genetically modified mice do not comprise an HCV core protein, structural protein E1 (E1), structural protein E2 (E2), nonstructural protein 2 (NS2), nonstructural protein 4B (NS4B), nonstructural protein 5A (NS5A), or nonstructural protein 5B (NS5B). In some embodiments, the genetically modified mice described above comprise a promoter that is a mouse major urinary promoter (MUP). In some embodiments, the genetically modified mice described above have an exogenous nucleic acid construct that further comprises a nucleic acid encoding a NS3 protease cleavage site. In some embodiments, the genetically modified mice described above have a nucleic acid that encodes an NS3 protease cleavage site that is joined to said NS3 gene. In some embodiments, the genetically modified mice described above have an exogenous nucleic acid construct that further comprises a nucleic acid encoding a secretory signal. In some embodiments, the genetically modified mice described above comprise an exogenous nucleic acid construct that further comprises a nucleic acid encoding a signal molecule. In some embodiments, the genetically modified mice described above comprise an NS3 gene that is codon optimized. In some embodiments, the genetically modified mice described above comprise an NS4A gene that is codon optimized. In some embodiments, the genetically modified mice described above have an increased sensitivity to TNF-alpha after contact with an inhibitor of a p38 MAP kinase, as compared to a genetically modified mouse, created as described herein, that has not been contacted with said inhibitor. In some embodiments, the inhibitor is SB203580.

In some embodiments, the genetically modified mice described above comprise at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 micrograms NS3 protein per gram of liver tissue. In some embodiments, the genetically modified mice described above comprise more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 micrograms NS3 protein per gram of liver tissue. In some embodiments, the genetically modified mice described above comprise between about 0.1-1.0, 0.5-1.5, 1.0-2.0, 1.5-2.5, 2.0-3.0, 2.5-3.5, 3.0-4.0, 3.5-4.5, 4.0-5.0, 4.5-5.5, 5.0-6.0, 5.5-6.5, 6.0-7.0, 6.5-7.5, 7.0-8.0, 7.7-8.5, 8.0-9.0, 8.5-9.5, 9.0-10.0 micrograms NS3 protein per gram of liver tissue.

Accordingly, aspects of the invention relate to an isolated totipotent mouse cell comprising an exogenous nucleic acid construct that comprises a mouse major urinary promoter (MUP) operably linked to a gene encoding an hepatitis C virus (HCV) nonstructural protein 3 (NS3). In some embodiments, the isolated totipotent mouse cell further comprises a nonstructural protein 4A (NS4A). Some embodiments include the isolated totipotent mouse cell as described above, with the proviso that said isolated totipotent cell does not comprise an HCV core protein, structural protein E1 (E1), structural protein E2 (E2), nonstructural protein 2 (NS2), nonstructural protein 4B (NS4B), nonstructural protein 5A (NS5A), or nonstructural protein 5B (NS5B).

Other aspects of the invention concern methods of making and using the genetically modified mice created as described herein. By one approach, a method of using a genetically modified mouse to identify a compound that inhibits HCV replication is provided wherein said method comprises providing a genetically modified mouse, created as described herein; contacting said genetically modified mouse with a compound; and analyzing the expression of NS3, NS3 protease activity, or the sensitivity of said genetically modified mouse to TNF-alpha, after contact with said compound, whereby said compound that inhibits HCV replication is identified by the ability of said compound to inhibit expression of NS3, inhibit protease activity of NS3, or restore TNF-alpha sensitivity in said genetically modified mouse. A pharmaceutical or dietary supplement comprising the compound identified by the method above is also an embodiment. In some embodiments, the compound is a p38 MAP kinase inhibitor. In some embodiments, the compound is SB203580 or SB202190.

A method of inhibiting HCV infection is also provided, wherein said method comprises identifying a subject infected with HCV; and providing said subject a composition comprising a p38 MAP kinase inhibitor. In some embodiments, the p38MAP kinase inhibitor is selected from the group consisting of SB 203580, SB 202190, KN62, U0126, PD 98059, Wortmannin, rapamycin, Ro 31-8220, Bis-1, Go 6976, UCN01, Indirubin-3'-monoxime, kenpaullone, alsterpaullone, PP1, PP2, SU 6656, SP 600125, ML-9, PD 169316, p38 MAP Kinase inhibitor, SB202190 hydrochloride, SB 203580 hydrochloride, SB 203580 Iodo, SC68376, SKF-86002, ZM 3363772, Anti-p38/HOG-1 antibody, and anti-p38 MAP Kinase antibody. In some embodiments, the inhibitor is SB203580 or SB202190. In some embodiments, the inhibitor is a suppressor of cytokine signaling-1 (SOCS1). In some embodiments, the method further comprises measuring the inhibition of HCV in said subject. Accordingly, aspects of the invention concern the use of a p38 MAP kinase inhibitor for the preparation of a medicament for the treatment or prevention of HCV infection. In some uses, the p38 inhibitor is SB203580 or SB202190.

BRIEF DESCRIPTION OF THE DRAWINGS

FIG. 13A is a sequence displaying key residues and relevant binding areas of the NS3 protein.

FIG. 13B is a sequence displaying key residues and relevant binding areas of the NS4A protein. The arrow shows the NS3/4A cleavage site (i.e., . . . T↓STW . . . ).

FIG. 14D is a diagram of the sequences of one embodiment of FIG. 14C.

FIG. 18E shows the results of a Western blot that compares the expression levels of various proteins in wild-type mice and NS3/4A transgenic mice following treatment with LPS.

FIG. 18F shows the results of a Western blot that compares the expression levels of various proteins in wild-type mice and NS3/4A transgenic mice following treatment with alpha-IFN.

FIG. 18G shows the results of a Western blot that compares the expression levels of various proteins in wild-type mice and NS3/4A transgenic mice following treatment with gamma-IFN.

DETAILED DESCRIPTION OF THE INVENTION

Figure 1:
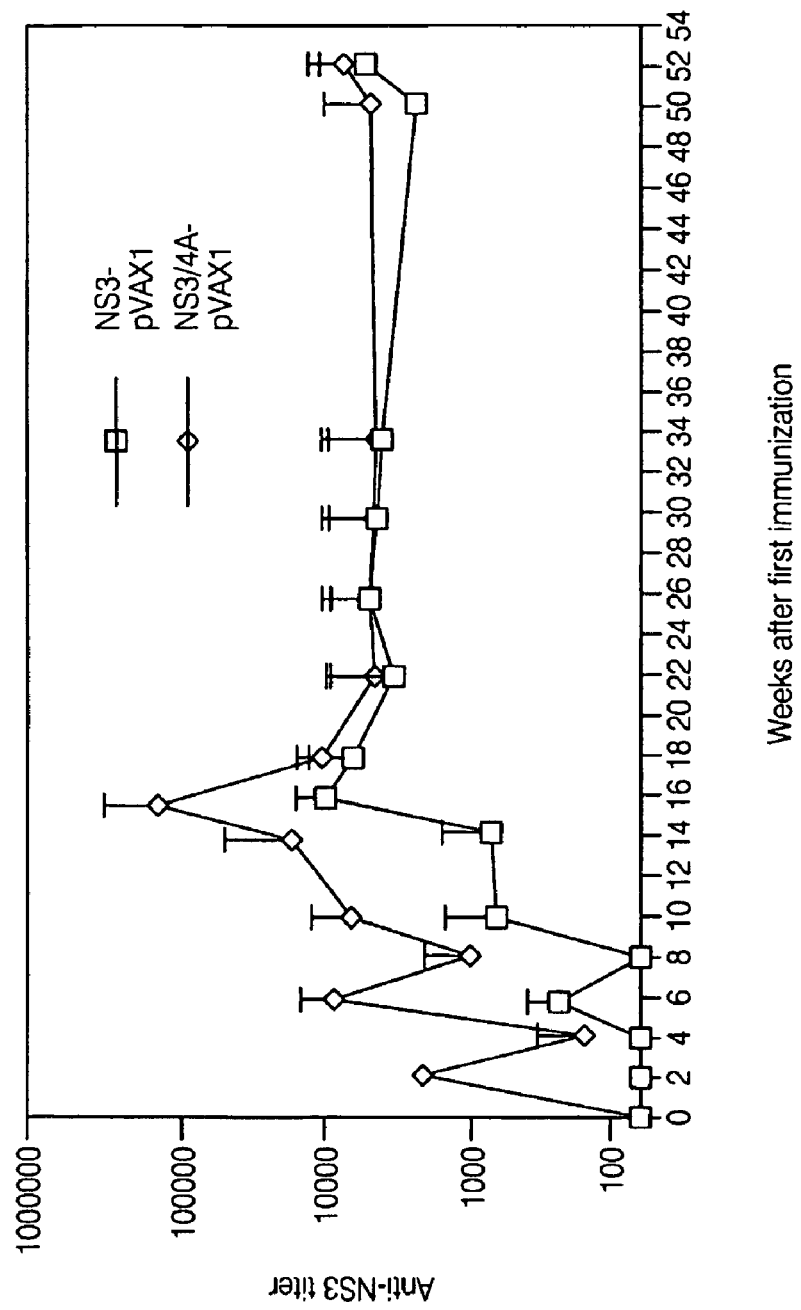
FIG. 1 is a graph demonstrating the antibody titer in H-2$^d$ mice against NS3 as a function of time after the first intra muscular immunization. Diamonds denote antibody titer in mice immunized with NS3/4A-pVAX and squares denote antibody titer in mice immunized with NS3-pVAX.

Transgenic mice comprising an exogenous nucleic acid construct that comprises a hepatitis C virus (HCV) nonstructural protein 3 (NS3) and nonstructural protein 4A (NS4A) have been created. These genetically modified mice express appreciable amounts of NS3 and/or NS4A proteins in the liver (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 micrograms NS3 and/or NS4A protein per gram of liver tissue). The HCV NS3/4A transgenic mice created, as described herein, also have a reduced sensitivity or an increased resistance to TNF-alpha, as compared to wild-type mice of the same variety that have not been genetically modified to contain NS3/4A. That is, some of the NS3/4A-containing genetically modified mice survive a lethal dose of TNF-alpha but said transgenic mice revert to a TNF-alpha sensitive phenotype in the presence of a p38 MAP kinase inhibitor, such as SB203580 or SB202190. That is, some of the genetically modified mice created as described herein, which have a reduced sensitivity or increased resistance to TNF-alpha, can be induced to become as sensitive to TNF-alpha as a wild-type mouse of the same variety by contacting the genetically modified mouse with an inhibitor of p38 MAP kinase.

The genetically modified mice that express NS3/4A are used as models for HCV infection and provide an in vivo system for the identification of compounds that inhibit HCV replication and/or HCV infection. In some embodiments, signal molecules (e.g., luciferase, lac z, or green fluorescent protein) and secretory signals (e.g., IG kappa) can be included on said exogenous nucleic acid constructs used to create said genetically modified mice so as to facilitate the analysis and testing of said compounds for anti-HCV activity. By some approaches, the genetically modified mice, created as described herein, are contacted with a compound and the expression of NS3, NS3 protease activity, or TNF-alpha sensitivity is analyzed. Compounds that inhibit HCV replication (e.g., inhibitors of NS3 expression or protease activity or compounds that restore TNF-alpha sensitivity) are identified using the methods described herein and said identified compounds (e.g., p38 MAP kinase inhibitors such as, SB203580 or SB202190) are incorporated into pharmaceuticals and/or dietary supplements, which can be provided to HCV infected individuals or individuals at risk of becoming infected with HCV. That is, aspects of the invention described herein concern the use of p38 MAP kinase inhibitors such as, SB203580 or SB202190, to prepare a medicament for the treatment and/or prevention of HCV infection and methods of using said medicaments in HCV treatment or prophylactic methods. The section below describes some of the nucleic acids used to create the genetically modified mice described herein.

Nucleic Acid and Peptide Embodiments

A new isolate of HCV was identified and a nucleic acid encoding NS3/4A was cloned and sequenced (SEQ. ID. NO. 1). (See EXAMPLE 1). A Genebank search revealed that the cloned sequence had the greatest homology to HCV sequences but was only 93% homologous to the closest HCV relative (accession no. AJ 278830). A truncated mutant of the novel NS3/4A peptide and NS3/4A mutants, which lack a proteolytic cleavage site, (as well as corresponding nucleic acids) were also created. The use of a Semliki forest virus (SFV) replicon (wtNS3/4A-SFV) to enhance mRNA amplification resulted in improved immunogenicity as evidenced through higher levels of NS3-specific antibodies. This also resulted in a more rapid priming of cytotoxic T lymphocytes. Further, mice immunized with the NS3/4A enhanced mRNA amplification construct were found to prime NS3-specific CTLs more effectively and exhibit better in vivo tumor inhibiting immune responses than mice immunized with wild-type NS3/4A containing constructs.

The nucleic acid of SEQ. ID. NO.: 1, a wild-type of HCV NS3/4A, was then analyzed for codon usage and the sequence was compared to the codons that are most commonly used in human cells. Because HCV is a human pathogen, it was unexpected to discover that the virus had not yet evolved to use codons that are most frequently found to encode human proteins (e.g., optimal human codons). A total of 435 nucleotides were replaced to generate the codon-optimized synthetic NS3/4A nucleic acid.

A codon-optimized nucleic acid encoding NS3/4A was created and found to be immunogenic. (See also U.S. patent application Ser. Nos. 09/930,591; 09/929,955; and 10/307, 047), all of which are herein expressly incorporated by reference in their entireties). The NS3/4A peptide (SEQ. ID. NO.: 36) encoded by the codon-optimized nucleic acid sequence was 98% homologous to HCV-1 and contained a total of 15 different amino acids. The codon optimized nucleic acid (MSLF1 or coNS3/4A) (SEQ. ID. NO.: 35) was found to be more efficiently translated in vitro than the native NS3/4A and mice immunized with the coNS3/4 containing construct generated significantly more NS3/4A specific antibodies than mice immunized with a wild-type NS3/4A containing construct. (See EXAMPLE 2). Further, mice immunized with the coNS3/4A containing construct were found to prime NS3-specific CTLs more effectively and exhibit better in vivo tumor inhibiting immune responses than mice immunized with wild-type NS3/4A containing constructs. (See EXAMPLES 3-16).

Accordingly, several nucleic acid embodiments include nucleotides encoding the HCV peptides described herein (SEQ. ID. NOs.: 2-11 or SEQ. ID. NO.: 36) or a fragment thereof (e.g., SEQ. ID. NOs.: 14 and 15) containing any number of consecutive amino acids between at least 25-100 (e.g., 25, 35, 45, 55, 65, 75, 85, 95, or 100 amino acids in length). Some embodiments for example, include genomic DNA, RNA, and cDNA encoding these HCV peptides. The HCV nucleotide embodiments not only include the DNA sequences shown in the sequence listing (e.g., SEQ. ID. NO.: 1 or SEQ. ID. NO.: 35) but also include nucleotide sequences encoding the amino acid sequences shown in the sequence listing (e.g., SEQ. ID. NOs.: 2-11 or SEQ. ID. NO.: 36) and any nucleotide sequence that hybridizes to the DNA sequences shown in the sequence listing under stringent conditions (e.g., hybridization to filter-bound DNA in 0.5 M NaHPO$_4$, 7.0% sodium dodecyl sulfate (SDS), 1 mM EDTA at 50° C.) and washing in 0.2×SSC/0.2% SDS at 50° C. and any nucleotide sequence that hybridizes to the DNA sequences that encode an amino acid sequence provided in the sequence listing (SEQ. ID. NOs.: 2-11 or SEQ. ID. NO.: 36) under less stringent conditions (e.g., hybridization in 0.5 M NaHPO$_4$, 7.0% sodium dodecyl sulfate (SDS), 1 mM EDTA at 37° C. and washing in 0.2×SSC/0.2% SDS at 37° C.).

The nucleic acid embodiments of the invention also include fragments, modifications, derivatives, and variants of the sequences described above. Desired embodiments, for example, include nucleic acids having at least 100 consecutive nucleotides of one of the novel HCV sequences or a sequence complementary thereto and preferred fragments include at least 200 consecutive nucleotides of a nucleic acid encoding the NS3/4A molecule of SEQ. ID. NO.: 2 or SEQ. ID. NO.: 36 or a mutant NS3/4A molecule of SEQ. ID. NOs.: 3-13 or a sequence complementary thereto.

In this regard, the nucleic acid embodiments described herein can have any number of consecutive nucleotides between about 30 to approximately 2112 consecutive nucleotides of SEQ. ID. NO.: 1 or SEQ. ID. NO.: 35. Some DNA fragments, for example, include nucleic acids having at least, more than, or equal to 30, 30-50, 50-100, 100-200, 200-300, 300-400, 400-500, 500-600, 600-700, 700-800, 800-900, 900-1000, 1000-1500, 1500-2079, or 1500-2112 consecutive nucleotides of SEQ. ID. NO.: 1 or SEQ. ID. NO.: 35 or a complement thereof. These nucleic acid embodiments can also be altered by substitution, addition, or deletion so long as the alteration does not significantly affect the structure or function (e.g., ability to serve as an immunogen) of the HCV nucleic acid. Due to the degeneracy of nucleotide coding sequences, for example, other DNA sequences that encode substantially the same HCV amino acid sequence as depicted in SEQ. ID. NOs.: 2-13 or SEQ. ID. NO.: 36 can be used in some embodiments. These include, but are not limited to, nucleic acid sequences encoding all or portions of HCV peptides (SEQ. ID. NOs.: 2-13) or nucleic acids that complement all or part of this sequence that have been altered by the substitution of different codons that encode a functionally equivalent amino acid residue within the sequence, thus producing a silent change, or a functionally non-equivalent amino acid residue within the sequence, thus producing a detectable change. Accordingly, the nucleic acid embodiments of the invention are said to be comprising, consisting of, or consisting essentially of nucleic acids encoding any one of SEQ. ID. NOs.: 2-27 or SEQ. ID. NO.: 36 in light of the modifications above.

By using the nucleic acid sequences described above, probes that complement these molecules can be designed and manufactured by oligonucleotide synthesis. Desirable probes comprise a nucleic acid sequence of (SEQ. ID. NO.: 1) that is unique to this HCV isolate. These probes can be used to screen cDNA from patients so as to isolate natural sources of HCV, some of which may be novel HCV sequences in themselves. Screening can be by filter hybridization or by PCR, for example. By filter hybridization, the labeled probe preferably contains at least 15-30 base pairs of the nucleic acid sequence of (SEQ. ID. NO.: 1) that is unique to this NS3/4A peptide. The hybridization washing conditions used are preferably of a medium to high stringency. The hybridization can be performed in 0.5M NaHPO$_4$, 7.0% sodium dodecyl sulfate (SDS), 1 mM EDTA at 42° C. overnight and washing can be performed in 0.2×SSC/0.2% SDS at 42° C. For guidance regarding such conditions see, for example, Sambrook et al., 1989, *Molecular Cloning, A Laboratory Manual*, Cold Springs Harbor Press, N.Y.; and Ausubel et al., 1989, *Current Protocols in Molecular Biology*, Green Publishing Associates and Wiley Interscience, N.Y.

HCV nucleic acids can also be isolated from patients infected with HCV using the nucleic acids described herein. (See also EXAMPLE 1). Accordingly, RNA obtained from a patient infected with HCV is reverse transcribed and the resultant cDNA is amplified using PCR or another amplification technique. The primers are preferably obtained from the NS3/4A sequence (SEQ. ID. NO.: 1).

For amplification of mRNAs, it is within the scope of the invention to reverse transcribe mRNA into cDNA followed by PCR (RT-PCR); or, to use a single enzyme for both steps as described in U.S. Pat. No. 5,322,770. Another technique involves the use of Reverse Transcriptase Asymmetric Gap Ligase Chain Reaction (RT-AGLCR), as described by Marshall R. L. et al. (*PCR Methods and Applications* 4:80-84, 1994).

Briefly, RNA is isolated, following standard procedures. A reverse transcription reaction is performed on the RNA using an oligonucleotide primer specific for the most 5' end of the amplified fragment as a primer of first strand synthesis. The resulting RNA/DNA hybrid is then "tailed" with guanines using a standard terminal transferase reaction. The hybrid is then digested with RNAse H, and second strand synthesis is primed with a poly-C primer. Thus, cDNA sequences upstream of the amplified fragment are easily isolated. For a review of cloning strategies which can be used, see e.g., Sambrook et al., 1989, supra.

In each of these amplification procedures, primers on either side of the sequence to be amplified are added to a suitably prepared nucleic acid sample along with dNTPs and a thermostable polymerase, such as Taq polymerase, Pfu polymerase, or Vent polymerase. The nucleic acid in the sample is denatured and the primers are specifically hybridized to complementary nucleic acid sequences in the sample. The hybridized primers are then extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188, all of which are expressly incorporated by reference in their entireties.

The primers are selected to be substantially complementary to a portion of the nucleic acid sequence of (SEQ. ID. NO.: 1) that is unique to this NS3/4A molecule, thereby allowing the sequences between the primers to be amplified. Preferably, primers can be any number between at least 16-20, 20-25, or 25-30 nucleotides in length. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers described herein preferably range between 10% and 75%, more preferably between 35% and 60%, and most preferably between 40% and 55%. The appropriate length for primers under a particular set of assay conditions can be empirically determined by one of skill in the art.

The spacing of the primers relates to the length of the segment to be amplified. In the context of the embodiments described herein, amplified segments carrying nucleic acid sequence encoding HCV peptides can range in size from at least about 25 bp to the entire length of the HCV genome. Amplification fragments from 25-1000 bp are typical, fragments from 50-1000 bp are preferred and fragments from 100-600 bp are highly preferred. It will be appreciated that amplification primers can be of any sequence that allows for specific amplification of the NS3/4A region and can, for example, include modifications such as restriction sites to facilitate cloning.

The PCR product can be subcloned and sequenced to ensure that the amplified sequences represent the sequences of an HCV peptide. The PCR fragment can then be used to isolate a full length cDNA clone by a variety of methods or can be used to create the exogenous nucleic acid constructs described herein. For example, the amplified fragment can be labeled and used to screen a cDNA library, such as a bacteriophage cDNA library. Alternatively, the labeled fragment can be used to isolate genomic clones via the screening of a genomic library. Additionally, an expression library can be constructed utilizing cDNA synthesized from, for example, RNA isolated from an infected patient. In this manner, HCV gene products can be isolated using standard antibody screening techniques in conjunction with antibodies raised against the HCV gene product.

Embodiments of the invention also include (a) DNA vectors that contain any of the foregoing nucleic acid sequence and/or their complements (i.e., antisense); (b) DNA expression vectors that contain any of the foregoing nucleic acid sequences operatively associated with a regulatory element that directs the expression of the nucleic acid; and (c) genetically engineered host cells that contain any of the foregoing nucleic acid sequences operatively associated with a regulatory element that directs the expression of the coding sequences in the host cell. These recombinant constructs are capable of replicating autonomously in a host cell. Alternatively, the recombinant constructs can become integrated into the chromosomal DNA of a host cell. Such recombinant polynucleotides typically comprise an HCV genomic or cDNA polynucleotide of semi-synthetic or synthetic origin by virtue of human manipulation. Therefore, recombinant nucleic acids comprising these sequences and complements thereof that are not naturally occurring are provided.

Although nucleic acids encoding an HCV peptide or nucleic acids having sequences that complement an HCV gene as they appear in nature can be employed, they will often be altered, e.g., by deletion, substitution, or insertion, and can be accompanied by sequence not present in humans. As used herein, regulatory elements include, but are not limited to, inducible and non-inducible promoters, enhancers, operators and other elements known to those skilled in the art that drive and regulate expression. Such regulatory elements include, but are not limited to, MUP, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast-mating factors.

In addition, recombinant HCV peptide-encoding nucleic acid sequences and their complementary sequences can be engineered so as to modify their processing or expression. For example, and not by way of limitation, the HCV nucleic acids described herein can be combined with a promoter sequence and/or ribosome binding site, or a signal sequence can be inserted upstream of HCV peptide-encoding sequences so as to permit secretion of the peptide and thereby facilitate harvesting or bioavailability. Additionally, a given HCV nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. (See EXAMPLE 1). Any technique for mutagenesis known in the art can be used, including but not limited to, in vitro site-directed mutagenesis. (Hutchinson et al., *J. Biol. Chem.*, 253:6551 (1978)). The nucleic acids encoding the HCV peptides, described above, can be manipulated using conventional techniques in molecular biology so as to create recombinant constructs that express the HCV peptides.

Further, nucleic acids encoding other proteins or domains of other proteins can be joined to nucleic acids encoding an HCV peptide so as to create a fusion protein. Nucleotides encoding fusion proteins can include, but are not limited to, a full length NS3/4A sequence (SEQ. ID. NO.: 2 or SEQ. ID. NO.: 36), mutant NS3/4A sequences (e.g., SEQ. ID. NOs.: 3-11) or a peptide fragment of an NS3/4A sequence fused to an unrelated protein or peptide, such as for example, polyhistidine, hemagglutinin, an enzyme, fluorescent protein, or luminescent protein, as discussed below.

The embodied HCV peptides or derivatives thereof, include but are not limited to, those containing as a primary amino acid sequence all of the amino acid sequence substantially as depicted in the Sequence Listing (SEQ. ID. NOs.: 2-11 and SEQ. ID. NO.: 36) and fragments of SEQ. ID. NOs.: 2-11 and SEQ. ID. NO.: 36 that are at least four amino acids in length (e.g., SEQ. ID. NOs.: 14-16) including altered sequences in which functionally equivalent amino acid residues are substituted for residues within the sequence resulting in a silent change. Preferred fragments of a sequence of SEQ. ID. NOs.: 2-11 and SEQ. ID. NO.: 36 are at least four amino acids and comprise amino acid sequence unique to the discovered NS3/4A peptide or mutants thereof including altered sequences in which functionally equivalent amino acid residues are substituted for residues within the sequence resulting in a silent change. The HCV peptides can be, for example, at least about 30-704 amino acids in length (e.g., any number between 25-30, 30-40, 40-50, 50-100, 100-150, 150-250, 250-500 or 500-704 amino acids in length). Preferred peptides include a functional NS3 protease.

Embodiments also include HCV peptides that are substantially identical to those described above. That is, HCV peptides that have one or more amino acid residues within SEQ. ID. NOs.: 2-11 and SEQ. ID. NO.: 36 and fragments thereof that are substituted by another amino acid of a similar polarity that acts as a functional equivalent, resulting in a silent alteration. Further, the HCV peptides can have one or more amino acid residues fused to SEQ. ID. NOs.: 2-11 and SEQ. ID. NO.: 36 or a fragment thereof so long as the fusion does not significantly alter the structure or function (e.g., immunogenic properties or protease activity) of the HCV peptide. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine. Accordingly, the peptide embodiments of the invention are said to be consisting essentially of SEQ. ID. NOs.: 2-27 and SEQ. ID. NO.: 36 in light of the modifications described above.

The HCV peptides described herein can be prepared by chemical synthesis methods (such as solid phase peptide synthesis) using techniques known in the art such as those set forth by Merrifield et al., *J. Am. Chem. Soc.* 85:2149 (1964), Houghten et al., *Proc. Natl. Acad. Sci. USA*, 82:51:32 (1985), Stewart and Young (*Solid phase peptide synthesis*, Pierce Chem. Co., Rockford, Ill. (1984), and Creighton, 1983, *Proteins: Structures and Molecular Principles*, W.H. Freeman & Co., N.Y. Such polypeptides can be synthesized with or without a methionine on the amino terminus. Chemically synthesized HCV peptides can be oxidized using methods set forth in these references to form disulfide bridges.

While the HCV peptides described herein can be chemically synthesized, it can be more effective to produce these polypeptides by recombinant DNA technology. Such methods can be used to construct expression vectors containing the HCV nucleotide sequences described above, for example, and appropriate transcriptional and translational control signals. These methods include, for example, in vitro recombinant DNA techniques, synthetic techniques, and in vivo genetic recombination. Alternatively, RNA capable of encoding an HCV nucleotide sequence can be chemically synthesized using, for example, synthesizers. See, for example, the techniques described in *Oligonucleotide Synthesis*, 1984, Gait, M. J. ed., IRL Press, Oxford. Accordingly, several embodiments concern cells (e.g., totipotent cells) and cell lines that have been engineered to express the embodied HCV peptides. For example, some cells are made to express the HCV peptides of SEQ. ID. NOs.: 2-11 and SEQ. ID. NO.: 36 or fragments of these molecules (e.g., SEQ. ID. NOs.: 14-26), preferably fragments that contain a functional NS3 protease.

A variety of host-expression vector systems can be utilized to express the embodied HCV peptides. Suitable expression systems include, but are not limited to, microorganisms such as bacteria (e.g., *E. coli* or *B. subtilis*) transformed with recombinant bacteriophage DNA, plasmid DNA or cosmid DNA expression vectors containing HCV nucleotide sequences; yeast (e.g., *Saccharomyces, Pichia*) transformed with recombinant yeast expression vectors containing the HCV nucleotide sequences; insect cell systems infected with recombinant virus expression vectors (e.g., baculovirus) containing the HCV sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing HCV sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the HCV gene product being expressed. For example, when a large quantity of such a protein is to be produced, for the generation of pharmaceutical compositions of HCV peptide or for raising antibodies to the HCV peptide, for example, vectors which direct the expression of high levels of fusion protein products that are readily purified can be desirable. Such vectors include, but are not limited, to the *E. coli* expression vector pUR278 (Ruther et al., *EMBO J.*, 2:1791 (1983), in which the HCV coding sequence can be ligated individually into the vector in frame with the lacZ coding region so that a fusion protein is produced; pIN vectors (Inouye & Inouye, *Nucleic Acids Res.*, 13:3101-3109 (1985); Van Heeke & Schuster, *J. Biol. Chem.*, 264:5503-5509 (1989)); and the like. The pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The HCV coding sequence can be cloned individually into nonessential regions (for example the polyhedrin gene) of the virus and placed under control of an AcNPV promoter (for example the polyhedrin promoter). Successful insertion of an HCV gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (See e.g., Smith et al., *J. Virol.* 46: 584 (1983); and Smith, U.S. Pat. No. 4,215,051, herein expressly incorporated by reference in its entirety).

In mammalian host cells, a number of viral-based expression systems can be utilized. In cases where an adenovirus is used as an expression vector, the HCV nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the HCV gene product in infected hosts. (See e.g., Logan & Shenk, *Proc. Natl. Acad. Sci. USA* 81:3655-3659 (1984)). Specific initiation signals can also be required for efficient translation of inserted HCV nucleotide sequences. These signals include the ATG initiation codon and adjacent sequences.

However, in cases where only a portion of the HCV coding sequence is inserted, exogenous translational control signals, including, perhaps, the ATG initiation codon, can be provided. Furthermore, the initiation codon can be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bittner et al., *Methods in Enzymol.*, 153:516-544 (1987)).

In addition, a host cell strain can be chosen, which modulates the expression of the inserted sequences, or modifies and processes the gene product in the specific fashion desired. Such modifications (e.g., glycosylation) and processing (e.g., cleavage) of protein products are important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and WI38.

For long-term, high-yield production of recombinant proteins, stable expression is preferred. For example, cell lines that stably express the HCV peptides described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the HCV gene product.

A number of selection systems can be used, including but not limited to the herpes simplex virus thymidine kinase (Wigler, et al., *Cell* 11:223 (1977), hypoxanthine-guanine phosphoribosyltransferase (Szybalska & Szybalski, *Proc. Natl. Acad. Sci. USA* 48:2026 (1962)), and adenine phosphoribosyltransferase (Lowy, et al., *Cell* 22:817 (1980)) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980); O'Hare, et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin, et al., *J. Mol. Biol.* 150:1 (1981)); and hygro, which confers resistance to hygromycin (Santerre, et al., *Gene* 30:147 (1984)).

The sequences, constructs, vectors, clones, and other materials comprising the embodied HCV nucleic acids and peptides can be in enriched or isolated form. As used herein, "enriched" means that the concentration of the material is many times its natural concentration, for example, at least about 2, 5, 10, 100, or 1000 times its natural concentration, advantageously 0.01%, by weight, preferably at least about 0.1% by weight. Enriched preparations from about 0.5% or more, for example, 1%, 5%, 10%, and 20% by weight are also contemplated. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated.

Embodiments of the invention also include NS3/4A fusion proteins or nucleic acids encoding these molecules. For instance, production and purification of recombinant protein may be facilitated by the addition of auxiliary amino acids to form a "tag". Such tags include, but are not limited to, His-6, Flag, Myc and GST. The tags may be added to the C-terminus, N-terminus, or within the NS3/4A amino acid sequence. Further embodiments include NS3/4A fusion proteins with amino or carboxy terminal truncations, or internal deletions, or with additional polypeptide sequences added to the amino or carboxy terminal ends, or added internally. Other embodiments include NS3/4A fusion proteins, or truncated or mutated versions thereof, where the residues of the NS3/4A proteolytic cleavage site have been substituted. Such substitutions include, but are not limited to, sequences where the P1' site is a Ser, Gly, or Pro, or the P1 position is an Arg, or where the P8 to P4' sequence is Ser-Ala-Asp-Leu-Glu-Val-Val-Thr-Ser-Thr-Trp-Val (SEQ. ID. NO.: 15).

A fusion protein containing NS3/4A, as described herein, can be readily purified by utilizing an antibody specific for the fusion protein being expressed. For example, a system described by Janknecht et al. allows for the ready purification of non-denatured fusion proteins expressed in human cell lines. (Janknecht, et al., *Proc. Natl. Acad. Sci. USA* 88: 8972-8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers.

More embodiments concern an immunogen comprising the NS3/4A fusion protein, or a truncated, mutated, or modified version thereof, capable of eliciting an enhanced immune response against NS3. The immunogen can be provided in a substantially purified form, which means that the immunogen has been rendered substantially free of other proteins, lipids, carbohydrates or other compounds with which it naturally associates.

Some embodiments comprise at least one of the HCV nucleic acids or HCV peptides (e.g., SEQ. ID. NOs.: 1-27, 35, or 36) joined to a support. Preferably, these supports are manufactured so as to create a multimeric agent. These multimeric agents provide the HCV peptide or nucleic acid in such a form or in such a way that a sufficient affinity to the molecule is achieved. A multimeric agent having an HCV nucleic acid or peptide can be obtained by joining the desired molecule to a macromolecular support. A "support" can be a termed a carrier, a protein, a resin, a cell membrane, a capsid or portion thereof, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An HCV nucleic acid or peptide can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the HCV nucleic acid or peptide by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, HCV nucleic acid or peptide can be covalently bound to carriers including proteins and oligo/polysaccarides (e.g. cellulose, starch, glycogen, chitosane, the gal antigen, Gal alpha (1,3) Gal beta, or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the HCV nucleic acid or peptide. For example, cyanogen bromide activated matrices, epoxy activated matrices, thio and thiopropyl gels, nitrophenyl chloroformate and N-hydroxy succinimide chloroformate linkages, or oxirane acrylic supports are used. (Sigma).

Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, capsids that display the desired HCV peptide or nucleic acid, and Chromosorb® (Johns-Manville Products, Denver Co.). Ligand conjugated Chromosorb® (Synsorb-Pk) has been tested in humans for the prevention of hemolytic-uremic syndrome and was reported as not presenting adverse reactions. (Armstrong et al. *J Infectious Diseases* 171.1042-1045 (1995)). For some embodiments, a "naked" carrier (i.e., lacking an attached HCV nucleic acid or peptide) that has the capacity to attach an HCV nucleic acid or peptide in the body of a organism is administered. By this approach, a "prodrug-type" therapy is envisioned in which the naked carrier is administered separately from the HCV nucleic acid or peptide and, once both are in the body of the organism, the carrier and the HCV nucleic acid or peptide are assembled into a multimeric complex.

The insertion of linkers, (e.g., "λ linkers" engineered to resemble the flexible regions of λ phage) of an appropriate length between the HCV nucleic acid or peptide and the support are also contemplated so as to encourage greater flexibility of the HCV peptide, hybrid, or binding partner and thereby overcome any steric hindrance that can be presented by the support. The determination of an appropriate length of linker that allows for an optimal cellular response or lack thereof, can be determined by screening the HCV nucleic acid or peptide with varying linkers in the assays detailed in the present disclosure.

A composite support comprising more than one type of HCV nucleic acid or peptide is also envisioned. A "composite support" can be a carrier, a resin, or any macromolecular structure used to attach or immobilize two or more different HCV nucleic acids or peptides. As above, the insertion of linkers, such as λ linkers, of an appropriate length between the HCV nucleic acid or peptide and the support is also contemplated so as to encourage greater flexibility in the molecule and thereby overcome any steric hindrance that can occur. The determination of an appropriate length of linker that allows for an optimal cellular response or lack thereof, can be determined by screening the HCV nucleic acid or peptide with varying linkers in the assays detailed in the present disclosure.

In other embodiments, the multimeric and composite supports discussed above can have attached multimerized HCV nucleic acids or peptides so as to create a "multimerized-multimeric support" and a "multimerized-composite support", respectively. A multimerized ligand can, for example, be obtained by coupling two or more HCV nucleic acids or peptides in tandem using conventional techniques in molecular biology. The multimerized form of the HCV nucleic acid or peptide can be advantageous for many applications because of the ability to obtain an agent with a higher affinity, for example. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized HCV nucleic acid or peptide and the support can encourage greater flexibility and limit steric hindrance presented by the support. The determination of an appropriate length of linker can be determined by screening the HCV nucleic acids or peptides in the assays detailed in this disclosure. Embodiments also include vaccine compositions and immunogen preparations comprising the NS3/4A nucleic acids or peptides as described herein and, optionally, an adjuvant (e.g., ribavirin).

In some embodiments, the constructs described herein are useful for the identification of HCV protease inhibitors. There are many different methods by which one can detect the cleavage or absence of cleavage of the NS3/4A protein, and thereby, determine whether or not any given compound possesses the ability to inhibit the NS3 protease. In some embodiments, the NS3/4A construct contains a secretory sequence connected to a signal molecule (detectable marker, indicator, or other similar item), and thus is referred to as a PADSI (protease activity dedependent secreted indicator) construct. Preferably, the indicator is a secreted indicator whose level of secretion is dependent upon protease activity. Thus, by monitoring secretion of the indicator, one may indirectly monitor the activity of the protease. This approach allows one to test various candidate protease inhibitors to determine their ability to cleave NS3/4A. This data can then be recorded on a media for subsequent analysis and rational drug design (e.g., strength of inhibition of the NS3 protease, duration of action, various methods of delivery of the inhibitor, etc can be recorded). As will be appreciated by one of skill in the art, various amounts of the NS3, NS4A, NS4B, or other sections of protein may also be incorporated in the constructs. As will be discussed in greater detail below, there are two general forms of PADSI constrcuts—negative PADSIs and positive PADSIs.

Some of these protease inhibitor-based constructs are directed to NS3 proteases, NS3/4A or sections or derivatives thereof and, optionally, may be associated with detectable markers and secretory signals. By some approaches, as will be discussed below, the activity of protease inhibitors can be monitored through the relative presence or absence of the detectable marker outside a cell harboring the construct (e.g., in the blood of a transgenic organism), and optionally the amount of secreted marker can be compared to the amount of marker retained in the cells (e.g., in the liver cells of a transgenic organism).

As will be appreciated by one of skill in the art, while the terms "venous" or "venous blood" are used in the present application, the terms are not meant to denote any particular limitation as far blood from veins, arteries, or other blood flow systems. Rather, all that is meant by the term "venous," unless otherwise specifically denoted herein, is that the marker, for example, is outside the cell harboring the construct. Thus, venous can include any solution, at any point in an organism, whether it be aterial, venous, or otherwise.

In some embodiments, the PADSI construct is not the entire NS3/4A protein, but comprises a minimal NS3/4A cleavage (proteolytic) site. Any amount of the cleavage site can be used, as long as the section can be cleaved by an NS3 or NS3/4A protein. Additionally, the section of protein encoding for the cleavage site should not be so large as to allow for self cleavage (in embodiments where this is not desired). However, as will be appreciated by one of skill in the art, the entire NS3/4A complex could be used as part of the construct, as long as it cannot cleave itself; thus, NS3 protease inactive variants may also be used.

In some embodiments, the PADSI proteins include NS3/4A variants that are NS3 protease inactive. In other words, the NS3/4A section of the PADSI protein will not autocatalytically cleave the NS3/4A peptide bond. Such a variant PADSI protein is useful as a means of controlling when the NS3 protease cleaves the NS3/4A peptide bond. While the variant NS3/4A will not cleave its own bond, an active NS3 or NS3/4A protein can still act upon the NS3/4A variant in order to cleave the bond.

The variants can be made in a variety of ways. Guidance can be provided by the crystal structures of the NS3/4A complexes. Guidance can also be found in FIG. 13A and FIG. 13B, which show the active-site residues of NS3 (*), His-1083, Asp-1107, and Ser-1165, for example. Substitutions at these sites will result in the prevention of cleavage at NS3/4A, NS4A/4B, NS4B/5A, and NS5A/B (see, for example, Tomei et al., J. Virol. 1993, 67:3338-3344; Manabe et al., Virology, 1994, 198:636-644; Grakoui et al., J. Virol., 1993, 67: 2832-2843; Eckart et al., Biochem. Biophys. Res Commun., 1993, 192:399-406; Bartenschlager et al., J. Virol., 1993, 67:3835-3844; Hijikata, et al., J. Virol., 1993, 67:4665-4675.) Additionally, guidance can be found in the art, such as position 1685 in NS4A, which, when changed to a Gln from an Arg, results in a NS4A peptide with inhibitory effects on NS3. (Shimizu et al., J. Virol., 1996, 70:127-132).

As will be appreciated by one of skill in the art, multiple variations may be included in any single PADSI construct. Thus, in one embodiment, the variant PADSI protein is not only unable to cleave the NS3/4A peptide bond, but the NS3 and NS4A proteins will not associate with each other, apart from through the peptide bond.

Additionally, as understood by one of skill in the art, these molecules may be especially useful for high throughput (HTP) screening as large numbers of possible candidate protease inhibitors may be added either simultaneously or sequentially at high rates and the NS3/4A PADSI proteins are amenable to the identification of protease inhibitors in a HTP format. While one of ordinary skill in the art will recognize that these proteins can be applied to many HTP systems, systems that readily allow the visualization of changes in the amount of detectable marker (e.g., a fluorescence marker) inside and/or outside of a cell are particularly useful. For example, chip based technology where the PADSI proteins are readily observable when they are attached to a fixed surface may be particularly useful. Retention or loss of the detectable marker from the construct will be an appropriate indicator of the effectiveness of the protease inhibitor. Alternatively, the PADSI proteins may be expressed in cells and the cells themselves may serve as a fixed platform overwhich candidate protease inhibitors can be applied. As mentioned supra, some embodiments include codon optimized sequences and, as discussed further below, these constructs can be used in transgenic mice. The next section describes several negative PADSI constructs that can be used to identify protease inhibitors.

Figure 14A:
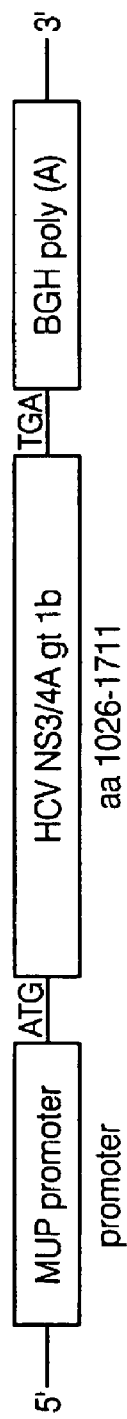
FIG. 14A is a schematic representation of the linearized fragment (pMUP-NS3/4A) used for microinjection to produce the transgenic mice.
Figure 14B:
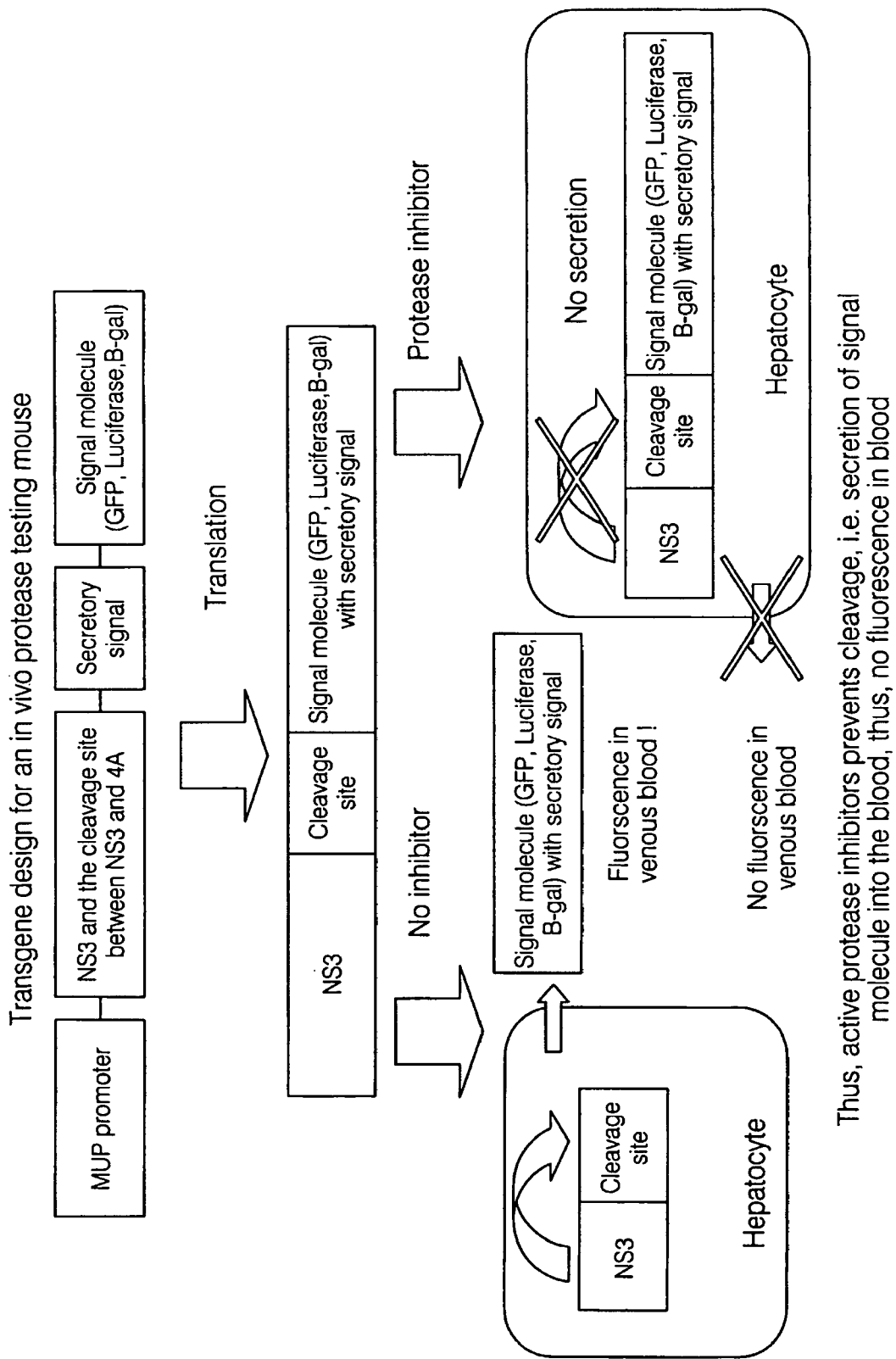
FIG. 14B is a schematic representation of the linearized fragment of a PADSI construct (pMUP-NS3-cleavage site-secretory signal-signal molecule) used for the detection of protease inhibitors.
Figure 14C:
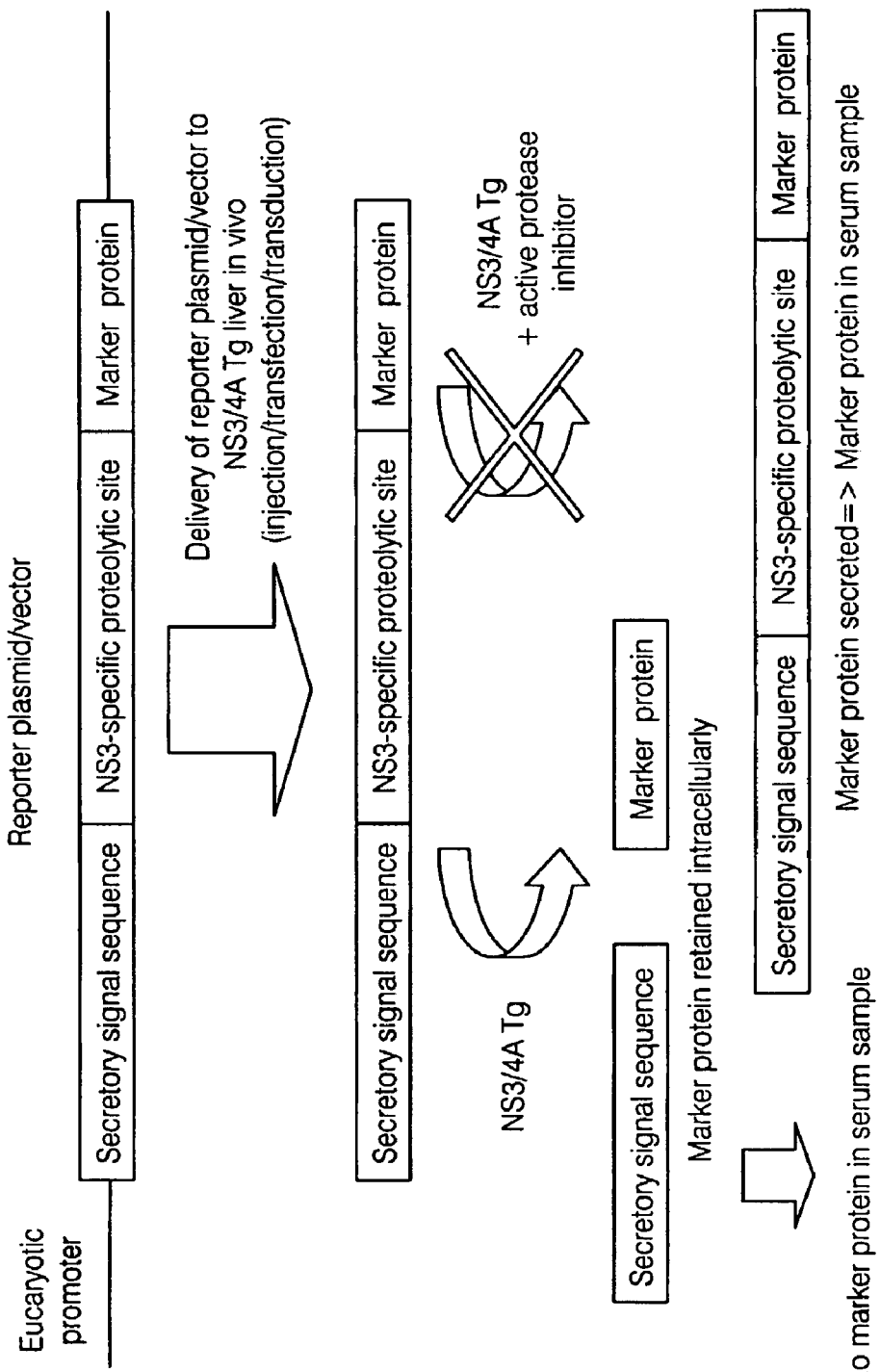
FIG. 14C is a schematic representation of the linearized fragment of an alternative PADSI construct (pMUP-NS3-cleavage site-secretory signal-signal molecule) used for the detection of protease inhibitors.

A schematic of a negative PADSI construct is shown in FIG. 14B, which can be compared to other constructs shown in FIGS. 14A and 14C. The construct is called a negative PADSI because the absence of the detectable marker outside of a cell harboring the PASDSI construct (e.g., the venous blood of a transgenic organism) indicates that the candidate protease inhibitor is effective. Generally speaking, this construct has a NS3 section, a cleavage site section, a secretory signal, and a signal molecule (detectable marker). Cleavage at the cleavage site results in the separation of the secretory signal peptide from the signal molecule (detectable marker). In the absence of NS3 protein, the signal molecule, which is attached to a secretory signal, is able to leave the cell harboring the PADSI construct (e.g., if the construct is expressed in a transgenic organism, the construct may enter the venous blood where it can be detected). Thus, cleavage of the PADSI fusion protein will result in the distribution of the signal molecule to areas outside of the cell but in the presence of a protease inhibitor, the signal molecule is retained in the cells harboring the PADSI construct. The PADSI constructs need not fluoresce. That is, in some embodiments, the detectable marker is GFP, Luciferase, or Beta-gal, or any other detectable marker known to those of skill in the art.

In some embodiments, the PADSI construct encodes a fusion protein comprising NS3 connected to a protease cleavage site, which can optionally be connected to the first approximately 5-10, 10-15, 15-20, 20-25, 25-30, 30-35, 35-40, 40-50, or 50 or more consecutive amino acids of NS4A. Connected to the 3 prime section of this optional part of the nucleic acid encoding NS4A is a secretory sequence, which is further connected to a signal molecule sequence (e.g., a detectable marker). Both the nucleic acid and amino acid constructs are contemplated, as are their presence in a transgenic organism (e.g., a mouse).

In some embodiments, the PADSI is a positive PADSI construct. In these embodiments, the presence of the detectable marker in the venous blood or outside the cell that harbors the construct will be a positive indication that the candidate protease inhibitor can prevent (e.g., reduce) cleavage of the NS3/4A molecule at the protease cleavage site. An example of a construct for a positive PADSI is shown in FIG. 14C and an example of the sequences selected for such a construct are shown in FIG. 14D. The positive PADSI construct described in FIG. 14C comprises a secretory signal sequence, a NS3-specific proteolytic site, and a marker protein, which are connected in the depicted manner or some equivalently functional manner. This construct can be delivered to a cell (e.g. a liver cell in a mouse) that is already expressing a NS3 or an NS3/4A construct such that liberated NS3 can cleave the positive PADSI construct and thereby release the detectable marker allowing secretion outside of the cell (e.g., into the blood of the mouse). Delivery of the positive PADSI construct or a positive PADSI protein may be by injection, transfection, or transduction. In the presence of a protease inhibitor, however, cleavage of the NS3-specific proteolytic site is prevented, marker protein and secretory signal sequence is not released and the fusion protein is retained within the cell (e.g., within the liver cells of a mouse). By monitoring the amount of detectable marker present outside of the cell harboring the construct (e.g., in the venous blood of a NS3/4A transgenic organism that receives the positive PADSI construct), one is able to determine the amount of protease activity that is inhibited. Unlike the previous embodiment, a greater amount of marker protein outside of the cell harboring the PADSI construct (e.g., in the venous blood of a transgenic organism) indicates a more efficient protease inhibitor.

As will be appreciated by one of skill in the art, not all of the cleaved marker may exit cell, even in the absence of a protease inhibitor. Thus, for both the negative PADSI and the positive PADSI constructs, changes in the relative amounts of the detectable marker can indicate the activity of a protease inhibitor. In some embodiments, any significant change in the amount of a detectable marker inside or outside of a cell harboring the PADSI construct can be sufficient. For example, 0-1, 1-10, 10-30, 30-60, 60-100, 100-200, 200-500, 500-1000, or greater percent increase, or decrease (0-1, 1-2, 2-5, 5-10, 10-20, 20-40, 40-60, 60-80, 80-90, 90-95, 95-98, 98-99, 99-100 percent) in the level of a detectable marker, either external to the original host cell (e.g., venous blood) or internal to the original host cell, can indicate that the candidate agent is an efficient protease inhibitor. In some embodiments, for example, a change in amount of marker detected is expressed as a ratio between the amount of detectable marker observed in the cell harboring the PADSI construct (e.g., liver cell of a transgenic organism) and the amount of detectable marker observed outside the cell harboring the PADSI construct (e.g., in the venous blood of the transgenic organism). By venous blood, is meant is that the detectable marker is on the opposite side of the cell membrane of the cell containing the construct or the PADSI protein.

Expression data (e.g., expression levels and ratios) for a particular candidate HCV inhibitor (e.g., a candidate protease inhibitor) can be recorded on a media (e.g., on a hard drive of a computer) and databases containing this information for a plurality of candidate HCV inhibitors can be assembled. By comparing the data assembled for various candidate HCV inhibitors, patterns of structure/function indicia can be recorded and, accordingly, candidate compounds can be assembled into groups that share similar structure/function indicia. Approaches in rational drug design can then be used to generate new candidate agents, which can be analyzed in the assays described herein, the data recorded and assembled into databases, and the process can be repeated. In this manner, an evolutionary approach to identify agents that inhibit HCV replication and infection can be employed based on an itterative or cyclical development process.

The MUP promoter shown in FIG. 14B is a tissue-specific promoter in that it expresses a construct in the liver of an organism. Other tissue specific promoters, constitutive promoters and inducible promoters can be used with embodiments described herein, as well. When the MUP promoter is used to drive expression of one of the PADSI constructs, however, the construct is expressed in liver cells. Thus, a change in the localization of the fluorescence, from the liver to the venous blood, or vice versa, can facilitates identification of protease inhibitors.

In some embodiments, the entire NS3 protein is encoded by the nucleic acid construct. This allows the NS3 protein to cleave the NS3/4A cleavage site. As discussed herein, variants of particular NS3 proteins, such as nonenzymatic variants, may be used for the NS3 section of the construct. In the present disclosure, the use of the term "PADSI" refers to a construct that contains a minimal NS3 cleavage site (e.g., comprising at least the "TS" motif). Other PADSIs can also be created, for example NS4A and 4B PADSIs, which are referred to as "NS4A/4B PADSIs." A sufficient amount of the cleavage site and surrounding residues is maintained so as to allow cleavage of the fusion peptide. For example, cleavage domains that can be used in the embodiments described herein can comprise CMSADLEVVTSTWVLVGGVL SEQ. ID. No. 74 or fragments thereof that comprise the (TS) cleavage site, such as, MSADLEVVTSTWVLVGGVL, SEQ. ID. No. 75, SADLEVVTSTWVLVGGVL, SEQ. ID. No. 47, ADLEVVTSTWVLVGGVL, SEQ. ID. No. 48, DLEVVTSTWVLVGGVL, SEQ. ID. No. 49, LEVVTSTWVLVGGVL, SEQ. ID. No. 50, EVVTSTWVLVGGVL, SEQ. ID. No. 51, VVTSTWVLVGGVL, SEQ. ID. No. 52, VTSTWVLVGGVL, SEQ. ID. No. 53, TSTWVLVGGVL, SEQ. ID. No. 54, TSTWVLVGGV, SEQ. ID. No. 55, TSTWVLVGG, SEQ. ID. No. 56, TSTWVLVG, SEQ. ID. No. 57, TSTWVLV, SEQ. ID. No. 58, TSTWVL , SEQ. ID. No. 59, TSTWV, SEQ. ID. No. 60, TSTW, SEQ. ID. No. 61, TST, TS, CMSADLEVVTS, SEQ. ID. No. 62, MSADLEVVTS, SEQ. ID. No. 63, SADLEVVTS, SEQ. ID. No. 64, ADLEVVTS, SEQ. ID. No. 65, DLEVVTS, SEQ. ID. No. 66, LEVVTS, SEQ. ID. No. 67, EVVTS, SEQ. ID. No. 68, VVTS, SEQ. ID. No. 69, VTS. Preferred cleavage domains to be incorporated in embodiments described herein comprise LEVVTSTWVL, SEQ. ID. No. 70, EVVTSTWVL, SEQ. ID. No. 71, or VVTSTWVL, SEQ. ID. No. 72.

In some embodiments, only the NS3/4A cleavage site is included in the construct. In another embodiment, part of the NS4A or NS3 nucleic acid section is also incorporated in the construct. For example, a nucleic acid encoding 2, 3, 4, 5, 6, 7, 8, 9, 10, 11, 12, 13, 14, 15, 16, 17, 18, 19, or 20 consecutive amino acids of any one of the peptides above or CMSADLEVVTSTWVLVGGVL, SEQ. ID. No. 73, or a fragment of NS3/4A that comprises the cleavage site (TS) may be included in the nucleic acid construct. More of the NS4A protein may be included, as long as it does not interfere with the desired effects of the secretory signal and the signal molecule. Other cleavage sites may also be used if the protease activity of those sites is of interest.

Any type of secretory signal may be used, as long as it is sufficient to move the signal molecule out of the cell. An example of a secretory signal includes Ig kappa. In some embodiments, the secretory signal is located close to the end of the cleaved NS3/4A product, thus allowing the secretory signal and the signal molecule attached to it to more readily diffuse out of the cell. Examples of possible signal molecules include green fluorescent protein (GFP), Luciferase and Beta-galactosidase. Several such signal sequences are known in the art, however. Exemplary sequences include, but are not limited to, GenBank Accession numbers, U49181 (luciferase), U73901 (GFP), and sequences in U.S. Pat. Nos. 5,625,048; 5,777,079; 5,804,387; 5,981,200; 6,066,476; 6,319,669 (GFP); 5,670,356; 5,604,123; and 5,229,285 (luciferase) all of which are hereby expressly incorporated by reference in their entireties (see also the attached sequences). Any molecule that can diffuse from the cell when associated with a secretory signal could be used in the embodiments described herein.

As discussed supra, in some embodiments, the PADSI nucleic acids and proteins described above can be used to detect whether or not a candidate protease inhibitor is functioning to stop the activity of the NS3 protease in vivo. When a MUP promoter-driven construct is expressed in an animal, such as a transgenic mouse, the resulting protein product may comprise a NS3 protein with a cleavage site, connected to a secretory signal and a signal molecule. In the absence of a protease inhibitor, NS3 will cleave the cleavage site, allowing the secretory signal and signal molecule to be released from the NS3, allowing the signal molecule to leave the hepatocytes and to diffuse to the venous blood. Thus, when a protease inhibitor is absent in the animal, the signal molecule is present in the venous blood. In the presence a protease inhibitor, however, cleavage is prevented and the signal molecule remains localized within the hepatocytes. Therefore, by monitoring the presence or absence of a signal molecule in the venous blood, one is able to determine if, and to what degree, the candidate protease inhibitors are able to prevent cleavage of NS3/4A. One may look in other areas as well as the venous blood, in particular when other tissue-specific promoters are used. In fact, any location outside of the cells that produced the PADSI protein will indicate the level of activity of the NS3/4A protease and the protease inhibitor. Preferably, the luciferase marker is used with the constructs above, which allows one to analyze protease activity in vivo using whole animal screening, in addition to the blood analysis mentioned above. Accordingly, in some embodiments, when luciferase is detected in the animal outside of the liver or outside of liver cells, the protease is not inhibited by the candidate protease inhibitor and when the luciferase remains localized to the liver, then the protease inhibitor is effective at disrupting cleavage of NS3/4A.

Several options are available with the systems described herein. For example, the NS3 PADSI construct can be expressed in its proper cell type, (liver cells) so that candidate inhibitors must be able to inhibit protease activity in the infected cell type and under physiological conditions. Additionally, there is an internal control for signal, because all of the PADSI mice will exhibit the signal molecule and it is only the localization of the signal molecule that changes. Additionally, if the signal molecule is fluorescent (e.g., luciferase), one may simply look for fluorescence in the blood of the mouse (e.g., whole animal screening) and no sample need be withdrawn from the organism. In some embodiments, the above constructs are adapted so that they can be used to detect the cleavage of other HCV peptides, such as NS4B and NS5. The following section provides more detail on the transgenic organisms described herein.

Transgenic Organisms

The HCV gene products described herein can be expressed in plants, insects, and animals so as to create a transgenic organism. Desirable transgenic plant systems having an HCV peptide include *Arabadopsis*, maize, and *Chlamydomonas*. Desirable insect systems having an HCV peptide include, but are not limited to, *D. melanogaster* and *C. elegans*. Animals of any species, including, but not limited to, amphibians, reptiles, birds, mice, hamsters, rats, rabbits, guinea pigs, pigs, micro-pigs, goats, dogs, cats, and non-human primates, e.g., baboons, monkeys, and chimpanzees can be used to generate transgenic animals having an embodied HCV molecule. These transgenic organisms desirably exhibit germline transfer of HCV peptides described herein.

Any technique known in the art is preferably used to introduce the HCV transgene into animals to produce the founder lines of transgenic animals or to knock out or replace existing HCV genes. Several methods to produce transgenic animals have become conventional in the-art. Such techniques also include, but are not limited to pronuclear microinjection (Hoppe, P. C. and Wagner, T. E., 1989, U.S. Pat. No. 4,873,191; and U.S. Pat. No. 4,736,866, issued Apr. 12, 1998 to Leder); retrovirus mediated gene transfer into germ lines (Van der Putten et al., *Proc. Natl. Acad. Sci., USA* 82:6148-6152 (1985)) and U.S. Pat. Pub. 20040019920, published Jan. 29, 2004 to Bremel et al.; gene targeting in embryonic stem cells (Thompson et al., *Cell* 56:313-321 (1989)); electroporation of embryos (Lo, *Mol. Cell. Biol.* 3:1803-1814 (1983); and sperm-mediated gene transfer (Lavitrano et al., *Cell* 57:717-723 (1989)); see also Gordon, *Transgenic Animals, Intl. Rev. Cytol.* 115:171-229 (1989).

In one embodiment, the transgenic organism is created by microinjection. Once a construct is decided upon, it will be inserted into a cell. Each construct must first be in the linear form to be inserted into the cell. Therefore, if the construct has been inserted into a vector, linearization is accomplished by digesting the DNA with a suitable restriction endonuclease selected to cut only within the vector sequence and not within the construct sequence. For insertion, the construct is added to the ES cells under appropriate conditions for the insertion method chosen, as is known to the skilled artisan. For example, if the ES cells are to be electroporated, the ES cells and construct DNA are exposed to an electric pulse using an electroporation machine and following the manufacturer's guidelines for use. After electroporation, the ES cells are typically allowed to recover under suitable incubation conditions. The cells are then screened for the presence of the construct as explained above. Where more than one construct is to be introduced into the ES cell, each construct can be introduced simultaneously or one at a time.

After suitable ES cells containing the construct in the proper location have been identified by the selection techniques outlined above, the cells can be inserted into an embryo. Insertion may be accomplished in a variety of ways known to the skilled artisan, however a preferred method is by microinjection. For microinjection, about 10-30 cells are collected into a micropipet and injected into embryos that are at the proper stage of development to permit integration of the foreign ES cell containing the construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (1986) Current Topics in Devel. Biol. 20:357-371.

While any embryo at the right stage of development is suitable for use, preferred embryos are male. In mice, the preferred embryos also have genes coding for a coat color that is different from the coat color encoded by the ES cell genes. In this way, the offspring can be screened easily for the presence of the construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the construct using Southern blots and/or PCR as described above. Offspring that appear to be mosaics may then be crossed to each other, if they are believed to carry the construct in their germ line, in order to generate homozygous animals. Homozygotes may be identified by Southern blotting of equivalent amounts of genomic DNA from mice that are the product of this cross, as well as mice that are known heterozygotes and wild type mice.

Other means of identifying and characterizing the construct offspring are available. For example, Northern blots can be used to probe the mRNA for the presence or absence of transcripts encoding either the gene, the marker gene, or both. In addition, Western blots can be used to assess the level of expression of the NS3/4A gene in various tissues of the offspring by probing the Western blot with an antibody against the NS3/4A protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the construct gene product.

The discussion below and the examples that follow describe the creation of a NS3/4A HCV transgenic mouse. (See EXAMPLES 18-36). The NS3/4A transgenic mouse was created without the Cre/Lox-P system. The transgenic mouse, created by the methods described herein, was found to produce both the NS3 and NS4A proteins. Furthermore, the proteins are produced in these mice in surprisingly large amounts, making the NS3 readily identifiable. Additionally, the transgenic mice created as described herein exhibit an HCV appropriate phenotype that is not so overwhelming so as to endanger the life of the model organism, namely livers with increased weight and a lower number of nuclei per area unit indicating enlarged cells. Additionally, the NS3/4A transgenic mice display a reduced likelihood of having intra-hepatic inflammatory foci and other phenotypes as will be discussed infra. While NS3/4A expression may not appear to cause a prominent phenotype in the liver of these mice, expression of NS3/4A protein does alter the intrahepatic distribution of immune cells in these animals. These phenotypes and others as described below provide evidence that the present description teaches the first successful transgenic HCV model.

In some embodiments, a genetically modified non-human mammal that comprises an allele that comprises a gene from a hepatitis C virus is provided. The hepatitis C virus gene can be codon optimized. In some embodiments, the genetically modified non-human mammal further comprises a NS3 gene. In some embodiments, the genetically modified non-human mammal further comprises a NS4A gene. In some embodiments, the genetically modified non-human mammal comprises both a NS3 gene and a NS4A gene. In some embodiments, the genetically modified non-human mammal has the further proviso that no other hepatitis C virus gene is in an allele of the non-human mammal, apart from the group that consists of: a NS3 gene a NS4A gene, and a combination of the two genes.

In a preferred embodiment, a vector that comprises a mouse major urinary promoter and at least one hepatitis C virus gene is provided. The hepatitis C virus gene is selected from the group that consists of: NS3, NS4A, and a combination of NS3 and NS4A. In some aspects, a vector that comprises a promoter and a codon optimized hepatitis C virus gene is provided. In some embodiments, the codon optimized hepatitis C virus gene is selected from the group that consists of: a NS4A gene, a NS3 gene, and a combination of a NS4A gene and a NS3 gene. In some aspects a vector that comprises a hepatitis C virus gene and a Semliki forest virus replicon is provided. In some embodiments, the hepatitis C virus gene is selected from the group that consists of: a NS4A gene, a NS3 gene, and a combination of a NS4A gene and a NS3 gene.

Accordingly, one aspect of the present invention relates to a transgenic non-human mammal (e.g., a mouse) comprising an exogenous DNA sequence stably integrated in its genome, wherein said exogenous DNA sequence comprises a mouse major urinary promoter (MUP) operably linked to an HCV NS3 gene and a method of making said genetically modified non-human mammal, as described herein. By one approach, for example, the genetically modified mouse is created by providing a construct that comprises a mouse major urinary promoter (MUP) operably linked to an HCV NS3 gene, transferring said construct to a totipotent cell, and transferring said totipotent containing said construct to a pseudo pregnant mouse, whereby said pseudo pregnant mouse gives birth to the genetically modified mouse describe herein. In some embodiments, the totipotent cell is a fertilized oocyte. In some embodiments, the totipotent cell is an embryonic stem cell. In some embodiments, the totipotent cell is a stem cell and in some embodiments the totipotent cell is a cell of a blastocyst.

In some embodiments, the construct used in the method of making a genetically modified non-human mammal, further comprises an NS4A gene operably linked to said MUP promoter. In another embodiment the construct further comprises a nucleic acid encoding a NS3 protease cleavage site. In another embodiment said nucleic acid encoding said NS3 protease cleavage site is joined to said NS3 gene. In another embodiment, said NS3 protease cleavage site is joined to said NS4A gene. In one embodiment, said construct further comprises a secretory signal joined to said NS3 gene and said NS3 protease cleavage site. In yet another embodiment said construct further comprises a signal molecule joined to said secretory signal, said NS3 gene, and said NS3 protease cleavage site.

In some embodiments, the transgenic non-human mammal containing an exogenous DNA further comprises an HCV NS4A gene operably linked to said MUP promoter. In another embodiment, the transgenic non-human mammal containing an exogenous DNA further comprises a nucleic acid encoding a NS3 protease cleavage site. In another embodiment, the transgenic non-human mammal containing an exogenous DNA wherein said nucleic acid encoding said NS3 protease cleavage site is joined to said NS3 gene. In one embodiment the present invention relates to a transgenic non-human mammal containing an exogenous DNA wherein said nucleic acid encoding said NS3 protease cleavage site is joined to said NS4a gene. In one embodiment, the invention relates to a transgenic non-human mammal containing an exogenous DNA as described above further comprising a nucleic acid encoding a secretory signal joined to the NS3 gene and the NS3 protease cleavage site. In another embodiment, the transgenic non-human mammal containing an exogenous DNA as described above further comprising further comprises a signal molecule joined to the secretory signal, the NS3 gene and the NS3 protease cleavage site.

In some embodiments, any of the genes described above are codon optimized for expression in a non-human mammal, in particular mice or humans. In a special embodiment the NS3 gene is codon optimized for expression in humans. In another special embodiment the NS3 gene and the NS4A gene are codon optimized for expression in humans.

Some embodiments relate to a transgenic non-human mammal according to the present invention comprising a phenotype of survival after contact with an amount of TNF-alpha that is lethal for a wild type non-human mammal of the same variety. In another embodiment said transgenic non-human mammal further comprises a phenotype of reversion to TNF-alpha sensitivity after contact with an inhibitor of p38 MAP kinase. In one embodiment, said inhibitor is SB203580. Some embodiments concern a transgenic non-human mammal according to the present invention comprising a phenotype of a reduced amount of intra-heptic CD4+ T cells, as compared to a non-human mammal of the same variety. Some embodiments concern a transgenic non-human mammal according to the present invention comprising a phenotype of a reduced amount of type I and II dendritic cells, as compared to a non-human mammal of the same variety.

In some aspects, a genetically modified mouse that comprises an allele that comprises a NS3 gene and a NS4A gene that allow the genetically modified mouse to express a NS3 protein and a NS4A protein is provided. In some embodiments, the NS3 protein produced by a liver of a genetically modified non human mammal is produced in an amount between about 0.1 to about 8 micrograms per gram of liver tissue, such as between 0.1 to 7 micrograms, between 0.1 to 6 micrograms, between 0.1 to 5 micrograms, between 0.1 to 4 micrograms between 0.1 to 3 micrograms, between 0.1 to 3 micrograms, between 0.1 to 2 micrograms, between 0.1 to 1 micrograms, between 1 to 7 micrograms, between 2 to 7 micrograms, between 3 to 7 micrograms, between 4 to 7 micrograms, between 5 to 7 micrograms, between 6 to 7 micrograms, between 7 to 8 micrograms. In some embodiments, the NS3 protein produced by a liver of a genetically modified mouse is at least 8 micrograms per gram of liver tissue.

In some embodiments, the NS3 protein expressed is detectable via a western blot. In some embodiments, the NS3 protein expressed is restricted to expression in the cytoplasm of hepatocytes. In some embodiments, the genetically modified mouse has a liver with a significantly increased weight relative to a mouse without NS3 protein being expressed in the mouse. In some embodiments, the genetically modified mouse has a lower number of nuclei per area unit in its liver tissue relative to a mouse without NS3 protein being expressed in the mouse.

Some embodiments concern a nucleic acid construct, the protein capable of being encoded by the nucleic acid construct, and/or a transgenic organism, such as a non-human mammal, expressing or that comprises any of the above. In some embodiments the protease whose activity is being monitored is the NS3 protease, and the protein being cleaved is the NS3/4A cleavage site, or sections thereof.

In some embodiments, the construct comprises a nucleic acid that encodes a NS3 peptide, comprising the NS3/4A cleavage site, joined to a secretory signal, which is attached to a signal molecule (e.g., an indicator molecule or marker protein). Following translation, a fusion protein, as depicted in FIG. 14B, is created. In the absence of protease inhibitor, the resulting fusion peptide will cleave itself, via the NS3 protein, at the NS3/4A cleavage site. This cleavage will allow the signal molecule to be secreted out of a cell that harbors the fusion peptide (e.g., into the bloodstream of a transgenic organism harboring the construct). In contrast, when a protease inhibitor is present, NS3 will not cleave the fusion peptide and the detectable marker (also known as a signal molecule, indicator, or marker protein) will not be secreted. These constructs and related embodiments are referred to as Protease Activity Dependent Secreted Indicators (PADSI). In the exemplary embodiment, the presence of a liberated detectable marker outside of the cell (e.g., in the venous blood of a organism containing the fusion peptide) will indicate that cleavage has occurred and that a protease inhibitor is not present. This particular form of a PADSI is called a negative PADSI, as it is the absence (or relative absence) of the indicator outside of the cell harboring the construct (e.g., in the venous blood) that indicates an active protease inhibitor.

In other embodiments, the presence of the indicator in the venous blood (or outside of the cell) will indicate the presence of an effective protease inhibitor. For example, the construct may be that described in FIG. 14C. In this embodiment the construct comprises a secretory signal attached to a NS3/4A proteolytic site that is attached to a marker protein (signal molecule, indicator, detectable marker or similar term). This construct is then placed into a system that has, or can have, active NS3 present. For example, a transgenic non-human mammal discussed herein expressing the NS3/4A construct can be used. In this embodiment, in the absence of inhibitor, the fusion peptide will be cleaved by NS3 and secretion of the marker protein into the blood stream will occur. In contrast, when a protease inhibitor is present, cleavage will not occur and fluorescence in the blood stream will not be observed. This embodiment is termed a positive PADSI, as the presence of fluorescence, in the venous blood, indicates the presence of an active protease inhibitor. Of course, as will be appreciated by one of skill in the art, the presence or absence of an indicator need not be binary and any statistically significant change can indicate the presence of an inhibitor.

As will be appreciated by one of skill in the art, these constructs may be expressed in vivo and the presence or absence of the detectable marker (indicator) in the venous blood can be determined without drawing blood from the non-human mammal. For example, in a positive PADSI, a transgenic non-human mammal that expresses NS3 can be provided a positive PADSI construct that will express the NS3/4A cleavage site along with the secretory signal and the detectable marker. In one embodiment, the PADSI construct is only expressed in the liver. In the absence of any NS3 protease inhibitor, the positive PADSI construct will be cleaved keeping the indicator inside the cell and allowing the secretory signal to leave the cell. In this state, the venous blood of the organism will not have a significant amount of marker. However, when a NS3 protease inhibitor is added, cleavage of the NS3/4A cleavage site will not occur, allowing the secretory signal to pull the detectable marker out of the cell, into the venous blood. Thus, any section of the non-human mammal that allows one to monitor the detectable marker in the venous blood through the skin of the non-human mammal can be observed to determine the activity associated with the protease inhibitor. Additionally, a similar in vivo approach may be applied with the negative PADSI constructs, in which case, one correlates the absence of an indicator with the level of activity of the protease inhibitor.

As will be appreciated by one of skill in the art, these PADSI constructs indicate activity based upon secretion and one is not limited to examination in transgenic non-human mammal. That is, various in vivo and in vitro tests may also be applied. For example, as mentioned supra, any time the indicator is detected outside of a cell harboring the construct, one can determine the activity of a candidate protease inhibitor. Additionally, viruses or other systems can be used to induce an organism to express the NS3 protein.

Other embodiments include a transgenic non-human mammal expressing the combination of NS3/NS4A fusion protein. The nucleic acids described above can be used to generate model HCV transgenic non-human mammal. The nucleic acids were expressed stably and at high levels in transgenic mice. These mice exhibited livers with increased weight and a lower number of nuclei per area unit indicating enlarged cells. Additionally, the presence of intra-hepatic inflammatory foci were less common in the NS3/4A transgenic mice. As such, these transgenic mice are useful as, among other things, model organisms for HCV analysis. In one embodiment, a transgenic mouse comprises the wild-type NS3/4A gene. In another embodiment, a transgenic mouse comprises the codon optimized NS3/4A gene.

In some embodiments, the transgenic non-human mammal displays a biochemical phenotype. For example, the transgenic mice can display an increased level of suppressor of cytokine activation-1 (SOCS1), increased immunity or resistance to TNF-alpha or TNF-alpha-induced lethality, and/or lower IRF-3 levels. More embodiments concern methods of treating or preventing HCV replication and infection by providing molecules that modulate the expression, phosphorylation, or activity of these proteins or proteins that are members of a phosphorylation cascade involving p38 MAP kinase.

It was found that the NS3/4A complex interferes with TNF receptor signalling in a p38 MAPK dependent way. This was demonstrated by showing that a NS3/4A transgenic phenotype, e.g., resistance to TNFα induced cytotoxicity, was reverted to wild-type by providing an inhibitor of p38 MAP kinase signaling. Until the present disclosure, a TNF-a signal transduction cascade involving NS3/4A was unknown. Further, these findings provide evidence that molecules that directly or indirectly inhibit p38 MAP kinase signaling can inhibit HCV replication and infection. The NS3/4A-transgenic mice described in the examples herein also provide a new and rapid way to identify inhibitors of p38 MAP kinase and thereby identify inhibitors of HCV replication and infection. By monitoring the sensitivity to TNFα in the presence and absence of candidate agents that inhibit p38 MAP kinase, for example, one can identify compounds that inhibit HCV replication and infection. By one approach, for example, an amount of TNF-alpha that is lethal to a wild-type mouse is provided to a NS3/4A transgenic mouse. Next, an amount of a candidate agent is then provided to the transgenic mouse and a reversion to TNF-alpha sensitivity (e.g., death or damage of the mouse) indicates that the candidate inhibits HCV replication and infection In more embodiments, a transgenic non-human mammal comprises a PADSI NS3/4A protein or nucleic acid encoding said protein and this transgenic non-human mammal is used to identify HCV protease inhibitors. Through the use of a PADSI NS3/4A protein, for example, one may, determine if a candidate protease inhibitor inhibits, reduces or prevents NS3/4A protease activity in vivo by observing the fluorescence of the tissue of the mouse when candidate protease inhibitor compounds are provided. For example, various candidate NS3 protease inhibitors can be administered to the transgenic mouse and the presence of the detectable marker in the venous blood is detected through the surface of the organism via a CCD. A decrease in the level of detectable marker will indicate that one of the candidate protease inhibitors is actually an effective protease inhibitor is described in the Examples. Accordingly, novel protease inhibitors can be identified. The following section provides more detail on the NS3/4A transgenic mice described herein.

NS3/4A Transgenic Mice

Unlike wild-type mice, the NS3/4A transgenic mice ("NS3/4A-Tg") created as described herein were found to exhibit several characteristics associated with an impaired immunity. It was observed, for example, that NS3/4A-Tg mice had a reduced number of spontaneously appearing intra-hepatic inflammatory foci. Accordingly, the immune cells present in the liver were further analyzed. In a first set of experiments, flow cytometry was used to analyze the percent of non-parenchymal immune cell populations in the liver and this analysis revealed that the NS3/4A-Tg mice had a minute increase in intra-hepatic NK cells but a marked reduction in CD4+ T cells (see EXAMPLE 31, FIG. 17A). The observed lack of inflammatory foci in the NS3/4A-Tg mice detected by histology may be a result of the reduced amount of CD4+ T cells. This reduced amount of intra-hepatic CD4+ T cells was confirmed by analysing the presence of different intra-hepatic immune markers using an RNAse protection assay ("RPA"). In these experiments, it was determined that the CD4+ cell mRNA levels were reduced in NS3/4A-Tg as compared to wild-type mice. (See EXAMPLE 32).

Next, a closer look was taken at the CD11c positive dendritic cell (DC) populations in the transgenic mouse livers. It has recently been shown that three to four distinct DC populations can be detected in the mouse liver (Jomantaite, I. et al., Hepatic dendritic cell subsets in the mouse. *Eur J Immunol* 34:355-365 (2004); Lian, Z. X. et al., Heterogeneity of dendritic cells in the mouse liver: identification and characterization of four distinct populations, *J Immunol* 170:2323-2330 (2003)). The CD11c+hepatic DCs can be divided into three distinct populations by quantifying the surface expression of CD11b, MHC-II, and Ly6C/G. This revealed that the CD11c+/CD11b-/MHC-IIint/Ly6C/G+population also termed type I/II, similar in phenotype and function to plasmacytoid DCs of a lymphoid origin (Colonna et al., *Nat Immunol*, 5:1219-1226 (2004)), was significantly reduced in the NS3/4A-Tg livers as compared to wild-type mice (see FIG. 17B, EXAMPLE 31). This DC population is a major producer of type-I IFN and a reduction of this cell type impairs the intra-hepatic immune response to viral pathogens.

Several NS3/4A transgenic mice were also examined to determine if they exhibited a functional impairment of the intra-hepatic immunity. Groups of transgenic and non-transgenic mice were treated with several different agents that are known to cause immune mediated liver damage and the results were recorded.

Figure 18A:
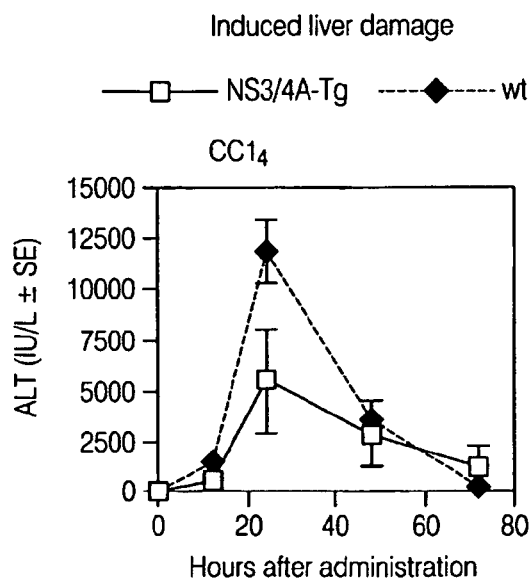
FIG. 18A is a graph showing the extent of $CCl_4$-induced liver damage in wild-type and NS3/4A transgenic mice.

In a first set of experiments, the NS3/4A-transgenic mice were contacted with $CCl_4$ and it was observed that the NS3/4A-Tg mice exhibited a reduced sensitivity to toxic liver damage, as compared to wild-type mice. (see EXAMPLE 33, FIG. 18A). While $CCl_4$ initially causes toxic liver damage, a large part of the following inflammatory response is mediated through TNF-α (see Morio et al., Distinct roles of tumor necrosis factor-alpha and nitric oxide in acute liver injury induced by carbon tetrachloride in mice, *Toxicol Appl Pharmacol*, 172:44-51 (2001); Simeonova, P. P. et al., The role of tumor necrosis factor-alpha in liver toxicity, inflammation, and fibrosis induced by carbon tetrachloride, *Toxicol Appl Pharmacol* 177:112-120 (2001)).

Figure 18B:
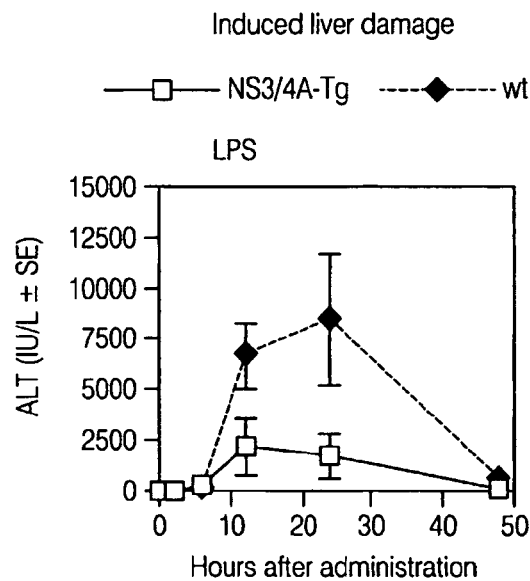
FIG. 18B is a graph showing the extent of LPS-induced liver damage in wild-type and NS3/4A transgenic mice.

Next, the activation of the TOLL-like receptor (TLR) 4 was tested by providing LPS and GalN to the NS3/4A-Tg and wild-type mice. (See Akira et al., Toll-like receptor signaling, *Nat Rev Immunol*, 4:499-511 (2004)). These experiments revealed that LPS-induced liver damage was also significantly reduced in the NS3/4A-Tg mice as compared to wld-type mice. (see EXAMPLE 33, FIG. 18B). Since the main mediator of the LPS response is TNF-α, and since TNF-α is also involved in $CCl_4$-mediated liver damage, similar pathways that do not directly involve TNF-α were then analyzed to determine if they too were affected in the transgenic mice.

Figure 18C:
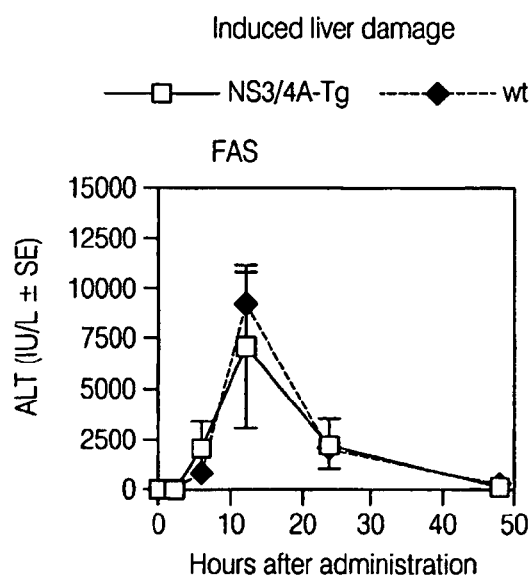
FIG. 18C is a graph showing the extent of FAS-induced liver damage in wild-type and NS3/4A transgenic mice.
Figure 18D:
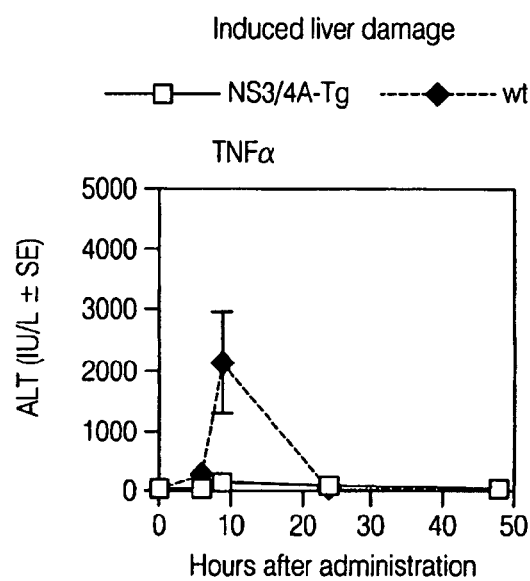
FIG. 18D is a graph showing the extent of TNF-alpha-induced liver damage in wild-type and NS3/4A transgenic mice.

Intravenous injection of the FAS mAb Jo2, which causes massive apoptosis in liver cells, was conducted in NS3/4A-Tg and wild-type mice. These experiments revealed that the antibody induced comparable liver damage in the NS3/4A-Tg and wild-type mice, indicating that FAS-mediated apoptotic pathways were intact in the Tg mice (see EXAMPLE 33, FIG. 18C). Finally, a direct injection of TNF-α in NS3/4A-Tg and wild-type mice revealed that the NS3/4A-Tg mice exhibited significantly reduced liver damage (see EXAMPLE 33, FIG. 18D). Accordingly, the data from these experiments provided strong evidence that the major defect in the intra-hepatic immunity in the NS3/4A-transgenic mice involved TNF-α.

Soluble TNF-α acts through the TNF receptor 1 (TNFR1), or p55, a receptor that is expressed on adult murine hepatocytes. (See Kamiya, A. & Gonzalez, F. J., TNF-alpha regulates mouse fetal hepatic maturation induced by oncostatin M and extracellular matrices, *Hepatology*, 40:527-536 (2004)). Thus, a major defect in the intra-hepatic immunity in the NS3/4A-Tg mice is a reduced sensitivity to liver damage conferred by TNF-α through TNFR1 directly, or indirectly through LPS.

As appreciated by one of skill in the art, by determining the relevant pathway(s) through which TNF-alpha activity is altered in the NS3/4A-Tg mice, one can determine the proteins that NS3, NS4A, or NS3/4A interact. Accordingly, new targets for the development of anti-HCV compounds can be identified using the NS3/4A-Tg mice described herein.

Figure 20:
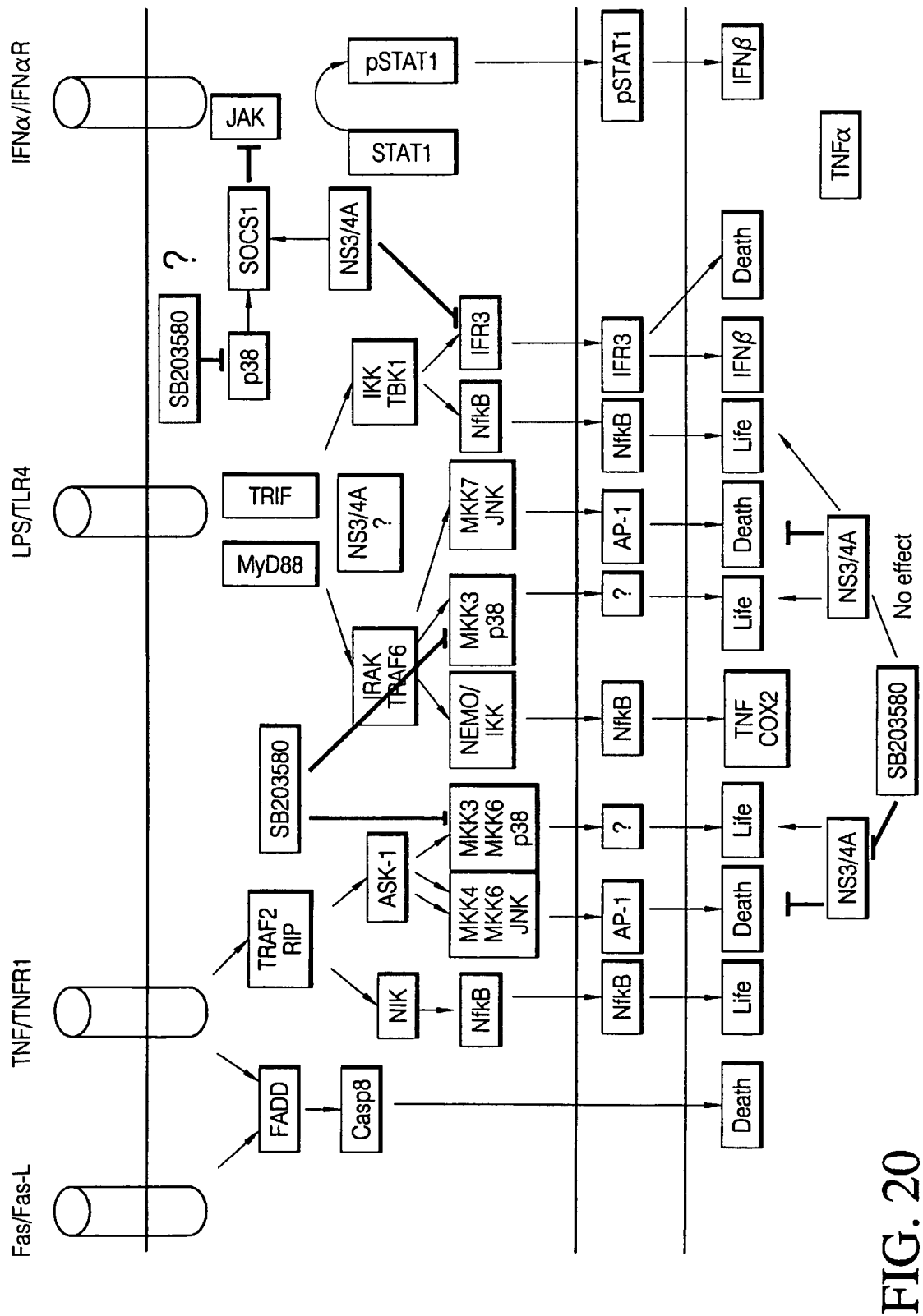
FIG. 20 is a flow chart showing various pathways involved with FAS, TNF-alpha, LPS, and IFN-alpha signal transduction. Protein-protein interactions are shown using arrows (denoting activating interactions) or bars (denoting inhibiting interactions).

TNF-α mediated TNFR1 activation leads either directly to apoptosis through caspases, or to activation of the transcriptional complex IKK/NfkB (see FIG. 20). TRAF2/RIP in turn activates ASK-1, which signals through either the JNK or the p38 MAP kinases (hereinafter "p38"). Activation of TLR4 leads to signalling either through MyD88 or through an MyD88-independent pathway. (See Palsson-McDermott, E. M. & O'Neill, L. A., Signal transduction by the lipopolysaccharide receptor, Toll-like receptor-4, *Immunology* 113:153-162 (2004)). TLR4 mainly acts through TNF-alpha by IKK/ NfkB activation through MyD88 signalling, whereas TLR4-induced IFN signalling is mediated through the MyD88-independent pathway and IRF3. (See Doughty, L., Nguyen, K., Durbin, J. & Biron, C., A role for IFN-alpha beta in virus infection-induced sensitization to endotoxin, *J Immunol*, 166:2658-2664 (2001)). Signalling through IFNα acts directly on the IFNα receptor that signals through IRF3 to STAT1 and initiates trancription of IFN-responsive genes. (See Biron, C.A. Interferons alpha and beta as immune regulators—a new look, *Immunity* 14:661-664 (2001)).

The actions of both TNFα and LPS described above can be blocked by activation of the suppressor of cytokine activation-1 (SOCS1). (See Nakagawa, R. et al., SOCS-1 participates in negative regulation of LPS responses. *Immunity* 17:677-687 (2002); Sass, et al., TNF/TNF receptor 1 inducible cytoprotective proteins in the mouse liver: relevance of suppressors of cytokine signaling, *Biochem J*. (2004)). As such, various tests were performed on the NS3/4A-Tg mice to determine the pathway(s) NS3/4A was involved. NS3/4A-Tg Mice were given LPS, IFNα, or IFNγ and their livers were removed at short intervals thereafter and the nuclear fraction was isolated and analyzed by Western blot.

Several lines of evidence indicated that signalling in the NS3/4A Tg livers was impaired. First, treatment with LPS revealed that the activation of nuclear phosphorylated STAT1 and STAT2 was reduced in the NS3/4A-Tg livers. (See EXAMPLE 34). Since phosphorylated STAT1 is a mediator of the cellular response to LPS, this is consistent with a reduction of LPS-mediated liver disease. Second, the basal levels of SOCS1 were higher in the NS3/4A-Tg mice although LPS treatment induced comparable levels of SOCS1 in non-transgenic and transgenic mice (see EXAMPLE 34). Third, LPS treatment induced PP2A in the transgenic but not in the non-transgenic mice. Since TNF-α signalling can be inhibited by increased de-phosphorylation, the increase in PP2A is consistent with a reduced TNF-α response (as PP2A, which can be activated by p38, functions to inhibit MKK4 activation, from TNA-alpha, of JNK1, which would otherwise lead to apoptosis. (See Avdi et al., J. Biol. Chem., 277:40687-40696 (2002)). Thus, reduced levels of phosphorylated STAT1 and STAT2, possibly caused by increased dephosphorylation by activation of PP2A following LPS treatment, is fully consistent with a reduced liver damage following LPS and TNF-α treatment in the NS3/4A-Tg mice. Interestingly, a similar inhibition of STAT1 induced by activation of PP2A has been observed in a transgenic mouse expressing the full length HCV genome. (See Duong, et al., Hepatitis C virus inhibits interferon signaling through up-regulation of protein phosphatase 2A, *Gastroenterology*, 126:263-277 (2004)). These findings indicate that the NS3/4A complex is responsible for PP2A induced inactivation of STAT1 and STAT2.

The IFN-signalling pathways were then evaluated to determine if they were affected in the NS3/4A-transgenic mice. Following IFNα treatment, it was noted that nuclear IRF3 levels were reduced in the NS3/4A-Tg mice (see EXAMPLE 34), which confirms previous in vitro observations. (see Foy, E. et al., Regulation of Interferon Regulatory Factor-3 by the Hepatitis C Virus Serine Protease, *Science* (2003)). It was again noted that the NS3/4A-transgenic mice had increased basal levels of SOCS1, and that IFNα treatment induced increased levels of SOCS1, as compared to non-transgenic mice (see EXAMPLE 34). These data indicate that the previous observations that NS3/4A interferes with IFNα-signalling has been reproduced in vivo. Also, these data indicate that the reduced sensitivity of the NS3/4A-Tg livers to LPS, TNFα, and IFNα involve activation of SOCS1.

Following IFNγ treatment a delay in the activation of nuclear STAT1 was observed (see EXAMPLE 34). However, no other marker seemed to be significantly impaired after IFNγ treatment, since activation of the IFNγR directly activates STAT1. The following section discusses the discovery that a p38 MAP kinase blocker reverts the phenotype of the NS3/4A Tg mouse to that of a wild-type mouse.

NS3/4a Transgenic Mice are Resistant to TNF-Alpha, which can be Reversed by Inhibiting P38

Figure 19A:
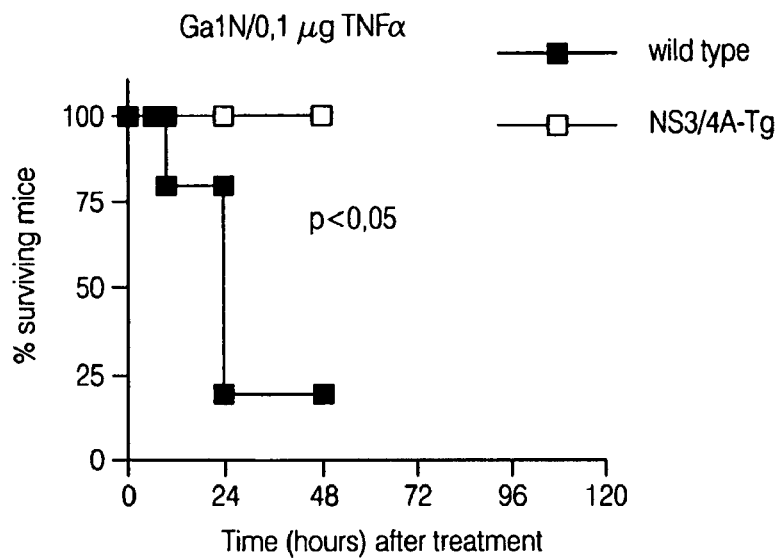
FIG. 19A is a graph showing the percent survival of wild-type mice and NS3/4A transgenic mice after administration of TNF-alpha.

Initially, the TNF-α sensitivity of the NS3/4A-transgenic mice and wild-type mice was compared. Injections of TNF-α (5 μg/kg) killed 80% of the non-transgenic mice within 24 hours, however, all NS3/4A-Tg mice survived this lethal TNF-α dose. (See EXAMPLE 35, FIG. 19A; p<0.05, Fisher's exact test). Since TNFR1 signalling is mediated through both the MKK4/7 and JNK, or the MKK3/6 and p38 pathways, the effect of p38 inhibitors on the NS3/4A-transgenic was investigated. The results of these experiments showed that inhibition of p38 reverted the TNF-α resistant phenotype of the NS3/4A-Tg mice to the wild-type sensitivity (see EXAMPLE 35, FIG. 19B). Notably, inhibition of p38 did not alter the TNF-alpha sensitivity of the wild type mice (see FIG. 19C). The results of these experiments provide evidence that the modulation of TNFR1 signalling in the NS3/4A-Tg mice is dependent on p38 MAP kinase activity. The following section provides more detail on the use of the transgenic organisms created as described herein to identify compounds that inhibit HCV proliferation, replication or infection.

Use of NS3/4a Transgenic Mice to Identify Inhibitors of HCV

Several embodiments concern a method of identifying a compound that inhibits hepatitis C virus replication, proliferation, or infection. Some methods comprise the steps of providing a genetically modified non-human mammal described herein, contacting a test compound to the non-human mammal, and analyzing the presence or absence of a marker that indicates that the compound inhibits hepatitis C virus replication, proliferation, or infection in a human. Accordingly, a reduction in the presence of the marker identifies the compound as one that inhibits hepatitis C virus replication, proliferation, or infection. In some embodiments, the reduction in hepatitis C virus replication is identified by comparing the liver or cell thereof of the non-human mammal treated with the test compound to a liver or cell thereof of a second non-human mammal. The second non-human mammal can be a wild-type mouse or an NS3/4A-Tg mouse that was not treated with the test compound.

Thus, in some embodiments, a method of using the genetically modified non-human mammal (e.g., a NS3/4A-Tg mouse) to identify a molecule that inhibits HCV replication is provided, wherein said method comprises providing the genetically modified non-human mammal, created as described herein, contacting said genetically modified non-human mammal with a candidate molecule, and determining whether said molecule inhibits the activity of NS3, whereby said molecule that inhibits HCV replication is identified by the ability of said molecule to inhibit the activity of NS3. In other embodiments, said genetically modified non-human mammal further comprises a nucleic acid encoding a signal molecule, a secretory signal, and an NS3 protease cleavage site. In some embodiments, said signal molecule is luciferase. In other embodiments, said determining step is performed by analyzing the presence or absence of the signal molecule outside a liver cell. In yet other embodiments, said determining step is performed by analyzing the presence or absence of the signal molecule inside a liver cell. The methods described above can be used to analyze various candidate compounds so as to identify molecules that inhibit p38 MAP kinase.

The compounds identified by the methods above, (e.g., kinase inhibitors, in particular p38 kinase inhibitors) can be incorporated into a composition (e.g., pharmaceutical or dietary supplement) that is formulated for human administration and said compositions can be provided to a subject in need of an agent that inhibits HCV replication and infection or an agent that otherwise improves the health or wellness of the subject (e.g., improves the function of the liver or immune system). In some embodiments, the inhibition of HCV replication in said subject is measured before and/or after providing said composition. Accordingly, methods of treating and preventing HCV replication and/or infection are provided whereby a subject in need of an agent that inhibits HCV replication and/or infection is provided a kinase inhibitor (e.g., a p38 kinase inhibitor).

Accordingly, the data provided herein demonstrate that the NS3//NS4A-transgenic mice can be used as a rapid in vivo model to screen for inhibitors of HCV (e.g., inhibitors of the p38 MAP kinase). For example, any compound or treatment that results in the NS3/4A transgenic mice exhibiting a wild-type phenotype (e.g., susceptibility to TNF-alpha induced cell death) can also be a compound useful for the treatment or prevention of HCV infection, as the compound will have displayed the ability to prevent an NS3/4A-based disruption in vivo. Thus, aspects of the present invention relate to methods of using the genetically modified non-human mammals (e.g., mice) to identify a molecule that inhibits HCV replication, wherein said methods comprise providing the genetically modified non human mammal created as described herein, contacting said genetically modified non-human mammal with a molecule; and determining whether said molecule increases the sensitivity of said genetically modified non-human mammal to TNF-alpha (e.g., TNF-alpha-induced cell death). In some embodiments, said molecule is a p38 MAP kinase inhibitor. In other embodiments, said inhibitor is selected from the group consisting of SB 203580, SB 202190, KN62, U0126, PD 98059, Wortmannin, rapamycin, Ro 31-8220, Bis-1, Go 6976, UCN01, Indirubin-3'-monoxime, kenpaullone, alsterpaullone, PP1, PP2, SU 6656, SP 600125, ML-9, PD 169316, p38 MAP Kinase inhibitor, SB202190 hydrochloride, SB 203580 hydrochloride, SB 203580 Iodo, SC68376, SKF-86002, ZM 3363772, Anti-p38/HOG-1 antibody, and anti-p38 MAP Kinase antibody. In a presently preferred embodiment said molecule is SB203580. In another presently preferred embodiment said molecule is SB202190. In more embodiments, said molecule is selected from the group consisting of a SOCS1 inhibitor, an IFR3 enhancer, type-1 IFN, typeI/II hepatic DC, STAT1 activator, STAT2 activator, siRNA to SOCS1, siRNA to p38, siRNA to PP2A, a blocking antibody to SOCS1, a blocking antibody to p38, a blocking antibody to PP2A, an activating antibody to IFR3, an activating antibody to STAT1, an activating antibody to STAT2, and a PP2A inhibitor. In still more embodiments, said molecule is a suppressor of cytokine signaling-1 (SOCS1) inhibitor.

The compounds identified by the methods above, (e.g., kinase inhibitors, in particular p38 kinase inhibitors) can be incorporated into a composition (e.g., pharmaceutical or dietary supplement) that is formulated for human administration and said compositions can be provided to a subject in need of an agent that inhibits HCV replication and infection or an agent that otherwise improves the health or wellness of the subject (e.g., improves the function of the liver or immune system). In some embodiments, the inhibition of HCV replication in said subject is measured before and/or after providing said composition. Accordingly, methods of treating and preventing HCV replication and/or infection are provided whereby a subject in need of an agent that inhibits HCV replication and/or infection is provided a kinase inhibitor (e.g., a p38 kinase inhibitor).

These results also demonstrate that the NS3/NS4A-transgenic mice, created as described herein, can be used as a rapid in vivo model to screen inhibitors of the p38 MAP kinase. Additionally, the mice can be used as a rapid in vivo system to screen candidate treatments directed to HCV. For example, any compound or treatment that results in the NS3/4A transgenic mice exhibiting a wild-type phenotype (e.g., susceptibility to TNF-alpha induced cell death) can also be a candidate compound for HCV prevention, as the compound will have displayed the ability to prevent an NS3/4A-based disruption in vivo.

In some embodiments, a NS3/4A transgenic mouse can be used to screen candidate inhibitors of p38 MAP kinase. As shown above, the present NS3/4A-Tg mice demonstrate an increased or high resistance to cell death mediated by TNF-alpha. Thus, NS3/4A transgenic mice that receive TNF-alpha have a much lower risk of death or cell damage than wild-type mice. It appears that this interaction occurs through p38, as the inhibition of p38 results in NS3/4A transgenic mice exhibiting wild-type sensitivity to TNF-alpha (e.g., cell death and mouse death). As such, a compound administered to a NS3/4A transgenic mouse (e.g., a candidate p38 inhibitor), in conjunction with a wild-type lethal amount of TNF-alpha that results in the NS3/4A transgenic mouse dying indicates that the candidate molecule is an effective inhibitor of p38 activity (e.g., SB203580) and also a compound that can be formulated into an anti-HCV pharmaceutical.

The term "wild-type lethal amount" can be used to describe the amount of a substance that would typically kill, or measurably increase the risk of death, of a wild-type mouse or cell, but not necessarily kill a NS3/4A transgenic mouse or cell. This amount can be an $LD_{50}$-based amount, where half of the population of wild-type mice would be dead, or it can be based on some other expected amount of death (e.g., the 80% death induced by TNF-alpha, as described above). The exact percent or risk of death need not be limited to any set amount, as long as a difference in the expected percent dead and the actual percent dead can be observed. The term "control lethal amount" denotes the amount required to kill a certain percentage of a control animals, i.e., the animal need not be a wild-type mouse. The term "wild-type lethal substance" denotes that a wild-type mouse can die from the administration of the substance to the mouse, while implying that a transgenic mouse (e.g., NS3/4A-Tg) would not have the same risk of death from the same amount of the substance.

In some embodiments, positive controls are run with the above test to make certain that the candidate compound is not lethal for other reasons. For example, a wild-type mouse can be provided the candidate compound to make certain it is not acting through other mechanisms. As appreciated by one of skill in the art, the positive indication of a candidate p38 inhibitor can vary, and can include, for example, mouse death, or cell death. Also, as demonstrated above, there are numerous proteins that change expression level due to NS3/4A expression. Detection of these changes in protein expression or activation can also allow one to determine if the candidate compound or treatment is effective in either inhibiting p38, or as an anti-HCV agent. Other techniques in which one examines the level of activity of proteins downstream of p38 can also be useful. Thus, both a method for screening for p38 inhibitors and a composition for doing so is provided. In one embodiment, the NS3/4A transgenic mouse has a consistent and steady level of TNF-alpha in its system so that it can be used continuously to test for candidate compositions.

As will be appreciated by one of skill in the art, the fact that NS3/4A-Tg mice exhibit a resistance to TNF-alpha relative to wild type mice is one phenotype of the NS3/4A-Tg mice. There are many other phenotypes described herein as well (e.g., increased SOCS1 levels), which can be analyzed in the methods described herein to identify compositions that inhibit HCV. In some embodiments, these other phenotypes are examined, instead of analyzing TNF-alpha mediated cell death. These phenotypes are generally termed "NS3/4A phenotypes." The compounds that are administered to the mouse to induce phenotypes are termed "NS3/4A phenotype inducing substances." Thus, TNF-alpha is one example of a NS3/4A phenotype inducing substance, as administration of TNF-alpha to the mouse results in a phenotype (e.g., reduced likelihood of cell and mouse death). In some embodiments, using the guidance provided above, one can test for other NS3/4A phenotype inducing substances. Thus, phenotypes other than cell death or phenotypes other than those relating to TNF-alpha can be observed.

In some embodiments, the phenotype observed is an activity level of various proteins in a pathway, for example, as shown above. Thus, a phenotype can be an elevated activity of a protein in a NS3/4A Tg can be used as a phenotype. "Activity" can encompass the kinetic rates associated with how quickly an enzyme may catalyze a reaction, which can be altered through events such as phosphorylation. Activity can also encompass the absolute level or amount of the protein present in a system. If intended to be separated, the terms can be denoted as enzymatic activity and protein expression respectively or other similar such terms.

As will be appreciated by one of skill in the art, compounds or techniques that result in the NS3/4A-Tg mouse exhibiting a wild-type phenotype can be effective HCV treatments. An HCV "treatment" can encompass both a method of treating HCV and a composition for treating HCV (e.g., a medicament). In some embodiments, HCV treatments can prevent the onset of symptoms or infection. In some embodiments, HCV treatments can also reduce symptoms associated with the disease, as well as reverse the course of the HCV infection. Regimens for treating or preventing HCV can vary dramatically. However, in light of the present disclosure, the identification and analysis of other kinase modulatory molecules that reduce HCV replication and infection are straightforward. In some embodiments, compounds that revert a NS3/4A phenotype of the NS3/4A transgenic mouse to a wild-type phenotype can be used to identify molecules for incorporation into a HCV medicament that if formulated for human administration (e.g., prepared according to cGMP standards). As appreciated by one of skill in the art, a HCV treatment need not completely remove all symptoms or aspects of HCV infection. In some embodiments, only some of the symptoms are reduced, such as a reduced amount of protein expressed in a patient who is receiving the treatment. In other embodiments, all of the symptoms are eliminated. In other embodiments, even the proteins associated with the HCV virus itself are eliminated. Thus, by "treat," what is meant is a reduction in a HCV related symptom, (e.g., HCV replication or persistence of the virus) rather than the removal of all HCV related effects. Additionally, as appreciated by one of skill in the art, the preventative nature of a compound designed to prevent HCV infection need not be absolute. In some embodiments, the treatments (e.g., methods or medicaments) can only reduce the risk of infection by some percent, for example, more than zero to 1, 1-10, 10-20, 20-30, 30-50, 50-60, 60-70, 70-80, 80-90, 95-99, and 99-100 percent reduction in risk of infection. In other embodiments, the treatments only delay the onset of initial or additional symptoms.

A "candidate" HCV treatment, p38 inhibitor, etc. denotes that the compound or method may be useful in the treatment or prevention of HCV or p38 activity. A "treatment," etc., when not modified by the term "candidate," denotes that the composition or method does alter the symptoms of HCV, inhibit p38 activity, etc. As will be appreciated by one of skill in the art, compounds that are treatments can also have other adverse side effects or be less effective in certain patients; however, such adjustments only require routine modifications and testing, as the risk of adverse side effects is common to almost all forms of medication.

Particular guidance for testing, characterizing, and using the candidate HCV treatments is provided herein in the description and in the Examples. Additional guidance is provided in FIG. 20. In particular, compounds that have previously been known to alter the indicated pathways for NS3/4A activity can be tested in the methods provided herein. Additionally, FIG. 20 can also be used to determine steps at which NS3/4A can act and thus provide guidance to one of skill in the art as to which later steps in the cascade should be activated to compensate for the inhibition or stimulation induced by NS3/4A. Additional pathways known to one of skill in the art can also be examined. These pathways have been discussed above. Additionally, it is believed that NS3/4A can have multiple influences. First, as previously proposed in vitro, NS3/4A can impair IFNα signalling through IRF3 in vivo, possibly through SOCS1. Additionally, NS3/4A can cause resistance to TNF-α mediated apoptosis due to p38, which up-regulates PP2A, which in turn blocks TNFR1-signalling through the MKK4-JNK pathway. This pathway is demonstrated in Avdi et al. (*J. of Biol. Chem.*, 277:40687-40696 (2002)) involving TNF-alpha, p38 MAP kinase, and PP2A and can also be used to determine possible proteins that are of interest in preventing or treating HCV. In particular, in this pathway, the balance between TNFR1 signalling through the pro-apoptotic MKK4/7-JNK, and the anti-apoptotic MKK3/6-p38 MAPK pathways, can be disturbed. Thus, the TNF-α resistant phenotype of the NS3/4A-Tg mice can be due to a p38-mediated activation of PP2A that blocks JNK-induced apoptosis. Kins et al., Activation of the ERK and JNK signaling pathways caused by neuron-specific inhibition of PP2A in transgenic mice, *Am J Pathol*, 163:833-843 (2003)). This theory is not intended to limit the scope of the various embodiments.

By "revert to wild-type" it is meant that a NS3/4A phenotype in a NS3/4A transgenic is made more similar to the wild-type phenotype. In some embodiments, reverting to a wild-type phenotype indicates that a HCV treatment has been identified. A NS3/4A phenotype is a characteristic that the NS3/4A transgenic exhibits that the wild-type does not exhibit, e.g, a different level of SOCS1 expression or an immunity to TNF-alpha induced death). Many such differences are noted above and in the figures and any of these differences can be used as a phenotype.

The above disclosed screening methods and the transgenic organisms described herein can also be used to screen for candidate HCV treatments, as compounds that are effective in reversing the phenotype in the transgenic mice can also reverse the phenotype of HCV in HCV infected organisms. Thus, the above compositions and methods applicable to p38 inhibition can be useful for HCV prevention and treatment. For example SB203580, or analogs thereof can be used as an inhibitor of p38 and to treat or prevent HCV. Additional compositions that may be used with the embodiments described herein include, but are not limited to: antisense RNA, siRNA to p38 MAP kinase, SB 203580, SB 202190, KN62, U0126, PD 98059, Wortmannin, rapamycin, Ro 31-8220, Bis-1, Go 6976, UCN01, Indirubin-3'-monoxime, kenpaullone, alsterpaullone, PP1, PP2, SU 6656, SP 600125, ML-9, PD 169316, p38 MAP Kinase inhibitor, SB202190 hydrochloride, SB 203580 hydrochloride, SB 203580 Iodo, SC68376, SKF-86002, ZM 3363772, Anti-p38/HOG-1 antibody, and anti-p38 MAP Kinase antibody, as well as, any inhibitors obtained by the identification methods disclosed herein.

Alternatively, other selective inhibitors to p38 MAPk, for example via blocking ATP binding, can be used. In some embodiments, the HCV treatment relates to the readjustment of a protein or enzyme that is altered in the NS3/4A transgenic mouse, as described herein (e.g., SOCS1). More examples of compounds that can be used to inhibit proliferation of HCV in an afflicted subject include, but are not limited to, a SOCS1 inhibitor, an IFR3 enhancer, type-1 IFN, typeI/II hepatic DC, STAT1 activator, STAT2 activator, siRNA to SOCS1, antisense RNA, miRNA and siRNA to p38 or to PP2A, a PP2A inhibitor, an inhibiting antibody (e.g., it acts as an inhibitor for the protein to which it binds) for any of the above inhibitors, and an activating antibody (e.g., it acts as an enhancer or activates the protein to which it binds) for any of the above activators. In some embodiments, any compound that alters, modifies, or modulates any of the activities of a molecule depicted in FIG. 20 may be formulated into an anti-HCV pharmaceutical for human administration.

Following the initial screening of a candidate HCV inhibitory compound, (e.g., once the compound demonstrates that it can induce TNF-alpha sensitivity in a NS3/4A transgenic mouse), additional screening steps can be performed. For example, the compound can be tested to make certain that it does not induce death in wild-type mice. The compound can be analyzed to determine its effectiveness in preventing or treating HCV or HCV related symptoms in an HCV infected subject (e.g., a human).

The general method for screening for candidate p38 inhibitors can also be used to screen for agents to treat or prevent HCV. The procedure is similar to that described in the Examples. Agents that make a NS3/4A mouse react to TNF-alpha in the same manner that a wild-type mouse reacts to TNF-alpha are selected as HCV treatments. These selected treatments can then be examined with more traditional and routine techniques known to one of skill in the art to determine how effective they are in preventing or treating HCV. Unlike EXAMPLE 37, candidate HCV treatments can include any compound that results in the reversion of the phenotype to a wild-type phenotype. In other words, a HCV treatment can function at a level beneath a p38 kinase, for example by inhibiting later steps in a pathway.

In some embodiments, rather than a NS3/4A transgenic mouse, another NS3/4A model system is used. For example, in some embodiments, a cell culture is used instead of an entire organism. Thus, a cell expressing NS3/4A protein is administered a wild-type lethal amount of TNF-alpha, alternatively, the cells may create their own TNF-alpha. Then candidate p38 inhibitors are applied to the cells. Cells will primarily die if the candidate p38 inhibitor is a p38 inhibitor (assuming the candidate inhibitor does not kill the wild-type cells when it is administered to the wild-type cells alone). In addition to cell death, one can examine the altered protein levels demonstrated above, as well as the various cytokine levels. In some embodiments, the cells are liver cells. In other embodiments, the cells are any type of cell that can express NS3/4A as desired.

In some embodiments, the testing is done in a mouse, but the mouse is not a traditional transgenic mouse. For example, in some embodiments, the mouse is a transient transgenic. That is, one or more of the constructs described herein is provided to said mouse (e.g., an NS3/4A expression construct containing a signal sequence and a secretory sequence is provided by injection). Once an NS3/4A-containing construct has been provided to said mouse, for example, the test compound is contacted with said transiently transgenic mouse and the presence or absence of NS3 protease activity or TNF-alpha sensitivity is analyzed. While this can result in a mouse with a NS3/4A phenotype for a relatively brief period of time, as demonstrated above, the lethality due to TNF-alpha can take as little as hours, even in the NS3/4A background mouse, in the presence of a p38 inhibitor. Thus, a transient transgenic can be sufficient for the methods of identifying compounds that inhibit HCV, described herein.

In some embodiments, the compositions, cells, and transgenic NS3/4A mice described above are used to determine the pathways in a cell that are influenced or impacted by NS3/4A expression. For example, rather than using SB203580, which targets p38, an inhibitor to any of the other proteins involved in the cascade (e.g., those shown in FIG. 20) can be used. In other words, any compound to a given protein that reverts the NS3/4A phenotype (e.g., TNF-alpha resistance) to the wild-type phenotype (e.g., TNF-alpha susceptibility) will demonstrate that the protein is influenced by the presence of NS3/4A. Thus, the entirety of the pathway(s) that NS3/4A impacts can readily be elucidated by the routine application of the present teachings. EXAMPLE 39 provides a demonstration of this embodiment.

The present invention also relates to approaches to identify other proteins involved in the NS3/4A phenotype. As described in EXAMPLE 39 alternative inhibitors or enhancers (i.e., SOCS1) can be administered. In one embodiment, the various proteins are tested until the precise protein that interacts with NS3/4A is identified. This protein is then used as a target for development of a HCV treatment. Of course, given the present disclosure, HCV treatments based on these proteins can be readily developed. For example, rather than adding SB203580 to the NS3/4A-Tg (along with TNF-alpha), SOCS1 siRNA or microRNA can be administered. If the siRNA results in the death of the transgenic mouse, then SOCS1 will be shown to be involved in the NS3/4A phenotype. This also would mean that SOCS1 would be a target for HCV treatments (e.g., SOCS1 antibodies, competitive binders, etc.).

In some embodiments, a method is contemplated in which one uses a composition that reverses an altered activity level induced by NS3/4A, as shown in FIG. 20. This can be directly, for instance by preventing an interaction between NS3/4A, for example through an antibody. Antibodies that bind to the proteins identified in FIG. 20 as possibly interacting directly with NS3/4A can be made. Alternatively, this could be through altering the activity of another protein either above or below the protein that interacts with NS3/4A. For example, it could be achieved by preventing the activation of a precursor or preventing the over-activation or uneractivation of later steps in the cascade. Guidance and description of which step(s) is provided in FIG. 20 and in the discussion and Examples. FIG. 20 displays the order and interaction between the various proteins. Arrows indicate activation, while flat bars indicate inhibition. Thus, if NS3/4A results in an inhibition of a particular enzyme, then a method or composition that activates or stimulates later steps in that same cascade can be useful for inhibiting HCV. One application of this method in the treatment of HCV is described in the Examples below.

Accordingly, many of the above described transgenic organisms may be used to test the efficacy of potential anti-HCV drugs in vivo. In some embodiments, the transgenic animals used are NS3/4A transgenic mice. In some embodiments, the transgenic animals used are coNS3/4A transgenic mice. In some embodiments, the transgenic animals used are positive or negative PADSI NS3/4A transgenic mice. In some embodiments, the transgenic animals used are variant positive or negative PADSI NS3/4A transgenic mice. In some embodiments, the transgenic animals used are variant positive or negative PADSI coNS3/4A transgenic mice. In some embodiments, any of the transgenic animals described above may be used as models for isolating candidate protease inhibitors. In a preferred embodiment, the transgenic animal displays a visible phenotype indicating that the organism is producing NS3/4A proteins. In some embodiments, the transgenic organism displays an enlarged liver. In some embodiments, the transgenic organism displays a form of steatosis.

Detection of whether or not the candidate protease inhibitor functions as a protease inhibitor can be performed by many different methods. For example, since the transgenic animal described above displays a phenotype that is similar to a human infected with HCV, similar phenotypes may be used to determine if the transgenic animal. Additionally, as the cleaving of the NS3/4A peptide bond is required for the cleaving of several other protein products of the HCV protein, one may detect the activity of the NS3/4A protease by detecting the amount of cleaved NS3/4A peptide in the transgenic organism. Additionally, one may test for other cleaved products as well, such as 4A/4B, 4B/5A, and 5A/5B, for example. In some embodiments, these cleaved products are detected by using antibodies directed to each half of the protein product, as described in the Examples.

As appreciated by one of skill in the art, many other products can also be present in the transgenic organism. In some embodiments, the transgenic organism has other genes in its alleles. In a preferred embodiment, the transgenic organism is only transgenic for the NS3 protease and for the NS4A enhancer. The other proteins to be cleaved may be added before, simultaneously, or after the addition of the candidate protease inhibitor to the transgenic organism. By doing this, one knows precisely how much initial protein material one has and what form it is in. The NS4A/4B, 4B/5A, and 5A/5B can also be added by viral vector. Of course, as the transgenic organism contains the NS3/4A gene, the proteolytic activity of NS3/4A on its own NS3/4A peptide bond requires no additional genes. As appreciated by one of skill in the art, and as described herein, the PADSI constructs need not be fluorescent. For example, Beta-galactosidase can be used as a marker for protease activity.

In some embodiments, multiple transgenic organisms are tested in each set of experiments. This may be done in order for enough sample to be isolated at each stage of the experiment, especially in situations in which organism sacrifice may be required in order to obtain enough sample. In some embodiments, multiple candidate compounds are administered at one time in a pool of candidate compounds. A positive response will result in subfractions of the pool being administered to determine which compounds are responsible for the inhibition of the protease activity.

In some embodiments, a successful protease inhibitor will be one which shows any decrease in the amount of cleaved product examined. In some embodiments, a candidate protease inhibitor will be considered a protease inhibitor if it reduces the amount of cleaved protein product by at least or more than 1%, 2%, 3%, 4-5%, 6-10%, 11-20%, 20-30%, 30-40%, 40-50%, 50-60%, 60-70%, 70-80%, 90-95%, 95-96%, 97%, 98%, 99%, 99-100%. In some embodiments, a candidate protease inhibitor will be considered a protease inhibitor if it displays an ability to decrease the amount of proteolytic activity, and causes little harm to the transgenic organism. In some embodiments, "little harm" is a relative term, thus, a candidate protease inhibitor that causes less harm to an organism than an HCV infection would cause is considered a protease inhibitor. In some embodiments, little harm means that the protease inhibitor causes less or the same amount of harm to a patient as compared to other similar drugs relating to HCV treatments. In some embodiments, the harm caused can be severe, such as resulting in tissue and cell death, but the damage is limited to areas that are infected with the HCV.

The protease inhibitor identified using the methods described herein may be used to treat HCV or prevent HCV from spreading in an organism. By "treat," what is meant is that when the protease inhibitor is administered in an effective dose to a patient, an effect caused by HCV is reduced. In some embodiments, the physical manifestations of HCV are reduced by the application of the protease inhibitor. In some embodiments, the amount of cleaved protein product from HCV proteins is reduced. In some embodiments, the rate of cleaving of the proteins of the HCV is reduced. Treatment does not require the elimination of all symptoms or the prevention of all proteolytic activity. In some embodiments, the protease inhibitor can be used to reduce the symptoms or the amount of HCV present in a host. In another embodiment, the protease inhibitor can be used to help ameliorate the symptoms and problems associated with HCV infection. The next section provides more detail on approaches to screen PADSI transgenic organisms.

Screening with PADSI Transgenic Organisms

The various PADSI constructs discussed above can be used to identify inhibitor of HCV. In some embodiments, a transgenic organism that has the ability to produce a PADSI protein is used to screen candidate inhibitors for their ability to inhibit protease activity. In some embodiments, this is done within an organism that is transgenic for the PADSI construct. However, the organism need not be transgenic for the PADSI construct itself. For example, as shown in the embodiment in FIG. 14C of the positive PADSI construct. In this embodiment, a mouse that is transgenic for the NS3/4A construct can be used as a host and the PADSI construct can be delivered to the host's liver at a desired time and with the appropriate promoter, or directly in protein form.

In some embodiments, the blood of a negative PADSI transgenic organism is examined to determine if a detectable marker, which is released from hepatocytes via NS3 and/or NS3/4A protease activity, is present in nonhepatocytes. The presence of the signal molecule in nonhepatocyte cells can indicate that the NS3/4A complex (or NS3, as appropriate) is still proteolytically active. When a functional inhibitor is administered to the transgenic organism, the inhibitor will reduce the amount of signal molecule (the secreted indicator) present in nonhepatocytes. In some embodiments, the presence of a protease inhibitor will be demonstrated by the fact that there is a greater amount of signal molecule in the hepatocytes than in the venous blood. In another embodiment, the presence of an inhibitor will be demonstrated by the fact that there is a reduction in the amount of signal molecule present in nonhepatocytes. Any significant amount of reduction will be sufficient, for example, reductions to 99, 99-90, 90-70, 70-50, 50-30, 30-10, 10-5, 5-1, or less will be sufficient to demonstrate that there is a protease inhibitor in the transgenic organism.

Methods of detecting the signal peptide are known in the art and will vary based upon the particular peptide and the amount of signal molecule one starts with, among other factors. For example, if the signal molecule is fluorescent, then fluorescent measurements can be made. For example, venous blood, can be taken, or whole body screening can be performed. In the later, where there are sufficient signal molecules present (or, as appropriate, absent), fluorescent readings through the skin can be possible without withdrawing a blood sample from the transgenic organism.

In some embodiments, the mice are not killed in order to determine if the candidate protease inhibitor is effective. In some embodiments, the level of signal molecule, or secreted indicator is determined by non-invasive means. Any suitable method may be used. For example, a CCD may be used to detect the presence of the signal molecule in various tissue, as demonstrated by Wu et al., (Mol. Ther., 4:297-306, (2001)), herein incorporated by reference in its entirety. In some embodiments, the CCD is positioned for detection of the signal molecule anywhere that fluorescence of venous blood is detectable through the surface of the organism. As discussed above, the signal molecule will be present in nonhepatocytes, e.g., the blood, unless an effective protease inhibitor is administered to the mouse, at which point the signal molecule will be relatively limited to the cells that create the PADSI. Thus, in some embodiments, a CCD at the surface of the organism's skin will be able to detect the presence of the signal molecule in nonhepatocytes, which will be indicative of a lack of a protease inhibitor. For example, in the blood of a vein or artery near the surface of the skin. Likewise, the CCD will also be able to detect the absence of the signal molecule at the surface of the organism's skin, thus indicating the presence of a protease inhibitor.

In some embodiments, methods of delivery of protease inhibitors are tested. One may administer a known protease inhibitor to a PADSI model or transgenic via a variety of methods to see if the known protease inhibitor can effectively make its way to the hepatocytes. As the level of signal molecule in the venous blood will decrease (or increase as appropriate) when the inhibitor makes it into the hepatocytes, one can monitor the effectiveness of the delivery method as a function of the absence of signal molecule in the blood.

In some embodiments, delivery compositions for protease inhibitors are tested. In order to test various delivery compositions, one may administer a known protease inhibitor with a variety of different delivery compounds. As the level of signal molecule in the venous blood will decrease when the inhibitor makes it into the hepatocytes, one can monitor the effectiveness of the delivery composition as a function of the absence of signal molecule in the blood. One possible example of a delivery composition would be an antibody targeted to hepatocytes, which may improve the delivery of the protease inhibitor to the hepatocytes.

In another embodiment, the positive PADSI construct is used to screen for protease inhibitors. The procedure can involve the same constructs described above for the positive PADSI constructs, the same NS3/4A transgenic mouse described herein, and the same detection procedures described above. One difference between the method of screening with this PADSI mouse and the above method involving a negative PADSI mouse is that in analyzing the amount of detectable marker present in the venous blood of the mouse, or external to the liver cells, that an increase in the amount of detectable marker in the venous blood will indicate that the candidate protease inhibitor is functioning as a protease inhibitor.

As exemplified below (see particulary EXAMPLE 46) the positive PADSI construct can be used to screen for NS3 protease inhibitors. A PADSI construct, as shown in FIG. 14C, is created. In particular, the construct shown in FIG. 14D is used. The detectable marker is luciferase. A NS3 transgenic mouse is created, as described herein. The amount of detectable marker in the blood system of the transgenic mouse is detected. Then, the positive PADSI construct is delivered, through approaches known in the art, to the transgenic mouse so that there are positive PADSI protein constructs in the liver cells of the NS3 transgenic mouse. Following this, various candidate NS3 protease inhibitors are administered to the transgenic mouse and the presence of the detectable marker in the venous blood is detected through the surface of the organism via a CCD. An increase in the level of detectable marker will indicate that one of the candidate protease inhibitors is actually an effective protease inhibitor. As will be appreciated by one of skill in the art, for the positive PADSI, the NS3/4A cleavage site may contain different amounts of the NS3 protein or the NS4A protein, as long as the NS3 protein is not autocatalytic under normal circumstance. Thus, in one embodiment, an entire NS3 protein is used, although it is catalytically inactive. The section below describes the manufacture of compositions that comprise the HCV nucleic acids, HCV peptides, NS3 protease inhibitors, kinase inhibitors, and compounds identified by the methods described herein.

Therapeutic Compositions and Dietary Supplements

The NS3 protease inhibiting agents identified by the methods described herein can be suitable for incorporation into pharmaceuticals or dietary supplements that treat or prevent HCV replication or infection in subjects or improve the general health and welfare of subjects infected with HCV. The active ingredients described herein can be processed in accordance with conventional methods to produce medicinal agents and dietary supplements for administration to subjects, e.g., mammals including humans. The active ingredients can be incorporated into a pharmaceutical or dietary supplement product with and without modification. Further, the manufacture of pharmaceuticals or dietary supplement that deliver the compounds of this invention by several routes are aspects of the invention. For example, and not by way of limitation, DNA, RNA, and viral vectors having sequence encoding the NS3 protease modulators or kinase inhibitors are used with embodiments. Nucleic acids encoding NS3 protease modulators or kinase inhibitors can be administered alone or in combination with other active ingredients.

The peptides and nucleic acids described herein are also useful as immunogens, which can be administered alone or in conjunction with an adjuvant. Preferred embodiments include compositions that comprise one or more of the nucleic acids and/or peptides described above with or without an adjuvant (e.g., ribavirin, see e.g., U.S. Pat. No. 6,680,059, herein expressly incorporated by reference in its entirety). That is, some of the compositions described herein are prepared with or without an adjuvant and comprise, consist, or consist essentially of a NS3/4A peptide (SEQ. ID. NO.: 2 or SEQ. ID. NO.: 36) or fragments thereof that are any number of consecutive amino acids between at least 30 or more (e.g., 30-50, 50-70, 70-90, 90-150, 150-200, 200-500, or more amino acids in length) (e.g., SEQ. ID. NOs.: 14 and 15) or a nucleic acid encoding one or more of these molecules (e.g., SEQ. ID. NO.: 35 or a fragment thereof that is any number of consecutive nucleotides between at least 30-2112 (e.g., 30-50, 50-100, 100-200, 200-500, 500-1000, 1000-1500, 1500-2079, or 1500-2112 consecutive nucleotides in length). Additional compositions are prepared with or without an adjuvant and comprise, consist, or consist essentially of one or more of the NS3/4A mutant peptides (SEQ. ID. NOs.: 3-13) and fragments thereof that are any number of consecutive amino acids between at least 30-500 (e.g., 30-50, 50-70, 70-90, 90-150, 150-200, 200-500, amino acids in length).

Embodiments of the invention also include methods of making and using the compositions above. Some methods involve the making of nucleic acids encoding NS3/4A, codon-optimized NS3/4A, mutant NS34A, fragments thereof that are any number of consecutive nucleotides between at least 30-100 (e.g., 30-40, 40-50, 50-60, 60-75, 75-90, or 90-2000, or more consecutive nucleotides in length), peptides corresponding to said nucleic acids, constructs comprising said nucleic acids, and cells containing said compositions. Preferred methods, however, concern the making of vaccine compositions or immunogenic preparations that comprise, consist, or consist essentially of the newly discovered NS3/4A fragment, codon-optimized NS3/4A, or an NS3/4A mutant (e.g., a truncated mutant or a mutant lacking a proteolytic cleavage site), or a fragment thereof or a nucleic acid encoding one or more of these molecules, as described above. Preferred fragments for use with the methods described herein include SEQ. ID. NOs.: 12-27 and fragments of SEQ. ID. NO.: 35 that contain at least 30 consecutive nucleotides. The compositions described above can be made by providing an adjuvant (e.g., ribavirin), providing an HCV antigen (e.g., a peptide comprising an HCV antigen such as (SEQ. ID. NOs.: 2-11 or 36) or a fragment thereof such as, SEQ. ID. NOs.: 12-26 or a nucleic acid encoding one or more of said peptides), and mixing said adjuvant and said antigen so as to formulate a composition that can be used to enhance or facilitate an immune response in a subject to said antigen.

The compounds of this invention can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's* Pharmaceutical Sciences, 15th Edition, Easton:Mack Publishing Company, pages 1405-1412 and 1461-1487 (1975) and The National *Formulary* XIV, 14th Edition, Washington, American Pharmaceutical Association (1975). The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular formulation having a compound described herein can vary based on the individual needs of the patient and the treatment or preventative measure sought. Efficacy and toxicity of such compounds can be determined by standard pharmaceutical procedures in cell cultures or experimental animals, e.g., ED50 (the dose therapeutically effective in 50% of the population). For example, NS3 protease inhibiting agents identified by the in vitro or in vivo screens discussed above, can be administered to the transgenic mouse models described above and the effect on the HCV phenotype in the mouse can be determined. The data obtained from these assays is then used in formulating a range of dosage for human use. The dosage of such compounds lies preferably within a range of circulating concentrations that include the ED50 with no toxicity. The dosage varies within this range depending upon type of compound, the dosage form employed, sensitivity of the patient, and the route of administration.

Normal dosage amounts of a composition described herein may vary from approximately 1 to 100,000 micrograms, up to a total dose of about 10 grams, depending upon the route of administration. Desirable dosages include 250 μg, 500 μg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, Ig, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g.

In some embodiments, the dose of the composition preferably produces a tissue or blood concentration or both from approximately 0.1 μM to 500 mM. Desirable doses produce a tissue or blood concentration or both of about 1 to 800 μM. Preferable doses produce a tissue or blood concentration of greater than about 10 μM to about 500 μM. Preferable doses are, for example, the amount of composition required to achieve a tissue or blood concentration or both of 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 145 μM, 150 μM, 160 μM, 170 μM, 180 μM, 190 μM, 200 μM, 220 μM, 240 μM, 250 μM, 260 μM, 280 μM, 300 μM, 320 μM, 340 μM, 360 μM, 380 μM, 400 μM, 420 μM, 440 μM, 460 μM, 480 μM, and 500 μM. A constant infusion of a composition described herein can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the fertility defect, age of the patient, age, and weight of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the pharmaceuticals and dietary supplements of the invention include, but are not limited to, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions described herein that are suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al.

Compositions described herein that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions described herein that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds of the invention.

Compositions described herein that are suitable for gastrointestinal administration include, but are not limited to, pharmaceutically acceptable powders, pills or liquids for ingestion and suppositories for rectal administration. Due to the ease of use, gastrointestinal administration, particularly oral, is a preferred embodiment.

In some embodiments, the compositions described herein are administered with an adjuvant. Such adjuvants include, but are not limited to, ribavirin, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are also potentially useful adjuvants.

In some embodiments, a compound with an increased ability to induce an immune response is contemplated. For example, by providing an adjuvant (e.g., ribavirin), providing an HCV antigen (e.g., a peptide comprising an HCV antigen such as a NS3/4A protein (e.g., SEQ. ID. NOs.: 2-11 or 36) or a fragment thereof such as, SEQ. ID. NOs.: 12-26 or a nucleic acid encoding one or more of said peptides), and mixing said adjuvant and said antigen so as to formulate a composition that can be used to enhance or facilitate an immune response in a subject to said antigen.

In some embodiments, a method of treatment, using the NS3/4A constructs described herein and an adjuvant is contemplated. For example, the expression construct for NS3/4A is introduced into the subject in a mixture of adjuvant (e.g., ribavirin) or in conjunction with an adjuvant (e.g., ribavirin). For example, the adjuvant (e.g., ribavirin) is administered shortly after the expression construct at the same site. Alternatively, RNA encoding the HCV polypeptide antigen of interest is provided to the subject in a mixture with ribavirin or in conjunction with an adjuvant (e.g., ribavirin).

One particularly useful adjuvant has proven to be Ribavirin. Nucleoside analogs have been widely used in anti-viral therapies due to their capacity to reduce viral replication. (Hosoya et al., *J. Inf. Dis.*, 168:641-646 (1993)). Ribavirin (1-β-D-ribofuranosyl-1,2,4-triazole-3-carboxamide) is a synthetic guanosine analog that has been used to inhibit RNA and DNA virus replication. (Huffman et al., *Antimicrob. Agents. Chemother.*, 3:235 (1973); Sidwell et al., *Science*, 177:705 (1972)). Ribavirin has been shown to be a competitive inhibitor of inositol mono-phosphate (IMP) dehydrogenase (IMPDH), which converts IMP to IMX (which is then converted to GMP). De Clercq, *Anti viral Agents: characteristic activity spectrum depending on the molecular target with which they interact*, Academic press, Inc., New York N.Y., pp. 1-55 (1993). Intracellular pools of GTP become depleted as a result of long term ribavirin treatment.

In addition to antiviral activity, investigators have observed that some guanosine analogs have an effect on the immune system. (U.S. Pat. Nos. 6,063,772 and 4,950,647). Ribavirin has been shown to inhibit functional humoral immune responses (Peavy et al., *J. Immunol.*, 126:861-864 (1981); Powers et al., *Antimicrob. Agents. Chemother.*, 22:108-114 (1982)) and IgE-mediated modulation of mast cell secretion. (Marquardt et al., *J. Pharmacol. Exp. Therapeutics*, 240:145-149 (1987)). Some investigators report that a daily oral therapy of ribavirin has an immune modulating effect on humans and mice. (Hultgren et al., *J. Gen. Virol.*, 79:2381-2391 (1998) and Cramp et al., *Gastron. Enterol.*, 118:346-355 (2000)). As disclosed in U.S. Pat. No. 6,680,059, to Sallberg et al., issued on Jan. 20, 2004, ribavirin has been shown to have particularly beneficial effects for HCV peptides, herein incorporated by reference in its entirety. Additional information can also be found in U.S. application Ser. No. 09/705,547 having a filing date of Nov. 3, 2000; U.S. Application No.: 20040092730, published May 13, 2004, U.S. Application No.: 20040086529, published May 6, 2004, U.S. Application No.: 20030206919, published Nov. 6, 2003, 20020155124, published Oct. 24, 2002, and U.S. Application No.: 20020136740, published Sep. 26, 2002 all of which are also expressly incorporated by reference in their entireties.

Since many adjuvants, including ribavirin, have been on the market for several years, many dosage forms and routes of administration are known. All known dosage forms and routes of administration can be provided within the context of the embodiments described herein. Preferably, an amount of adjuvant that is effective to enhance an immune response to an antigen in an animal can be considered to be an any amount that is sufficient to achieve a blood serum level of antigen approximately 0.25-12.5 µg/ml in the animal, preferably, about 2.5 µg/ml. In some embodiments, the amount of adjuvant is determined according to the body weight of the animal to be given the vaccine. Accordingly, the amount of adjuvant in a particular formulation can be any amount between about 0.1-6.0 mg/kg body weight. That is, some embodiments have an amount of adjuvant that corresponds to any amount between 0.1-1.0 mg/kg, 1.1-2.0 mg/kg, 2.1-3.0 mg/kg, 3.1-4.0 mg/kg, 4.1-5.0 mg/kg, 5.1, and 6.0 mg/kg body weight of an animal. More conventionally, some of the compositions described herein contain any amount between about 0.25 mg-2000 mg of adjuvant. That is, some embodiments have approximately 250 µg, 500 µg, 1 mg, 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, and 2 g of adjuvant.

In some approaches described herein, the exact amount of adjuvant and/or HCV antigen is chosen by the individual physician in view of the patient to be treated. Further, the amounts of adjuvant can be added in combination to or separately from the same or equivalent amount of antigen and these amounts can be adjusted during a particular vaccination protocol so as to provide sufficient levels in light of patient-specific or antigen-specific considerations. In this vein, patient-specific and antigen-specific factors that can be taken into account include, but are not limited to, the severity of the disease state of the patient, age, and weight of the patient, diet, time and frequency of administration, drug combination(s), reaction sensitivities, and tolerance/response to therapy.

Accordingly, in some embodiments, a pharmaceutical composition for treating a patient infected by a hepatitis C virus is provided, wherein the composition comprises a compound that intereferes with the effects related to expression of NS3 in a genetically modified non-human mammal described above. In some embodiments, an anti-HCV pharmaceutical formulated for human administration comprising a p38 MAP kinase inhibitor. In one embodiment, said p38 inhibitor is SB203580. Some embodiments relate to a method of making the anti-HCV pharmaceutical comprising providing a p38 MAP kinase inhibitor and formulating said p38 MAP kinase inhibitor for human administration. In one embodiment said p38 MAP kinase inhibitor is SB203580. Some embodiments relate to a method of using the anti-HCV pharmaceutical to inhibit HCV replication comprising identifying a subject in need of a compound that inhibits HCV; and providing said subject a p38 MAP kinase inhibitor. In one embodiment said p38 inhibitor is SB203580. In another embodiment the inhibition of HCV in said subject is measured.

EXAMPLES

Example 1

The NS3/4A sequence was amplified from the serum of an HCV-infected patient (HCV genotype 1a) using the Polymerase Chain Reaction (PCR). Total RNA was extracted from serum, and cDNA synthesis and PCR were performed according to standard protocols (Chen M et al., *J. Med. Virol.* 43:223-226 (1995)). The cDNA synthesis was initiated using the antisense primer "NS4KR" (5'-CCG TCT AGA TCA GCA CTC TTC CAT TTC ATC-3' (SEQ. ID. NO.: 28)). From this cDNA, a 2079 base pair DNA fragment of HCV, corresponding to amino acids 1007 to 1711, which encompasses the NS3 and NS4A genes, was amplified. A high fidelity polymerase (Expand High Fidelity PCR, Boehringer-Mannheim, Mannheim, Germany) was used with the "NS3KF" primer (5'-CCT GAA TTC ATG GCG CCT ATC ACG GCC TAT-3' (SEQ. ID. NO.: 29) and the NS4KR primer. The NS3KF primer contained a EcoRI restriction enzyme cleavage site and a start codon and the primer NS4KR contained a XbaI restriction enzyme cleavage site and a stop codon.

The amplified fragment was then sequenced (SEQ. ID. NO.: 1). Sequence comparison analysis revealed that the gene fragment was amplified from a viral strain of genotype 1a. A computerized BLAST search against the Genbank database using the NCBI website revealed that the closest HCV homologue was 93% identical in nucleotide sequence.

The amplified DNA fragment was then digested with EcoRI and XbaI, and was inserted into a pcDNA3.1/His plasmid (Invitrogen) digested with the same enzymes. The NS3/4A-pcDNA3.1 plasmid was then digested with EcoRI and Xba I and the insert was purified using the QiaQuick kit (Qiagen, Hamburg, Germany) and was ligated to a EcoRI/Xba I digested pVAX vector (Invitrogen) so as to generate the NS3/4A-pVAX plasmid.

The rNS3 truncated mutant was obtained by deleting NS4A sequence from the NS3/4A DNA. Accordingly, the NS3 gene sequence of NS3/4A-pVAX was PCR amplified using the primers NS3KF and 3'NotI (5'-CCA CGC GGC CGC GAC GAC CTA CAG-3' (SEQ. ID. NO.: 30)) containing EcoRI and Not I restriction sites, respectively. The NS3 fragment (1850 bp) was then ligated to a EcoRI and Not I digested pVAX plasmid to generate the NS3-pVAX vector. Plasmids were grown in TOP10 *E. coli* cells (Invitrogen). The plasmids were sequenced and were verified by restriction cleavage and the results were as to be expected based on the original sequence.

Table 1 describes the sequence of the proteolytic cleavage site of NS3/4A, referred to as the breakpoint between NS3 and NS4A. This wild-type breakpoint sequence was mutated in many different ways so as to generate several different NS3/4A breakpoint mutants. Table 1 also identifies these mutant breakpoint sequences. The fragments listed in Table 1 are preferred immunogens that can be incorporated with or without an adjuvant (e.g., ribavirin) into a composition for administration to an animal so as to induce an immune response in said animal to HCV.

To change the proteolytic cleavage site between NS3 and NS4A, the NS3/4A-pVAX plasmid was mutagenized using the QUICKCHANGE™ mutagenesis kit (Stratagene), following the manufacturer's recommendations. To generate the "TPT" mutation, for example, the plasmid was amplified using the primers 5'-CTGGAGGTCGTCACGCCTAC-CTGGGTGCTCGTT-3' (SEQ. ID. NO.: 31) and 5'-AC-CGAGCACCCAGGTAGGCGTGACGACCTCCAG-3' (SEQ. ID. NO.: 32) resulting in NS3/4A-TPT-pVAX. To generate the "RGT" mutation, for example, the plasmid was amplified using the primers 5'-CTGGAGGTCGTCCGCGG-TACCTGGGTGCTCGTT-3' (SEQ. ID. NO.: 33) and 5'-AC-CGAGCACCCAGGTACC-GCGGACGACCTCCAG-3' (SEQ. ID. NO.: 34) resulting in NS3/4A-RGT-pVAX. All mutagenized constructs were sequenced to verify that the mutations had been correctly made. Plasmids were grown in competent TOP10 *E. coli*. The following section describes the codon optimization of the NS3/4A gene.

Codon Optimization:

The sequence of the previously isolated and sequenced unique NS3/4A gene (SEQ. ID. NO.: 1) was analyzed for codon usage with respect to the most commonly used codons in human cells. A total of 435 nucleotides were replaced to optimize codon usage for human cells. The sequence was sent to Retrogen Inc. (6645 Nancy Ridge Drive, San Diego, Calif. 92121) and they were provided with instructions to generate a full-length synthetic codon optimized NS3/4A gene. The codon optimized NS3/4A gene had a sequence homology of 79% within the region between nucleotide positions 3417-5475 of the HCV-1 reference strain. A total of 433 nucleotides differed. On an amino acid level, the homology with the HCV-1 strain was 98% and a total of 15 amino acids differed.

The full length codon optimized 2.1 kb DNA fragment of the HCV gene encoding amino acids 1007 to 1711, which encompass NS3 and NS4A, was amplified by the polymerase chain reaction (PCR) using high fidelity polymerase (Expand High Fidelity PCR, Boehringer-Mannheim, Mannheim, Germany). The amplicon was then inserted into a Bam HI and Xba I digested pVAX vector (Invitrogen, San Diego), which generated the MSLF1-pVAX plasmid. All expression constructs were sequenced. Plasmids were grown in competent TOP10 *E. Coli*. The plasmid DNA used for in vivo injection was purified using Qiagen DNA purification columns, according to the manufacturers instructions (Qiagen GmbH, Hilden, FRG). The concentration of the resulting plasmid DNA was determined spectrophotometrically (Dynaquant, Pharmacia Biotech, Uppsala, Sweden) and the purified DNA was dissolved in sterile phosphate buffer saline (PBS) at concentrations of 1 mg/ml.

TABLE 1

| Plasmid | Deduced amino acid sequence | |
|---|---|---|
| *NS3/4A-pVAX | TKYMTCMSADLEVV<u>TST</u>WVLVGGVL | (SEQ. ID. NO.: 14) |
| NS3/4A-TGT-pVAX | TKYMTCMSADLEVV<u>TGT</u>WVLVGGVL | (SEQ. ID. NO.: 16) |
| NS3/4A-RGT-pVAX | TKYMTCMSADLEVV<u>RGT</u>WVLVGGVL | (SEQ. ID. NO.: 17) |
| NS3/4A-TPT-pVAX | TKYMTCMSADLEVV<u>TPT</u>WVLVGGVL | (SEQ. ID. NO.: 18) |
| NS3/4A-RPT-pVAX | TKYMTCMSADLEVV<u>RPT</u>WVLVGGVL | (SEQ. ID. NO.: 19) |
| NS3/4A-RPA-pVAX | TKYMTCMSADLEVV<u>RPA</u>WVLVGGVL | (SEQ. ID. NO.: 20) |
| NS3/4A-CST-pVAX | TKYMTCMSADLEVV<u>CST</u>WVLVGGVL | (SEQ. ID. NO.: 21) |
| NS3/4A-CCST-pVAX | TKYMTGMSADLEVC<u>CST</u>WVLVGGVL | (SEQ. ID. NO.: 22) |
| NS3/4A-SSST-pVAX | TKYMTCMSADLEVS<u>SST</u>WVLVGGVL | (SEQ. ID. NO.: 23) |
| NS3/4A-SSSSCST-pVAX | TKYMTCMSADSSSS<u>CST</u>WVLVGGVL | (SEQ. ID. NO.: 24) |
| NS3A/4A-VVVVTST-pVAX | TKYMTCMSADVVVV<u>TST</u>WVLVGGVL | (SEQ. ID. NO.: 25) |
| NS5-pVAX | ASEDVVC<u>CSM</u>SYTWTG | (SEQ. ID. NO.: 27) |
| NS5A/B-pVAX | SSEDVVC<u>CSM</u>WVLVGGVL | (SEQ. ID. NO.: 26) |

*The wild type sequence for the NS3/4A fragment is NS3/4A-pVAX.
The NS3/4A breakpoint is identified by underline, wherein the P1 position corresponds to the first Thr (T) and the P1' position corresponds to the next following amino acid the NS3/4A-pVAX sequence.
In the wild type NS3/4A sequence the NS3 protease cleaves between the P1 and P1' positions.

Characterization of the Codon Optimized NS3/4a Gene and SFV Expression Vectors

The expression of NS3 and NS3/4A proteins from wtNS3/4A and coNS3/4A plasmids, were analyzed in an in vitro transcription and translation assay. The following example describes some of the experiments in greater detail.

Example 2

This example showed that the NS3/4A proteins could be correctly translated from the wtNS3/4A and coNS3/4A plasmids. To ensure that the wtNS3/4A and coNS3/4A genes were intact and could be translated, an in vitro transcription assay is using the prokaryotic T7 coupled reticulocyte lysate system (TNT; Promega, Madison, Wis.) was performed as previously described (Lazdina U et al. *J Gen Virol* 2001; 82:1299-1308 (2001); Frelin L et al., *Gene Ther.*, 10:686-699 (2003)). To compare the translation efficiency from the two plasmids the amount input DNA was diluted in serial dilutions (6 ng to 1 ng) prior to addition to the TNT assay. The results showed that the coNS3/4A plasmid gave detectable NS3 and NS3/4A protein at a higher plasmid dilution than the wtNS3/4A plasmid (See FIGS. 1A and 1B).

To compare the expression levels by another approach, HepG2 cells were transiently transfected with the wtNS3/4A and the coNS3/4A plasmids. The HepG2 cells were transiently transfected by standard protocols. In brief, HepG2 cells were plated into 25 cm$^2$ wells (0.5×10$^6$) in DMEM medium the day before transfection. Two μg of each plasmid DNA construct (wtNS3/4A and coNS3/4A) was transfected into HepG2 cells using Fugene 6 Transfection Reagent (Roche). After transfection, the HepG2 cells were incubated for 24-48 hrs.

Cell lysates were analysed by immunoprecipitation followed by SDS-PAGE. In brief, transient transfected HepG2 cells were lysed in RIPA buffer (0.15 M NaCl, 50 mM Tris, 1% Triton-X 100, 1% Na-deoxycholate and 1% SDS). The cell lysates were immunoprecipitated with protein A sepharose and anti-NS3 polyclonal antibody overnight at 4° C. The washed pellets were re-suspended in SDS sample buffer, heated at 100° C. for 5 minutes prior to SDS-PAGE analysis on 4-12% Bis-Tris gel (Invitrogen) and electrotransferred onto Nitrocellulose membranes. These experiments revealed that the coNS3/4A plasmid generated 11-fold higher expression levels of the NS3 protein when compared to the wtNS3/4A plasmid, as determined by densitometry and a standard curve of recombinant NS3.

Since the wtNS3/4A and the coNS3/4A plasmids are identical in size it is unlikely that there are any major differences in transfections efficiencies between the plasmids. The enhanced expression of the wtNS3 gene seen when including NS4A in the SFV replicon system has been reported previously (Frelin et al., 2003). Staining of coNS3/4A plasmid transfected, and SFV infected, BHK cells revealed a similar perinuclear and cytoplasmic distribution of the NS3 as previously observed, confirming an unchanged subcellular localization. It was discovered that the construct "NS3/4A-pVAX" was significantly more immunogenic in vivo than the construct "NS3-pVAX". Surprisingly, it was also discovered that the codon-optimized NS3/4A containing construct ("MSLF1-pVAX") was more immunogenic in vivo than NS3/4A pVAX. The example below describes these experiments.

Example 3

To determine whether a humoral immune response was elicited by the NS3-pVAX and NS3/4A-pVAX vectors, the expression constructs described in Example 1 were purified using the Qiagen DNA purification system, according to the manufacturer's instructions and the purified DNA vectors were used to immunize groups of four to ten Balb/c mice. The plasmids were injected directly into regenerating tibialis anterior (TA) muscles as previously described (Davis et al., *Human Gene Therapy* 4(6):733 (1993)). In brief, mice were injected intramuscularly with 50 μl/TA of 0.01 mM cardiotoxin (Latoxan, Rosans, France) in 0.9% sterile NaCl. Five days later, each TA muscle was injected with 50 μl PBS containing either rNS3 or DNA.

Inbred mouse strains C57/BL6 (H-2b), Balb/C(H-2d), and CBA (H-2k) were obtained from the breeding facility at Möllegard Denmark, Charles River Uppsala, Sweden, or B&K Sollentuna Sweden. All mice were female and were used at 4-8 weeks of age. For monitoring of humoral responses, all mice received a booster injection of 50 μl/TA of plasmid DNA every fourth week. In addition, some mice were given recombinant NS3 (rNS3) protein, which was purified, as described herein. The mice receiving rNS3 were immunized no more than twice. All mice were bled twice a month.

Enzyme immunosorbent assays (EIAs) were used to detect the presence of murine NS3-specific antibodies. These assays were performed essentially as described (Chen et al., *Hepatology* 28(1): 219 (1998), herein expressly incorporated by reference in its entirety). Briefly, rNS3 was passively adsorbed overnight at 4° C. to 96-well microtiter plates (Nunc, Copenhagen, Denmark) at 1 μg/ml in 50 mM sodium carbonate buffer (pH 9.6). The plates were then blocked by incubation with dilution buffer containing PBS, 2% goat serum, and 1% bovine serum albumin for one hour at 37° C. Serial dilutions of mouse sera starting at 1:60 were then incubated on the plates for one hour. Bound murine serum antibodies were detected by an alkaline phosphatase conjugated goat anti-mouse IgG (Sigma Cell Products, Saint Louis, Mo.) followed by addition of the substrate pNPP (1 tablet/5 ml of 1M Diethanol amine buffer with 0.5 mM MgCl$_2$). The reaction was stopped by addition of 1M NaOH and absorbency was read at 405 nm.

After four weeks, four out of five mice immunized with NS3/4A-pVAX had developed NS3 antibodies, whereas one out of five immunized with NS3-pVAX had developed antibodies (FIG. 1). After six weeks, four out of five mice immunized with NS3/4A-pVAX had developed high levels (>104) of NS3 antibodies (mean levels 10800±4830) and one had a titer of 2160. Although all mice immunized with NS3-pVAX developed NS3 antibodies, none of them developed levels as high as that produced by the NS3/4A-pVAX construct (mean levels 1800±805). The antibody levels elicited by the NS3/4A fusion construct were significantly higher than those induced by NS3-pVAX at six weeks (mean ranks 7.6 v.s 3.4, p<0.05, Mann-Whitney rank sum test, and p<0.01, Students t-test). Thus, immunization with either NS3-pVAX or NS3/4A-pVAX resulted in the production of NS3-specific antibodies, but the NS3/4A containing construct was a more potent immunogen. The following example describes a similar experiment that compared the immunogenicity of NS3/4A-pVAX and MSLF1-pVAX.

Example 4

A similar experiment was conducted to compare the immunogenicity of the NS3/4A-pVAX and MSLF1-pVAX constructs. To better resemble a future vaccination schedule in humans, however, the plasmids were delivered to groups of ten mice using a gene gun. In brief, plasmid DNA was linked to gold particles according to protocols supplied by the manufacturer (Bio-Rad Laboratories, Hercules, Calif.). Prior to immunization, the injection area was shaved and the immunization was performed according to the manufacturer's protocol. Each injection dose contained 4 μg of plasmid DNA. Immunizations were performed on weeks 0, 4, and 8.

The MSLF1 gene was found to be more immunogenic than the native NS3/4A gene since NS3-specific antibodies were significantly higher in mice immunized with the MSLF1-pVAX construct at two weeks after the second and third immunization (TABLE 2). These results confirmed that MSLF1-pVAX was a more potent B cell immunogen than NS3/4A-pVAX. In the next example, the intrinsic immunogenicity of the NS3 genes was examined.

TABLE 2

| Immunogen | Week | No. of injections | Mean NS3 titre | SD | Mann-Whitney |
|---|---|---|---|---|---|
| NS3/4A | 2 | 1 | 0 | 0 | NS |
| MSLF1 | 2 | 1 | 0 | 0 | |
| NS3/4A | 6 | 2 | 0 | 0 | $p < 0.0002$ |
| MSLF1 | 6 | 2 | 2484 | 3800 | |
| NS3/4A | 10 | 3 | 60 | 0 | $p < 0.0001$ |
| MSLF1 | 10 | 3 | 4140 | 4682 | |

Example 5

To test the intrinsic immunogenicity of the different NS3 genes groups of BALB/c ($H-2^d$) mice were immunized with the wtNS3/4A, coNS3/4A DNAs, or wtNS3/4A-SFV vectors. Doses of 4 μg DNA were administered using the gene gun and doses of $10^7$ SFV particles were injected subcutaneously (s.c.). The mice were boosted after four weeks. The mice immunized with the wtNS3/4A-SFV developed antibodies already after the first injection indicating a potent immunogenicity (see FIGS. 2A and 2B). At two weeks after the second immunization most mice immunized with the coNS3/4A or wtNS3/4A-SFV vectors had developed mean antibody levels over $10^3$. (See FIGS. 2A and 2B). In contrast, none of the mice immunized with the wtNS3/4A plasmid had developed detectable NS3-specific antibodies at six weeks. Thus, both codon optimization and mRNA amplification by SFV resulted in an increased B cell immunogenicity of the NS3/4A gene.

Figure 2A:
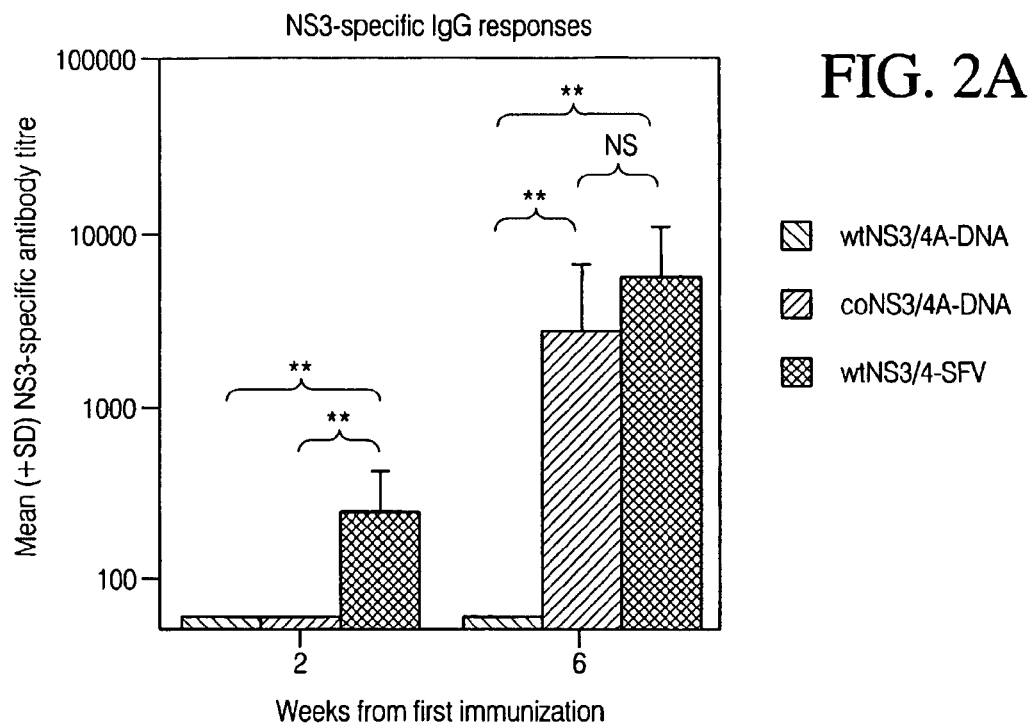
FIG. 2A is a bar graph demonstrating NS3-specific responses.
Figure 2B:
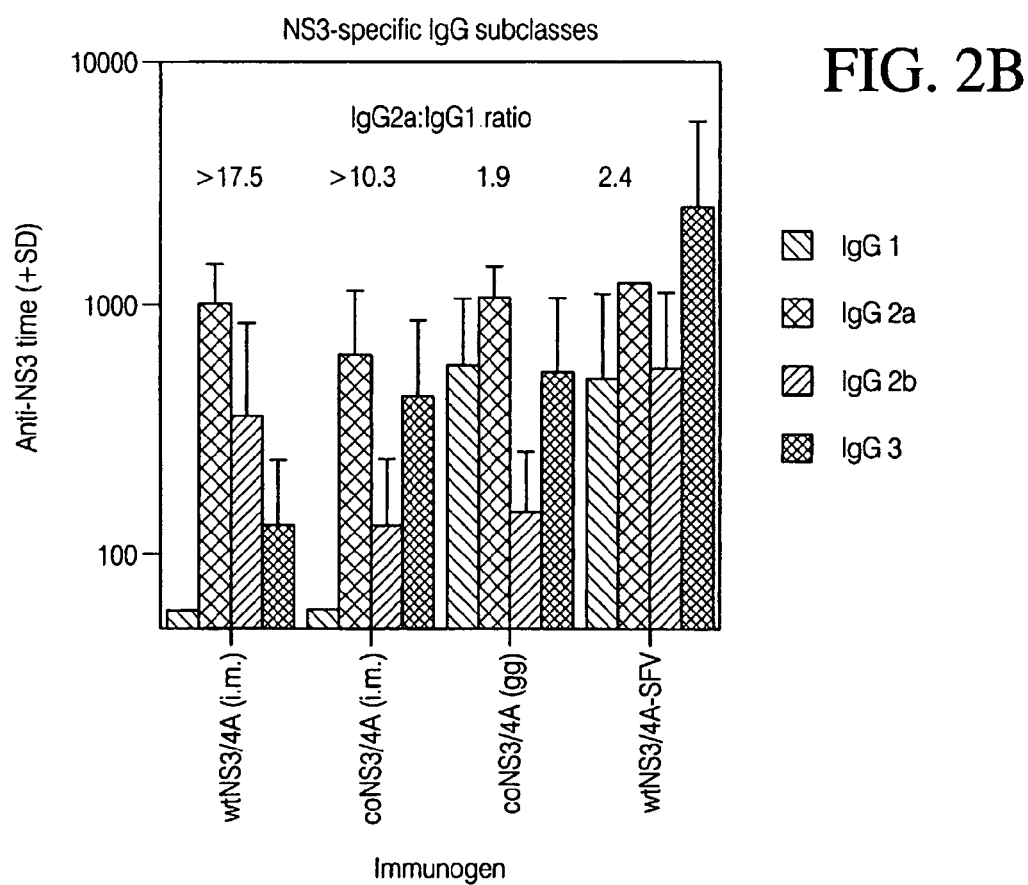
FIG. 2B is a bar graph demonstrating NS3-specific IgG subclasses.

To indirectly compare the T helper 1 (Th1) and Th2-skewing of the T cell response primed by wtNS3/4A, coNS3/4A, and wtNS3/4A-SFV immunizations the levels of NS3-specific IgG1 (Th2) and IgG2a (Th1) antibodies were analyzed (see FIGS. 2A and 2B). The IgG2a/IgG1-ratio in mice immunized with rNS3 with or without adjuvant was always <1 regardless of the murine haplotype (Sallberg M et al., *J Gen Virol.*, 77:2721-2728 (1996)), signaling a Th2-dominated response Schirmbeck R., et al., *Intervirology*, 44:115-123 (2001). In contrast, mice immunized i.m. with the wtNS3, wtNS3/4A DNA, or coNS3/4A plasmids had Th1-skewed Th-cell responses evidenced by IgG2a/IgG1 ratios of >1. Thus, codon optimization did not change the IgG subclass distribution. When genetically immunizing BALB/c mice with NS3/4A using the gene gun the subclass ratio indicated a mixed Th1/Th2 response.

This result is fully consistent with previous reports indicated a less Th1-like response primed by gene gun immunization (Schirmbeck et al., *Intervirology*, 44:115-123 (2001)). It should be noted that the codon optimized plasmid did not display increased in vitro stimulatory capacity of B cells compared to the native plasmid, indicating that no major immune stimulatory motifs had been lost or introduced. The example below describes experiments that were performed to determine if mutant NS3/4A peptides, which lack a proteolytic cleavage site, could elicit an immune response to NS3.

Example 6

To test if the enhanced immunogenicity of NS3/4A could be solely attributed to the presence of NS4A, or if the NS3/4A fusion protein in addition had to be cleaved at the NS3/4A junction, another set of experiments were performed. In a first experiment, the immunogenicity of the NS3-pVAX, NS3/4A-pVAX, and mutant NS3/4A constructs were compared in Balb/c mice. Mice were immunized on week 0 as described above, and, after two weeks, all mice were bled and the presence of antibodies to NS3 at a serum dilution of 1:60 was determined (TABLE 3). Mice were bled again on week 4. As shown in TABLE 3, all the constructs induced an immune response; the mutant constructs, for example, the NS3/4A-TGT-pVAX vector was comparable to the NS3-pVAX vector (4/10 vs. 0/10; NS, Fisher's exact test). The NS3/4A-pVAX vector, however, was more potent than the mutant constructs.

TABLE 3

| | No. of antibody responders to the respective immunogen after one 100 μg i.m immunization | | |
|---|---|---|---|
| Weeks from 1st immunization | NS3-pVAX | wild-type NS3/4A-pVAX | mutant example NS3/4A-TGT-pVAX |
| 2 | 0/10 | 17/20 | 4/10 |
| 4 | 0/10 (<60) | 20/20 (2415 ± 3715) 55% > $10^3$ 10% > $10^4$ | 10/10 (390 ± 639) 50% > $10^2$ 10% > $10^3$ |

During the chronic phase of infection, HCV replicates in hepatocytes, and spreads within the liver. A major factor in combating chronic and persistent viral infections is the cell-mediated immune defense system. CD4+ and CD8+ lymphocytes infiltrate the liver during the chronic phase of HCV infection, but they are incapable of clearing the virus or preventing liver damage. In addition, persistent HCV infection is associated with the onset of hepatocellular carcinoma (HCC). Examples 7 and 8 describe experiments that were performed to determine whether the NS3, NS3/4A, and coNS3/4A constructs were capable of eliciting a T-cell mediated immune response against NS3.

Example 7

Figure 3:
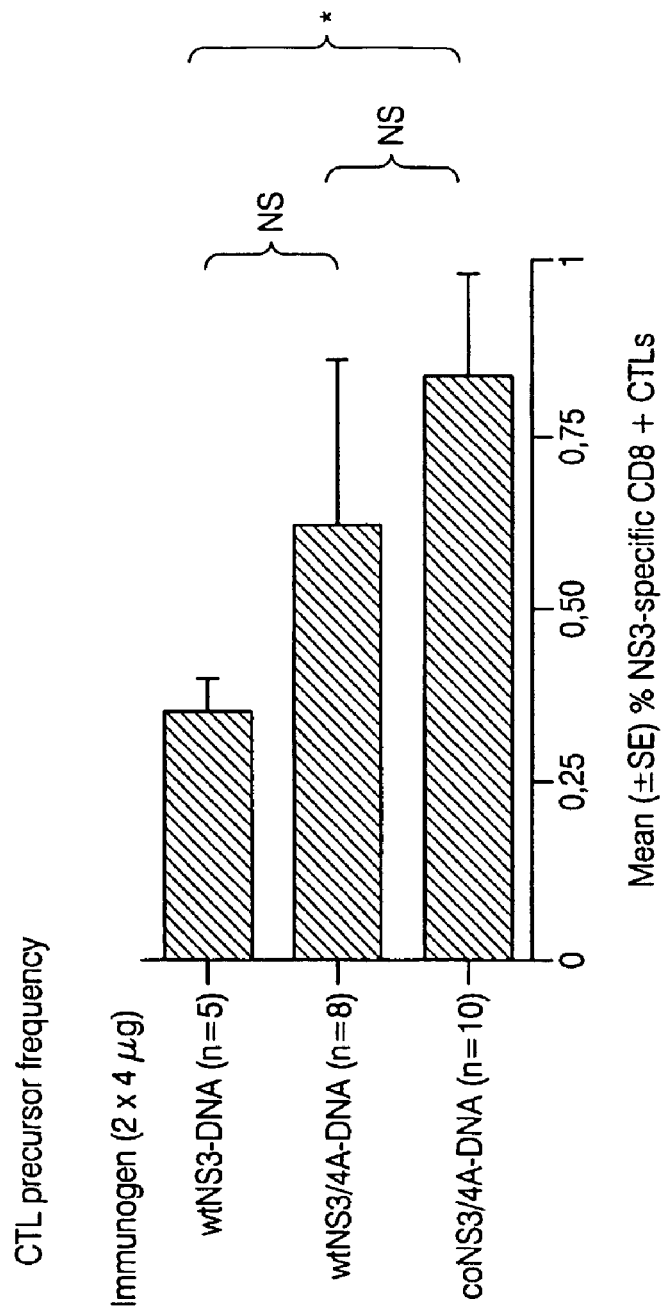
FIG. 3 is a bar graph demonstrating CTL precursor frequency for wtNS3, wtNS3/4A and coNS3/4A.

This example demonstrates the effect of codon optimization and mRNA amplification on priming NS3-specific cytoxic T lymphocytes (CTLs). First the frequency of NS3-specific CTLs that could be primed by gene gun immunization using the wtNS3, wtNS3/4A and coNS3/4A expressing plasmids was estimated. The coNS3/4A plasmid primed higher precursor frequencies of NS3-specific CTL as compared to the wtNS3 gene enforcing the importance of NS4A (see FIG. 3). No statistical difference in CTL precursor frequencies was noted between the wtNS3/4A and coNS3/4A expressing plasmids when analyzed directly ex vivo (see FIG. 3). A single immunization with the coNS3/4A plasmid or wtNS3/4A-SFV primed around 1% of peptide-specific CTLs.

The specificity of the detection was confirmed by a five-day restimulation in vitro with the NS3-peptide by which very high precursor frequencies were observed after immunization with the coNS3/4A gene. (See FIG. 3).

Figure 4A:
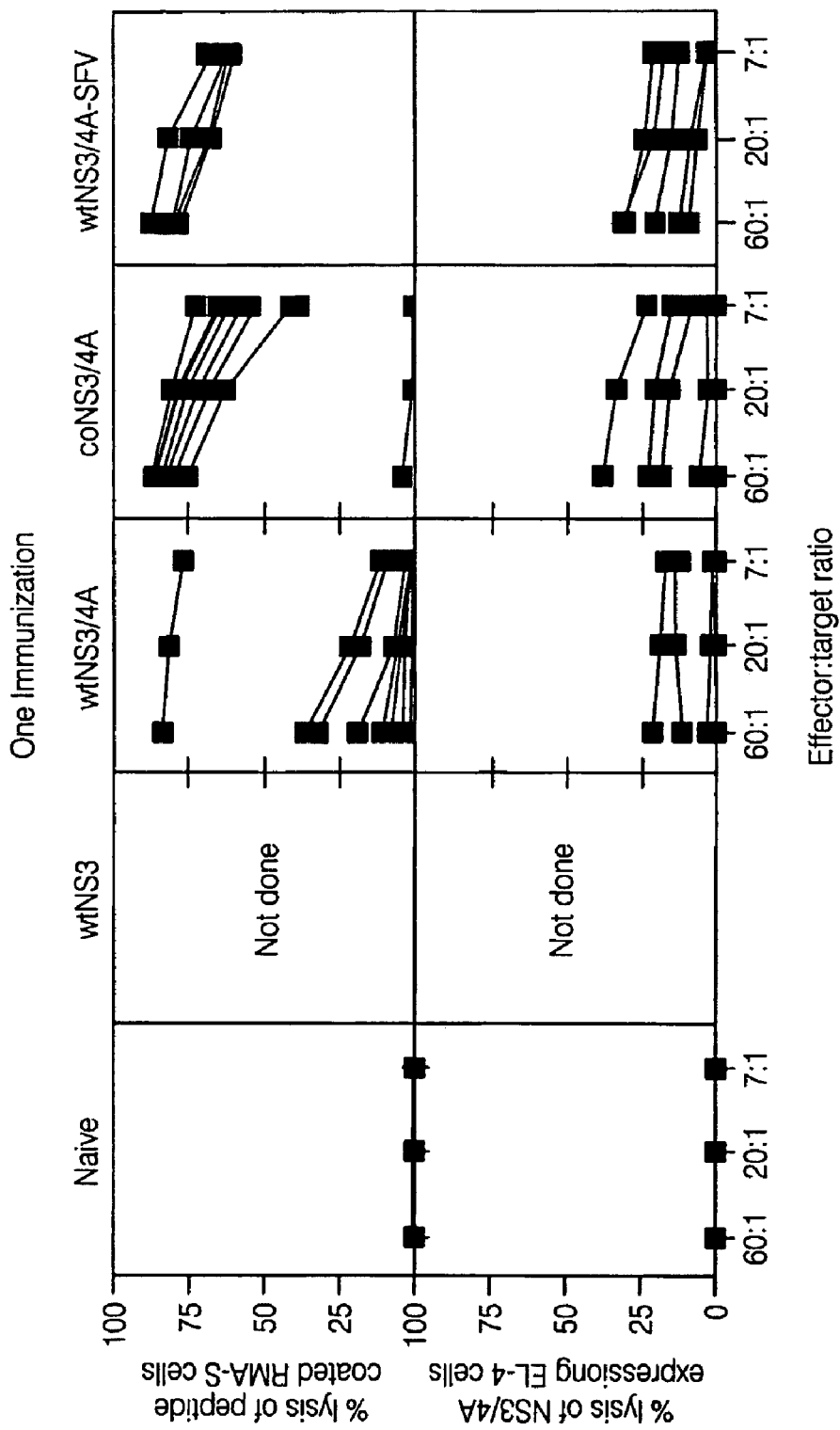
FIG. 4A is a graph demonstrating the priming, following a single immunization, of in vitro detectable CTLs in H-2b mice by gene gun immunization of the various constructs.
Figure 4B:
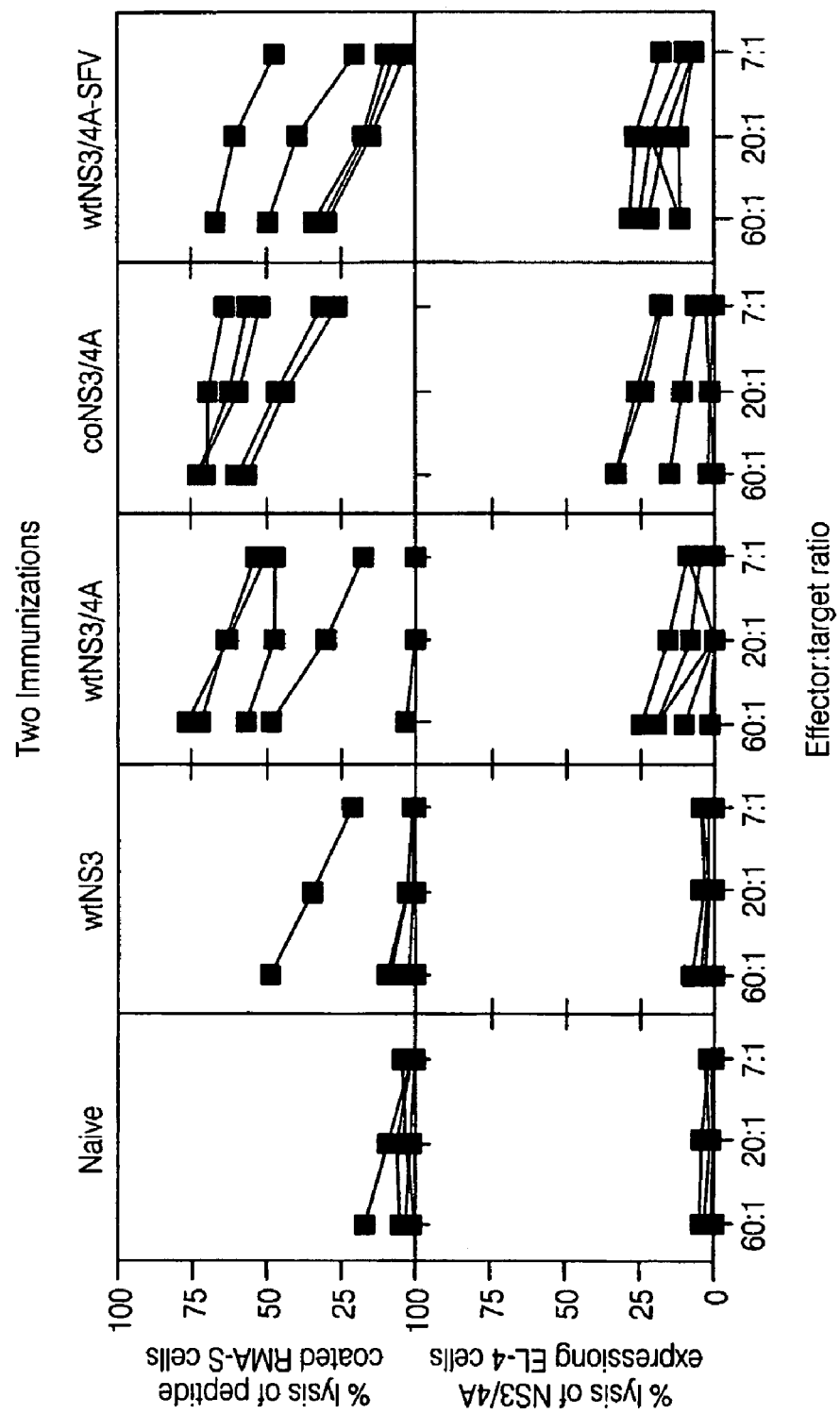
FIG. 4B is a graph demonstrating the priming, following two immunizations, of in vitro detectable CTLs in H-2b mice by gene gun immunization of the various constructs.

To directly compare the in vitro lytic activity of the NS3-specific CTLs primed by different vectors, a standard $^{51}$Cr-release assay was performed after one or two immunizations. The lytic activity of the in vivo primed CTLs were assayed on both NS3-peptide loaded H-2 $D^b$ expressing RMA-S cells and EL-4 cells stably expressing NS3/4A. After one dose, the coNS3/4A plasmid and the wtNS3/4A-SFV vector was clearly more efficient than the wtNS3/4A plasmid in priming CTLs that lysed NS3-peptide coated target cells. (See FIGS. 4A & 4B). Thus, also the CTL priming event is enhanced by codon optimization or mRNA amplification of the NS3/4A gene. The difference was less clear when using the NS3/4A-expressing EL-4 cells presumably since this assay is less sensitive. After two immunizations all NS3/4A vectors seemed to prime NS3-specific CTLs with a similar efficiency. (See FIG. 4B). However, the NS3/4A-containing vectors were clearly more efficient in priming NS3-specific CTLs as compared to the plasmid containing only the wtNS3 gene. In conclusion, codon optimization or mRNA amplification of the NS3/4A gene seems to allow for a more rapid priming of NS3-specific CTLs.

Example 8

To study whether the constructs described above were capable of eliciting a cell-mediated response against NS3, an in vivo tumor growth assay was performed. To this end, an SP2/0 tumor cell line (SP2/0-Ag14 myeloma cell line (H-2$^d$)) stably transfected with the NS3/4A gene was made. The SP2/0 cells were maintained in DMEM medium supplemented with 10% fetal calf serum (FCS; Sigma Chemicals, St. Louis, Mo.), 2 mM L-Glutamine, 10 mM HEPES, 100 U/ml Penicillin and 100 µg/ml Streptomycin, 1 mM non-essential amino acids, 50 µM β-mercaptoethanol, 1 mM sodium pyruvate (GIBCO-BRL, Gaithesburgh, Md.). The pcDNA3.1 plasmid containing the NS3/4A gene was linearized by BglII digestion. A total of 5 µg linearized plasmid DNA was mixed with 60 µg transfection reagent (Superfect, Qiagen, Germany) and the mixture was added to a 50% confluent layer of SP2/0 cells in a 35 mm dish. The transfection procedure was performed according to manufacturer's protocol.

Transfected cells were cloned by limiting dilution and selected by addition of 800 µg geneticin (G418)/ml complete DMEM medium after 14 days. A stable NS3/4A-expressing SP2/0 clone was identified using PCR and RT-PCR and/or a capture EIA using a monoclonal antibody to NS3. All EIAs for the detection of murine NS3 antibodies were essentially performed as follows. In brief, rNS3 (recombinant NS3 protein produced in *E. Coli*, dialyzed overnight against PBS, and sterile filtered) was passively adsorbed overnight at 4° C. to 96-well microtiter plates (Nunc, Copenhagen, Denmark) at 1 µg/ml in 50 mM sodium carbonate buffer (pH 9.6). The plates were then blocked by incubation with dilution buffer containing PBS, 2% goat serum, and 1% bovine serum albumin for one hour at +37° C. Serial dilutions of mouse sera starting at 1:60 were then incubated on the plates for one hour. Bound murine serum antibodies were detected by an alkaline phosphatase conjugated goat anti-mouse IgG (Sigma cell products, Saint Louis, Mo. USA) followed by addition of the substrate pNPP (1 tablet/5 ml of 1 M Diethanolamin buffer with 0.5 mM MgCl2). The reaction was stopped by addition of 1 M NaOH. Absorbance was then read at 405 nm.

The in vivo growth kinetics of the SP2/0 and the NS3/4A-SP2/0 cell lines were then evaluated in Balb/c mice. Mice were injected subcutaneously with $2 \times 10^6$ tumor cells in the right flank. Each day the size of the tumor was determined through the skin. The growth kinetics of the two cell lines was comparable. The mean tumor sizes did not differ between the two cell lines at any time point, for example. (See TABLE 4).

TABLE 4

| Mouse ID | Tumor cell line | Maximum in vivo tumor size at indicated time point | | | | | | | | |
|---|---|---|---|---|---|---|---|---|---|---|
| | | 5 | 6 | 7 | 8 | 11 | 12 | 13 | 14 | 15 |
| 1 | SP2/0 | 1.6 | 2.5 | 4.5 | 6.0 | 10.0 | 10.5 | 11.0 | 12.0 | 12.0 |
| 2 | SP2/0 | 1.0 | 1.0 | 2.0 | 3.0 | 7.5 | 7.5 | 8.0 | 11.5 | 11.5 |
| 3 | SP2/0 | 2.0 | 5.0 | 7.5 | 8.0 | 11.0 | 11.5 | 12.0 | 12.0 | 13.0 |
| 4 | SP2/0 | 4.0 | 7.0 | 8.0 | 10.0 | 13.0 | 15.0 | 16.5 | 16.5 | 17.0 |
| 5 | SP2/0 | 1.0 | 1.0 | 3.0 | 4.0 | 5.0 | 6.0 | 6.0 | 6.0 | 7.0 |
| | Group mean | 1.92 | 3.3 | 5.0 | 6.2 | 9.3 | 10.1 | 10.7 | 11.6 | 12.1 |
| 6 | NS3/4A-SP2/0 | 1.0 | 2.0 | 3.0 | 3.5 | 4.0 | 5.5 | 6.0 | 7.0 | 8.0 |
| 7 | NS3/4A-SP2/0 | 2.0 | 2.5 | 3.0 | 5.0 | 7.0 | 9.0 | 9.5 | 9.5 | 11.0 |
| 8 | NS3/4A-SP2/0 | 1.0 | 2.0 | 3.5 | 3.5 | 9.5 | 11.0 | 12.0 | 14.0 | 14.0 |
| 9 | NS3/4A-SP2/0 | 1.0 | 1.0 | 2.0 | 6.0 | 11.5 | 13.0 | 14.5 | 16.0 | 18.0 |
| 10 | NS3/4A-SP2/0 | 3.5 | 6.0 | 7.0 | 10.5 | 15.0 | 15.0 | 15.0 | 15.5 | 20.0 |
| | Group mean | 1.7 | 2.7 | 3.7 | 5.7 | 9.4 | 10.7 | 11.4 | 12.4 | 14.2 |
| | p-value of student's t-test comparison between group means | 0.7736 | 0.6918 | 0.4027 | 0.7903 | 0.9670 | 0.7986 | 0.7927 | 0.7508 | 0.4623 |

The example below describes experiments that were performed to determine whether mice immunized with the NS3/4A constructs had developed a T-cell response against NS3.

Example 9

To examine whether a T-cell response was elicited by the NS3/4A immunization, the capacity of an immunized mouse's immune defense system to attack the NS3-expressing tumor cell line was assayed. The protocol for testing for in vivo inhibition of tumor growth of the SP2/0 myeloma cell line in Balb/c mice has been described in detail previously (Encke et al., *J. Immunol.* 161:4917 (1998), herein expressly incorporated by reference in its entirety). Inhibition of tumor growth in this model is dependent on the priming of cytotoxic T lymphocytes (CTLs). In a first set of experiments, groups of ten mice were immunized i.m. five times with one month intervals with either 100 μg NS3-pVAX or 100 μg NS3/4A-pVAX. Two weeks after the last immunization $2 \times 10^6$ SP2/0 or NS3/4A-SP2/0 cells were injected into the right flank of each mouse. Two weeks later the mice were sacrificed and the maximum tumor sizes were measured. There was no difference between the mean SP2/0 and NS3/4A-SP2/0 tumor sizes in the NS3-pVAX immunized mice. (See TABLE 5).

TABLE 5

| Mouse ID | Immunogen | Dose (μg) | Tumor cell line | Tumor growth | Maximum tumor size (mm) |
|---|---|---|---|---|---|
| 1 | NS3-pVAX | 100 | SP2/0 | Yes | 5 |
| 2 | NS3-pVAX | 100 | SP2/0 | Yes | 15 |
| 3 | NS3-pVAX | 100 | SP2/0 | No | — |
| 4 | NS3-pVAX | 100 | SP2/0 | Yes | 6 |
| 5 | NS3-pVAX | 100 | SP2/0 | Yes | 13 |
| Group total | | | | 4/5 | 9.75 ± 4.992 |
| 6 | NS3-pVAX | 100 | NS3/4A-SP2/0 | Yes | 9 |
| 7 | NS3-pVAX | 100 | NS3/4A-SP2/0 | Yes | 8 |
| 8 | NS3-pVAX | 100 | NS3/4A-SP2/0 | Yes | 7 |
| 9 | NS3-pVAX | 100 | NS3/4A-SP2/0 | No | — |
| 10 | NS3-pVAX | 100 | NS3/4A-SP2/0 | No | — |
| | | | | 3/5 | 8.00 ± 1.00 |

Unpaired t-test for Max diam
Grouping Variable: Column 1
Hypothesized Difference = 0
Row exclusion: NS3DNA-Tumor-001213

| | Mean Diff. | DF | t-Value | P-Value |
|---|---|---|---|---|
| NS3-sp2, NS3-spNS3 | 1.750 | 5 | 0.58 | 0.584 |

Group Info for Max diam
Grouping Variable: Column 1
Row exclusion: NS3DNA-Tumor-001213

| | Count | Mean | Variance | Std. Dev. | Std. Err |
|---|---|---|---|---|---|
| NS3-sp2 | 4 | 9.750 | 24.917 | 4.992 | 2.496 |
| NS3-spNS3 | 3 | 8.000 | 1.000 | 1.000 | 0.57 |

Note:
Statistical analysis (StatView): Student's t-test on maximum tumor size. P-values < 0.05 are considered significant.

To analyze whether administration of different NS3 containing compositions affected the elicitation of a cell-mediated immune response, mice were immunized with PBS, rNS3, a control DNA, or the NS3/4A construct, and tumor sizes were determined, as described above. The NS3/4A construct was able to elicit a T-cell response sufficient to cause a statistically significant reduction in tumor size (See TABLE 6).

TABLE 6

| Mouse ID | Immunogen | Dose (μg) | Tumor cell line | Anti-NS3 | Tumor growth | Maximum tumor size (mm) |
|---|---|---|---|---|---|---|
| 1 | NS3-pVAX | 10 | NS3/4A-SP2/0 | <60 | + | 12.0 |
| 2 | NS3-pVAX | 10 | NS3/4A-SP2/0 | <60 | + | 20.0 |
| 3 | NS3-pVAX | 10 | NS3/4A-SP2/0 | 60 | + | 18.0 |
| 4 | NS3-pVAX | 10 | NS3/4A-SP2/0 | <60 | + | 13.0 |
| 5 | NS3-pVAX | 10 | NS3/4A-SP2/0 | <60 | + | 17.0 |
| Group mean | | | | 60 | 5/5 | 16.0 ± 3.391 |
| 6 | NS3-pVAX | 100 | NS3/4A-SP2/0 | 2160 | + | 10.0 |
| 7 | NS3-pVAX | 100 | NS3/4A-SP2/0 | <60 | − | — |
| 8 | NS3-pVAX | 100 | NS3/4A-SP2/0 | <60 | − | — |
| 9 | NS3-pVAX | 100 | NS3/4A-SP2/0 | 360 | − | — |
| 10 | NS3-pVAX | 100 | NS3/4A-SP2/0 | <60 | + | 12.5 |
| Group mean | | | | 1260 | 2/5 | 11.25 ± 1.768 |
| 11 | NS3/4A-pVAX | 10 | NS3/4A-SP2/0 | <60 | + | 10.0 |
| 12 | NS3/4A-pVAX | 10 | NS3/4A-SP2/0 | <60 | − | — |
| 13 | NS3/4A-pVAX | 10 | NS3/4A-SP2/0 | <60 | − | — |
| 14 | NS3/4A-pVAX | 10 | NS3/4A-SP2/0 | <60 | + | 13.0 |
| 15 | NS3/4A-pVAX | 10 | NS3/4A-SP2/0 | <60 | + | 13.5 |
| Group mean | | | | <60 | 3/5 | 12.167 ± 1.893 |
| 16 | NS3/4A-pVAX | 100 | NS3/4A-SP2/0 | 60 | + | 10.0 |
| 17 | NS3/4A-pVAX | 100 | NS3/4A-SP2/0 | 360 | − | — |
| 18 | NS3/4A-pVAX | 100 | NS3/4A-SP2/0 | 2160 | + | 8.0 |
| 19 | NS3/4A-pVAX | 100 | NS3/4A-SP2/0 | 2160 | + | 12.0 |
| 20 | NS3/4A-pVAX | 100 | NS3/4A-SP2/0 | 2160 | + | 7.0 |

TABLE 6-continued

| | | | | | | |
|---|---|---|---|---|---|---|
| Group mean | | | | 1380 | 4/5 | 9.25 ± 2.217 |
| 36 | p17-pcDNA3 | 100 | NS3/4A-SP2/0 | <60 | + | 20.0 |
| 37 | p17-pcDNA3 | 100 | NS3/4A-SP2/0 | <60 | + | 7.0 |
| 38 | p17-pcDNA3 | 100 | NS3/4A-SP2/0 | <60 | + | 11.0 |
| 39 | p17-pcDNA3 | 100 | NS3/4A-SP2/0 | <60 | + | 15.0 |
| 40 | p17-pcDNA3 | 100 | NS3/4A-SP2/0 | <60 | + | 18.0 |
| Group mean | | | | <60 | 5/5 | 14.20 ± 5.263 |
| 41 | rNS3/CFA | 20 | NS3/4A-SP2/0 | >466560 | + | 13.0 |
| 42 | rNS3/CFA | 20 | NS3/4A-SP2/0 | >466560 | − | — |
| 43 | rNS3/CFA | 20 | NS3/4A-SP2/0 | >466560 | + | 3.5 |
| 44 | rNS3/CFA | 20 | NS3/4A-SP2/0 | >466560 | + | 22.0 |
| 45 | rNS3/CFA | 20 | NS3/4A-SP2/0 | >466560 | + | 17.0 |
| Group mean | | | | 466560 | 4/5 | 17.333 ± 4.509 |
| 46 | PBS | — | NS3/4A-SP2/0 | <60 | + | 10.0 |
| 47 | PBS | — | NS3/4A-SP2/0 | <60 | + | 16.5 |
| 48 | PBS | — | NS3/4A-SP2/0 | 60 | + | 15.0 |
| 49 | PBS | — | NS3/4A-SP2/0 | <60 | + | 21.0 |
| 50 | PBS | — | NS3/4A-SP2/0 | <60 | + | 15.0 |
| 51 | PBS | — | NS3/4A-SP2/0 | <60 | − | — |
| Group mean | | | | 60 | 5/6 | 15.50 ± 3.937 |

Unpaired t-test for Largest Tumor size
Grouping Variable: group
Hypothesized Difference = 0

| | Mean Diff. | DF | t-Value | P-Value |
|---|---|---|---|---|
| p17-sp3-4, NS3-100-sp3-4 | 2.950 | 5 | .739 | .4933 |
| p17-sp3-4, NS3/4-10-sp3-4 | 2.033 | 6 | .628 | .5532 |
| p17-sp3-4, NS3-10-sp3-4 | −1.800 | 8 | −.643 | .5383 |
| p17-sp3-4, NS3/4-100-sp3-4 | 4.950 | 7 | 1.742 | .1250 |
| p17-sp3-4, PBS-sp3-4 | −1.300 | 8 | −.442 | .6700 |
| p17-sp3-4, rNS3-sp3-4 | −3.133 | 6 | −.854 | .4259 |
| NS3-100-sp3-4, NS3/4-10-sp3-4 | −.917 | 3 | −.542 | .6254 |
| NS3-100-sp3-4, NS3-10-sp3-4 | −4.750 | 5 | −1.811 | .1299 |
| NS3-100-sp3-4, NS3/4-100-sp3-4 | 2.000 | 4 | 1.092 | .3360 |
| NS3-100-sp3-4, PBS-sp3-4 | −4.250 | 5 | −1.408 | .2183 |
| NS3-100-sp3-4, rNS3-sp3-4 | −6.083 | 3 | −1.744 | .1795 |
| NS3/4-10-sp3-4, NS3-10-sp3-4 | −3.833 | 6 | −1.763 | .1283 |
| NS3/4-10-sp3-4, NS3/4-100-sp3-4 | 2.917 | 5 | 1.824 | .1277 |
| NS3/4-10-sp3-4, PBS-sp3-4 | −3.333 | 6 | −1.344 | .2274 |
| NS3/4-10-sp3-4, rNS3-sp3-4 | −5.167 | 4 | −1.830 | .1412 |
| NS3-10-sp3-4, NS3/4-100-sp3-4 | 6.750 | 7 | 3.416 | .0112 |
| NS3-10-sp3-4, PBS-sp3-4 | .500 | 8 | .215 | .8350 |
| NS3-10-sp3-4, rNS3-sp3-4 | −1.333 | 6 | −.480 | .6480 |
| NS3/4-100-sp3-4, PBS-Sp3-4 | −6.250 | 7 | −2.814 | .0260 |
| NS3/4-100-sp3-4, rNS3-sp3-4 | −8.083 | 5 | −3.179 | .0246 |
| PBS-sp3-4, rNS3-sp3-4 | −1.833 | 6 | −.607 | .5662 |

Note:

Statistical analysis (StatView): Student's t-test on maximum tumor size. P-values < 0.05 are considered as significant.

The example below describes more experiments that were performed to determine whether the reduction in tumor size can be attributed to the generation of NS3-specific T-lymphocytes.

Example 10

In the next set of experiments, the inhibition of SP2/0 or NS3/4A-SP2/0 tumor growth was again evaluated in NS3/4A-pVAX immunized Balb/c mice. In mice immunized with the NS3/4A-pVAX plasmid, the growth of NS3/4A-SP2/0 tumor cells was significantly inhibited as compared to growth of the non-transfected SP2/0 cells. (See TABLE 7). Thus, NS3/4A-pVAX immunization elicits CTLs that inhibit growth of cells expressing NS3/4A in vivo.

TABLE 7

| Mouse ID | Immunogen | Dose (μg) | Tumor cell line | Tumor growth | Maximum tumor size (mm) |
|---|---|---|---|---|---|
| 11 | NS3/4A-pVAX | 100 | SP2/0 | No | — |
| 12 | NS3/4A-pVAX | 100 | SP2/0 | Yes | 24 |
| 13 | NS3/4A-pVAX | 100 | SP2/0 | Yes | 9 |
| 14 | NS3/4A-pVAX | 100 | SP2/0 | Yes | 11 |
| 15 | NS3/4A-pVAX | 100 | SP2/0 | Yes | 25 |
| | | | | 4/5 | 17.25 ± 8.421 |
| 16 | NS3/4A-pVAX | 100 | NS3/4A-SP2/0 | No | — |
| 17 | NS3/4A-pVAX | 100 | NS3/4A-SP2/0 | Yes | 9 |
| 18 | NS3/4A-pVAX | 100 | NS3/4A-SP2/0 | Yes | 7 |
| 19 | NS3/4A-pVAX | 100 | NS3/4A-SP2/0 | Yes | 5 |
| 20 | NS3/4A-pVAX | 100 | NS3/4A-SP2/0 | Yes | 4 |
| | | | | 4/5 | 6.25 ± 2.217 |

Unpaired t-test for Max diam
Grouping Variable: Column 1
Hypothesized Difference = 0
Row exclusion: NS3DNA-Tumor-001213

| | Mean Diff. | DF | t-Value | P-Value |
|---|---|---|---|---|
| NS3/4-sp2, NS3/4-spNS3 | 11.000 | 6 | 2.526 | 0.044 |

Group Info for Max diam
Grouping Variable: Column 1
Row exclusion: NS3DNA-Tumor-001213

| | Count | Mean | Variance | Std. Dev. | Std. Err |
|---|---|---|---|---|---|
| NS3/4-sp2 | 4 | 17.250 | 70.917 | 8.421 | 4.211 |
| NS3/4-spNS3 | 4 | 6.250 | 4.917 | 2.217 | 1.109 |

Note:
Statistical analysis (StatView): Student's t-test on maximum tumor size. P-values < 0.05 are considered significant.

In another set of experiments, the inhibition of NS3/4A-expressing SP2/0 tumor growth was evaluated in MSLF1-pVAX immunized Balb/c mice. In brief, groups of mice were immunized with different immunogens (4 μg of plasmid) using a gene gun at weeks zero, four, eight, twelve, and sixteen. Two weeks after the last immunization approximately $1 \times 10^6$ NS3/4A-expressing SP2/0 cells were injected s.c into the right flank of the mouse. The kinetics of the tumor growth was then monitored by measuring the tumor size through the skin at days seven, 11, and 13. The mean tumor sizes were calculated and groups were compared using the Mann-Whitney non-parametric test. At day 14 all mice were sacrificed.

Figure 5:
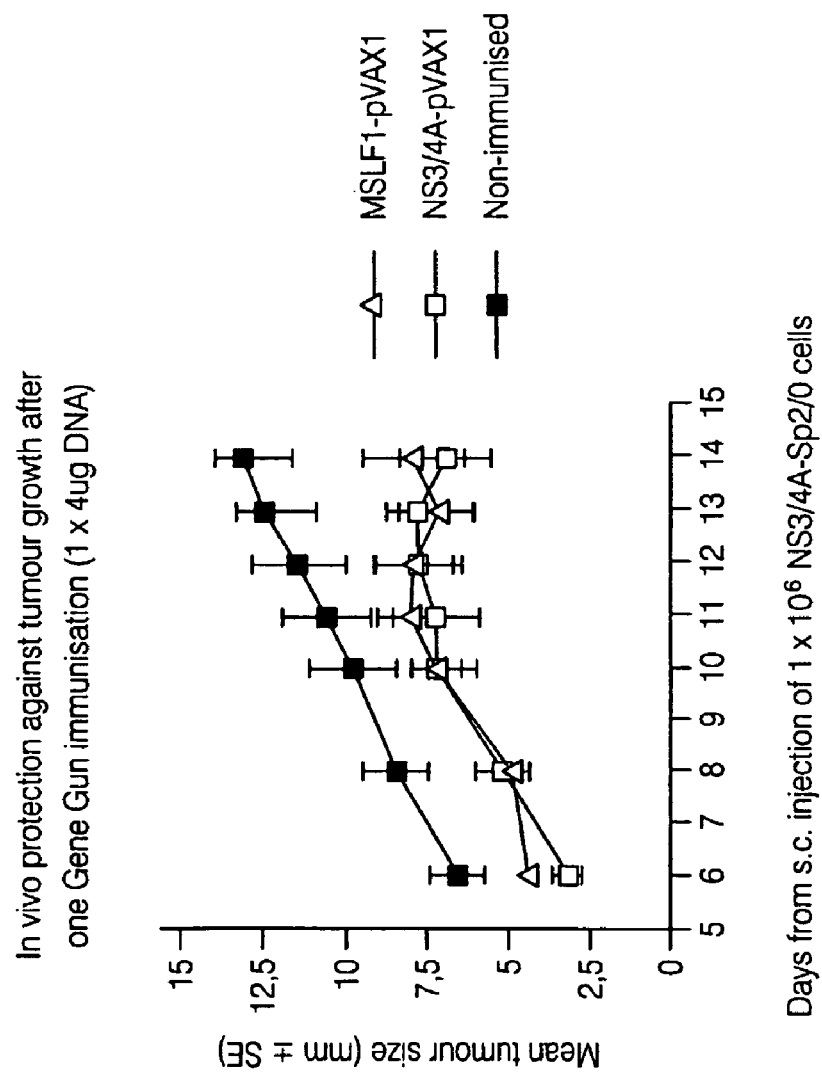
FIG. 5 shows the in vivo protection conferred by one gene gun immunization of NS3/4A-pVAX1 (4 μg) or MSLF1-pVAX1 (4 μg). Mice were immunized with the respective plasmid and 14 days later the mice were challenged with an NS3/4A expressing SP2/0 cell line (approximately 10$^6$ cells/mouse). Tumor size was then measured through the skin daily following day 6 post-challenge and the data plotted.
Figure 6:
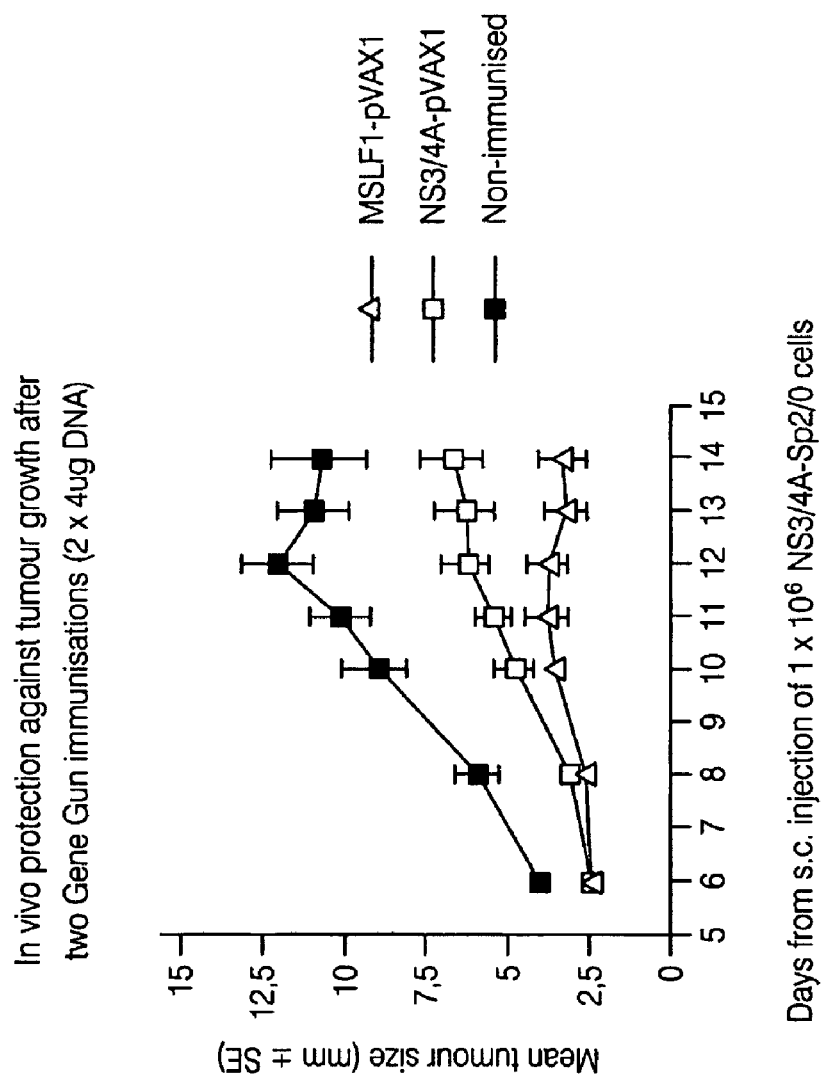
FIG. 6 shows the in vivo protection conferred by two gene gun immunizations of NS3/4A-pVAX1 (4 μg) or MSLF1-pVAX1 (4 μg). Mice were immunized with the respective plasmid at weeks zero and week four and, 14 days after the last immunization, the mice were challenged with an NS3/4A expressing SP2/0 cell line (approximately 10$^6$ cells/mouse). Tumor size was then measured through the skin daily following day 6 post-challenge and the data plotted.
Figure 7:
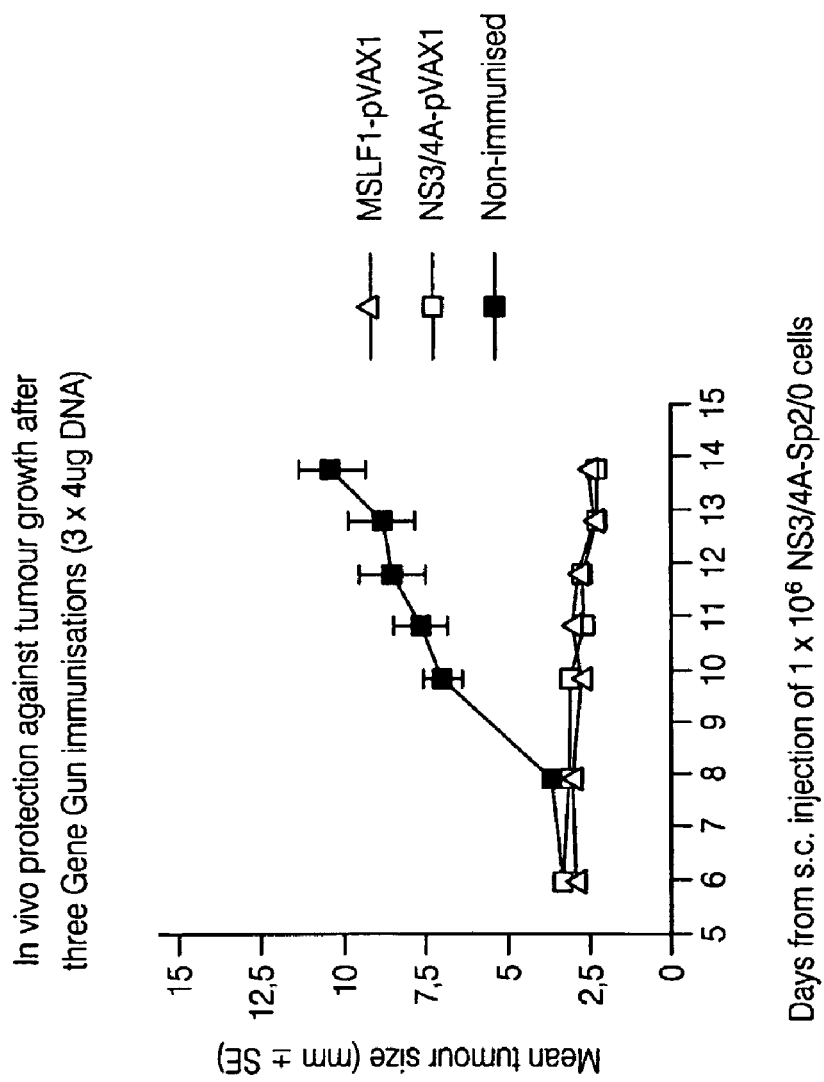
FIG. 7 shows the in vivo protection conferred by three gene gun immunizations of NS3/4A-pVAX1 (4 μg) or MSLF1-pVAX1 (4 μg). Mice were immunized with the respective plasmid at weeks zero, week four, and week eight and, 14 days after the last immunization, the mice were challenged with an NS3/4A expressing SP2/0 cell line (approximately 10$^6$ cells/mouse). Tumor size was then measured through the skin daily following day 6 post-challenge and the data plotted.

After only a single immunization, tumor inhibiting responses were observed. (See FIG. 5 and TABLE 8). After two immunizations, both the NS3/4A-pVAX and MSLF1-pVAX plasmids primed tumor-inhibiting responses. (See FIG. 6 and TABLE 9). The tumors were significantly smaller in mice immunized with the coNS3/4A gene, however, as compared to the native NS3/4A gene. After three injections, both plasmids effectively primed comparable tumor inhibiting responses. (See FIG. 7 and TABLE 10). These experiments provided evidence that the MSLF-1 gene was more efficient in activating tumor inhibiting immune responses in vivo than NS3/4A-pVAX.

TABLE 8

| Group | MSLF1-pVAX1 | NS3/4A-pVAX1 | Non-immunized |
|---|---|---|---|
| MSLF1-pVAX1 | — | N.S. | p < 0.05 |
| NS3/4A-pVAX1 | N.S. | — | p < 0.05 |
| Non-immunized | p < 0.05 | p < 0.05 | — |

TABLE 9

| Group | MSLF1-pVAX1 | NS3/4A-pVAX1 | Non-immunized |
|---|---|---|---|
| MSLF1-pVAX1 | — | p < 0.05 | p < 0.01 |
| NS3/4A-pVAX1 | p < 0.05 | — | p < 0.01 |
| Non-immunized | p < 0.01 | p < 0.01 | — |

TABLE 10

| Group | MSLF1-pVAX1 | NS3/4A-pVAX1 | Non-immunized |
|---|---|---|---|
| MSLF1-pVAX1 | — | N.S. | p < 0.01 |
| NS3/4A-pVAX1 | N.S. | — | p < 0.01 |
| Non-immunized | p < 0.01 | p < 0.01 | — |

The example below describes experiments that were performed to analyze the efficiency of various NS3 containing compositions in eliciting a cell-mediated response to NS3.

Example 11

Figure 8B:
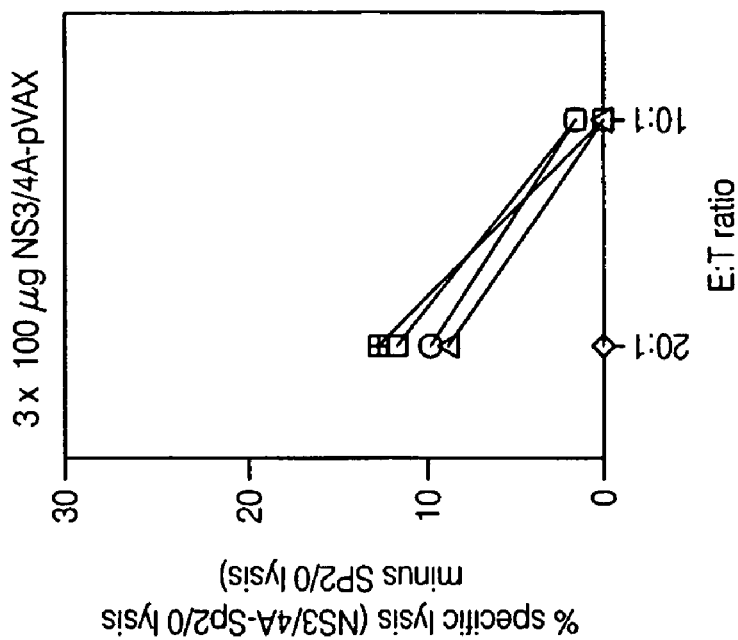
FIG. 8B is a graph demonstrating the percentage specific CTL-mediated lysis of SP2/0 target cells as a function of the effector to target ratio. Plasmid NS3/4A-pVAX was used as the immunogen.
Figure 8A:
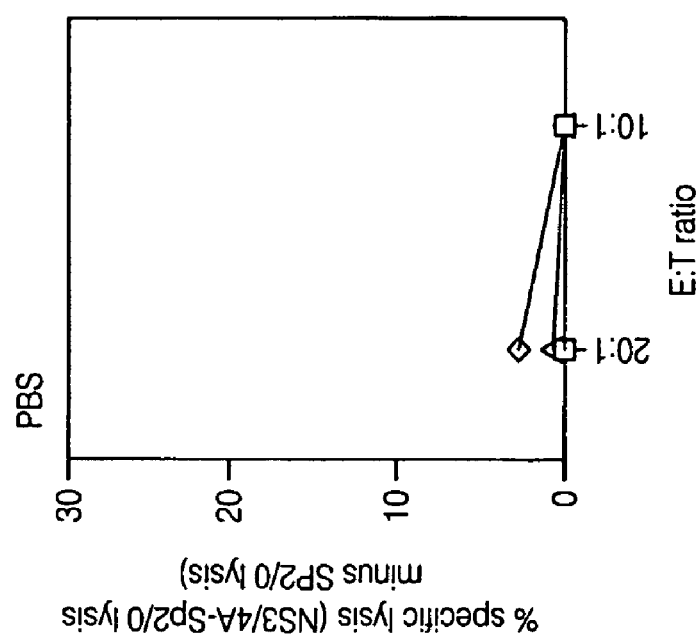
FIG. 8A is a graph demonstrating the percentage of specific CTL-mediated lysis of SP2/0 target cells as a function of the effector to target ratio. Phosphate Buffered Saline (PBS) was used as a control immunogen.

To determine whether NS3-specific T-cells were elicited by the NS3/4A immunizations, an in vitro T-cell mediated tumor cell lysis assay was employed. The assay has been described in detail previously (Sallberg et al., *J. Virol.* 71:5295 (1997), herein expressly incorporated by reference in its entirety). In a first set of experiments, groups of five Balb/c mice were immunized three times with 100 μg NS3/4A-pVAX i.m. Two weeks after the last injection the mice were sacrificed and splenocytes were harvested. Re-stimulation cultures with $3\times10^6$ splenocytes and $3\times10^6$ NS3/4A-SP2/0 cells were set. After five days, a standard $Cr^{51}$-release assay was performed using NS3/4A-SP2/0 or SP2/0 cells as targets. Percent specific lysis was calculated as the ratio between lysis of NS3/4A-SP2/0 cells and lysis of SP2/0 cells. Mice immunized with NS3/4A-pVAX displayed specific lysis over 10% in four out of five tested mice, using an effector to target ratio of 20:1 (See FIGS. 8A and 8B).

In a next set of experiments, the T cell responses to MSLF1-pVAX and NS3/4A-pVAX were compared. The ability of the two plasmids to prime in vitro detectable CTLs were evaluated in C57/BL6 mice since an H-2b-restricted NS3 epitope had been previously mapped. Groups of mice were immunized with the two plasmids and CTLs were detected in vitro using either peptide coated H-2b expressing RMA-S cells or NS3/4A-expressing EL-4 cells. Briefly, in vitro stimulation was carried out for five days in 25-ml flasks at a final volume of 12 ml, containing 5 U/ml recombinant murine IL-2 (mIL-2; R&D Systems, Minneapolis, Minn.). The restimulation culture contained a total of $40\times10^6$ immune spleen cells and $2\times10^6$ irradiated (10,000 rad) syngenic SP2/0 cells expressing the NS3/4A protein. After five days in vitro stimulation a standard $^{51}$Cr-release assay was performed. Effector cells were harvested and a four-hour $^{51}$Cr assay was performed in 96-well U-bottom plates in a total volume of 200 μl. A total of $1\times10^6$ target cells was labeled for one hour with 20 μl of $^{51}$Cr (5 mCi/ml) and then washed three times in PBS. Cytotoxic activity was determined at effector:target (E:T) ratios of 40:1, 20:1, and 10:1, using $5\times10^3$ $^{51}$Cr-labeled target cells/well.

Alternatively, splenocytes were harvested from C57BL/6 mice 12 days after peptide immunization and were resuspended in RPMI 1640 medium supplemented with 10% FCS, 2 mM L-Glutamine, 10 mM HEPES, 100 U/ml Penicillin and 100 μg/ml Streptomycin, 1 mM non-essential amino acids, 50 μM β-mercaptoethanol, 1 mM sodium pyruvate. In vitro stimulation was carried out for five days in 25 ml flasks in a total volume of 12 ml, containing $25\times10^6$ spleen cells and $25\times10^6$ irradiated (2,000 rad) syngeneic splenocytes. The restimulation was performed in the presence of 0.05 μM NS3/4A H-2 $D^b$ binding peptide (sequence GAVQNEVTL SEQ. ID. NO.: 37) or a control peptide H-2 $D^b$ peptide (sequence KAVYNFATM SEQ. ID. NO.: 38). After five days a $^{51}$Cr-release assay was performed. RMA-S target cells were pulsed with 50 μM peptide for 1.5 hrs at +37° C. prior to $^{51}$Cr-labelling, and then washed three times in PBS. Effector cells were harvested and the four hour $^{51}$Cr assay was performed as described. Cytotoxic activity was determined at the E:T ratios 60:1, 20:1, and 7:1 with $5\times10^3$ $^{51}$Cr-labeled target cells/well. By these assays, it was determined that the coNS3/4A gene primed higher levels of in vitro lytic activity compared to the NS3/4A-pVAX vector. (See FIG. 4A and FIG. 4B). Similar results were obtained with both the peptide coated H-2b expressing RMA-S cells and NS3/4A-expressing EL-4 cells.

Additional evidence that the codon-optimized coNS3/4A gene primed NS3-specific CTLs more effectively than the native NS3/4A gene was obtained using flow cytometry. The frequency of NS3/4A-peptide specific CD8+ T cells were analyzed by ex-vivo staining of spleen cells from NS3/4A DNA immunized mice with recombinant soluble dimeric mouse H-2 $D^b$:Ig fusion protein. Many of the monoclonal antibodies and MHC:Ig fusion proteins described herein were purchased from BDB Pharmingen (San Diego, Calif.); Anti-CD16/CD32 (Fc-block™, clone 2.4G2), FITC conjugated anti-CD8 (clone 53-6.7), FITC conjugated anti-H-2 Kb (clone AF6-88.5), FITC conjugated anti-H-2$D^b$ (clone KH95), recombinant soluble dimeric mouse H-2$D^b$:Ig, PE conjugated Rat-α Mouse IgG1 (clone X56).

Approximately, $2\times10^6$ spleen cells resuspended in 100 μl PBS/1% FCS (FACS buffer) were incubated with 1 μg/$10^6$ cells of Fc-blocking antibodies on ice for 15 minutes. The cells were then incubated on ice for 1.5 hrs with either 2 μg/$10^6$ cells of H-2 $D^b$:Ig preloaded for 48 hours at +4° C. with 160 nM excess of NS3/4A derived peptide (sequence GAVQNEVTL SEQ. ID. NO.: 37) or 2 μg/$10^6$ cells of unloaded H-2 $D^b$:Ig fusion protein. The cells were then washed twice in FACS buffer and resuspended in 100 μl FACS buffer containing 10 μl/100 μl PE conjugated Rat-α Mouse IgG1 secondary antibody and incubated on ice for 30 minutes. The cells were then washed twice in FACS buffer and incubated with 1 μg/$10^6$ cells of FITC conjugated α-mouse CD8 antibody for 30 minutes. The cells were then washed twice in FACS buffer and resuspended in 0.5 ml FACS buffer containing 0.5 μg/ml of PI. Approximately 200,000 events from each sample were acquired on a FACS Calibur (BDB) and dead cells (PI positive cells) were excluded from the analysis.

The advantage of quantifying specific CTLs by FACS analysis is that it bypasses the possible disadvantages of in vitro expansion of CTLs in vitro prior to analysis. Direct ex-vivo quantification of NS3-specific CTLs using NS3-peptide loaded divalent H-2 $D^b$:Ig fusion protein molecules revealed that the codon optimized MSLF-1 gene primed a effectively primed NS3-specific CTLs already after two immunizations, whereas the original NS3/4A gene did not. Thus, the optimized MSLF-1 gene effectively primes NS3-specific CTLs that are of higher frequency and of better functionality by all parameters tested, as compared to the original NS3/4A gene. The following example demonstrates which population of cells is the protector population.

Example 12

Figures 9A, 9B:
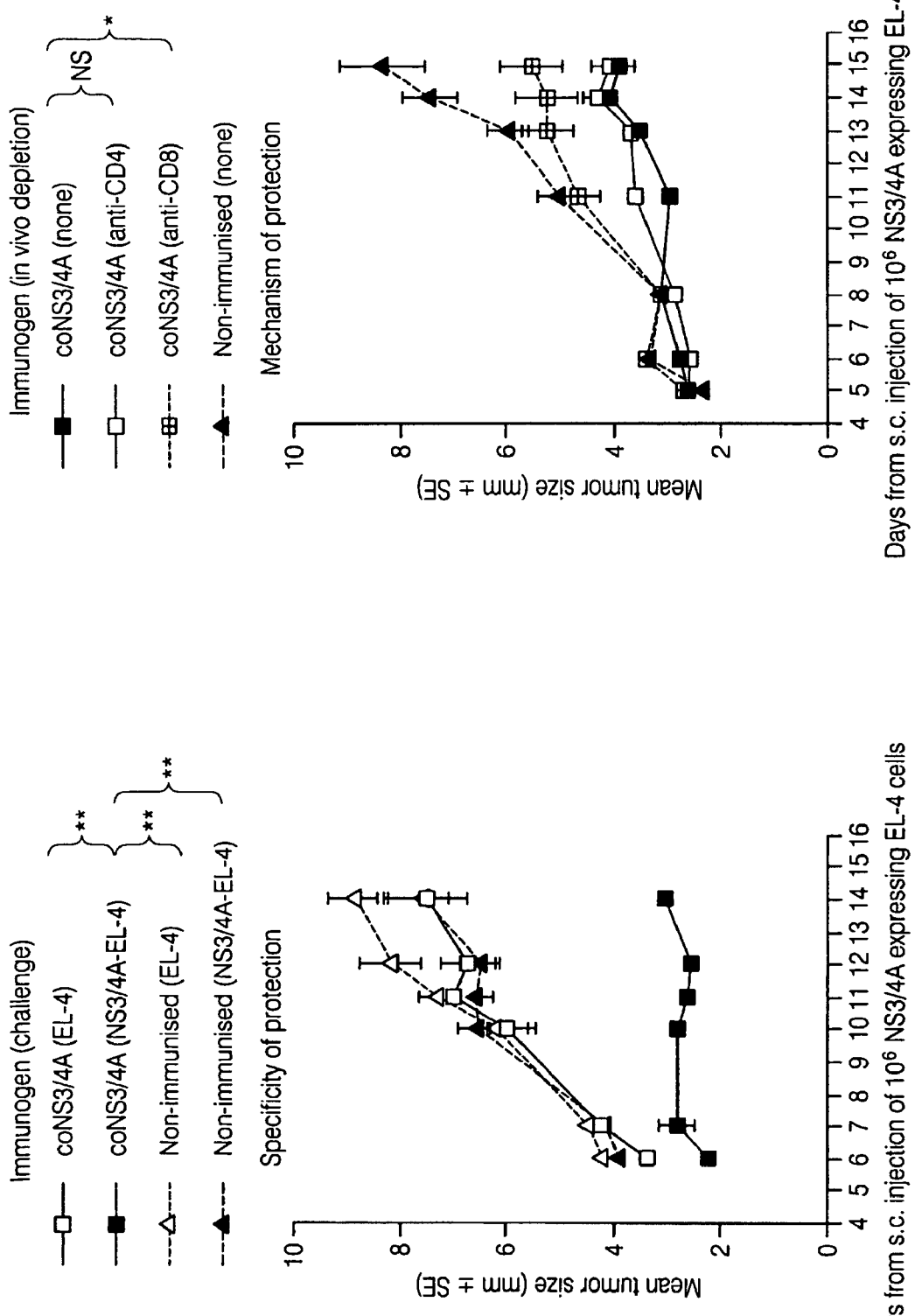
FIG. 9A is a graph demonstrating the specificity of protection for the constructs.
FIG. 9B is a graph demonstrating the in vivo functional effector cell population.
Figure 10A:
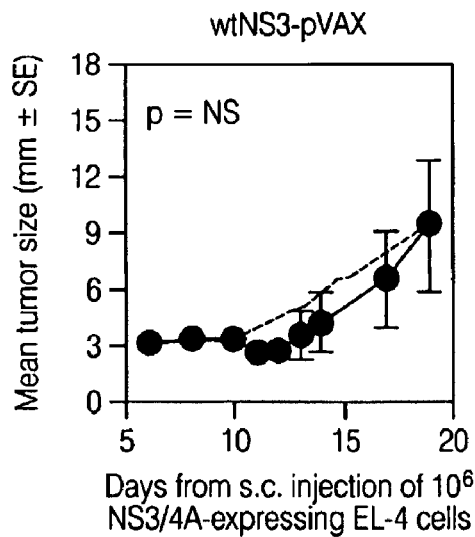
FIG. 10A is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10B:
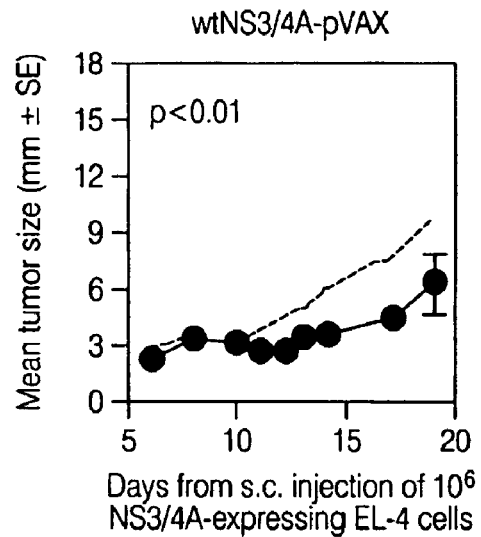
FIG. 10B is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10C:
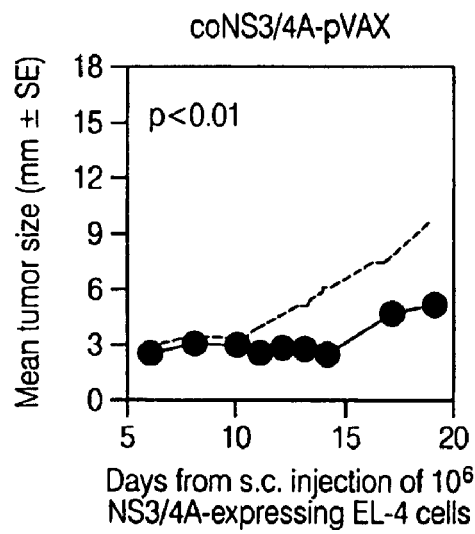
FIG. 10C is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10D:
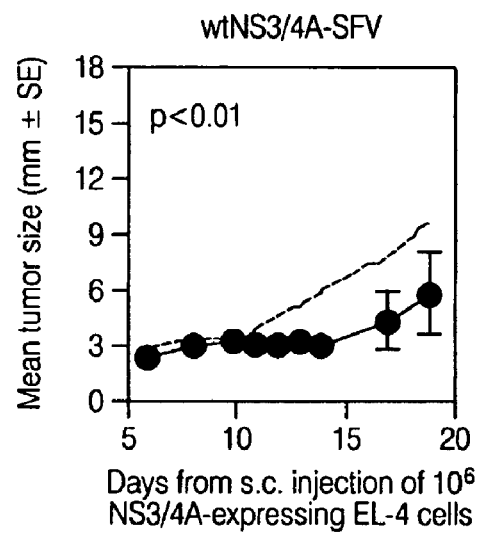
FIG. 10D is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10E:
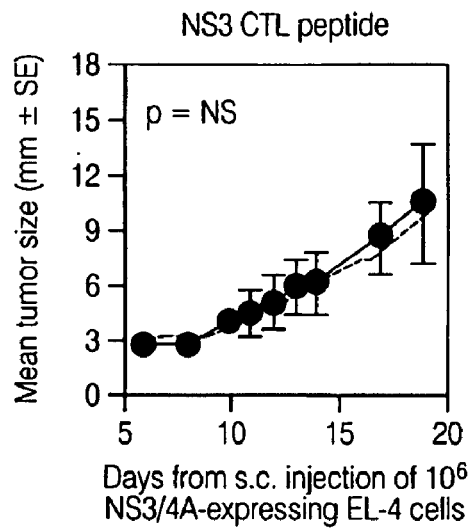
FIG. 10E is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10F:
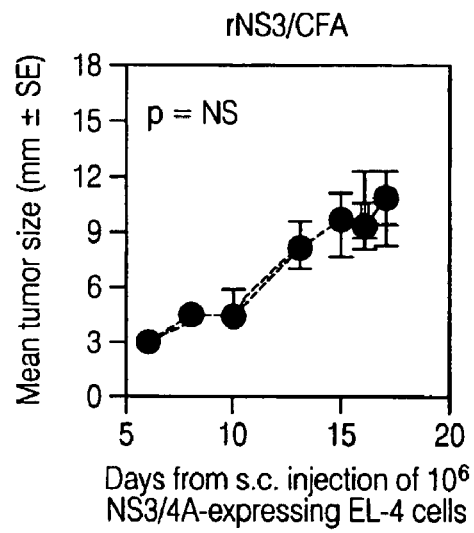
FIG. 10F is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10G:
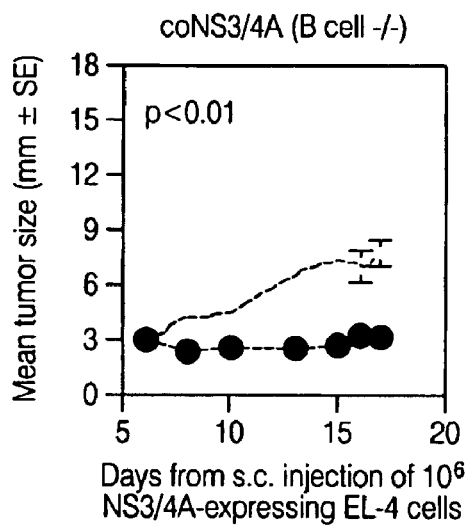
FIG. 10G is a graph demonstrating the ability of an immunogen to prime HCV NS3/4A-specific tumor inhibiting responses after a single immunization. As a negative control the mean data from the group immunized with the empty pVAX plasmid were plotted in the graph.
Figure 10H:
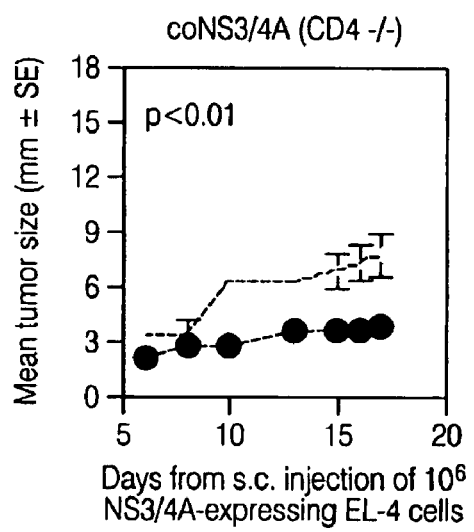
FIG. 10H is a graph demonstrating the ability of an immunogen to prime HCV NS3/4A-specific tumor inhibiting responses after a single immunization. As a negative control the mean data from the group immunized with the empty pVAX plasmid were plotted in the graph.

This example demonstrates a method by which one may determine which population of cells is the major protector population. In vitro depletion of CD4+ or CD8+ T cells of splenocytes from coNS3/4A plasmid immunized H-2b mice indicated that CD8+ T cells were the major effector cells in the $^{51}$Cr-release assay. To define the in vivo functional antitumor effector cell population, CD4+ or CD8+ T cells were depleted in mice immunized with the coNS3/4A plasmid one week prior to, and during, challenge with the NS3/4A-EL-4 tumor cell line. Analysis by flow cytometry revealed that 85% of CD4+ and CD8+ T cells had been depleted, respectively. This showed that in vivo depletion of CD4+ T cells had no significant effect on the tumor immunity (FIG. 9A). In contrast, depletion of CD8+ T cells in vivo significantly reduced the tumor immunity (p<0.05, ANOVA; FIG. 9B). Thus, NS3/4A-specific CD8+ CTLs are the major protective cell at the effector stage in the in vivo model for inhibition of tumor growth. The following example demonstrates the benefit of codon optimization in vivo.

Example 13

This example demonstrates the effect of codon optimization and mRNA amplification on priming in vivo functional NS3-specific CTLs. The tumor challenge model was used to evaluate how effective the different immunogens were in priming a protective immunity against growth of NS3/4A-EL4 tumor cells in vivo. To ensure that the effectiveness of the priming event was studied, all mice were immunized only once. Vectors containing NS3/4A were able to rapidly prime protective immune responses as compared to the immunized with the empty pVAX plasmid (p<0.05, ANOVA; FIG. 10). However, this was dependent on NS4A but independent on either codon optimization or mRNA amplification and indicates that C57BL/6 mice are easily protected against tumor growth using genetic immunization. The next example examines the prerequisites for priming of CD8+ CTL.

Example 14

To further clarify the prerequisites for priming of CD8+ CTL additional experiments were performed. First, C57BL/6 mice immunized with the NS3-derived CTL peptide were not protected against growth of NS3/4A-EL-4 tumors. Second, immunization with recombinant NS3 in adjuvant did not protect against tumor growth. To further characterize the priming event, groups of B cell (μMT; Kitamura D., et al., Nature, 350: 423-426 (1991)) or CD4 deficient C57BL/6 mice (Rahemtulla A et al., Nature, 353:180-184 (1991)) were immunized once with the coNS3/4A gene using gene gun, and challenged two weeks later (FIG. 10). Since both lineages were protected against tumor growth it appears that neither B cells nor CD4+ T cells were required for the priming of in vivo functional NS3/4A-specific CTLs (FIG. 10). In conclusion, the priming of in vivo tumor protective NS3/4A-specific CTLs in C57BL/6 mice requires NS4A and an endogenous expression of the immunogen. In the C57BL/6 mice the priming is less dependent on the gene delivery route and accessory cells such as B cells or CD4+ T cells. The fact that the priming of in vivo functional CTL by the coNS3/4A DNA plasmid was independent of CD4+ T helper cells may help to explain the speed by which the priming occurred.

Repeated experiments in C57BL/6 mice using the NS3/4A-EL-4 cell line have shown that protection against tumor growth is obtained already after the first immunization with the NS3/4A gene, independent of codon optimization or mRNA amplification (FIG. 10). Also, after two injections the immunity against NS3/4A-EL-4 tumor growth was even further enhanced, but only when NS4A was present. Thus, this model may therefore not be sufficiently sensitive to reveal subtle differences in the intrinsic immunogenicity of different immunogens. Thus, to better compare the immunogenicity of the wtNS3/4A and the coNS3/4A DNA plasmids additional experiments were performed in H-2$^d$ mice, were at least two immunizations seemed to be required for a tumor protective immunity. The following example examines if gene gun immunization impairs CTL priming.

Example 15

Figures 11A, 11B:
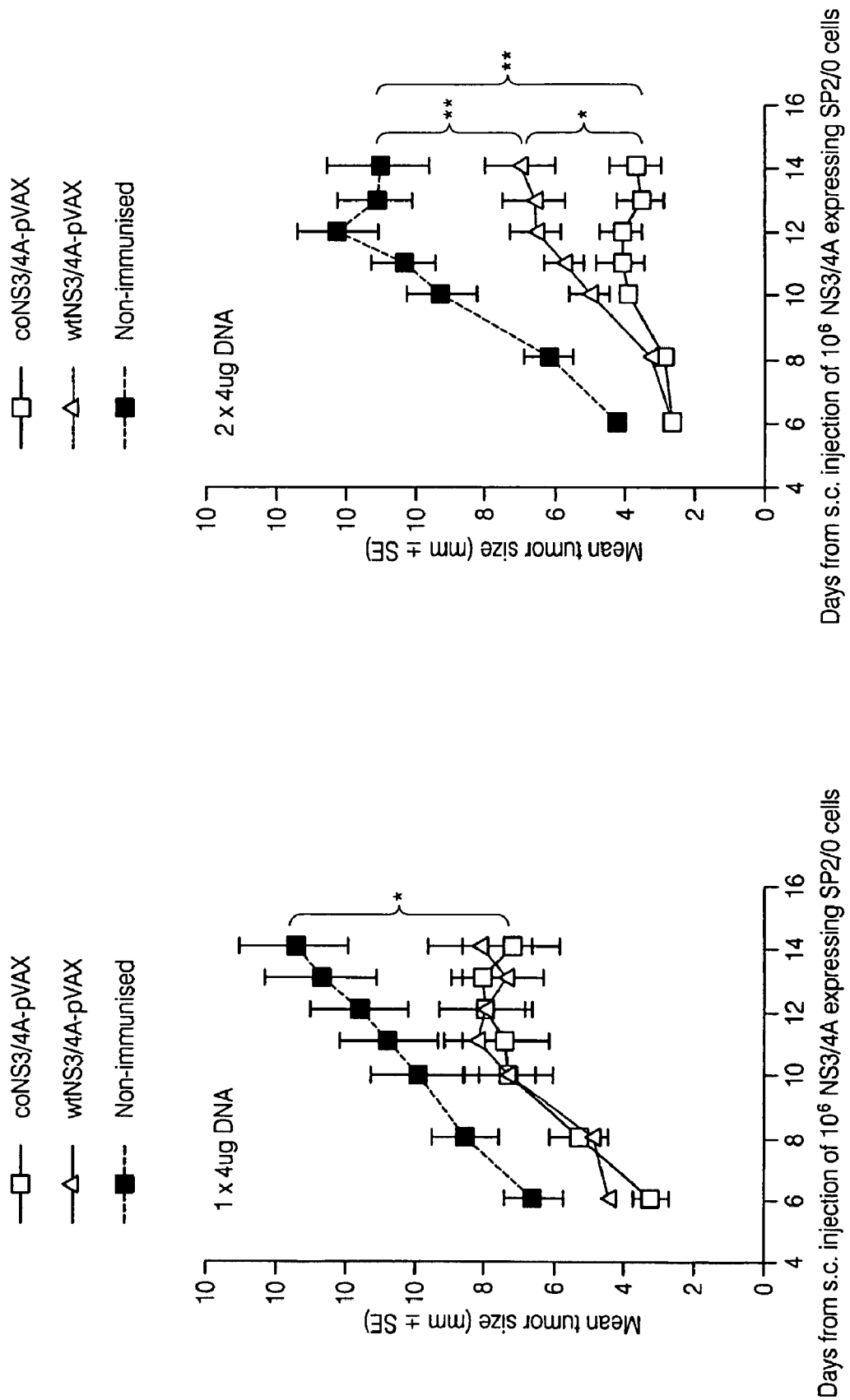
FIG. 11A is a graph of the efficiency of different plasmids in priming tumor-inhibiting immune responses with a single monthly immunization.
FIG. 11B is a graph of the efficiency of different plasmids in priming tumor-inhibiting immune responses with two monthly immunizations.
Figure 11C:
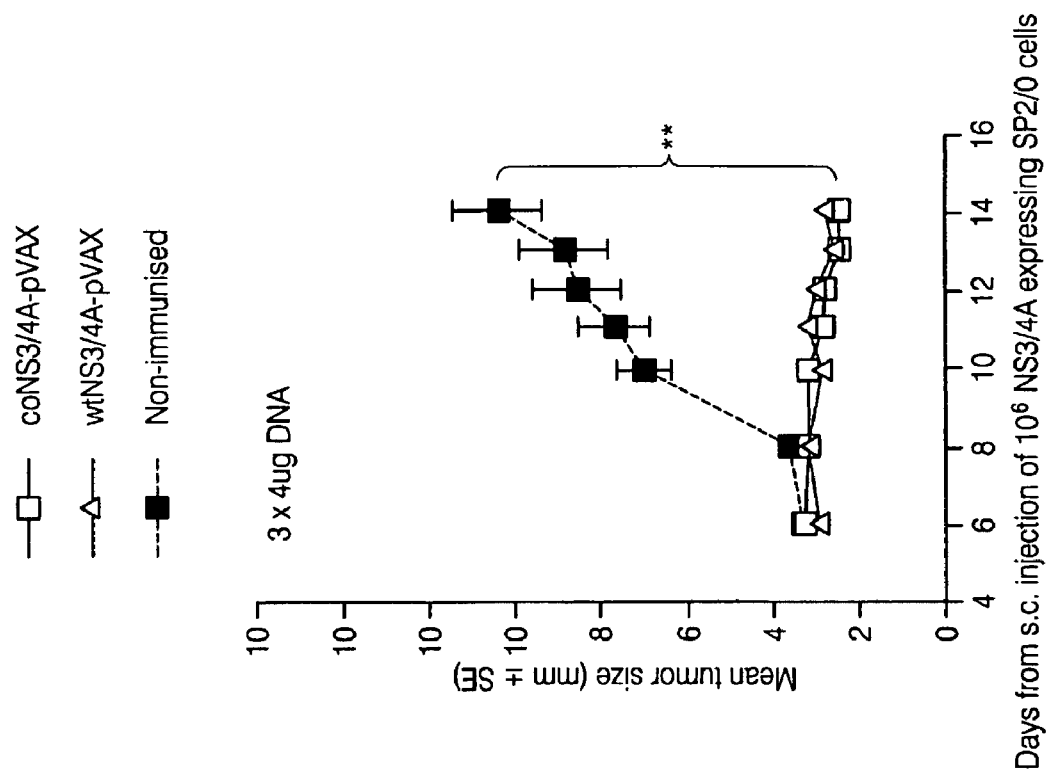
FIG. 11C is a graph of the efficiency of different plasmids in priming tumor-inhibiting immune responses with three monthly immunizations.

This example examines if it was possible that a Th2-like immunization route (gene gun) in the Th2-prone BALB/c mouse strain (Sadick M D et al., *J Exp Med.*, 171:115-127 (1990); Savelkoul H F. et al., *Eur J Immunol*, 18: 1209-1215 (1998)) may impair the ability to prime in vivo effective CTL responses. Groups of 10 BALB/c mice were immunized once, twice, or thrice with 4 μg of the respective DNA plasmid using the gene gun (FIG. 11). The mice were challenged two weeks after the last injection. From these experiments it became clear that the coNS3/4A plasmid primed an in vivo functional NS3/4A-specific tumor inhibiting immunity more rapidly than the wild type plasmid (FIG. 11). Two doses of the coNS3/4A primed a significantly better NS3/4A-specific tumor inhibiting immunity as compared to the wtNS3/4A plasmid (p<0.05, ANOVA; FIG. 11). After three doses the tumor inhibiting immunity was the same. Thus, the codon optimization of the NS3/4A gene prime NS3-specific CTLs more rapidly. The following example teaches how one can evalutate the effectiveness of an immunization.

Example 16

Figure 12:
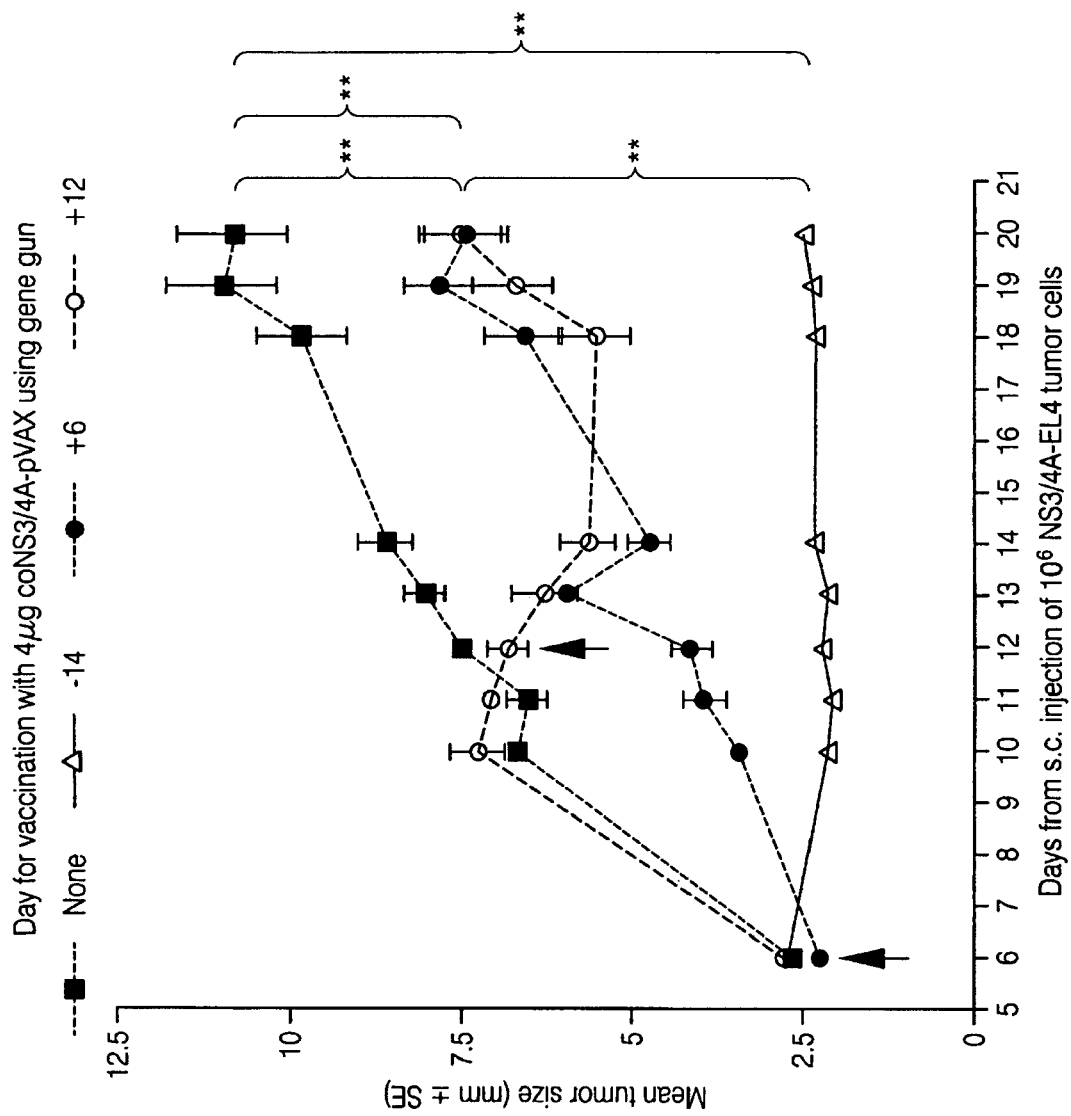
FIG. 12 is a graph demonstrating the effect of therapeutic vaccination with the coNS3/4A plasmid using a gene gun.

This example demonstrates how to evaluate the effect of therapeutic immunization after the injection of tumor cells. Groups of 10 C57BL/6 mice were challenged with 106 NS3/4A-EL-4 tumor cells. One group was immunized transdermally with of 4 μg coNS3/4A at six days, and another group at 12 days, after tumor challenge. After the therapeutic vaccination both groups had significantly smaller tumors as compared to the nonimmunized control group (p<0.01, respectively, ANOVA; FIG. 12). This shows that the vaccine rapidly primed CTLs that home to and infiltrate the NS3/4A-expressing tumors. Thus, gene gun immunization with the coNS3/4A plasmid is an effective therapeutic vaccine. The next example describes some of the peptide embodiments in greater detail.

Example 17

To characterize NS3/4A-pVAX, MSLF1-pVAX, and the NS3/4A mutant constructs, described in Example 1, the plasmids were transcribed and translated in vitro, and the resulting polypeptides were visualized by sodium dodecyl sulfate-polyacrylamide gel electrophoresis (SDS-PAGE). In vitro transcription and translation were performed using the T7 coupled reticulocyte lysate system (Promega, Madison, Wis.) according to the manufacturer's instructions. All in vitro translation reactions of the expression constructs were carried out at 30° C. with $^{35}$S-labeled methionine (Amersham International, Plc, Buckinghamshire, UK). The labeled proteins were separated by 12% SDS-PAGE and visualized by exposure to X-ray film (Hyper Film-MP, Amersham) for 6-18 hours.

The in vitro analysis revealed that all proteins were expressed to high amounts from their respective expression constructs. The rNS3 construct (NS3-pVAX vector) produced a single peptide of approximately 61 kDa, whereas, the mutant constructs (e.g., the TGT construct (NS3/4A-TGT-pVAX) and the RGT construct (NS3/4A-RGT-pVAX)) produced a single polypeptide of approximately 67 kDa, which is identical to the molecular weight of the uncleaved NS3/4A peptide produced from the NS3/4A-pVAX construct. The cleaved product produced from the expressed NS3/4A peptide was approximately 61 kDa, which was identical in size to the rNS3 produced from the NS3-pVAX vector. These results demonstrated that the expression constructs were functional, the NS3/4A construct was enzymatically active, the rNS3 produced a peptide of the predicted size, and the breakpoint mutations completely abolished cleavage at the NS3—NS4A junction.

To compare the translation efficiency from the NS3/4A-pVAX and MSLF1-pVAX plasmids, the amount of input DNA was serially diluted prior to addition to the assay. Serial dilutions of the plasmids revealed that the coNS3/4A plasmid gave stronger bands at higher dilutions of the plasmid than the wild-type NS3/4A plasmid, providing evidence that in vitro transcription and translation was more efficient from the coNS3/4A plasmid. The NS3/4A-pVAX and coNS3/4A plasmids were then analyzed for protein expression using transiently transfected Hep-G2 cells. Similar results were obtained in that the MSLF-1 gene provided more efficient expression of NS3 than the native NS3/4A gene.

Example 18

A full-length NS3/4A complementary DNA (cDNA) clone from a HCV genotype I infected patient was isolated as described in Lazdina et al. (2001). The NS3/4A (NS3/4A) gene fragment, corresponding to the amino acids 1026 to 1711 encompassing the NS3 and NS4A, was inserted into the BamHI and EcoRI sites of pMUP-11AS plasmid. A fragment containing the MUP promoter (Held et al. 1989) and NS3/4A (HindIII to EcoRI) was excised and cloned into the pVAX 1 (Invitrogen, San Diego) expression vector. Using HindIII and SwaI sites the MUP promoter, NS3/4A fragment, and BGH polyadenylation signal was excised from the pVAX1 vector to generate the transcriptional unit used for microinjection, designated pMUP-NS3/4A (illustrated in FIG. 14A). The entire pMUP-NS3/4A-BGH polyadenylation signal construct was sequenced prior to microinjection to confirm correct sequence.

The purified transgene construct was microinjected into fertilized oocytes from C57BL/6 (H–2$^b$) x CBA (H–2$^k$) mice, see FIG. 14. Potential founder mice were analyzed for the presence of transgene by polymerase chain reaction (PCR) and Southern blot of genomic tail DNA. For detection of NS3/4A by PCR, specific outer primers were used; for example, sense primer (5'-CCT GAA TTC ATG GCG CCT ATC ACG GCC TAT-3') (SEQ ID. NO.: 29) and antisense primer (5'-CCG TCT AGA TCA GCA CTC TTC CAT TTC ATC-3') (SEQ ID. NO.: 38) and inner primers; for example, sense primer (5'-GCATGCTCCCACCGGCAGCGGTAA-GAG-3') (SEQ ID. NO.: 28) and antisense primer (5'-CGCA-GAGGACAGACGAGTCAAACATGC - 3') (SEQ ID. NO.: 40). Mice were housed in microfiltered cages in a controlled and pathogen-free environment.

A total of 21 mice were born from mothers implanted with microinjected oocytes. Tail DNA from the founder mice was screened for the presence of the NS3/4A transgene by PCR and Southern blot. Six founder mice were identified by screening, all having the full-length NS3/4A fragment as determined by PCR. The full-length amplification of NS3/4A from transgenic mice tail DNA was determined by PCR. The appropriate bands appeared for the transgenic mouse and positive control. No bands were observed for the negative control or a non-transgenic mouse Example 19

This example provides a method for the visualization of genomic DNA, as described above. A Southern blot analysis of genomic DNA isolated from mouse tails was performed. In brief, 10 µg DNA was immobilized onto un-charged nylon membranes using a Bio-Dot apparatus (Bio-Rad Laboratories, Hercules, Calif.). A 1 kb gel-purified fragment of the NS3/4A DNA was labeled with [α-$^{32}$P]dATP by random priming procedure and used as a probe. The probe was hybridized with the membrane at 68° C. overnight and washed stringently. The genomic NS3/4A DNA was visualized by exposure of the membrane to X-ray film (Hyper film-MP, Amersham) for 12-72 hours. Six founder mice were identified by the above method Example 20

This example provides a method for the visualization of protein. Organ samples (100 mg) were homogenized and analyzed by immunoprecipitation followed by SDS-PAGE. In brief, organ homogenates were lysed in 1 mL radioimmune precipitation assay (RIPA) buffer (0.15 M NaCl, 50 mM Tris, 1% Triton-X 100, 1% Na-deoxycholate and 1% SDS). The homogenates were immunoprecipitated with protein A sepharose and anti-NS3 or anti-NS4A polyclonal antibody overnight at 4° C. The washed pellets were re-suspended in SDS sample buffer, heated at 100° C. for 5 minutes prior to SDS-PAGE analysis on 4-12% Bis-Tris gel (Invitrogen) and electrotransferred onto Nitrocellulose membranes. Detection of NS3/4A protein was done according to manufacturer's protocol by using a chemiluminiscence-linked Western blot kit (WesternBreeze; Invitrogen). NS3/4A protein expression was detected and quantified as a chemiluminiscent signal by using an NS3— or NS4A-specific polyclonal antibody. Chemiluminiscent signals were detected by the GeneGnome (Syngene, Cambridge, UK). As positive controls BHK-21, HeLa, and HepG2 cells were transfected by wild-type and codon-optimized NS3/4A plasmids (as taught in Wolk B et al., J. Virol., 74:2293-2304 (2000) and Tanji Y et al., J. Virol., 69:1575-1581 (1995)). Quantification of chemiluminiscence Western blots was performed on GeneGnome and units of intensity from each protein band was calculated and compared to a standard curve of rNS3.

All six DNA positive transgenic lineages were evaluated for NS3/4A protein expression. The age range of tested mice was from of one to 18 months of age. HCV NS3/4A protein expression was detected by immunoprecipitation and Western blot using a polyclonal NS3 or NS4A antibody. A band visualized in the livers of the transgenic mice was consistent with the 70 kDa HCV NS3 protein band seen in lysates from transiently transfected HepG2, HeLa or BHK-21 cells. The characterization of the NS3 protein expression included comparing the detection of NS3 protein in liver homogenates from transgenic mice with a molecular weight marker, (Magic Mark, Invitrogen) and Western blot analysis of immunoprecipitated HepG2 cells transient transfected with the codon optimised NS3/4A gene, and a non-transgenic littermate. A band for NS3 was detected only in transgenics and, a similar NS3 band, was detected from the codon optimized NS3/4A transfected HepG2 cells. NS3 protein expression was detected only in total protein preparations from livers of one out of the six transgenic mice lineages.

Additionally, NS3 protein expression was examined in different tissues of transgenic and non-transgenic mice by immunoprecipitation and Western blot. Liver, kidney, and spleen from a NS3/4A transgenic mouse was compared with the liver, kidney and spleen of a non-transgenic mouse. The only sample with an appropriately sized band for NS3 was found in the liver sample from the NS3/4A transgenic mouse, as well as the positive controls, such as HepG2 cells transfected with the coNS3/4A gene, and a recombinant NS3 protein.

A weak 6-8 kDa NS4A protein band in lysates from transient transfected BHK-21 cells was detected, but the NS4A protein band in liver homogenates from transgenic mice was not visualized. The reason for this inability to detect NS4A protein in mouse livers was due to technical reasons, as liver tissue is a highly homogenous and compact tissue. It is highly unlikely that NS4A is not expressed from the mono-cistronic expression construct. The full-length wtNS3/4A gene was detected in DNA from transgenic mouse livers by PCR. BHK-2 cells were transiently transfected with the codon optimized NS3/4A gene and a MOCK transfected control, as well as nontransgenic mice. Thus, this is the first transgenic mouse with a detectable expression of the HCV NS3 protein.

Additionally, transgene expression was restricted to the liver and was not detectable in other tissues, such as spleen, kidney, lungs, heart, brain and skin. This is consistent with the expected expression pattern of the MUP promoter. Non-transgenic mice were consistently negative for NS3 in all total protein preparations. Thus, the transgenic mice have a NS3 protein expression restricted to the liver.

Figure 15:
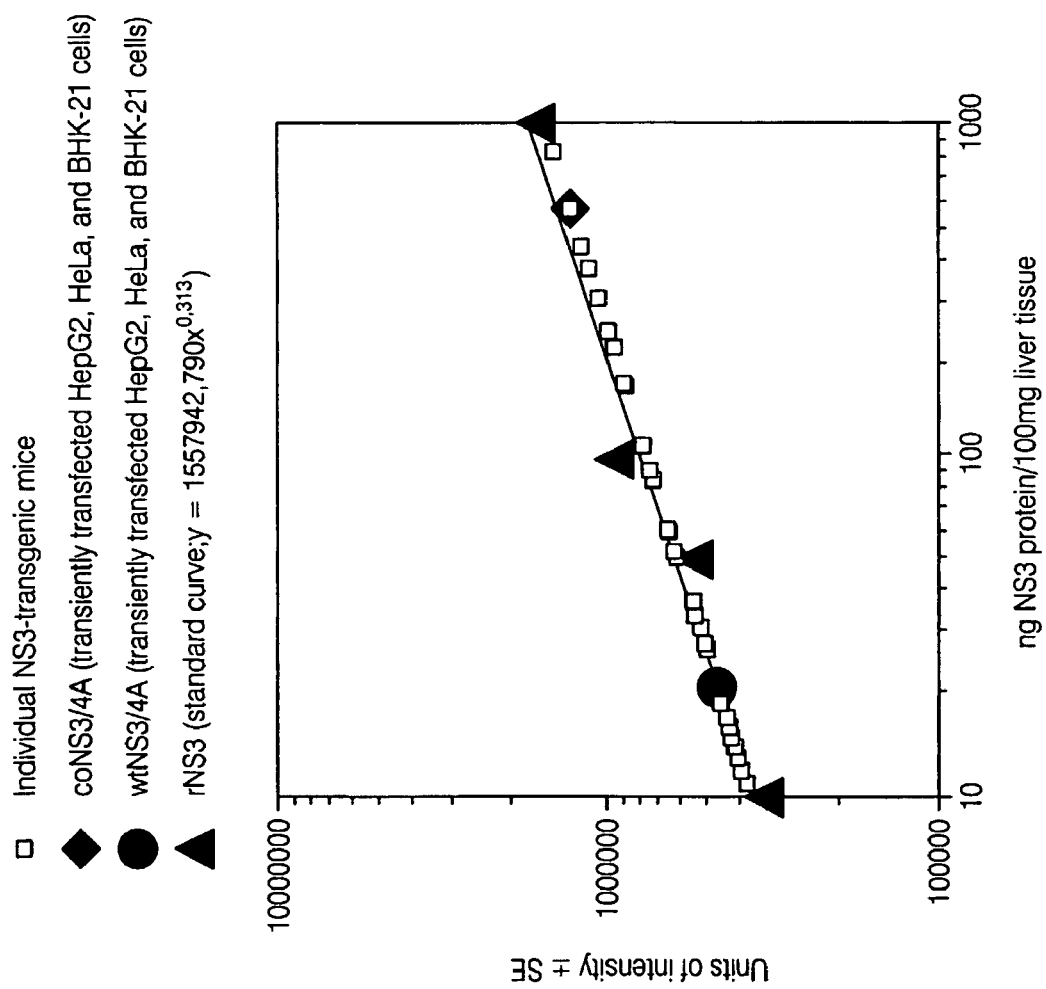
FIG. 15 is a chart that lists the NS3 protein expression levels in male transgenic mice.

NS3 protein expression was detected in both transgenic males and females by Western blot, despite the fact that expression levels are usually higher in males due the sex hormone regulated MUP promoter. (See Pang P S., et al., Embo J, 21:1168-1176 (2002)). Out of the 67 male transgenic mice tested, 43 mice (64%) were found to express NS3. Out of the 50 female transgenic mice that were tested, only 16% were found to express NS3. A wide range of protein expression among males was observed, which is consistent with observations from other transgenic mice that contain transgenes driven by the MUP promoter. The protein expression levels in male transgenic mice ranged from 0.11 to 8.1 µg/g liver (74-fold difference), and from 0.15 to 0.6 µg/g liver (4-fold difference) in female transgenic mice. Expression levels were quantified as units of intensity obtained from a standardized protein-band area, which was compared to a standard curve of rNS3 protein (FIG. 15). FIG. 15 is a chart quantifying NS3 protein expression levels in male transgenic mice. The amount NS3 protein in 100 mg of liver tissue was quantified from 44 individual transgenic mice, as described herein. Expression levels of NS3 were also quantified from HepG2, HeLa, and BHK-21 cells that were transiently transfected with the expression plasmids wild-type (wt) NS3/4A-pVAX1 or codon-optimized (co) NS3/4A-pVAX1. The wtNS3/4A dot represents a mean value±SD of nine different quantifications of NS3 protein after transient transfection and the coNS3/4A dot represents a mean value±SD of 14 different quantifications. The amount of rNS3 protein used to generate the standard curve was 5 µg, 1 µg, 0.1 µg, 0.05 µg, and 0.01 µg.

Example 21

This example provides a method by which mouse sera can be tested biochemically. Transgenic- and non-transgenic mice were bled retro-orbitally and sera was tested for alanine aminotransferase (ALT) and blood glucose levels. Serum was stored at −20° C. until tested. ALT values were measured using the Modular P equipment (Roche Diagnostics GmbH, Mannheim, Germany). Blood glucose levels were measured in serum from mice by using the Accu-Check® Sensor equipment (Roche Diagnostics). Serum from venous blood was used to analyse the ALT and glucose levels in female and male transgenic and non-transgenic mice. No consistent differences in ALT levels between the different groups were observed, indicating that the NS3/4A protein does not induce a spontaneous liver damage (TABLE 11).

TABLE 11

Phenotypic Characterization of the NS3/4A Transgenic Mice

| Age (months) | Mouse weight (g) ± SD | | Liver weight (g) ± SD | | % liver weight of body weight | | ALT (µKat/L) ± SD | | Glucose (mmol/L) ± SD | |
|---|---|---|---|---|---|---|---|---|---|---|
| | Non-Tg | Tg | Non-Tg | Tg | Non-Tg | Tg | Non-Tg | Tg | Non-Tg | Tg |
| 1-3 | 22.7 ± 3.2 (n = 57) | 23.7 ± 4.8 (n = 85) | 1.1 ± 0.2 (n = 57) | 1.3 ± 0.3** (n = 85) | 5.1 ± 0.4 (n = 57) | 5.5 ± 0.8** (n = 85) | 0.64 ± 0.43 (n = 15) | 0.66 ± 0.80 (n = 22) | 10.65 ± 3.04 (n = 25) | 10.79 ± 2.48 (n-31) |
| >17 | 41.7 ± 5.9 (n = 7) | 47.1 ± 9.6 (n = 12) | 2.0 ± 0.3 (n = 6) | 2.5 ± 0.5 (n-12) | 4.7 ± 0.5 (n = 6) | 5.3 ± 1.1 (n = 12) | 1.24 ± 1.81 (n = 7) | 1.56 ± 2.43 (n = 23) | 10.08 ± 2.21 (n = 6) | 10.48 ± 5.14 (n = 10) |

SD; standard deviation
*p < 0.05 compared with non-transgenic control group (Student's t-test)
**p < 0.01 compared with non-transgenic control group (Student's t-test)

Also, the serum glucose levels were found to be equal in transgenic and non-transgenic mice. Thus, intra-hepatic expression of the NS3/4A protein did not affect ALT or glucose levels in all of the transgenic mice. However, both serum levels of ALT and glucose were comparably small in the present study. Statistical differences were observed in subgroups regarding both ALT and glucose values.

Example 22

This example provides a method by which a histological analysis of a sample may be prepared. Mice were sacrificed and liver tissue was placed in formalin or OCT cryostat embedded compound (Tissue-Tek, Torrance, Calif., USA) and immediately snap-frozen in liquid nitrogen and then stored at −80° C. Formalin fixed liver samples were paraffin embedded, and sectioned. Four µm thick liver sections were mounted on slides and stained with Hematoxylin-Eosin dye. Liver sections were also stained with Periodic Acid Schiff's (PAS) for detection of basal membranes and glycogen accumulation, and by Sirius red staining for visualization of fibrosis. Frozen liver sections (four to seven μm thick) were stained using Oil red O to visualize lipid droplets and estimate the degree of macro- and micro steatosis. The different staining types were done according to standard procedures. All sections were analysed by a liver pathologist who was blinded to the status of the animal. Sections from different tissues were analysed blindly by a mouse pathologist to identify possible transgene-related changes outside the liver. The NS3 protein was visualized using an anti-human NS3 antibody.

The NS3 protein was only found in hepatocytes from NS3/4A transgenic mice. NS3 expression was consistently perinuclear and cytoplasmic. The immunohistochemical detection of HCV NS3 protein in liver was readily observable. Liver from a 17 months old transgenic mouse and an aged matched non-transgenic mouse was formalin fixed, sectioned, and stained using an anti-human NS3 antibody as described herein. Sections were photomicrographs obtained with a magnification of ×100, ×200, and ×400. NS3 staining was perinuclear and cytoplasmic, and localized to the hepatocytes.

Stained hepatocytes were localized both around the hepatic venules and portal tracts. The visualization pattern was consistent with the staining of NS3 in liver section from chronic infected humans (as shown in Erringthon et al., 1999). Thus, the NS3/4A-expression in the transgenic mice has a distribution and localization of the protein fully consistent with infected humans.

Example 23

The following example demonstrates how one can determine the percentage of hepatocytes expressing NS3 protein at detectable levels. The percentage of hepatocytes expressing the NS3 protein was determined by immunohistochemistry and calculated by examination of an average of 40 randomly chosen fields (400× magnification) in sections positively stained for NS3. Calculation of standardized surface areas indicated that approximately 1% of the hepatocytes expressed the NS3 protein at high enough levels to allow for detection by immunohistology.

Example 24

This example demonstrates an approach to conduct immunohistochemistry of a liver sample. Liver tissue was placed in formalin and embedded in paraffin; 4 μm sections were prepared. Paraffin-embedded sections were pre-treated with an avidin-biotin blocking kit (Vector, Vector Laboratories, Burlingame, Calif.) and then immunostained with a human anti-NS3 antibody. For detection, biotinylated anti-human IgG, followed by avidin-biotin peroxidase (Vector) was used. Microwave pre-treatment was also used for NS3 immunostaining. Thus allowing one to identify the presence of the NS3 protein and correlate its presence to a location in the sample. In some embodiments, mice that are transiently transfected with the above proteins or constructs are useful controls for analyzing or even performing some of the herein described techniques. The following example demonstrates one such transfection procedure.

Example 25

HepG2, HeLa or BHK-21 cells were transiently transfected by a standard protocol. Accordingly, cells were plated into 25 cm$^2$ wells ($0.5 \times 10^6$) in DMEM medium the day before transfection. Two μg of each plasmid DNA construct was transfected into HepG2, HeLa or BHK-21 cells using Fugene 6 Transfection Reagent (Roche). After transfection, the HepG2, HeLa or BHK-21 cells were incubated for 24-48 hrs. Cell lysates were prepared and NS3/4A protein expression was detected by chemiluminiscence with NS3— or NS4A-specific hyperimmune sera. The following example demonstrates a method of determining the significance of a given observed change.

Example 26

This example demonstrates a method by which the results of the present embodiments may be analyzed to determine if a particular change in protease activity is significant. Fisher's exact test was used for frequency analysis and Student's t-test and Mann-Whitney U-test were used for comparing values from two groups. For calculations of repeated measurements the area under the curve (AUC) and analysis of variance (ANOVA) was used. The calculations were performed using the Macintosh version of the StatView software (version 5.0). The following example demonstrates some of the observed characteristics of the NS3/4A transgenic mice.

Example 27

Figure 16B:
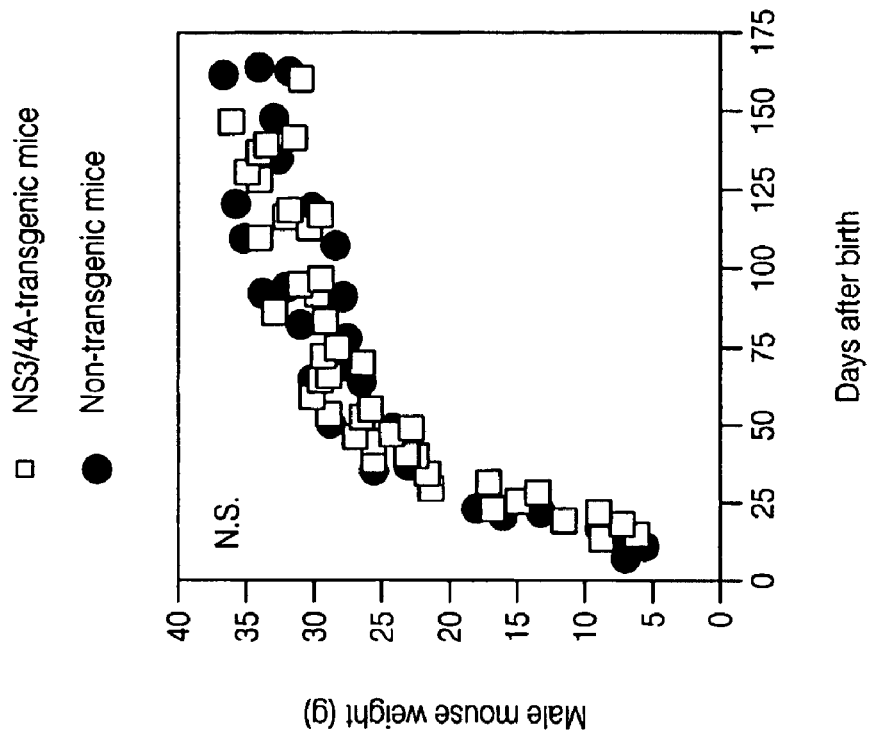
FIG. 16B is a graph showing the weight comparison of male NS3/4A-transgenic- and non-transgenic mice.
Figure 16A:
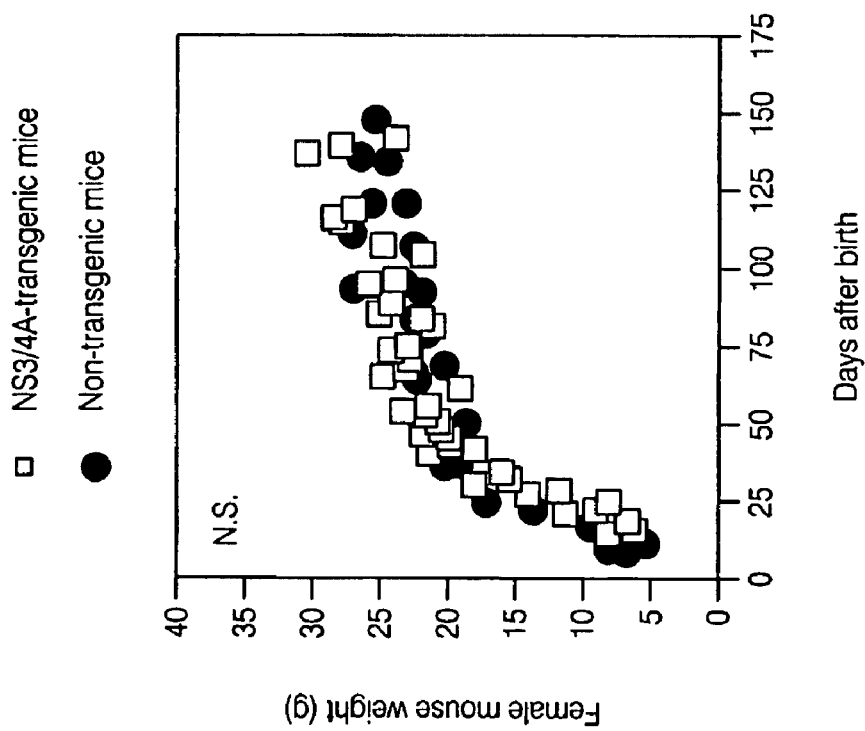
FIG. 16A is a graph showing the weight comparison of female NS3/4A-transgenic- and non-transgenic mice.

The following example describes several macroscopic and biochemcial observations on the transgenic mice. A difference in growth between transgenic and non-transgenic mice was not readily apparent. (see FIG. 16). FIGS. 16A and 16B are graphs showing the weight comparison of female NS3/4A-transgenic- and non-transgenic mice (FIG. 16A) and male NS3/4A-transgenic- and non-transgenic mice (FIG. 16B). Each dot represents a group of mice (one to seven mice). A total number of 33 female and 38 male NS3/4A-transgenic mice were weighed and 10 female and 14 male non-transgenic mice were weighed during the first five months after birth. Transgenic- and non-transgenic mouse weight in female and male groups were compared statistically using area under the curve (AUC) and analysis of variance (ANOVA).

Interestingly, the liver weight, as well as the percent liver weight of total body weight was significantly higher in the young transgenic mice (1-3 months old) as compared to age matched controls (males and females together; p<0.01; FIG. 16 and TABLE 11. The slight increase in liver weight was statistically different in young male mice but not in female mice, indicating that the increase is related to the expression levels of NS3/4A. Thus, the livers from NS3/4A transgenic were slightly enlarged. Despite this, there was no evidence of a spontaneously appearing liver pathology in the transgenic mice, as determined by either histology or by biochemistry. This observation indicates that this minor hepatomegaly does not predispose the organism for any pathology.

Sirius red staining of liver sections from Tg- and non-Tg mice revealed that no signs of fibrosis appeared within the first 17 months of age. Thus, intra-hepatic expression of NS3/4A does not noticably increase the incidence of fibrosis.

By staining the transgenic- and non-transgenic liver sections with glycogen and lipid-specific dyes (PAS and Oil red O;) it was found that the vacuoles in hepatocytes were filled with lipids. Liver sections were stained with Hematoxylin and Eosin and liver sections were stained with Oil red O according to standard procedures for visualization. However, transgenic and non-transgenic liver sections were stained for presence of NS3 protein by immunohistochemistry, as described herein. Sections were from 1 to 3 months old and >17 months old, with a magnification of ×100 and ×400. By the histological examination, it was found that both macrovesicular and microvesicular steatosis appeared and increased with age. No differences in the presence or grade of steatosis between transgenic- and non-transgenic mice (TABLE 12) was detected. Thus, surprisingly, intra-hepatic expression of NS3/4A in mouse hepatocytes did not result in a histologically detectable increase in steatosis.

toxylin and eosine stained sections revealed that vacuoles were present in the hepatocytes from both transgenic and non-transgenic mice. The cause of these vacuoles could either be fat or glycogen deposition. It is well known that inflammatory foci spontaneously appear in laboratory mice. Surprisingly, such spontaneously appearing foci, containing five

TABLE 12

Histological Characterization of the NSS3/4A Transgenic Mice

| Age (months) | Transgene status[†] | Number of inflammatory foci (>5 cells/foci) per ten fields[#] | | Micro vesicular steatosis | | Mean number of nuclei/standardized area ± SD[§] |
|---|---|---|---|---|---|---|
| 1-3 | High | 0/11*,** | 5/24 | 6/11 | 9/24 | 79.2 ± 13.5** (n = 24) |
|  | Low | 5/13* |  | 3/13 |  | (n = 24) |
|  | None | 7/14** |  | 5/14 |  | 112.4 ± 16.4** (n = 14) |
| >17 | High | 3/7 | 6/10 | 5/7 | 8/10 | 63.8 ± 10.7** (n = 10) |
|  | Low | 3/3 |  | 3/3 |  | (n = 10) |
|  | None | 8/8 |  | 6/8 |  | 81.5 ± 9.1** (n = 8) |
| All | High | 3/18** | 11/34* | 11/18 | 17/34 | 74.6 ± 14.4** (n-34) |
|  | Low | 8/16 |  | 6/16 |  | (n-34) |
|  | None | 15/22*,** |  | 11/22 |  | 101.2 ± 20.7** (n-22) |

SD; standard deviation.
*p < 0.05 (Fisher's exact test).
**p < 0.01 (Fisher's exact test).
[†]Western blot positive Tg mice (high), Western blot negative Tg mice (low), and non-Tg mice (none).
[#]Ten fields analyzed/section; 100 x.
[§]Four fields analyzed/section; 463 x.

The differences in liver weight and percent liver weight of total body weight were small, albeit statistically significant, between the transgenic- and non-transgenic groups. Thus, it is possible that the absence of a correlation was due to this minor increase in size to a histologically visible pathology or anomaly (TABLE 12). It cannot be excluded that the NS3/4A transgenic mice develop slightly enlarged livers due to a very mild steatosis, undetectable by histology, but that increases the size of the hepatocytes. The increased liver size may also be due to accumulation of glycogen within the hepatocytes. Regardless of the reason for the mild hepatomegaly it is clear that the hepatic NS3/4A-expression does not result in overt liver pathology. Thus, unexpectedly, and in contrast to other HCV transgenic mouse linages (for example, as described in Moriya, (1997); Moriya, (1998); Lemon, (2000); Lerat, (2002); Blindenbacher, (2003)), with the exception of NS5A (Majumder, (2002); Majumder, (2003)), NS3/4A does not cause an immediately detectabe overt spontaneous liver disease.

It was also noted that the NS3/4A-transgenic mice began to loose hair within two months of age. A histological analysis of the skin revealed a destruction of hair follicles. This destruction appeared at the same time and was of the same magnitude in males and females. NS3/4A expression was not detected in any skin sample, however, even in mice that were characterized as having high levels of NS3 expression in the liver.

Example 28

The following example provides a method for analyzing histological sections for the frequency of occurrence of inflamatory foci. Histological sections from transgenic and non-transgenic mouse livers were analysed at 1-3 and >17 months of age. The initial histological examination of hemaor more immune cells, were less commonly found in the NS3/4A-Tg mice compared to non-Tg mice (p<0.05, Fishers exact test; TABLE 12). In particular, NS3/4A-Tg mice expressing high levels of NS3/4A (i.e. positive by Western blot) had almost no inflammatory foci compared to non-Tg mice (p<0.01, Fishers exact test). These data indicate that NS3/4A expression in the transgenic mice effects the distribution of intra-hepatic immune cells.

It has been reported that NS3/4A, and not NS3 alone, interferes with the intracellular interferon signalling pathways (See, Foy et al., Science (2003)). Also, it has been shown that mice expressing the full HCV genome have a defective immune response to hepatic infection. (See, Duong F H, et al., Gastroenterology 126(1):263-77, (2002), Blindenbacher et al. Gastroenterology, 124(5):1465-75, (2003), Disson et al., Gastroenterology, 126(3):859-72 (2004). Thus, the presently observed reduction of inflammatory foci in the NS3/4A transgenic mice livers provides more evidence that the intra-hepatic immune defense system is compromised in the presence of HCV proteins.

Example 29

The following example demonstrates that the NS3/4A transgenics have enlarged livers due to the presence of larger cells. The number of nucleus per standardized surface area in liver, spleen, kidney and inguinal lymphnode sections was calculated. The number of nuclei in the transgenic livers was statistically lower as compared to non-transgenic livers, indicating the presence larger cells (p<0.01; TABLE 12). Importantly, the number of nuclei was lower in transgenic males as compared to transgenic females (70.1±14 v.s. 80.4±13; p<0.05, Student's t-test), and a similar difference was not seen when comparing non-transgenic males and females.

This finding indicates that the change is related to the expression levels of NS3/4A. Also, no such difference could be observed in the spleen, kidney, or inguinal lymphnodes, indicating a liver specific event had occurred in the transgenic mice. Thus, the slight enlargement of the livers in young mice was caused by an increased size of the cells, and the increase was related to the expression levels of NS3/4A. The following section describes the characterization of the transgenic mice in greater detail. In particular, more differences between the transgenic mice and wild-type mice are discussed.

Example 30

This example discloses the preparation of liver and spleen leukocytes. The male NS3/4A-transgenic (i.e., "NS3/4A-Tg") or wild-type (i.e., "Wt") mice (6-12 weeks old) were killed by $CO_2$ inhalation and their abdomens opened. First, the spleens were excised and placed in 5 ml of serum free AIM-V medium (Gibco-BRL). A 10 ml syringe connected to a 25 G needle was then gently inserted into the portal vein and the liver were perfused with 5-7 ml of PBS (pH 7.4, 20° C.) until the liver turn pale, whereafter it was excised and weighed. In each experiment, 100-125 mg liver tissue was taken for Western blot analysis and immunohistochemistry. The remaining liver tissue was placed in 5 ml of serum free AIM-V medium. Single cell suspension of the spleen was obtained by crushing the organ in medium. The red blood cells of the spleen were lysed by addition of Red blood lysis buffer (Sigma). Cells were then washed and resuspended in 5 ml of medium. The number of cells was determined by trypan blue dye exclusion. The liver cell suspension was prepared by crushing the organ in medium. The cell suspensions were then passed through a 70 µm cell strainer (Falcon). The liver cells were then centrifuged for 15 minutes at 200×g. The supernatant was discarded and the cell pellet was resuspended in 80% isotonic Percoll solution (Amerham-Biosciences) and overlaid with a 40% Percoll solution. The cells were then centrifuged for 20 minutes at 300×g. The cells located at the interphase were collected, washed in medium and thereafter counted by Trypan blue dye exclusion. The spleen cells and liver cells were then processed for flow cytometry as described below.

Example 31

Figure 17A:
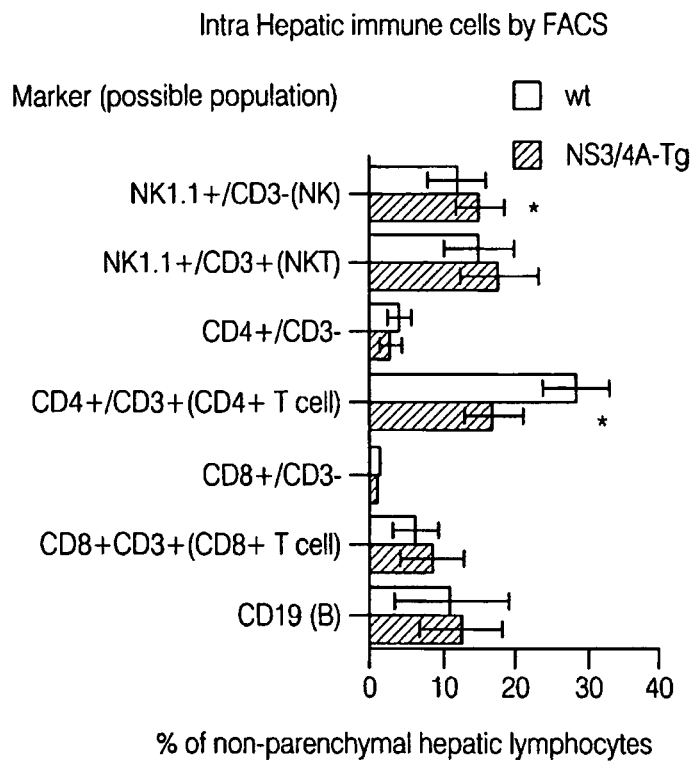
FIG. 17A is a bar graph comparing the intra hepatic immune cells of wild-type mice and NS3/4A transgenic mice.

This example describes the flow cytometry staining and analysis of the above samples. Spleen and liver cells were incubated for 20 min with Fc block (anti-CD16/CD32 clone 2.4G2). The cells were then incubated for 30 minutes on ice with fluorochrome or biotin-conjugated mAbs. After washing, cells stained with biotinylated antibodies were exposed to streptavidin conjugated phycoerythrin (PE) for 30 minutes on ice. The following antibodies (all purchased from BDB) were used: anti-CD16/CD32 clone 2.4G2; FITC conjugated anti-CD3 (145-2C11), anti-CD11c (HL3); PE conjugated anti-NK1.1 (PK136); Biotin conjugated anti-MHC class I-A/1-E (2G9), anti-CD4 (RM4-5); PerCP-Cy5.5 conjugated anti-CD11b (M1/70), anti-CD19 (1D3); APC conjugated anti-CD45 (Ly-5, 30-F11), anti-Ly 6C/G (RB6-8C5), anti-CD8 (53-6.7). Appropriate isotype controls (all from BD Biosciences) were used to check for background staining and for setting gates. A minimum of 50,000 propidium iodine negative (i.e., live cells) leukoocytes (CD45 positive cells backgated on forward/side scatter profile) were analysed per sample. FACS data were aquired on a FACSCalibur (BD Biosciences) and data analysed with CellQuest software (BD Biosciences). The results are shown in FIG. 17A. As can be seen from the results, there is a larger number of CD4+ T cells in the NS3/4A trangenic mice than in the wild-type mice.

Figure 17B:
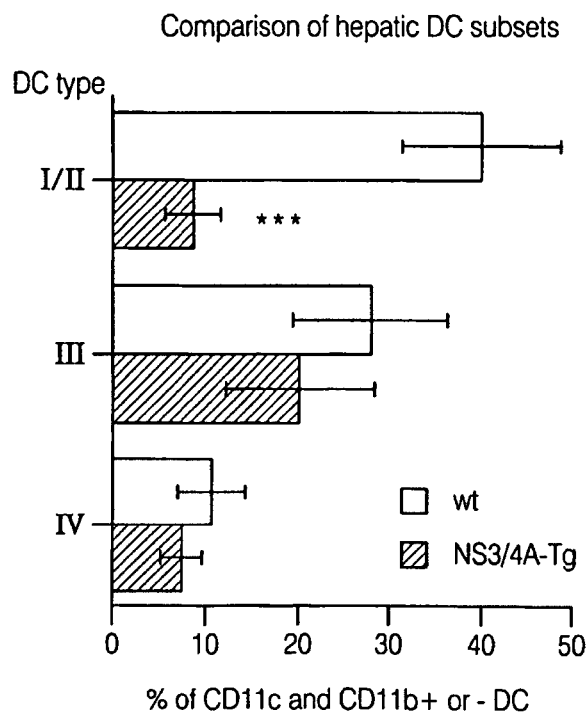
FIG. 17B is a bar graph comparing the various subtypes of hepatic DCs in wild-type and NS3/4A transgenic mice.

Additionally, a FACS analysis was also performed on the dendritic cells to determine the composition of the various subsets, using the antibodies discussed above. As shown in FIG. 17B, NS3/4A transgenic mice had significantly less type I/II cells. The following example describes a method for analyzing RNA levels in a cell.

Example 32

The example describes an Rnase Protection Assay (RPA). Total RNA was extracted from NS3/4A-Tg and wt-mice liver homogenates using TRIzol Reagent (Gibco-BRL) according to the manufacturers protocol. After the total RNA extraction, the RNA was further purified by the use of RNeasy columns (Qiagen) to yield a higher purity of the RNA. All RNA samples used in the Rnase Protection Assay had an $A_{260}/_{280}$ ratio of >1.9. Twenty micrograms of total RNA was assayed with the Multi-probe Rnase Protection Assay (RPA) system using Probe template set mCD-1 according to the manufacturers recommendations (BD Biosciences, Pharmingen, San Diego). In brief, RNA was hybridized overnight with $\{\alpha^{-32}P\}$dUTP labeled mCD-1 ($7\times10^5$ cpm) and digested with RNase A and T1. Rnase-protected probes were purified by phenol-extraction and resolved on a 4.75% denaturating polyacrylamide gel together with non-protected probe and then subjected to autoradiography. Using the undigested probes as markers, a standard curve of migration distance versus nucleotide lengths was plotted. This standard curve was used to identify the "Rnase protected" fragment lengths. The results of these experiments revealed that the amount of CD4+ cells was reduced in NS3/4A transgenic mice compared to wild-type mice.

Example 33

This Example describes several of the approaches used to induce hepatic injury in the NS3/4A-Tg mice and the techniques used to analyze the data. All NS3/4A-Tg or wild-type (Wt) mice used in these experiments were male and/or females between 6-12 weeks old. All groups of mice contained five to ten mice. Comparisons were done in age matched animals, excluding an age dependent difference when comparing groups. For the carbon tetrachloride ($CCl_4$) treatment, $CCl_4$ was diluted in 100 µL olive oil and administered intraperitoneal (i.p.) as a single dose to NS3/4A-Tg and Wt mice. Each mouse was treated with 10 mg (0.5 g/kg) $CCl_4$ (Sigma). Serum from individual mice was collected at various time intervals (12, 24, 48, and 72 hours) after $CCl_4$-treatment by retro-orbital bleeding. Serum alanine aminotransferase (ALT) values were measured to evaluate the extent of liver injury. For the lipopolysaccharide (LPS)/D-galactosamine (D-Gal) treatment, LPS/D-Gal was diluted/dissolved in 100 µL pyrogen-free PBS and administered i.p. as a single dose to NS3/4A-Tg and Wt mice. Each mouse was treated with 0.1 µg (5 µg/kg) LPS (Sigma) and 20 mg D-Gal (Sigma) per mouse. Serum from individual mice was collected at various time intervals (2, 6, 12, 24 and 48 hours) after LPS/D-Gal-treatment by retro-orbital bleeding. Serum ALT values were measured to evaluate the extent of liver injury. Alpha-mouse FAS monoclonal antibody (Jo2) treatment involved Jo2 monoclonal antibody that was diluted in 200 µL pyrogen-free PBS and administered intravenously (i.v.) to NS3/4A-Tg and Wt mice. Each mouse was treated with 2 µg (0.1 mg/kg) Jo2 monoclonal antibody (BD Pharmingen). Serum from individual mice was collected at various time intervals (2, 6, 12, 24, and 48 hours) after Jo2 monoclonal antibody-treatment by retro-orbital bleeding. Serum ALT values were measured to evaluate the extent of liver injury. For recombinant mouse (rm) tumor necrosis factor-α (TNF-α)/D-Gal treatment, rm TNF-α/D-Gal was diluted/dissolved in 100 μL pyrogen-free PBS containing 1 mg/mL bovine serum albumin (BSA; Sigma) and administered i.p. as a single dose to NS3/4A-Tg and Wt mice. Each mouse was treated with 0.1 μg (5 μg/kg) or 0.3 μg (15 μg/kg) TNF-α (BD Pharmingen) and 20 mg D-Gal (Sigma) per mouse. Animals were followed for survival after TNF-α/D-Gal-treatment and observed at different time intervals (6, 9, 24, 48, 72, 96, and 120 hours) after treatment. Serum from individual mice was collected at various time intervals (6, 9, 24, and 48 hours) after TNF-α/D-Gal-treatment by retro-orbital bleeding. Serum ALT values were measured to evaluate the extent of liver injury. For Concanavalin A (i.e., "Con A") treatment, Con A was dissolved in 200 μL pyrogen-free PBS and administered via an i.v. to NS3/4A-Tg and Wt mice. Each mouse was treated with 0.7 mg (35 mg/kg) Con A (Sigma). Serum from individual mice was collected at various time intervals (6, 9, 24, and 48 hours) after Con A-treatment by retro-orbital bleeding. Serum ALT values were measured to evaluate the extent of liver injury.

The results of the experiments above are presented in FIGS. 18A-D. As can be seen, the amount of liver damage in the wild-type mice in response to $CCL_4$, LPS, and TNF-alpha treatment was significantly higher than the amount of damage seen in the NS3/4A transgenic mice livers. The damage due to FAS treatment was approximately equivalent between wild-type and NS3/4A transgenics, however. The following Example describes how to determine proteins or pathways through which NS3/4A can interact to result in a phenotype or a disease symptom.

Example 34

This Example describes a method for analyzing the role of LPS in IFN-Induced Jak-STAT Signalling. In this set of experiments, aged-matched male NS3/4A-Tg and wild-type mice (6-12 weeks old) were used. Groups of 6 mice were either left untreated, injected i.p. with: LPS (0.2 μg/mouse)/D-Gal (20 mg/mouse), recombinant murine IFNα (rmIFNα; 1000 U/g mouse body weight; Sigma), or recombinant murine IFNγ (rmIFNγ; 10 μg/mouse; Sigma). The mice were sacrified 20, 40, and 80 minutes after injections. Whole cell extracts, cytoplasmic and nuclear extracts were prepared from liver cells as described below. Whole liver cell extracts and cytoplasmic/nuclear cell extracts were obtained from the same liver lobe throughout all experiments.

Whole liver cell extracts were generated by homogenizing the liver tissue sample in RIPA buffer (0.15 M NaCl, 50 mM Tris, 1% Triton-X 100, 1% Na-deoxycholate, 1% SDS, 0.2 mM PMSF, 1 mM $Na_3VO_4$, and 0.5 mM DTT). The homogenates were then incubated on ice for 20 minutes and centrifuged 12,000×g for 2 minutes. The supernatant was collected and stored at −80° C. until used in Western blot analysis.

Cytoplasmic/nuclear extracts were generated by a short homogenization on ice of the liver tissue sample in buffer A (10 mM HEPES-KOH pH 7.9, 1.5 mM $MgCl_2$, 10 mM KCl, 0.2 mM PMSF, 1 mM $Na_3VO_4$, and 0.5 mM DTT). The homogenates were the incubated on ice for 10 minutes, and then subsequently centrifuged for 2 minutes, 14.000×g at 4° C. The supernatant, containing the cytoplasmic cell fraction, was collected and stored at −80° C. until used in Western blot analysis. The remaining pellet was washed once with PBS containing 1 mM $Na_3VO_4$. Thereafter, the pellet was re-suspended in buffer C (20 mM HEPES-KOH pH 7.9, 1.5 mM $MgCl_2$, 420 mM NaCl, 0.2 mM EDTA pH 8.0, 25% Glycerol, 0.2 mM PMSF, 1 mM $Na_3VO_4$, and 0.5 mM DTT) by vortexing. The homogenate was incubated on ice for 30 minutes, then centrifuged for 2 minutes, 14.000×g at 4° C. The supernatant, containing the nuclear cell fraction, was collected and stored at −80° C. until used in Western blot analysis.

To analyze the liver extracts for the presence of HCV NS3/4A protein, the whole cell extract were immunoprecipitated and analysed by Western blot. For detections of IFN-induced signalling molecules; a total of 60 μg cytoplasmic or nuclear protein per sample was loaded onto a 4-12% SDS-PAGE gel. Membranes were probed with α-STAT1 (BD Biosciences), α-STAT2, α-STAT1pTyr (Upstate, Waltham, USA), α-STAT2pTyr, α-SOCS1 (Imgenex, San Diego, USA), α-IRF-3, α-TC-PTP, α-PP2Ac, and Histone 2B. Proteins were detected using HRP-conjugated secondary antibodies and visualized using a chemiluminescent detection kit (ECL Plus, Amersham Biosciences).

Treatment with LPS induced a reduction of the activation of nuclear phosphorylated STAT1 and STAT2 in the NS3/4A-Tg liver cells, as compared to liver cells from wild-type mice. Although the basal levels of SOCS1 were higher in the NS3/4A-Tg mice than wild-type mice, LPS treatment induced comparable levels of SOCS1 in non-transgenic and transgenic mice. Finally, LPS treatment induced PP2A activation in the NS3/4A transgenic mice but not in the non-transgenic mice. The results of these experiments are presented in FIG. 18E.

Following IFNα treatment, it was noted that nuclear IRF3 levels were reduced in the NS3/4A-Tg mice. It was again noted that the NS3/4A-transgenic mice had increased basal levels of SOCS1, and that IFNα treatment induced increased levels of SOCS1 as compared to non-transgenic mice. Treatment with gamma IFN resulted in a delay in the activation of nuclear STAT1. However, no other marker seemed to be significantly impaired after IFNγ treatment. The results of this Western blot analysis are presented in FIGS. 18F and 18G. The following Example discusses how an inhibitor or HCV treatment can be tested using the NS3/4A transgenic mouse.

Example 35

This Example discloses a method for administering and testing a p38 inhibitor, SB203580. This protocol can be used to test various candidate compounds to identify molelcules that inhibit p38 MAP kinase. These compounds and other kinase inhibitors, in particular a p38 kinase inhibitor, can be incorporated into a pharmaceutical that is formulated for human administration and said pharmaceuticals can be provided to a subject in need of an agent that inhibits HCV replication and infection. In some embodiments, the inhibition of HCV replication in said subject is measured before and/or after providing said kinase inhibitor. Accordingly, methods of treating and preventing HCV replication and/or infection are provided whereby a subject in need of an agent that inhibits HCV replication and/or infection is provided a kinase inhibitor (e.g., a p38 kinase inhibitor).

Figure 19B:
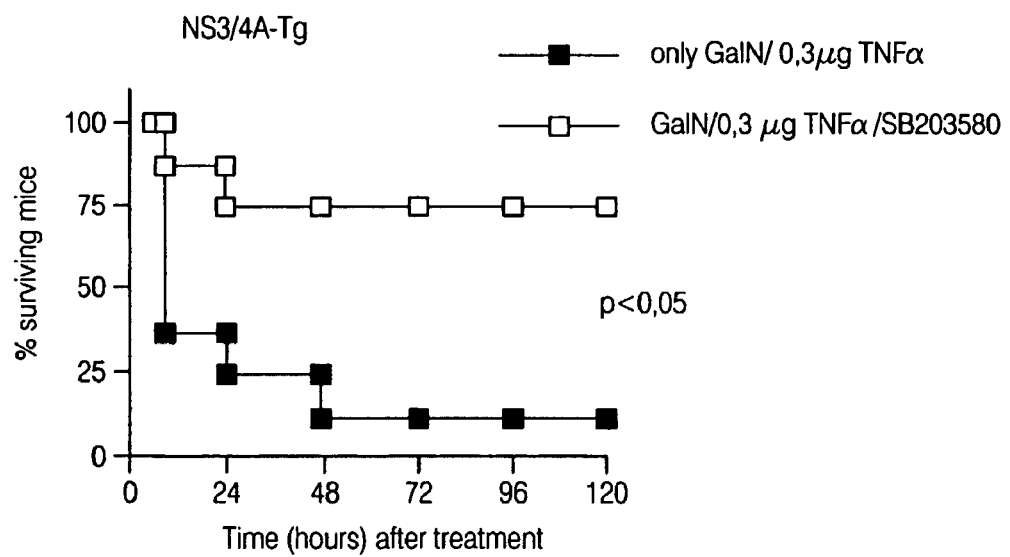
FIG. 19B is a graph showing the percent survival of NS3/4A transgenic mice after administration of TNF-alpha in the presence or absence of a p38 MAP kinase inhibitor.
Figure 19C:
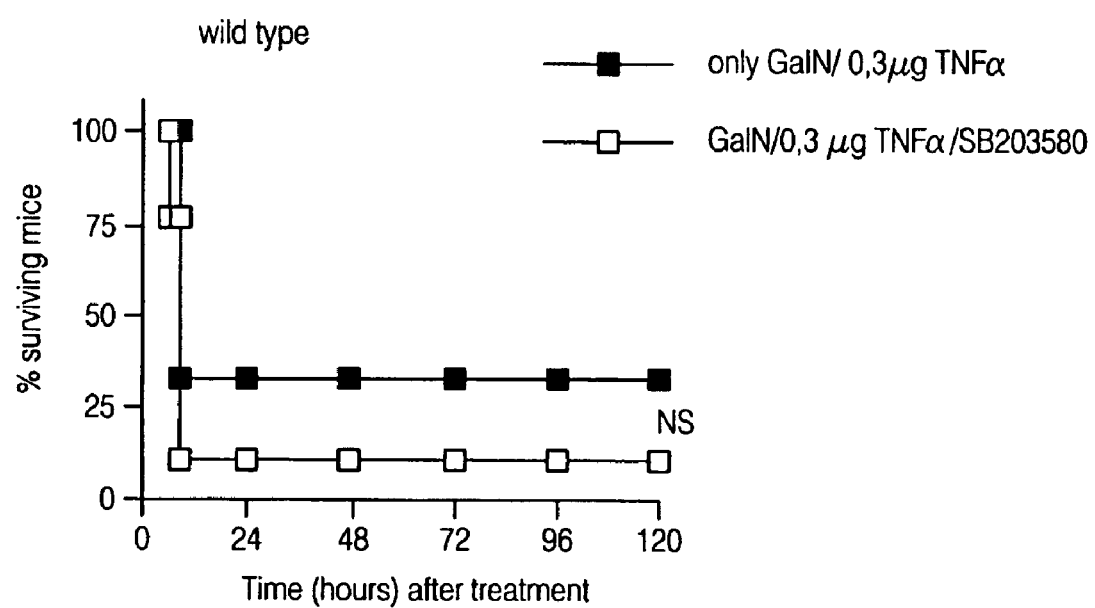
FIG. 19C is a graph showing the percent survival of wild-type mice after administration of TNF-alpha in the presence or absence of a p38 Map kinase inhibitor.

SB203580 (Calbiochem) was dissolved/diluted in sterile $dH_2O$ and administered to mice intra orally (i.o.). NS3/4A-Tg and Wt mice were pre-treated with 0.5 mg (25 mg/kg) SB203580 thirty minutes prior to challenge with rm TNF-α/D-Gal. Animals were followed for survival after TNF-α/D-Gal-treatment and observed at different time intervals (6, 9, 24, 48, 72, 96, and 120 hours) after treatment. The results are provided in FIGS. 19A through 19C. As can be seen in the graphs, while TNF alpha induced death in wild-type mice (e.g., at wild-type lethal doses), the compound did not kill NS3/4A transgenic mice at doses that were lethal for wild-type mice. As shown in FIG. 19B, however, when the p38 inhibitor SB203580 was provided to the NS3/4A transgenic mice the mice died, indicating that the TNF-alpha resitant phenotype of the transgenic mice had reverted to TNF-alpha sensitive phenotype seen with the wild-type mice. Additionally, as shown in FIG. 19C, the addition of SB203580 had no significant (NS denotes "not significant") impact on the survival rate of wild-type mice that have been provided TNF-alpha. The following Example teaches how the above data were statistically analyzed.

Example 36

This Example demonstrates how the data were analysed. Student- and Fisher's t-test were used for frequency analysis and Mann-Whitney U-test was used for comparing values from the two groups. For calculations of repeated measurements the area under the curve (AUC) and analysis of variance (ANOVA) was used. The calculations were performed using the Macintosh version of the StatView software (version 5.0).

As discussed above, NS3/4A-Tg mice almost completely lacked the spontaneous inflammatory foci. This indicated that the hepatic expression of NS3/4A interferes with the hepatic immunity. An extensive analysis of the intra-hepatic immune cell population revealed that the livers from the NS3/4A-Tg mice had reduced amounts of CD4+ T cells and plasmacytoide-like DCs. This is consistent with the absence of inflammatory foci and indicated that these mice have a functional deficit in the hepatic immunity. Transgenic mice were then treated with different agents that activate the hepatic immunity by different signal transduction pathways. These experiments revealed that the major immune defect was related to TNF-α, as evidenced by a reduced sensitivity and increased survival after treatment with $CCl_4$, LPS, and TNF-α. The transgenic mice did not show an altered sensitivity to FAS-mediated liver damage. Thus, the altered hepatic subsets of immune cells was accompanied by a reduced sensitivity to TNF-α-mediated liver damage. It appears that proteins other than NS3/4A are involved in this inhibition.

The reduced sensitivity to TNF-α signalling pathways in the NS3/4A-transgenic mice was explored on the molecular level. LPS treatment induced lower levels of phosphorylated STAT1 and STAT2 in the transgenic livers, as well as, increased levels of PP2A. This is fully consistent with the reduced sensitivity of TNF-α and with the observations from one of the full length HCV-transgenic linages. It was noted that the NS3/4A-transgenic mice had increased baseline levels of SOCS1, as well as, increased levels of SOCS1 and reduced levels of IRF3 in response to IFNα. Thus, the proposed inhibition of IRF3 could also be observed in vivo in the NS3/4A-Tg mice.

The HCV NS3/4A complex is involved in interfering with the hepatic immunity on many levels. The HCV NS3/4A complex alters the hepatic subsets of CD4+ T cells and DCs. Moreover, these findings are consistent with the previously observed inhibition of IFN-signalling in vitro and in vivo. In addition, it was found that the NS3/4A-transgenic mice also have an impaired functionality of the hepatic immunity mainly related to a reduced response to TNF-α-mediated signalling pathways.

One finding is the clear modulation of the response to exogenous TNF-alpha in the NS3/4A-transgenic mice. It was shown that hepatic expression of NS3/4A induces a reduced response to TNF-alpha-TNFR1 mediated signalling since the NS3/4A transgenic mice were resistant to liver-directed TNF-alpha. This resistance could effectively be reverted by a simultaneous administration of an inhibitor of the p38 MAP kinase.

In light of the above results, NS3/4A can either up-regulate signalling through the MKK3/6-p38 pathway, inhibit signalling through the FADD or JNK pathways, or operate through both pathways. NS3/4A can also proteolytically cleave one or more proteins related to signalling, or that the NS3/4A helicase/NTPase activity may interfere with the kinases, or other signal molecules. Also, albeit less likely, the p38 inhibitor can also affect the NS3/4A complex. A summary of some of these pathaways, and how NS3/4A can interact with these pathways in light of the current data is presented in FIG. 20.

Example 37

A general method for screening for agents that block p38 can be similar to that employed in Example 35, above. First, a candidate p38 inhibitor (agent, medicament, treatment, etc.) is administered to a NS3/4A transgenic mouse. Next, the NS3/4A transgenic mouse is provided a wild-type lethal amount of TNF-alpha. (In some embodiments this order can be reversed.) An example of an amount is a dose sufficient to kill 50% of the wild-type mice receiving it. Indication of a successful p38 inhibitor can be observed via observing the entire mouse (i.e., mouse death will demonstrate a p38 inhibitor), or, alternatively, on the level of tissue or cell death (via the procedures described above, for example). As a control, a wild-type mouse is administered the candidate p38 inhibitor to make certain that the candidate p38 inhibitor is killing the NS3/4A-Tg mouse in a manner relating to an effect from the NS3/4A protein expressed. The candidate p38 inhibitor, when applied to a wild-type mouse in amounts sufficient to reduce p38 activity, will not kill the wild-type mouse. Furthermore, a positive control with SB203580 and two negative controls, using TNF-alpha in a wild-type mouse and in a NS3/4A transgenic mouse can be used for comparisons as well, especially if protein levels are to be compared. The next Example discusses how the general method above can be used for discovering agents or drugs that treat or prevent HCV.

Example 38

The general method for screening for candidate p38 inhibitors can also be used to screen for agents to treat or prevent HCV. The procedure is similar to that described in the Examples above. Agents that make a NS3/4A mouse react to TNF-alpha in the same manner that a wild-type mouse reacts to TNF-alpha are selected as HCV treatments. These selected treatments can then be examined with more traditional and routine techniques known to one of skill in the art to determine how effective they are in preventing or treating HCV. Unlike the example above, candidate HCV treatments can include any compound that results in the reversion of the phenotype to a wild-type phenotype. In other words, a HCV treatment can function at a level beneath a p38 kinase, for example by inhibiting later steps in a pathway.

Example 39

This Example demonstrates how other proteins involved in the NS3/4A phenotype can be elucidated. The method is similar to Example 35 above, except an alternative inhibitor or enhacer to a different protein (i.e., SOCS1) is administered.

NS3/4A-Tg and Wt mice are administered SOCS1 siRNA prior to challenge with rm TNF-α/D-Gal. Animals are followed for survival after TNF-α/D-Gal-treatment and observed at different time intervals (6, 9, 24, 48, 72, 96, and 120 hours) after treatment. Additional amounts of SOCS1 siRNA can be administered to the animals. TNF-alpha can typically induce death in wild-type mice and will not be able to do so for the NS3/4A transgenics at a similar dose. However, the addition of the SOCS1 siRNA to the transgenic mice makes the NS3/4A transgenic mice again susceptible to the death inducing properties of TNF-alpha.

Example 40

A patient at risk of HCV symptoms is identified by routine methods (e.g., external symptoms, blood tests, lifestyle, etc.). The patient is administered an amount of an HCV treatment, as identified above, based on the particular patient and the severity of the HCV symptoms. Following a repeated course of treatment, if required, the patient's HCV related symptoms are reduced. In some applications, the reduction of viral lode or another indicator for HCV infection is measured.

Example 41

A patient in need of treatment of symptoms is identified by routine methods. The patient is administered an amount of a p38 inhibitor, as identified above, based on the particular patient and the severity of the HCV symptoms. Following a repeated course of treatment, if required, the patient's HCV related symptoms are reduced. In some applications, the reduction of viral lode or another indicator for HCV infection is measured.

Example 42

A patient in need of treatment of HCV s is identified by routine methods, as above. The patient is administered an amount of a SOCS1 inhibitor, as identified above, based on the particular patient and the severity of the HCV symptoms. Following a repeated course of treatment, if required, the patient's HCV related symptoms are reduced. In some applications, the reduction of viral lode or another indicator for HCV infection is measured.

Example 43

A patient in need of treatment of HCV related complications is identified by routine methods. The patient is administered an amount of SB203580, based on the particular patient and the severity of the HCV symptoms. Following a repeated course of treatment, if required, the patient's HCV related symptoms are reduced. In some applications, the reduction of viral lode or another indicator for HCV infection is measured. The next example describes more transgenic organisms that contain the constructs described herein.

Example 44

A full-length PADSI NS3/4A complementary DNA (cDNA) clone from a HCV genotype 1b infected patient will be isolated as described in Lazdina et al. (2001). The PADSI NS3/4A (PADSI NS3/4A) gene fragment, corresponding to the amino acids 1026 to 1711 encompassing the NS3 and NS4A as well as a luciferase gene connected to a secretory signal will be attached to the end of the NS3/4A construct at the cleavage site. This will be inserted into the BamHI and EcoRI sites of pMUP-11AS plasmid. A fragment containing the MUP promoter (Held et al. 1989) and NS3/4A (HindIII to EcoRI) will be excised and cloned into the pVAX1 (Invitrogen, San Diego) expression vector. Using HindIII and SwaI sites the MUP promoter, PADSI NS3/4A fragment, and BGH polyadenylation signal will be excised from the pVAX1 vector to generate the transcriptional unit to be used for microinjection, designated pMUP-PADSI NS3/4A (illustrated in FIG. 14B). The entire pMUP-PADSI NS3/4A-BGH polyadenylation signal construct will be sequenced prior to microinjection to confirm correct sequence.

The purified transgene construct will be microinjected into fertilized oocytes from C57BL/6 (H-$2^b$)×CBA (H-$2^k$) mice. Potential founder mice will be analyzed for the presence of transgene by polymerase chain reaction (PCR) and Southern blot of genomic tail DNA. For detection of NS3/4A by PCR, specific outer primers will be used; for example, sense primer (5'-CCT GAA TTC ATG GCG CCT ATC ACG GCC TAT-3'; SEQ ID. NO.: 41) and antisense primer (5'-CCG TCT AGA TCA GCA CTC TTC CAT TTC ATC-3) (SEQ ID. NO.: 42) and inner primers; for example, sense primer (5'-GCAT-GCTCCCACCGGCAGCGGTAAGAG-3'; SEQ ID. NO.: 43) and antisense primer (5'-CGCAGAGGACAGACGAGT-CAAACATGC-3'; SEQ ID. NO.: 44). Additionally, since the mice will be expressing luciferase, detection of incorporation of the gene can be done by probes for luciferase, or by looking for fluorescence at the luciferase emission spectra. The next section describes examples of methods by which the above mentioned transgenic animal can be used to test candidate reagents for their ability to inhibit the NS3 protease.

Example 45

This example demonstrates one example of how the negative PADSI construct can be used to screen for NS3 protease inhibitors. A PADSI construct as shown in FIG. 14B is created. The detectable marker is luciferase. A transgenic mouse expressing the PADSI construct is then generated. The amount of detectable marker in the blood system of the transgenic mouse is detected. Following this, various candidate NS3 protease inhibitors are administered to the transgenic mouse and the presence of the detectable marker in the venous blood is detected through the surface of the organism via a CCD. A decrease in the level of detectable marker will indicate that one of the candidate protease inhibitors is actually an effective protease inhibitor.

Example 46

This example describes how the positive PADSI construct can be used to screen for NS3 protease inhibitors. A PADSI construct, as shown in FIG. 14C, is created. In particular, the construct shown in FIG. 14D is used. The detectable marker is luciferase. A NS3 transgenic mouse is created, as described herein. The amount of detectable marker in the blood system of the transgenic mouse is detected. Then, the positive PADSI construct is delivered, through approaches known in the art, to the transgenic mouse so that there are positive PADSI protein constructs in the liver cells of the NS3 transgenic mouse. Following this, various candidate NS3 protease inhibitors are administered to the transgenic mouse and the presence of the detectable marker in the venous blood is detected through the surface of the organism via a CCD. An increase in the level of detectable marker will indicate that one of the candidate protease inhibitors is actually an effective protease inhibitor. As shown in the following example, there is also a considerable benefit to be had with the application of ribavirin with the coNS3/4A peptides.

Example 47

Figures 21A, 21B:
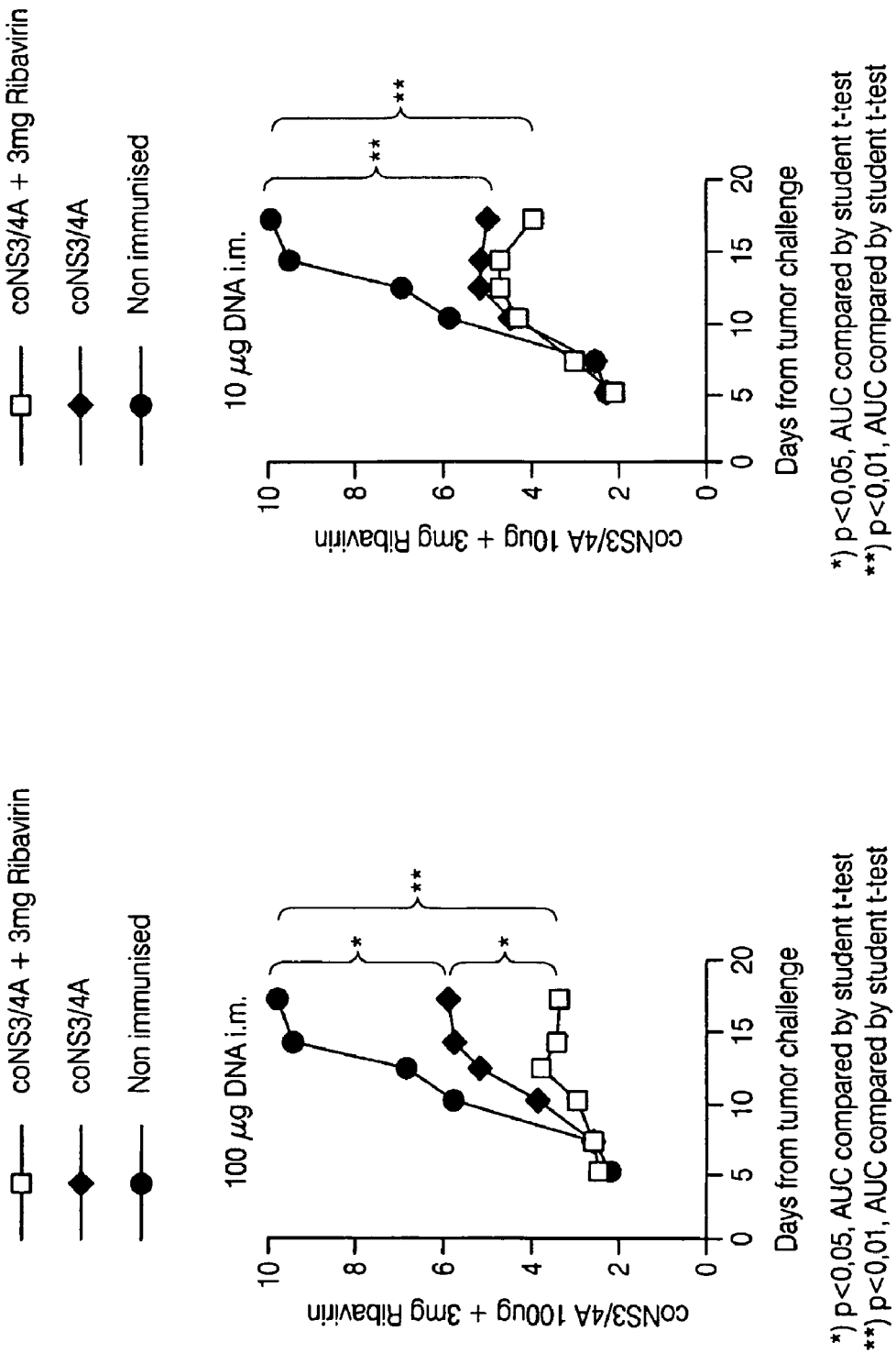
FIG. 21A is a graph showing the effect of an adjuvant with 100 micrograms of coNS3/4A.
FIG. 21B is a graph showing the effect of an adjuvant with 10 micrograms of coNS3/4A.
Figure 21C:
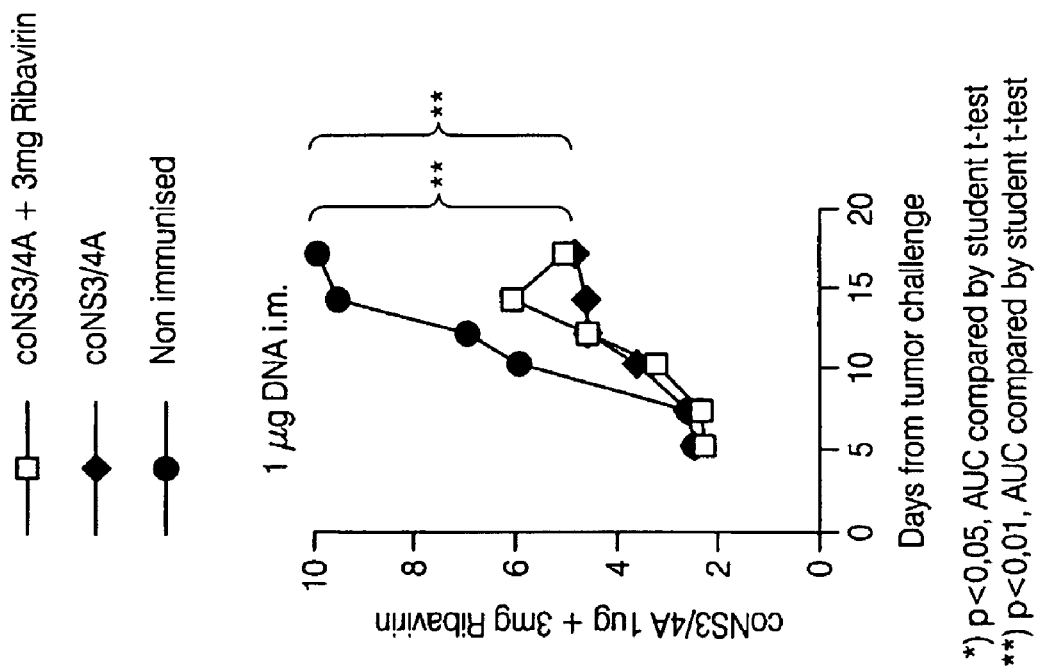
FIG. 21C is a graph showing the effect of an adjuvant with 1 microgram of coNS3/4A.

This example demonstrates the effectiveness of the adjuvant ribavirin in reducing the size of a tumor when combined with the codon optimized form of the NS3/4A peptides. In a method similar to that shown in Examples 10 and 15, described above involving tumor challenge experiments, the effectiveness of ribavirin on coNS3/4A in mice was also examined through a tumor challenge model. Either 100, 10, or 1 micrograms of coNS3/4A were injected into sets of 10 Balb/c mice. In each set, some mice were immunized with coNS3/4A alone, some were immunized with 3 mg ribavirin and coNS3/4A, and some were not immunized at all. Two weeks after the single immunization the mice were challenged with 1 million NS3/4A-expressing SP2/0 cells. Tumor size was then measured following this challenge to determine how well the initial immunization primed the immune system against cells expressing coNS3/4A. As can be seen in FIGS. 21A-C, the presence of ribavirin dramatically increased the effectiveness of the initial immunization. Additionally, it did so in a coNS3/4A dose dependent manner as low doses of the coNS3/4A construct displayed little effect (as shown in FIG. 21C), while large doses of coNS3/4A, with the same amount of ribavirin, showed substantially great effect (as shown in FIGS. 21B and 21C).

All references identified herein are hereby expressly incorporated by reference in their entireties. Definitions supplied herein control over definition incorporated by reference. Although the invention has been described with reference to embodiments and examples, it should be understood that various modifications can be made without departing from the spirit of the invention. Accordingly, the invention is limited only by the following claims.

What is claimed is:

1. A transgenic mouse whose genome comprises a transgene comprising a nucleic acid sequence encoding hepatitis C virus (HCV) nonstructural protein 3 (NS3) operably linked to a promoter, wherein the mouse exhibits reduced sensitivity to TNF-alpha as compared to a wild-type type mouse of the same variety, and wherein the mouse does not comprise a nucleic acid sequence encoding an HCV core protein, structural protein E1 (E1), structural protein E2 (E2), nonstructural protein 2 (NS2), nonstructural protein 4B (NS4B), nonstructural protein 5a (NS5A) or nonstructural protein 5B (NS5B).

2. The transgenic mouse of claim 1, further comprising a nucleic acid sequence encoding a HCV nonstructural protein 4A (NS4A).

3. The transgenic mouse of claim 1, wherein the promoter is a mouse major urinary promoter (MUP).

4. The transgenic mouse of claim 1, wherein the transgene further comprises a NS3 protease cleavage site operably linked to the nucleic acid sequence encoding HCV NS3.

5. The transgenic mouse of claim 1, wherein the transgene further comprises a nucleic acid sequence encoding a secretory signal operably linked to the nucleic acid sequence encoding HCV NS3.

6. The transgenic mouse of claim 1, wherein said mouse has an increased sensitivity to TNF-alpha after contact with an inhibitor of a p38 MAP kinase, as compared to a transgenic mouse of claim 1 that has not been contacted with said inhibitor.

7. The transgenic mouse of claim 6, wherein the inhibitor is SB203580.

8. The transgenic mouse of claim 1, wherein said mouse comprises at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 micrograms NS3 protein per gram of liver tissue.

9. The transgenic mouse of claim 1, wherein said mouse comprises more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 micrograms NS3 protein per gram of liver tissue.

10. The transgenic mouse of claim 1, wherein said mouse comprises between about 0.1-1.0, 0.5-1.5, 1.0-2.0, 1.5-2.5, 2.0-3.0, 2.5-3.5, 3.0-4.0, 3.5-4.5, 4.0-5.0, 4.5-5.5, 5.0-6.0, 5.5-6.5, 6.0-7.0, 6.5-7.5, 7.0-8.0, 7.7-8.5, 8.0-9.0, 8.5-9.5 or 9.0-10.0 micrograms NS3 protein per gram of liver tissue.

11. A method of using transgenic mouse to identify a compound that inhibits HCV replication comprising:
providing the transgenic mouse of claim 1;
contacting said transgenic mouse with a compound; and
analyzing the expression of NS3, NS3 protease activity, or the sensitivity of said transgenic mouse to TNF-alpha, after contact with said compound, whereby said compound that inhibits HCV replication is identified by the ability of said compound to inhibit expression of NS3, inhibit protease activity of NS3, or restore TNF-alpha sensitivity in said transgenic mouse.

12. A mouse embryonic stem (ES) cell comprising a transgene comprising a nucleic acid sequence encoding hepatitis C virus (HCV) nonstructural protein 3 (NS3) operably linked to a mouse major urinary promoter (MUP), and wherein the ES cell does not comprise a nucleic acid sequence encoding an HCV core protein, structural protein E1 (E1), structural protein E2 (E2), nonstructural protein 2 (NS2), nonstructural protein 4B (NS4B), nonstructural protein 5a (NS5A) or nonstructural protein 5B (NS5B).

13. The mouse ES cell of claim 12, further comprising a nucleic acid sequence encoding a HCV nonstructural protein 4A (NS4A).

* * * * *

UNITED STATES PATENT AND TRADEMARK OFFICE
CERTIFICATE OF CORRECTION

PATENT NO. : 7,566,812 B2
APPLICATION NO. : 11/660878
DATED : July 28, 2009
INVENTOR(S) : Sällberg et al.

It is certified that error appears in the above-identified patent and that said Letters Patent is hereby corrected as shown below:

On the Title Page Item (74), change "or" to --of--.

Sheet 4 of 30, Line 2, change "expressiong" to --expressing--.

Sheet 5 of 30, Line 2, change "expressiong" to --expressing--.

Column 5, Line 22, change "months ten" to --months, ten--.

Column 6, Lines 56-57, delete "The PADSI acid..........................for the PADSI nucleic acid."

And insert the same on col. 6, line 55, after "signal." as the continuation of the same paragraph.

Column 23, Line 34, change "chlorformate" to --chloroformate--.

Column 23, Line 45, change "J" to --J.--.

Column 24, Line 48, change "dedependent" to --dependent--.

Column 24, Line 62, change "constrcuts" to --constructs--.

Column 27, Line 55, change "itterative" to --iterative--.

Column 35, Line 47, change "infection" to --infection.--.

Column 37, Line 47, change "trancription" to --transcription--.

Column 48, Line 38, change "particulary" to --particularly--.

Column 50, Line 52, change "Ig," to --1 g,--.

Column 50, Line 53, change "5," to --5 g,--.

Column 61, Line 9, change "H-2 $D^b$" to --H-2$D^b$--.

Column 62, Line 29, change "MgCl2)." to --MgCl$_2$).--.

Column 69, Line 64, change "spleenocytes" to --splenocytes--.

Column 70, Line 7, change "H-2 $D^b$" to --H-2$D^b$--.

Column 70, Line 8, change "H-2 $D^b$" to --H-2$D^b$--.

Signed and Sealed this

Fifteenth Day of June, 2010

David J. Kappos
*Director of the United States Patent and Trademark Office*

Column 70, Line 28, change "H-2 $D^b$:Ig" to --H-2$D^b$:Ig--.

Column 70, Line 32, change "anti-H-2 Kb" to --anti-H-2$K^b$--.

Column 70, Line 40, change "H-2 $D^b$:Ig" to --H-2$D^b$:Ig--.

Column 70, Line 43, change "H-2 $D^b$:Ig" to --H-2$D^b$:Ig--.

Column 70, Line 59, change "H-2 $D^b$:Ig" to --H-2$D^b$:Ig--.

Column 71, Line 6, change "H-2b" to --H-$2^b$--.

Column 72, Line 34, change "evalutate" to --evaluate--.

Column 73, Line 34, change "I" to --1--.

Column 74, Line 6, change "mouse" to --mouse.--.

Column 74, Line 22, change "method" to --method.--.

Column 78, Line 26, change "biochemcial" to --biochemical--.

Column 79, Line 50, change "detectabe" to --detectable--.

Column 81, Line 57, change "1-E" to --I-E--.

Column 81, Line 65, change "aquired" to --acquired--.

Column 83, Line 41, change "untreated," to --un-treated,--.

Column 164, Line 16, in Claim 11, after "using" insert --a--.

SEQUENCE LISTING

```
<160> NUMBER OF SEQ ID NOS: 80

<210> SEQ ID NO 1
<211> LENGTH: 2061
<212> TYPE: DNA
<213> ORGANISM: Artificial Sequence
<220> FEATURE:
<223> OTHER INFORMATION: Hepatitis C virus NS3/4A coding region

<400> SEQUENCE: 1
atggcgccta tcacggccta tgcccagcag acaaggggcc ttttgggatg cataatcacc      60
agcttgaccg gccgggacaa aaaccaggtg gagggtgagg ttcagatcgt gtcaactgct     120
gcccagactt tcttggcaac ctgcattaac ggggtgtgtt ggactgtcta ccatggagcc     180
ggaacaagga ccattgcgtc acctaagggt cctgttatcc agatgtacac caatgtggac     240
caagacctcg taggctggcc cgctccccaa ggtgcccgct cattaacacc atgcacttgc     300
ggctcctcgg acctttacct ggtcacgagg cacgccgatg tcattcctgt gcgccgacgg     360
ggtgatggca ggggcagcct gctttcgccc cggcctatct cttacttgaa aggctcctcg     420
ggaggccctc tgctgtgccc cgcaggacat gccgtaggca tattcagagc cgcggtatgc     480
acccgtggag tggctaaggc ggtggacttc atccccgtag agagcttaga gacaaccatg     540
aggtccccgg tgttctcaga caactcctcc ccaccagcag tgcccagag ctaccaagtg      600 gcccacctgc atgctcccac cggcagcggt aagagcacca aggtcccggc cgcatacgca     660
gctcagggct acaaggtgct ggtgctcaac ccctccgttg ctgcaacaat gggctttggt     720
gcttacatgt ccaaggccca tgggattgat cctaacatca ggactggggt gaggacaatt     780
actactggca gcccgatcac gtattccacc tacggcaagt tccttgccga cggcgggtgt     840 tcaggggtg cttatgacat aataatttgt gacgagtgcc actccacgga tgcaacatcc     900
atcttgggca ttggcactgt ccttgaccaa gcagagaccg cggggcgag actgactgtg     960 ctcgccaccg ctacccctcc gggctccgtc actgtgcccc atcctaacat cgaggaggtt    1020
gctctgtcca ctaccggaga gatcccctt tatggcaagg ctattcccct tgaagcaatt    1080 aagggggga gacatctcat cttctgccac tcaaagaaga gtgcgacga gctcgccgca    1140 aaactggtcg cgttgggcgt caatgccgtg gcttactacc gcggccttga tgtgtccgtc    1200
atcccgacca gtggtgacgt tgtcgtcgtg gcaactgacg ccctcatgac cggctttacc    1260
ggcgacttcg attcggtgat agactgcaac acgtgtgtca cccagacagt cgacttcagc    1320
```

-continued

```
cttgaccota ccttcaccat tgagacaatc acgcttcccc aggatgctgt ctcccgtact    1380
caacgtcggg gtaggactgg cagagggaag ccaggcatct acagatttgt ggcaccgggg    1440
gagcgtcctt ctggcatgtt tgactcgtct gtcctctgcg agtgctatga cgcgggttgt    1500
gcttggtatg agcttacgcc cgccgagacc acagttaggc tacgagcata catgaacacc    1560
ccgggacttc ccgtgtgcca agaccatctt gaattttggg agggcgtctt tacgggtctc    1620
acccacatag acgcccactt cctatcccag acaaagcaga gtggggaaaa ccttccctat    1680
ctggtagcgt accaagccac cgtgtgcgct agagctcaag cccctccccc gtcgtgggac    1740
cagatgtgga agtgcttgat ccgtctcaag cccaccctcc atgggccaac acctctgcta    1800
tatagactgg gcgctgtcca gaatgaagtc accctgacgc acccagtcac caagtatatc    1860
atgacatgta tgtcggctga cctggaggtc gtcacgagta cctgggtgct cgttggcggc    1920
gttctggctg cttttgccgc gtattgccta tccacaggct gcgtggtcat agtaggtagg    1980
attgtcttgt ccggaaagcc ggcaatcata cccgacaggg aagtcctcta ccgggagttc    2040
gatgaaatgg aagagtgctg a                                               2061
```

<210> SEQ ID NO 2
<211> LENGTH: 686
<212> TYPE: PRT
<213> ORGANISM: Artificial Sequence
<220> FEATURE:
<223> OTHER INFORMATION: Hepatitis C virus NS3/4A peptide

<400> SEQUENCE: 2

```
Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
     50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220
```

-continued

```
Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
            245                 250                 255

Val Arg Thr Ile Thr Thr Gly Ser Pro Ile Thr Tyr Ser Thr Tyr Gly
        260                 265                 270

Lys Phe Leu Ala Asp Gly Gly Cys Ser Gly Gly Ala Tyr Asp Ile Ile
    275                 280                 285

Ile Cys Asp Glu Cys His Ser Thr Asp Ala Thr Ser Ile Leu Gly Ile
290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
```

```
                    645                 650                 655
Ile Val Gly Arg Ile Val Leu Ser Gly Lys Pro Ala Ile Ile Pro Asp
                660                 665                 670

Arg Glu Val Leu Tyr Arg Glu Phe Asp Glu Met Glu Glu Cys
            675                 680                 685

<210> SEQ ID NO 3
<211> LENGTH: 686
<212> TYPE: PRT
<213> ORGANISM: Artificial Sequence
<220> FEATURE:
<223> OTHER INFORMATION: Mutant Hepatitis C virus NS3

```
                  325                 330                 335
Ile Glu Glu Val Ala Leu Ser Thr Thr Gly Glu Ile Pro Phe Tyr Gly
                340                 345                 350
Lys Ala Ile Pro Leu Glu Ala Ile Lys Gly Gly Arg His Leu Ile Phe
            355                 360                 365
Cys His Ser Lys Lys Cys Asp Glu Leu Ala Ala Lys Leu Val Ala
        370                 375                 380
Leu Gly Val Asn Ala Val Ala Tyr Tyr Arg Gly Leu Asp Val Ser Val
    385                 390                 395                 400
Ile Pro Thr Ser Gly Asp Val Val Val Ala Thr Asp Ala Leu Met
                405                 410                 415
Thr Gly Phe Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
            435                 440                 445
Thr Ile Thr Leu Pro Gln Asp Ala Val Ser Arg Thr Gln Arg Arg Gly
    450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
                500                 505                 510
Arg Leu Arg Ala Tyr Met Asn Thr Pro Gly Leu Pro Val Cys Gln Asp
            515                 520                 525
His Leu Glu Phe Trp Glu Gly Val Phe Thr Gly Leu Thr His Ile Asp
        530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
                580                 585                 590
Leu His Gly Pro Thr Pro Leu Leu Tyr Arg Leu Gly Ala Val Gln Asn
            595                 600                 605
Glu Val Thr Leu Thr His Pro Val Thr Lys Tyr Ile Met Thr Cys Met
        610                 615                 620
Ser Ala Asp Leu Glu Val Val Thr Gly Thr Trp Val Leu Val Gly Gly
625                 630                 635                 640
Val Leu Ala Ala Leu Ala Ala Tyr Cys Leu Ser Thr Gly Cys Val Val
                645                 650                 655
Ile Val Gly Arg Ile Val Leu Ser Gly Lys Pro Ala Ile Ile Pro Asp
                660                 665                 670
Arg Glu Val Leu Tyr Arg Glu Phe Asp Glu Met Glu Glu Cys
            675                 680                 685

<210> SEQ ID NO 4
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 4

Met Ala Pro Ile Thr Ala Tyr Ala Gln Gln Thr Arg Gly Leu Leu Gly
```

-continued

```
  1               5                   10                  15
Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
             35                  40                  45

Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
             85                  90                  95

Pro Cys Thr Cys Gly Ser Ser Asp Leu Tyr Leu Val Thr Arg His Ala
             100                 105                 110

Asp Val Ile Pro Val Arg Arg Arg Gly Asp Gly Arg Gly Ser Leu Leu
             115                 120                 125

Ser Pro Arg Pro Ile Ser Tyr Leu Lys Gly Ser Ser Gly Gly Pro Leu
             130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
             165                 170                 175

Glu Thr Thr Met Arg Ser Pro Val Phe Ser Asp Asn Ser Ser Pro Pro
             180                 185                 190

Ala Val Pro Gln Ser Tyr Gln Val Ala His Leu His Ala Pro Thr Gly
             195                 200                 205

Ser Gly Lys Ser Thr Lys Val Pro Ala Ala Tyr Ala Ala Gln Gly Tyr
             210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
             245                 250                 255

Val Arg Thr Ile Thr Thr Gly Ser Pro Ile Thr Tyr Ser Thr Tyr Gly
             260                 265                 270

Lys Phe Leu Ala Asp Gly Gly Cys Ser Gly Gly Ala Tyr Asp Ile Ile
             275                 280                 285

Ile Cys Asp Glu Cys His Ser Thr Asp Ala Thr Ser Ile Leu Gly Ile
             290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
             325                 330                 335

Ile Glu Glu Val Ala Leu Ser Thr Thr Gly Glu Ile Pro Phe Tyr Gly
             340                 345                 350

Lys Ala Ile Pro Leu Glu Ala Ile Lys Gly Gly Arg His Leu Ile Phe
             355                 360                 365

Cys His Ser Lys Lys Lys Cys Asp Glu Leu Ala Ala Lys Leu Val Ala
             370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
             405                 410                 415

Thr Gly Phe Thr Gly Asp Phe Asp Ser Val Ile Asp Cys Asn Thr Cys
             420                 425                 430
```

```
Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
        450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Arg Gly Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 5
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 5

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110
```

-continued

```
Asp Val Ile Pro Val Arg Arg Gly Asp Gly Arg Gly Ser Leu Leu
            115                 120                 125
Ser Pro Arg Pro Ile Ser Tyr Leu Lys Gly Ser Ser Gly Pro Leu
        130                 135                 140
Leu Cys Pro Ala Gly His Ala Val Gly Ile Phe Arg Ala Ala Val Cys
145                 150                 155                 160
Thr Arg Gly Val Ala Lys Ala Val Asp Phe Ile Pro Val Glu Ser Leu
                165                 170                 175
Glu Thr Thr Met Arg Ser Pro Val Phe Ser Asp Asn Ser Ser Pro Pro
                180                 185                 190
Ala Val Pro Gln Ser Tyr Gln Val Ala His Leu His Ala Pro Thr Gly
                195                 200                 205
Ser Gly Lys Ser Thr Lys Val Pro Ala Ala Tyr Ala Ala Gln Gly Tyr
        210                 215                 220
Lys Val Leu Val Leu Asn Pro Ser Val Ala Ala Thr Met Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ser Pro Ile Thr Tyr Ser Thr Tyr Gly
                260                 265                 270
Lys Phe Leu Ala Asp Gly Gly Cys Ser Gly Gly Ala Tyr Asp Ile Ile
        275                 280                 285
Ile Cys Asp Glu Cys His Ser Thr Asp Ala Thr Ser Ile Leu Gly Ile
290                 295                 300
Gly Thr Val Leu Asp Gln Ala Glu Thr Ala Gly Ala Arg Leu Thr Val
305                 310                 315                 320
Leu Ala Thr Ala Thr Pro Pro Gly Ser Val Thr Val Pro His Pro Asn
                325                 330                 335
Ile Glu Glu Val Ala Leu Ser Thr Thr Gly Glu Ile Pro Phe Tyr Gly
                340                 345                 350
Lys Ala Ile Pro Leu Glu Ala Ile Lys Gly Gly Arg His Leu Ile Phe
        355                 360                 365
Cys His Ser Lys Lys Lys Cys Asp Glu Leu Ala Ala Lys Leu Val Ala
        370                 375                 380
Leu Gly Val Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
                405                 410                 415
Thr Gly Phe Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
        435                 440                 445
Thr Ile Thr Leu Pro Gln Asp Ala Val Ser Arg Thr Gln Arg Arg Gly
        450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
                500                 505                 510
Arg Leu Arg Ala Tyr Met Asn Thr Pro Gly Leu Pro Val Cys Gln Asp
        515                 520                 525
```

```
His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
                580                 585                 590

Leu His Gly Pro Thr Pro Leu Leu Tyr Arg Leu Gly Ala Val Gln Asn
                595                 600                 605

Glu Val Thr Leu Thr His Pro Val Thr Lys Tyr Ile Met Thr Cys Met
    610                 615                 620

Ser Ala Asp Leu Glu Val Val Thr Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
                660                 665                 670

Arg Glu Val Leu Tyr Arg Glu Phe Asp Glu Met Glu Glu Cys
                675                 680                 685

<210> SEQ ID NO 6
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 6

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu

-continued

```
Ser Gly Lys Ser Thr Lys Val Pro Ala Ala Tyr Ala Ala Gln Gly Tyr
    210                 215                 220
Lys Val Leu Val Leu Asn Pro Ser Val Ala Ala Thr Met Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ser Pro Ile Thr Tyr Ser Thr Tyr Gly
            260                 265                 270
Lys Phe Leu Ala Asp Gly Gly Cys Ser Gly Gly Ala Tyr Asp Ile Ile
                275                 280                 285
Ile Cys Asp Glu Cys His Ser Thr Asp Ala Thr Ser Ile Leu Gly Ile
    290                 295                 300
Gly Thr Val Leu Asp Gln Ala Glu Thr Ala Gly Ala Arg Leu Thr Val
305                 310                 315                 320
Leu Ala Thr Ala Thr Pro Pro Gly Ser Val Thr Val Pro His Pro Asn
                325                 330                 335
Ile Glu Glu Val Ala Leu Ser Thr Thr Gly Glu Ile Pro Phe Tyr Gly
            340                 345                 350
Lys Ala Ile Pro Leu Glu Ala Ile Lys Gly Gly Arg His Leu Ile Phe
                355                 360                 365
Cys His Ser Lys Lys Lys Cys Asp Glu Leu Ala Ala Lys Leu Val Ala
    370                 375                 380
Leu Gly Val Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
                405                 410                 415
Thr Gly Phe Thr Gly Asp Phe Asp Ser Val Ile Asp Cys Asn Thr Cys
            420                 425                 430
Val Thr Gln Thr Val Asp Phe Ser Leu Asp Pro Thr Phe Thr Ile Glu
                435                 440                 445
Thr Ile Thr Leu Pro Gln Asp Ala Val Ser Arg Thr Gln Arg Arg Gly
    450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
            500                 505                 510
Arg Leu Arg Ala Tyr Met Asn Thr Pro Gly Leu Pro Val Cys Gln Asp
    515                 520                 525
His Leu Glu Phe Trp Glu Gly Val Phe Thr Gly Leu Thr His Ile Asp
530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
                595                 600                 605
Glu Val Thr Leu Thr His Pro Val Thr Lys Tyr Ile Met Thr Cys Met
    610                 615                 620
Ser Ala Asp Leu Glu Val Val Arg Pro Thr Trp Val Leu Val Gly Gly
```

```
                    625                 630                 635                 640
Val Leu Ala Ala Leu Ala Ala Tyr Cys Leu Ser Thr Gly Cys Val Val
                        645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
            675                 680                 685

<210> SEQ ID NO 7
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 7

Met Ala Pro Ile Thr Ala Tyr Ala Gln Gln Thr Arg Gly Leu Leu Gly
 1                5                  10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu Ala Thr Cys
            35                  40                  45

Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
            115                 120                 125

Ser Pro Arg Pro Ile Ser Tyr Leu Lys Gly Ser Ser Gly Gly Pro Leu
        130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
```

|     |     |     |     | 305 |     |     |     | 310 |     |     |     | 315 |     |     |     | 320 |
| --- | --- | --- | --- | --- | --- | --- | --- | --- | --- | --- | --- | --- | --- | --- | --- | --- |
| Leu | Ala | Thr | Ala | Thr | Pro | Pro | Gly | Ser | Val | Thr | Val | Pro | His | Pro | Asn |     |
|     |     |     |     |     | 325 |     |     |     |     | 330 |     |     |     |     | 335 |     |
| Ile | Glu | Glu | Val | Ala | Leu | Ser | Thr | Thr | Gly | Glu | Ile | Pro | Phe | Tyr | Gly |     |
|     |     |     |     | 340 |     |     |     |     | 345 |     |     |     |     | 350 |     |     |
| Lys | Ala | Ile | Pro | Leu | Glu | Ala | Ile | Lys | Gly | Gly | Arg | His | Leu | Ile | Phe |     |
|     |     |     | 355 |     |     |     |     | 360 |     |     |     |     | 365 |     |     |     |
| Cys | His | Ser | Lys | Lys | Lys | Cys | Asp | Glu | Leu | Ala | Ala | Lys | Leu | Val | Ala |     |
|     |     | 370 |     |     |     |     | 375 |     |     |     |     | 380 |     |     |     |     |
| Leu | Gly | Val | Asn | Ala | Val | Ala | Tyr | Tyr | Arg | Gly | Leu | Asp | Val | Ser | Val |     |
| 385 |     |     |     |     | 390 |     |     |     |     | 395 |     |     |     |     | 400 |     |
| Ile | Pro | Thr | Ser | Gly | Asp | Val | Val | Val | Ala | Thr | Asp | Ala | Leu | Met |     |     |
|     |     |     |     | 405 |     |     |     |     | 410 |     |     |     |     | 415 |     |     |
| Thr | Gly | Phe | Thr | Gly | Asp | Phe | Asp | Ser | Val | Ile | Asp | Cys | Asn | Thr | Cys |     |
|     |     |     |     | 420 |     |     |     |     | 425 |     |     |     |     | 430 |     |     |
| Val | Thr | Gln | Thr | Val | Asp | Phe | Ser | Leu | Asp | Pro | Thr | Phe | Thr | Ile | Glu |     |
|     |     |     | 435 |     |     |     |     | 440 |     |     |     |     | 445 |     |     |     |
| Thr | Ile | Thr | Leu | Pro | Gln | Asp | Ala | Val | Ser | Arg | Thr | Gln | Arg | Arg | Gly |     |
|     |     | 450 |     |     |     |     | 455 |     |     |     |     | 460 |     |     |     |     |
| Arg | Thr | Gly | Arg | Gly | Lys | Pro | Gly | Ile | Tyr | Arg | Phe | Val | Ala | Pro | Gly |     |
| 465 |     |     |     |     | 470 |     |     |     |     | 475 |     |     |     |     | 480 |     |
| Glu | Arg | Pro | Ser | Gly | Met | Phe | Asp | Ser | Ser | Val | Leu | Cys | Glu | Cys | Tyr |     |
|     |     |     |     | 485 |     |     |     |     | 490 |     |     |     |     | 495 |     |     |
| Asp | Ala | Gly | Cys | Ala | Trp | Tyr | Glu | Leu | Thr | Pro | Ala | Glu | Thr | Thr | Val |     |
|     |     |     |     | 500 |     |     |     |     | 505 |     |     |     |     | 510 |     |     |
| Arg | Leu | Arg | Ala | Tyr | Met | Asn | Thr | Pro | Gly | Leu | Pro | Val | Cys | Gln | Asp |     |
|     |     |     | 515 |     |     |     |     | 520 |     |     |     |     | 525 |     |     |     |
| His | Leu | Glu | Phe | Trp | Glu | Gly | Val | Phe | Thr | Gly | Leu | Thr | His | Ile | Asp |     |
|     |     | 530 |     |     |     |     | 535 |     |     |     |     | 540 |     |     |     |     |
| Ala | His | Phe | Leu | Ser | Gln | Thr | Lys | Gln | Ser | Gly | Glu | Asn | Leu | Pro | Tyr |     |
| 545 |     |     |     |     | 550 |     |     |     |     | 555 |     |     |     |     | 560 |     |
| Leu | Val | Ala | Tyr | Gln | Ala | Thr | Val | Cys | Ala | Arg | Ala | Gln | Ala | Pro | Pro |     |
|     |     |     |     | 565 |     |     |     |     | 570 |     |     |     |     | 575 |     |     |
| Pro | Ser | Trp | Asp | Gln | Met | Trp | Lys | Cys | Leu | Ile | Arg | Leu | Lys | Pro | Thr |     |
|     |     |     |     | 580 |     |     |     |     | 585 |     |     |     |     | 590 |     |     |
| Leu | His | Gly | Pro | Thr | Pro | Leu | Leu | Tyr | Arg | Leu | Gly | Ala | Val | Gln | Asn |     |
|     |     |     | 595 |     |     |     |     | 600 |     |     |     |     | 605 |     |     |     |
| Glu | Val | Thr | Leu | Thr | His | Pro | Val | Thr | Lys | Tyr | Ile | Met | Thr | Cys | Met |     |
|     |     | 610 |     |     |     |     | 615 |     |     |     |     | 620 |     |     |     |     |
| Ser | Ala | Asp | Leu | Glu | Val | Val | Arg | Pro | Ala | Trp | Val | Leu | Val | Gly | Gly |     |
| 625 |     |     |     |     | 630 |     |     |     |     | 635 |     |     |     |     | 640 |     |
| Val | Leu | Ala | Ala | Leu | Ala | Ala | Tyr | Cys | Leu | Ser | Thr | Gly | Cys | Val | Val |     |
|     |     |     |     | 645 |     |     |     |     | 650 |     |     |     |     | 655 |     |     |
| Ile | Val | Gly | Arg | Ile | Val | Leu | Ser | Gly | Lys | Pro | Ala | Ile | Ile | Pro | Asp |     |
|     |     |     | 660 |     |     |     |     | 665 |     |     |     |     | 670 |     |     |     |
| Arg | Glu | Val | Leu | Tyr | Arg | Glu | Phe | Asp | Glu | Met | Glu | Glu | Cys |     |     |     |
|     |     |     | 675 |     |     |     |     | 680 |     |     |     | 685 |     |     |     |     |

<210> SEQ ID NO 8
<211> LENGTH: 686
<212> TYPE: PRT
<213> ORGANISM: Artificial Sequence
<220> FEATURE:
<223> OTHER INFORMATION: Mutant Hepatitis C virus NS3/4A

```
<400> SEQUENCE: 8

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
            115                 120                 125

Ser Pro Arg Pro Ile Ser Tyr Leu Lys Gly Ser Ser Gly Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
            195                 200                 205

Ser Gly Lys Ser Thr Lys Val Pro Ala Ala Tyr Ala Ala Gln Gly Tyr
            210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ala Thr Ser Ile Leu Gly Ile
            290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
            355                 360                 365

Cys His Ser Lys Lys Lys Cys Asp Glu Leu Ala Ala Lys Leu Val Ala
            370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
            405                 410                 415
```

-continued

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
            450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
            515                 520                 525

His Leu Glu Phe Trp Glu Gly Val Phe Thr Gly Leu Thr His Ile Asp
            530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
            595                 600                 605

Glu Val Thr Leu Thr His Pro Val Thr Lys Tyr Ile Met Thr Cys Met
            610                 615                 620

Ser Ala Asp Leu Glu Val Val Cys Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
            675                 680                 685

<210> SEQ ID NO 9
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 9

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
            35                  40                  45

Ile Asn Gly Val Cys Trp Thr Val Tyr His Gly Ala Gly Thr Arg Thr
        50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

-continued

```
Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
            115                 120                 125

Ser Pro Arg Pro Ile Ser Tyr Leu Lys Gly Ser Ser Gly Gly Pro Leu
            130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                    165                 170                 175

Glu Thr Thr Met Arg Ser Pro Val Phe Ser Asp Asn Ser Ser Pro Pro
                180                 185                 190

Ala Val Pro Gln Ser Tyr Gln Val Ala His Leu His Ala Pro Thr Gly
            195                 200                 205

Ser Gly Lys Ser Thr Lys Val Pro Ala Ala Tyr Ala Ala Gln Gly Tyr
            210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                    245                 250                 255

Val Arg Thr Ile Thr Thr Gly Ser Pro Ile Thr Tyr Ser Thr Tyr Gly
                260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ala Thr Ser Ile Leu Gly Ile
290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                    325                 330                 335

Ile Glu Glu Val Ala Leu Ser Thr Thr Gly Glu Ile Pro Phe Tyr Gly
                340                 345                 350

Lys Ala Ile Pro Leu Glu Ala Ile Lys Gly Gly Arg His Leu Ile Phe
            355                 360                 365

Cys His Ser Lys Lys Cys Asp Glu Leu Ala Ala Lys Leu Val Ala
            370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                    405                 410                 415

Thr Gly Phe Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Gly
450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                    485                 490                 495

Asp Ala Gly Cys Ala Trp Tyr Glu Leu Thr Pro Ala Glu Thr Thr Val
                500                 505                 510
```

```
Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
        530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
                580                 585                 590

Leu His Gly Pro Thr Pro Leu Leu Tyr Arg Leu Gly Ala Val Gln Asn
                595                 600                 605

Glu Val Thr Leu Thr His Pro Val Thr Lys Tyr Ile Met Thr Cys Met
        610                 615                 620

Ser Ala Asp Leu Glu Val Cys Cys Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
                660                 665                 670

Arg Glu Val Leu Tyr Arg Glu Phe Asp Glu Met Glu Glu Cys
        675                 680                 685

<210> SEQ ID NO 10
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 10

Met Ala Pro Ile Thr Ala Tyr Ala Gln Gln Thr Arg Gly Leu Leu Gly
1

-continued

```
Ala Val Pro Gln Ser Tyr Gln Val Ala His Leu His Ala Pro Thr Gly
        195                 200                 205
Ser Gly Lys Ser Thr Lys Val Pro Ala Ala Tyr Ala Ala Gln Gly Tyr
210                 215                 220
Lys Val Leu Val Leu Asn Pro Ser Val Ala Ala Thr Met Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ser Pro Ile Thr Tyr Ser Thr Tyr Gly
            260                 265                 270
Lys Phe Leu Ala Asp Gly Gly Cys Ser Gly Ala Tyr Asp Ile Ile
        275                 280                 285
Ile Cys Asp Glu Cys His Ser Thr Asp Ala Thr Ser Ile Leu Gly Ile
    290                 295                 300
Gly Thr Val Leu Asp Gln Ala Glu Thr Ala Gly Ala Arg Leu Thr Val
305                 310                 315                 320
Leu Ala Thr Ala Thr Pro Pro Gly Ser Val Thr Val Pro His Pro Asn
                325                 330                 335
Ile Glu Glu Val Ala Leu Ser Thr Thr Gly Ile Pro Phe Tyr Gly
        340                 345                 350
Lys Ala Ile Pro Leu Glu Ala Ile Lys Gly Gly Arg His Leu Ile Phe
        355                 360                 365
Cys His Ser Lys Lys Cys Asp Glu Leu Ala Ala Lys Leu Val Ala
    370                 375                 380
Leu Gly Val Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
                405                 410                 415
Thr Gly Phe Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
            435                 440                 445
Thr Ile Thr Leu Pro Gln Asp Ala Val Ser Arg Thr Gln Arg Arg Gly
        450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
            500                 505                 510
Arg Leu Arg Ala Tyr Met Asn Thr Pro Gly Leu Pro Val Cys Gln Asp
        515                 520                 525
His Leu Glu Phe Trp Glu Gly Val Phe Thr Gly Leu Thr His Ile Asp
    530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
                580                 585                 590
Leu His Gly Pro Thr Pro Leu Leu Tyr Arg Leu Gly Ala Val Gln Asn
        595                 600                 605
Glu Val Thr Leu Thr His Pro Val Thr Lys Tyr Ile Met Thr Cys Met
```

```
               610                 615                 620
Ser Ala Asp Leu Glu Val Ser Ser Thr Trp Val Leu Val Gly Gly
625                 630                 635

```
                290                 295                 300
Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
                340                 345                 350

Lys Ala Ile Pro Leu Glu Ala Ile Lys Gly Gly Arg His Leu Ile Phe
                355                 360                 365

Cys His Ser Lys Lys Cys Asp Glu Leu Ala Ala Lys Leu Val Ala
370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                405                 410                 415

Thr Gly Phe Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
                435                 440                 445

Thr Ile Thr Leu Pro Gln Asp Ala Val Ser Arg Thr Gln Arg Gly
450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
                500                 505                 510

Arg Leu Arg Ala Tyr Met Asn Thr Pro Gly Leu Pro Val Cys Gln Asp
                515                 520                 525

His Leu Glu Phe Trp Glu Gly Val Phe Thr Gly Leu Thr His Ile Asp
                530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
                580                 585                 590

Leu His Gly Pro Thr Pro Leu Leu Tyr Arg Leu Gly Ala Val Gln Asn
                595                 600                 605

Glu Val Thr Leu Thr His Pro Val Thr Lys Tyr Ile Met Thr Cys Met
610                 615                 620

Ser Ala Asp Ser Ser Ser Cys Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
                660                 665                 670

Arg Glu Val Leu Tyr Arg Glu Phe Asp Glu Met Glu Glu Cys
                675                 680                 685

<210> SEQ ID NO 12
<211> LENGTH: 632
<212> TYPE: PRT
<213> ORGANISM: Artificial Sequence
```

```
<220> FEATURE:
<223> OTHER INFORMATION: Hepatitis C virus NS3 peptide

<400> SEQUENCE: 12

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400
```

```
Ile Pro Thr Ser Gly Asp Val Val Val Ala Thr Asp Ala Leu Met
                405                 410                 415

Thr Gly Phe Thr Gly Asp Phe Asp Ser Val Ile Asp Cys Asn Thr Cys
        420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr
625                 630

<210> SEQ ID NO 13
<211> LENGTH: 54
<212> TYPE: PRT
<213> ORGANISM: Artificial Sequence
<220> FEATURE:
<223> OTHER INFORMATION: Hepatitis C virus NS4A peptide

<400> SEQUENCE: 13

Ser Thr Trp Val Leu Val Gly Gly Val Leu Ala Ala Leu Ala Ala Tyr
  1               5                  10                  15

Cys Leu Ser Thr Gly Cys Val Val Ile Val Gly Arg Ile Val Leu Ser
             20                  25                  30

Gly Lys Pro Ala Ile Ile Pro Asp Arg Glu Val Leu Tyr Arg Glu Phe
         35                  40                  45

Asp Glu Met Glu Glu Cys
     50

<210> SEQ ID NO 14
<211> LENGTH: 25
<212> TYPE: PRT
<213> ORGANISM: Artificial Sequence
<220> FEATURE:
<223> OTHER INFORMATION: Hepatitis C virus NS3/4A peptide

<400> SEQUENCE: 14

Thr Lys Tyr Met Thr Cys Met Ser Ala Asp Leu Glu Val Val Thr Ser
```

-continued

```
            1               5                   10                  15

Thr Trp Val Leu Val Gly Gly Val Leu
            20                  25

<210> SEQ ID NO 15
<211> LENGTH: 12
<212> TYPE: PRT
<213> ORGANISM: Artificial Sequence
<220> FEATURE:
<223> OTHER INFORMATION: Hepatitis C virus NS3/4A peptide

<400> SEQUENCE: 15

Ser Ala Asp Leu Glu Val Val Thr Ser Thr Trp Val
1               5                   10

<210> SEQ ID NO 16
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 16

Thr Lys Tyr Met Thr Cys Met Ser Ala Asp Leu Glu Val Val Thr Gly
1               5                   10                  15

Thr Trp Val Leu Val Gly Gly Val Leu
            20                  25

<210> SEQ ID NO 17
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 17

Thr Lys Tyr Met Thr Cys Met Ser Ala Asp Leu Glu Val Val Arg Gly
1               5                   10                  15

Thr Trp Val Leu Val Gly Gly Val Leu
            20                  25

<210> SEQ ID NO 18
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 18

Thr Lys Tyr Met Thr Cys Met Ser Ala Asp Leu Glu Val Val Thr Pro
1               5                   10                  15

Thr Trp Val Leu Val Gly Gly Val Leu
            20                  25

<210> SEQ ID NO 19
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 19

Thr Lys Tyr Met Thr Cys Met Ser Ala Asp Leu Glu Val Val Arg Pro
1               5                   10                  15
```

-continued

Thr Trp Val Leu Val Gly Gly Val Leu
            20                  25

<210> SEQ ID NO 20
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 20

Thr Lys Tyr Met Thr Cys Met Ser Ala Asp Leu Glu Val Val Arg Pro
1               5                   10                  15

Ala Trp Val Leu Val Gly Gly Val Leu
            20                  25

<210> SEQ ID NO 21
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 21

Thr Lys Tyr Met Thr Cys Met Ser Ala Asp Leu Glu Val Val Cys Ser
1               5                   10                  15

Thr Trp Val Leu Val Gly Gly Val Leu
            20                  25

<210> SEQ ID NO 22
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 22

Thr Lys Tyr Met Thr Cys Met Ser Ala Asp Leu Glu Val Cys Cys Ser
1               5                   10                  15

Thr Trp Val Leu Val Gly Gly Val Leu
            20                  25

<210> SEQ ID NO 23
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 23

Thr Lys Tyr Met Thr Cys Met Ser Ala Asp Leu Glu Val Ser Ser Ser
1               5                   10                  15

Thr Trp Val Leu Val Gly Gly Val Leu
            20                  25

<210> SEQ ID NO 24
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 24

Thr Lys Tyr Met Thr Cys Met Ser Ala Asp Ser Ser Ser Ser Cys Ser
1               5                   10                  15

Thr Trp Val Leu Val Gly Gly Val Leu
            20                  25

<210> SEQ ID NO 25
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 25

Thr Lys Tyr Met Thr Cys Met Ser Ala Asp Val Val Val Thr Ser
1               5                   10                  15

Thr Trp Val Leu Val Gly Gly Val Leu
            20                  25

<210> SEQ ID NO 26
<211> LENGTH: 18
<212> TYPE: PRT
<213> ORGANISM: Artificial Sequence
<220> FEATURE:
<223> OTHER INFORMATION: mutant Hepatitis C virus NS5A/B peptide

<400> SEQUENCE: 26

Ser Ser Glu Asp Val Val Cys Cys Ser Met Trp Val Leu Val Gly Gly
1               5                   10                  15

Val Leu

<210> SEQ ID NO 27
<211> LENGTH: 16
<212> TYPE: PRT
<213> ORGANISM: Artificial Sequence
<220> FEATURE:
<223> OTHER INFORMATION: Hepatitis C virus NS5 peptide

<400> SEQUENCE: 27

Ala Ser Glu Asp Val Val Cys Cys Ser Met Ser Tyr Thr Trp Thr Gly
1               5                   10                  15

<210> SEQ ID NO 28
<211> LENGTH: 30
<212> TYPE: DNA
<213> ORGANISM: Artificial Sequence
<220> FEATURE:
<223> OTHER INFORMATION: cloning oligonucleotide

<400> SEQUENCE: 28
ccgtctagat cagcactctt ccatttcatc                                      30

<210> SEQ ID NO 29
<211> LENGTH: 30
<212> TYPE: DNA
<213> ORGANISM: Artificial Sequence
<220> FEATURE:
<223> OTHER INFORMATION: cloning oligonucleotide

<400> SEQUENCE: 29
cctgaattca tggcgcctat cacggcctat                                      30

<210> SEQ ID NO 30
<211> LENGTH: 24
<212> TYPE: DNA
<213> ORGANISM: Artificial Sequence
<220> FEATURE:
<223> OTHER INFORMATION: cloning oligonucleotide

```
<400> SEQUENCE: 30
ccacgcggcc gcgacgacct acag                                              24

<210> SEQ ID NO 31
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 31
ctggaggtcg tcacgcctac ctgggtgctc gtt                                    33

<210> SEQ ID NO 32
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 32
accgagcacc caggtaggcg tgacgacctc cag                                    33

<210> SEQ ID NO 33
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 33
ctggaggtcg tccgcggtac ctgggtgctc gtt                                    33

<210> SEQ ID NO 34
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 34
accgagcacc caggtaccgc ggacgacctc cag                                    33

<210> SEQ ID NO 35
<211> LENGTH: 2078
<212> TYPE: DNA
<213> ORGANISM: Artificial Sequence
<220> FEATURE:
<223> OTHER INFORMATION: Codon optimized hepatitis C virus NS3/4A coding
      region
<220> FEATURE:
<221> NAME/KEY: CDS
<222> LOCATION: (12)...(2072)

<400> SEQUENCE: 35
gaattcgcac c atg gcc ccc atc acc gcc tac gcc cag cag acc cgc ggc        50
            Met Ala Pro Ile Thr Ala Tyr Ala Gln Gln Thr Arg Gly
              1               5                  10 ctg ctg ggc tgc atc atc acc agc ctg acc ggc cgc gac aag aac cag         98
Leu Leu Gly Cys Ile Ile Thr Ser Leu Thr Gly Arg Asp Lys Asn Gln
         15                  20                  25 gtg gag ggc gag gtg cag atc gtg agc acc gcc gcc cag acc ttc ctg        146
Val Glu Gly Glu Val Gln Ile Val Ser Thr Ala Ala Gln Thr Phe Leu
 30                  35                  40                  45
```

```
gcc acc tgc atc aac ggc gtg tgc tgg acc gtg tac cac ggc gcc ggc      194
Ala Thr Cys Ile Asn Gly Val Cys Trp Thr Val Tyr His Gly Ala Gly
             50                  55                  60 acc cgc acc atc gcc agc ccc aag ggc ccc gtg atc cag atg tac acc      242
Thr Arg Thr Ile Ala Ser Pro Lys Gly Pro Val Ile Gln Met Tyr Thr
             65                  70                  75 aac gtg gac cag gac ctg gtg ggc tgg ccc gcc ccc cag ggc gcc cgc      290
Asn Val Asp Gln Asp Leu Val Gly Trp Pro Ala Pro Gln Gly Ala Arg
         80                  85                  90 agc ctg acc ccc tgc acc tgc ggc agc agc gac ctg tac ctg gtg acc      338
Ser Leu Thr Pro Cys Thr Cys Gly Ser Ser Asp Leu Tyr Leu Val Thr
     95                 100                 105 cgc cac gcc gac gtg atc ccc gtg cgc cgc cgc ggc gac ggc cgc ggc      386
Arg His Ala Asp Val Ile Pro Val Arg Arg Arg Gly Asp Gly Arg Gly
110                 115                 120                 125 agc ctg ctg agc ccc cgc ccc atc agc tac ctg aag ggc agc agc ggc      434
Ser Leu Leu Ser Pro Arg Pro Ile Ser Tyr Leu Lys Gly Ser Ser Gly
                130                 135                 140 ggc ccc ctg ctg tgc ccc gcc ggc cac gcc gtg ggc atc ttc cgc gcc      482
Gly Pro Leu Leu Cys Pro Ala Gly His Ala Val Gly Ile Phe Arg Ala
                145                 150                 155 gcc gtg tgc acc cgc ggc gtg gcc aag gcc gtg gac ttc atc ccc gtg      530
Ala Val Cys Thr Arg Gly Val Ala Lys Ala Val Asp Phe Ile Pro Val
            160                 165                 170 gag agc ctg gag acc acc atg cgc agc ccc gtg ttc agc gac aac agc      578
Glu Ser Leu Glu Thr Thr Met Arg Ser Pro Val Phe Ser Asp Asn Ser
175                 180                 185 agc ccc ccc gcc gtg ccc cag agc tac cag gtg gcc cac ctg cac gcc      626
Ser Pro Pro Ala Val Pro Gln Ser Tyr Gln Val Ala His Leu His Ala
190                 195                 200                 205 ccc acc ggc agc ggc aag agc acc aag gtg ccc gcc gcc tac gcc gcc      674
Pro Thr Gly Ser Gly Lys Ser Thr Lys Val Pro Ala Ala Tyr Ala Ala
                210                 215                 220 cag ggc tac aag gtg ctg gtg ctg aac ccc agc gtg gcc gcc acc atg      722
Gln Gly Tyr Lys Val Leu Val Leu Asn Pro Ser Val Ala Ala Thr Met
                225                 230                 235 ggc ttc ggc gcc tac atg agc aag gcc cac ggc atc gac ccc aac atc      770
Gly Phe Gly Ala Tyr Met Ser Lys Ala His Gly Ile Asp Pro Asn Ile
            240                 245                 250 cgc acc ggc gtg cgc acc atc acc acc ggc agc ccc atc acc tac agc      818
Arg Thr Gly Val Arg Thr Ile Thr Thr Gly Ser Pro Ile Thr Tyr Ser
255                 260                 265 acc tac ggc aag ttc ctg gcc gac ggc ggc tgc agc ggc ggc gcc tac      866
Thr Tyr Gly Lys Phe Leu Ala Asp Gly Gly Cys Ser Gly Gly Ala Tyr
270                 275                 280                 285 gac atc atc atc tgc gac gag tgc cac agc acc gac gcc acc agc atc      914
Asp Ile Ile Ile Cys Asp Glu Cys His Ser Thr Asp Ala Thr Ser Ile
                290                 295                 300 ctg ggc atc ggc acc gtg ctg gac cag gcc gag acc gcc ggc gcc cgc      962
Leu Gly Ile Gly Thr Val Leu Asp Gln Ala Glu Thr Ala Gly Ala Arg
            305                 310                 315 ctg acc gtg ctg gcc acc gcc acc ccc ccc ggc agc gtg acc gtg ccc     1010
Leu Thr Val Leu Ala Thr Ala Thr Pro Pro Gly Ser Val Thr Val Pro
            320                 325                 330 cac ccc aac atc gag gag gtg gcc ctg agc acc acc ggc gag atc ccc     1058
His Pro Asn Ile Glu Glu Val Ala Leu Ser Thr Thr Gly Glu Ile Pro
335                 340                 345 ttc tac ggc aag gcc atc ccc ctg gag gcc atc aag ggc ggc cgc cac     1106
Phe Tyr Gly Lys Ala Ile Pro Leu Glu Ala Ile Lys Gly Gly Arg His
350                 355                 360                 365
```

-continued

| | |
|---|---|
| ctg atc ttc tgc cac agc aag aag aag tgc gac gag ctg gcc gcc aag<br>Leu Ile Phe Cys His Ser Lys Lys Lys Cys Asp Glu Leu Ala Ala Lys<br>370 375 380 | 1154 |
| ctg gtg gcc ctg ggc gtg aac gcc gtg gcc tac tac cgc ggc ctg gac<br>Leu Val Ala Leu Gly Val Asn Ala Val Ala Tyr Tyr Arg Gly Leu Asp<br>385 390 395 | 1202 |
| gtg agc gtg atc ccc acc agc ggc gac gtg gtg gtg gcc acc gac<br>Val Ser Val Ile Pro Thr Ser Gly Asp Val Val Val Ala Thr Asp<br>400 405 410 | 1250 |
| gcc ctg atg acc ggc ttc acc ggc gac ttc gac agc gtg atc gac tgc<br>Ala Leu Met Thr Gly Phe Thr Gly Asp Phe Asp Ser Val Ile Asp Cys<br>415 420 425 | 1298 |
| aac acc tgc gtg acc cag acc gtg gac ttc agc ctg gac ccc acc ttc<br>Asn Thr Cys Val Thr Gln Thr Val Asp Phe Ser Leu Asp Pro Thr Phe<br>430 435 440 445 | 1346 |
| acc atc gag acc atc acc ctg ccc cag gac gcc gtg agc cgc acc cag<br>Thr Ile Glu Thr Ile Thr Leu Pro Gln Asp Ala Val Ser Arg Thr Gln<br>450 455 460 | 1394 |
| cgc cgc ggc cgc acc ggc cgc ggc aag ccc ggc atc tac cgc ttc gtg<br>Arg Arg Gly Arg Thr Gly Arg Gly Lys Pro Gly Ile Tyr Arg Phe Val<br>465 470 475 | 1442 |
| gcc ccc ggc gag cgc ccc agc ggc atg ttc gac agc agc gtg ctg tgc<br>Ala Pro Gly Glu Arg Pro Ser Gly Met Phe Asp Ser Ser Val Leu Cys<br>480 485 490 | 1490 |
| gag tgc tac gac gcc ggc tgc gcc tgg tac gag ctg acc ccc gcc gag<br>Glu Cys Tyr Asp Ala Gly Cys Ala Trp Tyr Glu Leu Thr Pro Ala Glu<br>495 500 505 | 1538 |
| acc acc gtg cgc ctg cgc gcc tac atg aac acc ccc ggc ctg ccc gtg<br>Thr Thr Val Arg Leu Arg Ala Tyr Met Asn Thr Pro Gly Leu Pro Val<br>510 515 520 525 | 1586 |
| tgc cag gac cac ctg gag ttc tgg gag ggc gtg ttc acc ggc ctg acc<br>Cys Gln Asp His Leu Glu Phe Trp Glu Gly Val Phe Thr Gly Leu Thr<br>530 535 540 | 1634 |
| cac atc gac gcc cac ttc ctg agc cag acc aag cag agc ggc gag aac<br>His Ile Asp Ala His Phe Leu Ser Gln Thr Lys Gln Ser Gly Glu Asn<br>545 550 555 | 1682 |
| ctg ccc tac ctg gtg gcc tac cag gcc acc gtg tgc gcc cgc gcc cag<br>Leu Pro Tyr Leu Val Ala Tyr Gln Ala Thr Val Cys Ala Arg Ala Gln<br>560 565 570 | 1730 |
| gcc ccc ccc ccc agc tgg gac cag atg tgg aag tgc ctg atc cgc ctg<br>Ala Pro Pro Pro Ser Trp Asp Gln Met Trp Lys Cys Leu Ile Arg Leu<br>575 580 585 | 1778 |
| aag ccc acc ctg cac ggc ccc acc ccc ctg ctg tac cgc ctg ggc gcc<br>Lys Pro Thr Leu His Gly Pro Thr Pro Leu Leu Tyr Arg Leu Gly Ala<br>590 595 600 605 | 1826 |
| gtg cag aac gag gtg acc ctg acc cac ccc gtg acc aag tac atc atg<br>Val Gln Asn Glu Val Thr Leu Thr His Pro Val Thr Lys Tyr Ile Met<br>610 615 620 | 1874 |
| acc tgc atg agc gcc gac ctg gag gtg gtg acc agc acc tgg gtg ctg<br>Thr Cys Met Ser Ala Asp Leu Glu Val Val Thr Ser Thr Trp Val Leu<br>625 630 635 | 1922 |
| gtg ggc ggc gtg ctg gcc gcc ctg gcc gcc tac tgc ctg agc acc ggc<br>Val Gly Gly Val Leu Ala Ala Leu Ala Ala Tyr Cys Leu Ser Thr Gly<br>640 645 650 | 1970 |
| tgc gtg gtg atc gtg ggc cgc atc gtg ctg agc ggc aag ccc gcc atc<br>Cys Val Val Ile Val Gly Arg Ile Val Leu Ser Gly Lys Pro Ala Ile<br>655 660 665 | 2018 |
| atc ccc gac cgc gag gtg ctg tac cgc gag ttc gac gag atg gag gag<br>Ile Pro Asp Arg Glu Val Leu Tyr Arg Glu Phe Asp Glu Met Glu Glu | 2066 |

```
                        670             675             680             685
tgc tga tctaga                                                                  2078
Cys  *
```

<210> SEQ ID NO 36
<211> LENGTH: 686
<212> TYPE: PRT
<213> ORGANISM: Artificial Sequence
<220> FEATURE:
<223> OTHER INFORMATION: Codon optimized hepatitis c virus NS3/4A coding
      region

<400> SEQUENCE: 36

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
     50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335
```

-continued

```
Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
            355                 360                 365

Cys His Ser Lys Lys Cys Asp Glu Leu Ala Ala Lys Leu Val Ala
            370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
            450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
            485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
            515                 520                 525

His Leu Glu Phe Trp Glu Gly Val Phe Thr Gly Leu Thr His Ile Asp
            530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
            595                 600                 605

Glu Val Thr Leu Thr His Pro Val Thr Lys Tyr Ile Met Thr Cys Met
            610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
            645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
            675                 680                 685
```

<210> SEQ ID NO 37
<211> LENGTH: 9
<212> TYPE: PRT
<213> ORGANISM: Artificial Sequence
<220> FEATURE:
<223> OTHER INFORMATION: Artificial Peptide, NS3/4A H-2D Binding Peptide

<400> SEQUENCE: 37

```
Gly Ala Val Gln Asn Glu Val Thr Leu
 1               5
```

```
<210> SEQ ID NO 38
<211> LENGTH: 9
<212> TYPE: PRT
<213> ORGANISM: Artificial Sequence
<220> FEATURE:
<223> OTHER INFORMATION: Artificial Peptide, H-2D Control Peptide

<400> SEQUENCE: 38

Lys Ala Val Tyr Asn Phe Ala Thr Met
 1               5

<210> SEQ ID NO 39
<211> LENGTH: 27
<212> TYPE: DNA
<213> ORGANISM: Artificial Sequence
<220> FEATURE:
<223> OTHER INFORMATION: primers for transgenic analysis

<400> SEQUENCE: 39
gcatgctccc accggcagcg gtaagag                                      27

<210> SEQ ID NO 40
<211> LENGTH: 27
<212> TYPE: DNA
<213> ORGANISM: Artificial Sequence
<220> FEATURE:
<223> OTHER INFORMATION: primers for transgenic analysis

<400> SEQUENCE: 40
cgcagaggac agacgagtca aacatgc                                      27

<210> SEQ ID NO 41
<211> LENGTH: 30
<212> TYPE: DNA
<213> ORGANISM: Artificial Sequence
<220> FEATURE:
<223> OTHER INFORMATION: primers for transgenic analysis

<400> SEQUENCE: 41
cctgaattca tggcgcctat cacggcctat                                   30

<210> SEQ ID NO 42
<211> LENGTH: 30
<212> TYPE: DNA
<213> ORGANISM: Artificial Sequence
<220> FEATURE:
<223> OTHER INFORMATION: primers for transgenic analysis

<400> SEQUENCE: 42
ccgtctagat cagcactctt ccatttcatc                                   30

<210> SEQ ID NO 43
<211> LENGTH: 27
<212> TYPE: DNA
<213> ORGANISM: Artificial Sequence
<220> FEATURE:
<223> OTHER INFORMATION: primers for transgenic analysis

<400> SEQUENCE: 43
gcatgctccc accggcagcg gtaagag                                      27

<210> SEQ ID NO 44
<211> LENGTH: 27
<212> TYPE: DNA
<213> ORGANISM: Artificial Sequence
<220> FEATURE:
```

<223> OTHER INFORMATION: primers for transgenic analysis

<400> SEQUENCE: 44
cgcagaggac agacgagtca aacatgc                                         27

<210> SEQ ID NO 45
<211> LENGTH: 38
<212> TYPE: PRT
<213> ORGANISM: Hepatitis C virus

<400> SEQUENCE: 45

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe
        35

<210> SEQ ID NO 46
<211> LENGTH: 48
<212> TYPE: PRT
<213> ORGANISM: Artificial Sequence
<220> FEATURE:
<223> OTHER INFORMATION: Hepatitis B e antigen with an artificially
      introduced NS3/4A

<400> SEQUENCE: 46

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Leu Glu Val Val Thr Ser Thr Tr

```
<223> OTHER INFORMATION: Cleavage domain of NS4A/4B

<400> SEQUENCE: 49

Asp Leu Glu Val Val Thr Ser Thr Trp Val Leu Val Gly Gly Val Leu
 1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: Cleavage domain of NS4A/4B

<400> SEQUENCE: 50

Leu Glu Val Val Thr Ser Thr Trp Val Leu Val Gly Gly Val Leu
 1               5                  10                  15

<210> SEQ ID NO 51
<211> LENGTH: 14
<212> TYPE: PRT
<213> ORGANISM: Artificial Sequence
<220> FEATURE:
<223> OTHER INFORMATION: Cleavage domain of NS4A/4B

<400> SEQUENCE: 51

Glu Val Val Thr Ser Thr Trp Val Leu Val Gly Gly Val Leu
 1               5                  10

<210> SEQ ID NO 52
<211> LENGTH: 13
<212> TYPE: PRT
<213> ORGANISM: Artificial Sequence
<220> FEATURE:
<223> OTHER INFORMATION: Cleavage domain of NS4A/4B

<400> SEQUENCE: 52

Val Val Thr Ser Thr Trp Val Leu Val Gly Gly Val Leu
 1               5                  10

<210> SEQ ID NO 53
<211> LENGTH: 12
<212> TYPE: PRT
<213> ORGANISM: Artificial Sequence
<220> FEATURE:
<223> OTHER INFORMATION: Cleavage domain of NS4A/4B

<400> SEQUENCE: 53

Val Thr Ser Thr Trp Val Leu Val Gly Gly Val Leu
 1               5                  10

<210> SEQ ID NO 54
<211> LENGTH: 11
<212> TYPE: PRT
<213> ORGANISM: Artificial Sequence
<220> FEATURE:
<223> OTHER INFORMATION: Cleavage domain of NS4A/4B

<400> SEQUENCE: 54

Thr Ser Thr Trp Val Leu Val Gly Gly Val Leu
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Cleavage domain of NS4A/4B
```

```
<400> SEQUENCE: 55

Thr Ser Thr Trp Val Leu Val Gly Gly Val
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Cleavage domain of NS4A/4B

<400> SEQUENCE: 56

Thr Ser Thr Trp Val Leu Val Gly Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Cleavage domain of NS4A/4B

<400> SEQUENCE: 57

Thr Ser Thr Trp Val Leu Val Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Cleavage domain of NS4A/4B

<400> SEQUENCE: 58

Thr Ser Thr Trp Val Leu Val
1               5

<210> SEQ ID NO 59
<211> LENGTH: 6
<212> TYPE: PRT
<213> ORGANISM: Artificial Sequence
<220> FEATURE:
<223> OTHER INFORMATION: Cleavage domain of NS4A/4B

<400> SEQUENCE: 59

Thr Ser Thr Trp Val Leu
1               5

<210> SEQ ID NO 60
<211> LENGTH: 5
<212> TYPE: PRT
<213> ORGANISM: Artificial Sequence
<220> FEATURE:
<223> OTHER INFORMATION: Cleavage domain of NS4A/4B

<400> SEQUENCE: 60

Thr Ser Thr Trp Val
1               5

<210> SEQ ID NO 61
<211> LENGTH: 4
<212> TYPE: PRT
<213> ORGANISM: Artificial Sequence
<220> FEATURE:
<223> OTHER INFORMATION: Cleavage domain of NS4A/4B
```

```
<400> SEQUENCE: 61

Thr Ser Thr Trp
1

<210> SEQ ID NO 62
<211> LENGTH: 11
<212> TYPE: PRT
<213> ORGANISM: Artificial Sequence
<220> FEATURE:
<223> OTHER INFORMATION: Cleavage domain of NS4A/4B

<400> SEQUENCE: 62

Cys Met Ser Ala Asp Leu Glu Val Val Thr Ser
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Cleavage domain of NS4A/4B

<400> SEQUENCE: 63

Met Ser Ala Asp Leu Glu Val Val Thr Ser
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Cleavage domain of NS4A/4B

<400> SEQUENCE: 64

Ser Ala Asp Leu Glu Val Val Thr Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Cleavage domain of NS4A/4B

<400> SEQUENCE: 65

Ala Asp Leu Glu Val Val Thr Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Cleavage domain of NS4A/4B

<400> SEQUENCE: 66

Asp Leu Glu Val Val Thr Ser
1               5

<210> SEQ ID NO 67
<211> LENGTH: 6
<212> TYPE: PRT
<213> ORGANISM: Artificial Sequence
<220> FEATURE:
<223> OTHER INFORMATION: Cleavage domain of NS4A/4B

<400> SEQUENCE: 67
```

-continued

```
Leu Glu Val Val Thr Ser
 1               5

<210> SEQ ID NO 68
<211> LENGTH: 5
<212> TYPE: PRT
<213> ORGANISM: Artificial Sequence
<220> FEATURE:
<223> OTHER INFORMATION: Cleavage domain of NS4A/4B

<400> SEQUENCE: 68

Glu Val Val Thr Ser
 1               5

<210> SEQ ID NO 69
<211> LENGTH: 4
<212> TYPE: PRT
<213> ORGANISM: Artificial Sequence
<220> FEATURE:
<223> OTHER INFORMATION: Cleavage domain of NS4A/4B

<400> SEQUENCE: 69

Val Val Thr Ser
 1

<210> SEQ ID NO 70
<211> LENGTH: 10
<212> TYPE: PRT
<213> ORGANISM: Artificial Sequence
<220> FEATURE:
<223> OTHER INFORMATION: Cleavage domain of NS4A/4B

<400> SEQUENCE: 70

Leu Glu Val Val Thr Ser Thr Trp Val Leu
 1               5                  10

<210> SEQ ID NO 71
<211> LENGTH: 9
<212> TYPE: PRT
<213> ORGANISM: Artificial Sequence
<220> FEATURE:
<223> OTHER INFORMATION: Cleavage domain of NS4A/4B

<400> SEQUENCE: 71

Glu Val Val Thr Ser Thr Trp Val Leu
 1               5

<210> SEQ ID NO 72
<211> LENGTH: 8
<212> TYPE: PRT
<213> ORGANISM: Artificial Sequence
<220> FEATURE:
<223> OTHER INFORMATION: Cleavage domain of NS4A/4B

<400> SEQUENCE: 72

Val Val Thr Ser Thr Trp Val Leu
 1               5

<210> SEQ ID NO 73
<211> LENGTH: 20
<212> TYPE: PRT
<213> ORGANISM: Artificial Sequence
<220> FEATURE:
<223> OTHER INFORMATION: Cleavage domain of NS4A/4B

<400> SEQUENCE: 73
```

-continued

```
Cys Met Ser Ala Asp Leu Glu Val Val Thr Ser Thr Trp Val Leu Val
 1              5                   10                  15

Gly Gly Val Leu
            20

<210> SEQ ID NO 74
<211> LENGTH: 20
<212> TYPE: PRT
<213> ORGANISM: Hepatitis C virus

<400> SEQUENCE: 74

Cys Met Ser Ala Asp Leu Glu Val Val Thr Ser Thr Trp Val Leu Val
 1              5                   10                  15

Gly Gly Val Leu
            20

<210> SEQ ID NO 75
<211> LENGTH: 19
<212> TYPE: PRT
<213> ORGANISM: Artificial Sequence
<220> FEATURE:
<223> OTHER INFORMATION: Cleavage domain of NS4A/4B

<400> SEQUENCE: 75

Met Ser Ala Asp Leu Glu Val Val Thr Ser Thr Trp Val Leu Val Gly
 1              5                   10                  15

Gly Val Leu

<210> SEQ ID NO 76
<211> LENGTH: 180
<212> TYPE: PRT
<213> ORGANISM: Artificial Sequence
<220> FEATURE:
<223> OTHER INFORMATION: Hepatitis C virus NS3/4A coding region

<400> SEQUENCE: 76

Ala Pro Ile Thr Ala Tyr Ser Gln Gln Thr Arg Gly Leu Leu Gly Cys
 1              5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Pro Ala Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Ile Pro Val Glu Ser Met Glu
                165                 170                 175

Thr Thr Met Arg
```

```
                    180
```

<210> SEQ ID NO 77
<211> LENGTH: 54
<212> TYPE: PRT
<213> ORGANISM: Artificial Sequence
<220> FEATURE:
<223> OTHER INFORMATION: Hepatitis C virus NS3/4A coding region

<400> SEQUENCE: 77

Ser Thr Trp Val Leu Val Gly Gly Val Leu Ala Ala Leu Ala Ala Tyr
 1               5                  10                  15

Cys Leu Thr Thr Gly Ser Val Val Ile Val Gly Arg Ile Ile Leu Ser
            20                  25                  30

Gly Arg Pro Ala Val Ile Pro Asp Arg Glu Val Leu Tyr Gln Glu Phe
        35                  40                  45

Asp Glu Met Glu Glu Cys
    50

<210> SEQ ID NO 78
<211> LENGTH: 20
<212> TYPE: PRT
<213> ORGANISM: Artificial Sequence
<220> FEATURE:
<223> OTHER INFORMATION: Hepatitis C virus NS3/4A coding region

<400> SEQUENCE: 78

Tyr Gln Glu Phe Asp Glu Met Glu Glu Cys Ala Ser His Leu Pro Tyr
 1               5                  10                  15

Ile Glu Gln Gly
            20

<210> SEQ ID NO 79
<211> LENGTH: 20
<212> TYPE: PRT
<213> ORGANISM: Artificial Sequence
<220> FEATURE:
<223> OTHER INFORMATION: Hepatitis C virus NS3/4A coding region

<400> SEQUENCE: 79

Trp Ile Asn Glu Asp Cys Ser Thr Pro Cys Ser Gly Ser Trp Leu Arg
 1               5                  10                  15

Asp Val Trp Asp
            20

<210> SEQ ID NO 80
<211> LENGTH: 20
<212> TYPE: PRT
<213> ORGANISM: Artificial Sequence
<220> FEATURE:
<223> OTHER INFORMATION: Hepatitis C virus NS3/4A coding region

<400> SEQUENCE: 80

Glu Glu Ala Ser Glu Asp Val Val Cys Cys Ser Met Ser Tyr Thr Trp
 1               5                  10                  15

Thr Gly Ala Leu
            20